(12) United States Patent
Yang et al.

(10) Patent No.: US 9,260,382 B2
(45) Date of Patent: Feb. 16, 2016

(54) METHODS OF REDUCING VIRULENCE IN BACTERIA

(75) Inventors: Ching-Hong Yang, Mequon, WI (US); Xin Chen, Chapel Hill, NC (US); Eric J. Toone, Durham, NC (US)

(73) Assignees: UWM Research Foundation, Milwaukee, WI (US); Duke University, Durham, NC (US)

( * ) Notice: Subject to any disclaimer, the term of this patent is extended or adjusted under 35 U.S.C. 154(b) by 107 days.

(21) Appl. No.: 13/579,373

(22) PCT Filed: Feb. 16, 2011

(86) PCT No.: PCT/US2011/025082
§ 371 (c)(1),
(2), (4) Date: Aug. 16, 2012

(87) PCT Pub. No.: WO2011/103189
PCT Pub. Date: Aug. 25, 2011

(65) Prior Publication Data
US 2012/0322769 A1   Dec. 20, 2012

Related U.S. Application Data

(60) Provisional application No. 61/305,027, filed on Feb. 16, 2010, provisional application No. 61/332,385, filed on May 7, 2010.

(51) Int. Cl.
*A61K 31/40* (2006.01)
*A61K 31/4015* (2006.01)
(Continued)

(52) U.S. Cl.
CPC ............ *C07C 259/06* (2013.01); *A61K 31/05* (2013.01); *A61K 31/137* (2013.01); *A61K 31/165* (2013.01); *A61K 31/185* (2013.01); *A61K 31/192* (2013.01); *A61K 31/194* (2013.01);
(Continued)

(58) Field of Classification Search
CPC .......... A61K 31/4015; A61K 31/4164; A61K 31/175
USPC ............... 548/311.1, 452; 514/396, 412, 617; 564/305
See application file for complete search history.

(56) References Cited

U.S. PATENT DOCUMENTS

| 5,447,903 A | 9/1995 | Ort et al. |
| 5,994,077 A | 11/1999 | Valdivia et al. |

(Continued)

FOREIGN PATENT DOCUMENTS

| WO | WO 99/58714 | 11/1999 |
| WO | 02068610 | 9/2002 |

(Continued)

OTHER PUBLICATIONS

HCAPLUS abstract of Appukkuttan, et al., Tetrahedron Letters, HCAPLUS Accession # 2008:1017175, published 2008.*

(Continued)

*Primary Examiner* — Kamal Saeed
*Assistant Examiner* — Janet L Coppins
(74) *Attorney, Agent, or Firm* — Michael Best & Friedrich LLP

(57) ABSTRACT

A method of reducing virulence in a bacterium comprising at least one of a GacS/GacA-type system, a HrpX/HrpY-type system, a T3SS-type system, and a Rsm-type system, the method comprising contacting the bacterium with an effective amount of a compound described herein.

21 Claims, 33 Drawing Sheets

(51) Int. Cl.
| | |
|---|---|
| A61K 31/4164 | (2006.01) |
| A61K 31/175 | (2006.01) |
| C07C 259/06 | (2006.01) |
| A61K 31/05 | (2006.01) |
| A61K 31/137 | (2006.01) |
| A61K 31/165 | (2006.01) |
| A61K 31/185 | (2006.01) |
| A61K 31/192 | (2006.01) |
| A61K 31/194 | (2006.01) |
| A61K 31/196 | (2006.01) |
| A61K 31/216 | (2006.01) |
| A61K 31/255 | (2006.01) |
| A61K 31/277 | (2006.01) |
| A61K 31/341 | (2006.01) |
| A61K 31/343 | (2006.01) |
| A61K 31/381 | (2006.01) |
| A61K 31/4035 | (2006.01) |
| A61K 31/404 | (2006.01) |
| A61K 31/4172 | (2006.01) |
| A61K 31/4178 | (2006.01) |
| A61K 31/4406 | (2006.01) |
| A61K 31/4409 | (2006.01) |
| A61K 31/4439 | (2006.01) |
| A61K 31/662 | (2006.01) |
| A61K 31/683 | (2006.01) |
| C07C 211/29 | (2006.01) |
| C07C 215/54 | (2006.01) |
| C07C 233/65 | (2006.01) |
| C07C 235/34 | (2006.01) |
| C07C 237/20 | (2006.01) |
| C07C 243/32 | (2006.01) |
| C07C 259/08 | (2006.01) |
| C07C 309/24 | (2006.01) |
| C07C 309/68 | (2006.01) |
| C07D 209/14 | (2006.01) |
| C07D 209/48 | (2006.01) |
| C07D 209/86 | (2006.01) |
| C07D 213/56 | (2006.01) |
| C07D 233/64 | (2006.01) |
| C07D 307/52 | (2006.01) |
| C07D 307/79 | (2006.01) |
| C07D 333/24 | (2006.01) |
| C07D 333/60 | (2006.01) |
| C07D 403/06 | (2006.01) |
| C07D 405/06 | (2006.01) |
| C07F 9/38 | (2006.01) |

(52) U.S. Cl.
CPC ............ *A61K 31/196* (2013.01); *A61K 31/216* (2013.01); *A61K 31/255* (2013.01); *A61K 31/277* (2013.01); *A61K 31/341* (2013.01); *A61K 31/343* (2013.01); *A61K 31/381* (2013.01); *A61K 31/404* (2013.01); *A61K 31/4035* (2013.01); *A61K 31/4172* (2013.01); *A61K 31/4178* (2013.01); *A61K 31/4406* (2013.01); *A61K 31/4409* (2013.01); *A61K 31/4439* (2013.01); *A61K 31/662* (2013.01); *A61K 31/683* (2013.01); *C07C 211/29* (2013.01); *C07C 215/54* (2013.01); *C07C 233/65* (2013.01); *C07C 235/34* (2013.01); *C07C 237/20* (2013.01); *C07C 243/32* (2013.01); *C07C 259/08* (2013.01); *C07C 309/24* (2013.01); *C07C 309/68* (2013.01); *C07D 209/14* (2013.01); *C07D 209/48* (2013.01); *C07D 209/86* (2013.01); *C07D 213/56* (2013.01); *C07D 233/64* (2013.01); *C07D 307/52* (2013.01); *C07D 307/79* (2013.01); *C07D 333/24* (2013.01); *C07D 333/60* (2013.01); *C07D 403/06* (2013.01); *C07D 405/06* (2013.01); *C07F 9/3826* (2013.01); *C07C 2101/02* (2013.01)

(56) References Cited

U.S. PATENT DOCUMENTS

| | | | |
|---|---|---|---|
| 7,026,155 B2 | 4/2006 | Mahan et al. | |
| 7,196,085 B2 | 3/2007 | Martin et al. | |
| 7,339,043 B2 | 3/2008 | Cheung et al. | |
| 2002/0086332 A1 | 7/2002 | Mahan et al. | |
| 2002/0102246 A1 | 8/2002 | Schneider et al. | |
| 2003/0176364 A1 | 9/2003 | Ninkov | |
| 2007/0128328 A1 | 6/2007 | Tanada et al. | |
| 2009/0012128 A1 | 1/2009 | Tsuchida et al. | |
| 2010/0249234 A1 | 9/2010 | Yang et al. | |

FOREIGN PATENT DOCUMENTS

| | | | |
|---|---|---|---|
| WO | WO 2008/115118 | 9/2008 | |
| WO | WO 2008/124836 | 10/2008 | |
| WO | WO-2008/134836 A2 * | 10/2008 | ............ A61K 31/00 |

OTHER PUBLICATIONS

HCAPLUS abstract of Brewbaker, et al., J. Am. Chem. Society, HCAPLUS Accession # 1969:67319, published 1969.*
HCAPLUS abstract of Di Fabio, et al., Bio & Med. Chem. Letters, HCAPLUS Accession # 2003:795121, published 2003.*
HCAPLUS abstract of Eckhardt, et al., J. Clinical Chem & Clinical Biochem, HCAPLUS Accession # 1977:462286, published 1977.*
HCAPLUS abstract of Gadient, F., DE 2252080, HCAPLUS Accession # 1973:478370, published May 3, 1973.*
HCAPLUS abstract of Griffith, et al., Bioorganic & Med. Chem. Letters, HCAPLUS Accession #1993:254814, published 1993.*
HCAPLUS abstract of Hori, et al., EP 255695, HCAPLUS Accession # 1988:534833, published Feb. 10, 1988.*
HCAPLUS abstract of Jolidon et al., WO 2004007429, HCAPLUS Accession # 2004:60452, published Jan. 22, 2004.*
HCAPLUS abstract of Joung et al., Cancer Research, HCAPLUS Accession # 2006:459139, published 2006.*
HCAPLUS abstract of Lim et al., WO 2005040101, HCAPLUS Accession # 2005:395258, published May 6, 2005.*
HCAPLUS abstract of Mhatre et al., Indian J. Het. Chem., HCAPLUS Accession # 2000:545303, published 2000.*
HCAPLUS abstract of Tajima et al., WO 2006011669, HCAPLUS Accession # 2006:103803, published Feb. 2, 2006.*
HCAPLUS abstract of Thaler et al., J. Med. Chem, HCAPLUS Accession # 2009:1563803, published 2010.*
HCAPLUS abstract of Szmaszkovicz, J., U.S. Pat. No. 3,043,849, HCAPLUS Accession # 1962:483164, published Jul. 10, 1962.*
HCAPLUS abstract of Wagh et al., Asian J. Chem, HCAPLUS Accession # 2007:854258, published 2007.*
International Search Report and Written Opinion of International Searching Authority for Application No. PCT/US2008/059928 dated Nov. 21, 2008 (16 pages).
Office Action from the US Patent and Trademark Office for U.S. Appl. No. 12/595,148 dated Dec. 13, 2012 (12 pages).
First Office Action from the State Intellectual Property Office of China for Application No. 201180019127.2 dated Sep. 30, 2013 (18 pages).
Aiello, D. et al., "Discovery and characterization of inhibitors of Pseudomonas aeruginosa type III secretion," Antimicrob Agents Chemother. (2010) 54:1988-1999.
Alfano, J.R. et al., "The pseudomonas syringae Hrp pathogenicity island has a tripartite mosaic structure composed of a cluster of type III secretion genes bounded by exchangeable effector and conserved effector loci that contribute to parasitic fitness and pathogenicity in plants," Proc. Natl. Acad. Sci USA (2000) 97:4856-4861.

(56) References Cited

OTHER PUBLICATIONS

Alfano, J.R. et al., "Type III secretion system effector proteins: double agents in bacterial disease and plant defense," Annu. Rev. Phytopathol. (2004) 42:385-414.

Arlat, M. et al., "Transcriptional organization and expression of the large hrp gene-cluster of Pseudomonas solanacearum," Mol. Plant Microbe Interact. (1992) 5:187-193.

Bahrani, F.K. et al., "Secretion of Ipa proteins by shigella flexneri: inducer molecules and kinetics of activation," Inf. Immun. (1997) 65(10):4005-4010.

Bailey, L. et al., "Small molecule inhibitors of type III secretion in Yersinia block the chlamydia pneumoniae infection cycle," FEBS Lett. (2007) 581:587-595.

Barnard, F.M. et al., "Global regulation of virulence and the stress response by Csra in the highly adapted human gastric pathogen helicobacter pylori," Mol. Microbiol. (2004) 51:15-32.

Bauer, D.W. et al., "Erwinia chrysanthemi harpinEch: an elicitor of the hypersensitive response that contributes to soft-rot pathogenesis," Mol. Plant Microbe Interact. (1995) 8:484-491.

Bauer, D.W. et al., "*Erwinia chrysanthemi* hrp genes and their inolvementin soft rot pathogenesis and elicitation of the hypersensitive response," Mol. Plant Microbe Interact. (1994) 7:573-581.

Bell, K.S. et al., "Genome sequence of the enterobacterial phytopathogen *Erwinia carotovora* subsp. Atroseptica and characterization of virulence factors," Proc. Natl. Acad. Sci. USA (2004) 101:11105-11110.

Ben-Ami, R. et al., "Multinational survey of risk factors for infection with extended-spectrum beta-lactamase-producing enterobacteriaceae in nonhospitalized patients," Clin. Infect. Dis. (2009) 49:682-690.

Benghezal, M. et al., "Inhibitors of bacterial virulence identified in a surrogate host model," Cell Microbiol. (2007) 9:1336-1342.

Boccara, M. et al., "Genetic diversity and host range in strains of Erwinia chrysanthemi," Mol. Plant Microbe Interact. (1991) 4:293-299.

Brandl, M.T. et al., "Leaf age as a risk factor in contamination of lettuce with *Escherichia coli* O157:H7 and *Salmonella enterica*," Appl. Environ. Microbiol. (2008) 74:2298-2306.

Brandl, M.T., "Plant lesions promote the rapid multiplication of *Escherichia coli* O157:H7 on postharvest lettuce," Appl. Env. Microbiol. (2008) 74(17):5258-5289.

Brencic, A. et al., "Determination of the regulon and identification of novel Mrna targets of pseudomonas aeruginosa Rsma," Mol. Microbiol. (2009) 72:612-632.

Buell, C.R. et al., "The complete genome sequence of the arabidopsis and tomato pathogen *Pseudomonas syringae* pv tomato DC3000," Proc. Natl. Acad. Sci. USA (2003) 100:10181-10186.

Burrowes, E. et al., "Characterisation of the regulatory Rna Rsmb from pseudomonas aeruginosa Pao1," Res. Microbiol. (2005) 156:7-16.

Burrowes, E. et al., "Influence of the regulatory protein RsmA on cellular functions in pseudomonas aeruginosa PAO1, as revealed by transcriptome analysis," Microbiology (2006) 152:405-418.

Buttner, D. et al., "Who comes first? How plant pathogenic bacteria orchestrate type III secretion," Curr. Opin. Microbiol. (2006) 9:193-200.

Cegelski, L. et al., "The biology and future prospects of antivirulence therapies," Nat. Rev. Microbiol. (2008) 6:17-27.

Chancey, S.T. et al., "Survival of GacS/GacA mutants of the biological control bacterium Pseudomonas aureofaciens 30-84 in the wheat rhizosphere," Appl. Environ. Microbiol. (2002) 68:3308-3314.

Chang, J.H. et al., "Wake of the flood: ascribing functions to the wave of type III effector proteins of phytopathogenic bacteria," Curr. Opin. Microbiol. (2004) 7:11-18.

Charkowski, A. et al., The *Pseudomonas syringae* pv. tomato HrpW protein has domains similar to harpins and pectate lyases and can elicit the plant hypersensitive response and bind to pectate. Journal of bacteriology (1998) 180(19): 5211-5217.

Chatterjee, A. et al., "GacA, the response regulatory of a two-component system, acts as a mastery regulatory in *Pseudomonas syringae* pv. Tomato DC3000 by controlling regulatory RNA, transcriptional activators, and alternate sigma factors," Mol. Plant-Microbe Interact. (2003) 16:1106-1117.

Chatterjee, A. et al., "Regulation of Erwinia carotovora hrpL(Ecc) (sigma-L(Ecc)), which encodes an extracytoplasmic function subfamily of sigma factor required for expression of the HRP regulon," Mol. Plant-Microbe Interact. (2002) 15:971-980.

Chatterjee, A. et al., "RsmA and the quorum-sensing signal, N-[3-oxohexanoyl]-L-homoserine lactone, control the levels of rsmB RNA in *Erwinia carotovora* subsp. *carotovora* by affecting its stability," J. Bacteriol. (2002) 184:4089-4095.

Chellas-Gery, B. et al., "human Gcip interacts with Ct847, a novel chlamydia trachomatis type III secretion substrate, and is degraded in a tissue-culture infection model," Cell Microbiol. (2007) 9:2417-2430.

Coburn, B. et al., "Type III secretion systems and disease," Clin. Microbiol. Rev. (2007) 20:535-549.

Collmer, A. et al., "The role of pectic enzymes in plant pathogenesis," Ann. Rev. Phytopathol. (1986) 43:383-409.

Collmer, A. et al. Pseudomonas syringae Hrp type III secretion system and effector proteins. Proceedings of the National Academy of Sciences of the United States of America (2000) 97: 8770-8777.

Corey, E.J. et al., "Dimethyloxosulfonium methylide and dimethylsulfonium methylide. Formulation and application to organic synthesis," J. Am. Chem. Soc. (1965) 87:1353-1364.

Cui, Y. et al., "Effects of the two-component system comprising GacA and GacS of *Erwinia carotovora* subsp. *carotovora* on the production of global regulatory rsmB RNA, extracellular enzymes, and harpin ECC," Mol. Plant-Microbe Interact. (2001) 14:516-526.

Cui, Y. et al., "Identification of a global repressor gene, rsmA, of *Erwinia carotovora* subsp. *carotovora* that controls extracellular enzymes, N-(3-oxohexanoyl)-L-homoserine lactone, and pathogenicity in soft-rotting *Erwinia* spp.," J. Bacteriol. (1995) 177:5108-5115.

Cui, Y. et al., "rsmC of the soft-rotting bacterium *Erwinia carotovora* subsp. *carotovora* negatively controls extracellular enzyme and harpin(Ecc) production and virulence by modulating levels of regulatory RNA (rsmB) and RNA-binding protein (RsmA)," J. Bacteriol. (1999) 181:6042-6052.

Cunnac, S. et al., "Pseudomonas syringae type III secretion system effectors: repertoires in search of functions," Curr. Opin. Microbiol. (2009) 12:53-60.

Debroy, S. et al., "A family of conserved bacterial effectors inhibits salicylic acid-mediated basal immunity and promotes disease necrosis in plants," Proc. Natl. Acad. Sci. USA (2004) 101:9927-9932.

Dong, H. et al., "Harpin induces disease resistance in arabidopsis through the systemic acquired resistance pathway mediated by salicylic acid and the NIM1 gene," Plant J. (1999) 20:207-215.

Engel, J. et al., "Role of pseudomonas aeruginosa type III effectors in disease," Curr. Opin. Microbiol. (2009) 12:61-66.

Enninga, J. et al., "Imaging the assembly, structure and activity of type III secretion systems," Cell Microbiol. (2009) 11:1462-1470.

Fouts, D.E. et al., "Genomewide identification of *Pseudomonas syringae* pv. Tomato DC3000 promoters controlled by the HrpL alternative sigma factor," Proc. Natl. Acad. Sci. (2002) 99:2275-2280.

Francis, M.S. et al., "Regulation of type III secretion systems," Curr. Opin. Microbiol. (2002) 5:166-172.

Franza, T. et al., "Erwinia chrysanthemi requires a second iron transport route dependent of the siderophore achromobactin for extracellular growth and plant infection," Mol. Microbiol. (2005) 55(1):261-275.

Galan, J.E. et al., "Type III secretion machines: bacterial devices for protein delivery into host cells," Science (1999) 284:1322-1328.

Gilbert, P. et al., "Biocide usage in the domestic setting and concern about antibacterial and antibiotic resistance," J. Infect. (2001) 43:85-91.

Gould, I.M., "Antibiotic resistance: the perfect storm," Int. J. Antimicrob. Agents (2009) 34 Suppl. 3:S2-5.

Grant, S.R. et al., "Subterfuge and manipulation: type III effector proteins of phytopathogenic bacteria," Annu. Rev. Microbiol. (2006) 60:425-449.

(56) References Cited

OTHER PUBLICATIONS

Guo, M. et al., "The majority of the type III effector inventory of *Pseudomonas syringae* Pv. Tomato Dc3000 can suppress plant immunity," Mol. Plant Microbe Interact. (2009) 22:1069-1080.
Hawkey, P.M. et al., "The changing epidemiology of resistance," J. Antimicrob. Chemother. (2009) 64 Suppl 1:3-10.
Heeb, S. et al., "Regulatory roles of the GacS/GacA two-component system in plant-associated and other gram-negative bacteria," Mol. Plant-Microbe Interact. (2001) 14:1351-1363.
Heilig, S. et al., "Curtailing antibiotic use in agriculture: it is time for action: this use contributes to bacterial resistance in humans," West J. Med. (2002) 176:9-11.
Hentzner, M. et al., "Quorum sensing: a novel target for the treatment of biofilm infections," BioDrugs (2003) 17:241-250.
Hudson, D. L. et al., "Inhibition of type III secretion in *Salmonella enterica* serovar Typhimurium by small-molecule inhibitors," Antimicrob Agents Chemother (2007) 51:2631-2635.
Hugouvieux-Cotte-Pattat, N. et al., "Regulation of pectinolysis in Erwinia chrysanthemi," Annu. Rev. Microbiol. (1996) 50:213-257.
Hung, D.T. et al., "Small-molecule inhibitor of vibrio cholerae virulence and intestinal colonization," Science (2005) 310:670-674.
Hyytiainen, H. et al., "Global regulators ExpA (GacA) and KdgR modulate extracellular enzyme gene expression through the RsmA-rsmB system in *Erwinia carotovora* subsp. *carotovora*," Mol. Plant-Microbe Interact. (2001) 14:931-938.
Kalogeraki, V.S. et al., "The phenolic vir gene inducer ferulic acid is O-demethylated by the VirH2 protein of an agrobacterium tumefaciens Ti plasmid," Mol. Micro. (1999) 34(3):512-522.
Kauppi, A.M. et al., "Targeting bacterial virulence: inhibitors of type III secretion in Yersinia," Chem. Biol. (2003) 10:241-249.
Keyser, P. et al., "Blockers as alternatives to antibiotics: type III secretion inhibitors against gram-negative bacteria," J. Intern. Med. (2008) 264:17-29.
Kivi, M. et al., "A beef-associated outbreak of *Salmonella typhimurium* Dt104 in the Netherlands with implications for National and International policy," Epidemiol. Infect. (2007) 135:890-899.
Krawczyk, H. et al., "Knoevenagel reaction of diethylphosphonoacetic acid: a facile route to diethyl (E)-2-arylvinylphosphonates," Synthesis (2005) 17:2887-2896.
Lan, L. et al., "Genome-wide gene expression analysis of *Pseudomonas syringae* pv. Tomato DC3000 reveals overlapping and distinct pathways regulated by hrpL and hrpRS," Mol. Plant Microbe Interact. (2006) 19:976-987.
Lawhon, S.D. et al., "Global regulation by Csra in *Salmonella typhimurium*," Mol. Microbiol. (2003) 48:1633-1645.
Leveau, J.H. et al., "Predictive and interpretive simulation of green fluorescent protein expression in reporter bacteria," J. Bacteriol. (2001) 183:6752-6792.
Levy, S.B., "Antibiotic resistance—the problem intensifies," Adv. Drug Deliv. Rev. (2005) 57:1446-1450.
Li, S.W. et al., "Synthesis of a biochemically important aldehyde, 3,4-dihydroxyphenylacetaldehyde," Bioorg. Chem. (1998) 26:45-50.
Li, Y. et al., "Plant phenolic compound p-coumaric acid represses gene expression in the *Dickeya dadantii* Type III Secretion System," Appl. Environ. Microbiol. (2009) 75(5):1223-1228.
Lindeberg, M. et al., "Closing the circle on the discovery of genes encoding Hrp regulon members and type III secretion system effectors in the genomes of three model pseudomonas syringae strains," Mol. Plant-Microbe Interact (2006) 19:1151-1158.
Lister, P.D. et al., "Antibacterial-resistant Pseudomonas Aeruginosa: clinical impact and complex regulation of chromosomally encoded resistance mechanisms," Clin. Microbiol. Rev. (2009) 22:582-610.
Liu, Y. et al., "Characterization of a novel RNA regulator of *Erwinia carotovora* ssp. *carotovora* that controls production of extracellular enzymes and secondary metabolites," Mol. Microbiol. (1998) 29:219-234.

Login, F.H. et al., "The single transmembrane segment drives self-assembly of OutC and the formation of a functional type II secretion system in Erwinia chrysanthemi," J. Biol. Chem. (2006) 281:33152-33162.
Logue, C.M. et al., "*Salmonella* contamination of turkey from processing to final product—a process to product perspective," Foodborne Pathog. Dis. (2007) 4:491-504.
Lojkowska, E. et al., "Characterization of the pelL gene encoding a novel pectate lyase of Erwinia chrysanthemi 3937," Mol. Microbiol. (1995) 16:1183-1195.
Lopez-Solanilla, E. et al., "Relative effects on virulence of mutations in the sap, pel, and hrp loci of erwinia chrysanthemi," Mol. Plant Microbe Interact. (2001) 14:386-393.
Luzzatto, T. et al., "Priming of antimicrobial phenolics during induced resistance response towards pectobacterium carotovorum in the ornamental monocot calla lily," J. Agric. Food Chem. (2007) 55:10315-10322.
Lyon, G.J. et al., "Rational design of a global inhibitor of the virulence response in *Staphylococcus aureus*, based in part on localization of the site of inhibition to the receptor-histidine kinase, AgrC," Proc. Natl. Acad. Sci. (2000) 97:13330-13335.
Ma, B. et al., "Host range and molecular phylogenies of the soft rot enterobacterial genera *Pectobacterium* and *Dickeya*," Phytopathology (2007) 97:1150-1163.
Majdalani, N. et al., Bacterial small RNA regulators, Crit. Rev. Biochem. Mol. Biol. (2005) 40:93-113.
Matsumoto, H. et al., "Peh production, flagellum synthesis, and virulence reduced in *Erwinia carotovora* subsp. *carotovora* by mutation in a homologue of cyrR," Mol. Phant-Microbe Interact. (2003) 16:389-397.
Matsushita, M. et al., "Histidine kinases as targets for new antimicrobial agents," Bioorg. Med. Chem. (2002) 10:855-867.
McEwen, S.A. et al., "Antimicrobial use and resistance in animals," Clin. Infect. Dis. (2002) 34 Suppl. 3:S93-S106.
McManus, P.S. et al., "Antibiotic use in plant agriculture," Annu. Rev. Phytopathol. (2002) 40:443-465.
Mead, P.S. et al., "Food-related illness and death in the United States reply to Dr. Hedberg," Emerg. Infect. Dis. (1999) 5:841-842.
Merighi, M. et al., "Role of *Salmonella enterica* serovar typhimurium two-component system PreA/PreB in modulating PmrA-regulated gene transcription," J. Bacteriol. (2006) 188:141-149.
Metcalf, W.W. et al., "Conditionally replicative and conjugative plasmids carrying lacZ alpha for cloning, mutagenesis, and allele replacement in bacteria," Plasmid (1996) 35:1-13.
Metraux, J.P., "Recent breakthroughs in the study of salicylic acid biosynthesis," Trends Plant Sci. (2002) 7:332-334.
Miller, W.G. et al., "An improved GFP cloning cassette designed for prokaryotic transcriptional fusions," Gene (1997) 191:149-153.
Miller, W.G. et al., "Improved gfp and inaZ broad-host-range promoter-probe vectors," Mol. Plant-Microbe Interact. (2000) 13:1243-1250.
Montesano, M. et al., "Multiple defense signals induced by *Erwinia carotovora* ssp. *carotovora* in potato," Mol. Plant Pathol. (2005) 6:541-549.
Mota, L.J. et al., "Type III secretion: the bacteria-eukaryotic cell express," FEMS Microbiol. Lett. (2005) 252:1-10.
Mukherjee, A. et al., "Global regulation in *Erwinia* species by *Erwinia carotovora* rsmA, a homologue of *Escherichia coli* csrA: repression of secondary metabolites, pathogenicity and hypersensitive reaction," Microbiol. (1996) 142:427-434.
Mulcahy, H. et al., "The posttranscriptional regulatory RsmA plays a role in the interaction between pseudomonas aeruginosa and human airway epithelial cells by positively regulating the type III secretion system," Infect. Immun. (2006) 74:3012-3015.
Muschiol, S. et al., "Small molecule inhibitors of the yersinia type III secretion system impair the development of chlamydia after entry into host cells," BMC Microbiol. (2009) 9:75, 7 pages.
Muschiol, S. et al., "Small-molecule inhibitor of type III secretion inhibits different stages of the infectious cycle of chlamydia trachomatis," proc. Natl. Acad. Sci. USA (2006) 103:14566-14571.
Nasser, W. et al., "Pecs and Pct coregulate the synthesis of Hrpn and pectate lyases, two virulence determinants in erwinia chrysanthemi 3937," Mol. Plant Microbe Interact. (2005) 18:1205-1214.

(56) References Cited

OTHER PUBLICATIONS

Niimi, T. et al., "Design and synthesis of non-peptidic inhibitors for the Syk C-terminal SH2 domain based on structure-based in-silico screening," J. Med. Chem. (2001) 44:4737-4740.
Nordfelth, R. et al., "Small-molecule inhibitors specifically targeting type III secretion," Infect Immun (2005) 73:3104-3114.
Okinaka, Y. et al., "Identification of potential virulence genes in erwinia chrysanthemi 3937; transposon insertion into plant-upregulated genes," J. Gen. Plant Pathology (2006) 72:360-368.
Pan, N.J. et al., "Targeting type III secretion in Yersinia pestis," Antimicrob. Agents Chemother. (2009) 53:385-392.
Patel, B.A. et al.,"Palladium-catalyzed vinylic substitution reactions with carboxylic acid derivatives," J. Org. Chem. (1977) 42:3903-3907.
Peng, Q. et al., "Population behavior analysis of dspE and pelD regulation in Erwinia chrysanthemi 3937," Mol. Plant-Microbe Interact. (2006) 19:451-457.
Pfaffl, M.W. et al., "Relative expression software tool (REST) for group-wise comparison and statistical analysis of relative expression results in real-time PCR," Nucl. Acids Res. (2002) 30:e36.
Pinkner, J.S. et al., "Rationally designed small compounds inhibit pilus biogenesis in uropathogenic bacteria," proc. Natl. Acad. Sci. USA (2006) 103:17897-17902.
Raskin, I., "Role of salicyclic acid in plants," Annu. Rev. Plant Physiol. Plant Mol. Biol. (1992) 43:439-463.
Ravirala, R.S. et al., "Efflux pump gene expression in erwinia chrysanthemi is induced by exposure to phenolic acids," Molecular Plant-Microbe Interactions: MPMI (2007) 20(3):313-320.
Rietsch, A. et al., "Metabolic regulation of type III secretion gene expression in Pseudomonas aeruginosa," Mol. Microbiol. (2006) 59:807-820.
Roberts, N.J. et al., "Gentamicin use and pseudomonas and serratia resistance: effect of a surgical prophylaxis regimen," Antimicrob. Agents Chemother. (1978) 13:214-220.
Shah, J., "The salicylic acid loop in plant defense," Curr. Opin. Plant Biol. (2003) 6:365-371.
Tang, X. et al., "Regulation of the tyep III secretion system in phytopathogenic bacteria," Mol. Plant-Microbe Interact. (2006) 19:1159-1166.
Tardy, F. et al., "Comparative analysis of the five major erwinia chrysanthemi pectate lyases: enzyme characteristics and potential inhibitors," J. Bacteriol. (1997) 179:2503-2511.
Toth, I.K. et al., "Comparative genomics reveals what makes an entererobacterial plant pathogen," Annu. Rev. Phytopathol. (2006) 44:305-336.
Valecillos, A.M. et al., "The role of several multidrug resistance systems in Erwinia crysanthemi pathogeneis," Mol Plant Microbe Interact. (2006) 19:607-613.
Veenendaal, A.K.J. et al., "Small molecule T3SS inhibitors block assembly of the shigella type III secretion," J. Bacteriol. (2009) 191(2):563-570.
Vidal, S. et al., "Salicylic acid and the plant pathogen erwinia carotovora induce defense genes via antagonistic pathways," Plant J. (1997) 11:115-123.
Weber, E. et al., "The type III-dependent Hrp pilus is required for productive interaction of *Xanthomonas campestris* pv. Vesicatoria with pepper host plants," J. Bacteriol. (2005) 187:2458-2468.
Wei, Z.M. et al., "Regulation of hrp genes and type III protein secretion in erwinia amylovora by HrpX/HrpY, a novel two-component system, and HrpS," Mol. Plant Microbe Interact. (2000) 13:1251-1262.
Wiley, D.J. et al., "Induction of the Yersinia type 3 secretion system as an all-or-none phenomenon," J. Mol. Biol. (2007) 373:27-37.
Wolf, K. et al., "Treatment of chlamydia trachomatis with a small molecule inhibitor of the Yersini a type III secretion system disrupts progression of the chlamydial development cycle," Mol. Microbiol. (2006) 61(6):1543-1555.
Wright, A.C. et al., "Pathogens in raw foods: what the salad bar can learn from the raw bar," Curr. Opin. Biotechnol. (2009) 20:172-177.
Xiao, Y.X. et al., "Organizational and environmental regulation of the *Pseudomonas syringae* pv. *syringae* 61 hrp cluster," J. Bacteriol. (1992) 174:1734-1741.
Yahr, T.L. et al., "Transcriptional regulation of the pseudomonas aeruginosa type III secretion system," Mol. Microbiol. (2006) 62:631-640.
Yalpani, N. et al., "Pathway of salicylic acid biosynthesis in healthy and virus-inoculated tobacco," Plant Physiol. (1993) 103:315-321.
Yamazaki, A. et al., "Derivatives of Plant Phenolic Compound Affect the Type III Secretion system of Pseudomonas aeruginosa via a GacS—GacA Two-Component Signal Transduction System." Antimicrobial Agents and Chemotherapy (2012) 56(1): 36-43.
Yang, C.H. et al., "Hrp genes of erwinia chrysanthema 3937 are important virulence factors," Mol. Plant Microbe Interact. (2002) 15:472-480.
Yang, S. et al., "Dynamic regulation of GacA in type III secretion system, pectinase gene expression pellicle formation, and pathogenicity of *Dickeya dadantii* (*Erwinia chrysanthemi* 3937)," Mol. Plant. Microbe Int. (2008) 21(1):133-142.
Yang, S. et al., "Genome-wide identification of plant-upregulated genes of *Erwinia chrysanthemi* 3937 using a GFP-based IVET leaf array," Mol. Plant-Microbe Interact. (2004) 17:999-1008.
Yang, S. et al., "Global effect of indole-3-acetic acid biosynthesis on multiple virulence factors of Erwinia chrysanthemi 3937," Appl. Environ. Microbiol. (2007) 73:1079-1088.
Yang, S. et al., "Type III secretion system genes of *Dickeya dandantii* 3937 are induced by plant phenolic acids," Plos One (2008) 3(8):e2973, pp. 1-9.
Yap, M.N. et al., "Harpin mediates cell aggregation in Erwinia chrysanthemi 3937," J. Bacteriol. (2006) 188:2280-2284.
Yap, M.N. et al., "the Erwinia chrysanthemi type III secretion system is required for multicellular behavior," J. Bacteriol. (2005) 187:639-648.
Yip, C.K. et al., "Structural characterization of the molecular platform for type III secretion system assembly," Nature (2005) 435:702-707.
Zeng, Q. et al. "Regulatory mechanisms of exoribonuclease PNPase and regulatory small RNA on T3SS of Dickeya dadantii." Mol Plant Mmicrob Interact (2010) 23(10): 1345-55.
Zhang, X. et al., "A new procedure for preparation of carboxylic acid hydrazides," J. Org. Chem. (2002) 67:9471-9474.
Zhao, Y. et al., "Virulence systems of *Pseudomonas syringae* pv. Tomato promote bacterial speck disease in tomato by targeting the jasmonate signaling pathway," Plant J. (2003) 36:485-499.
Zou, L. et al. SlyA regulates type III secretion system (T3SS) genes in parallel with the T3SS master regulator HrpL in Dickeya dadantii 3937. Appl Environ Microbiol (2012) 78(8): 2888-95.
International Preliminary Report on Patentability for Application No. PCT/US2008/059928 dated Oct. 13, 2009 (8 pages).
International Preliminary Report on Patentability for Application No. PCT/US2011/025082 dated Aug. 21, 2012 (7 pages).
Office Action from the US Patent and Trademark Office for U.S. Appl. No. 12/595,148 dated Oct. 7, 2013 (13 pages).
Second Office Action from the State Intellectual Property Office of China for Application No. 201180019127.2 dated Jun. 5, 2014 (9 pages).
Office Action from the State Intellectual Property Office of China for Application No. 201180019127.2 dated Feb. 17, 2015 (10 pages).

* cited by examiner

Bacterial strains, plasmids, and primers used in this study.

| Strains, plasmids, and primers | Characteristics[a] or sequences[b] (5' to 3') | Reference or source |
|---|---|---|
| Strains | | |
| *E. coli* | | |
| S17-1 λ-*pir* | λ-*pir* lysogen of S17-1, Sp[r] | Victor de Lorenzo, Spain |
| *P. syringae* | | |
| DC3000 | Wild type, Rif[r] | (Cuppels 1986) |
| Plasmids | | |
| pPROBE-NT | pPROBE-gfp[AAV]; Promoter-probe vector, Km[r] | (Miller and Lindow 1997) |
| phrpA | pPROBE-NT derivative containing 496-bp *hrpA* promoter region, Km[r] | This study |
| Primers | | |
| Promoter amplification: | | |
| PhrpA-F (*Bam*HI) | TTT<u>GGATCC</u>CGATGTTTGCCCACTGCTG | This study |
| PhrpA-R (*Eco*RI) | ACA<u>GAATTC</u>CGTGTTGACACCCTGCAATG | This study |
| Real-Time PCR: | | |
| RTgap1-F | ATCGAAAGCGGCCTGATGAC | This study |
| RTgap1-R | CTCGGGATCATCGACTGGGT | This study |
| RTgyrA-F | TCAAGGACCTGCTGGAAGCC | This study |
| RTgyrA-R | CCGCCTGACCTTCAAGGATG | This study |
| RThrpW-F | CCGGCAAGATCAATGTGGTG | This study |
| RThrpW-R | TTTCGCCCTGGTCTCCGTTA | This study |

[a] Sp[r], Rif[r], and Km[r] indicate resistance to spectinomycin, rifampin, and kanamycin, respectively.
[b] Restriction sites incorporated into primers are underlined.

FIG. 31

The compounds screened for *Pseudomonas syringae* pv. *tomato* DC3000 (DC3000) *hrpA* inducers and inhibitors. Expression of DC3000 *hrpA* in HIM or HIM supplemented with different compounds.

| Phenolic compound (compound no.)[a] | Avg MFI ±SD[b] at: | |
|---|---|---|
| | 6 h | 9 h |
| DC3000 (pPROBE-NT) | 1.9±0.0 | 1.8±0.0 |
| DC3000 (phrpA) : | | |
| HIM | 69.8±1.3 | 109.2±3.3 |
| Yang001, *trans*-Cinnamic acid (TCA) | 17.9±0.6[*] | 34.8±0.3[*] |
| Yang034, Benzoic acid (BA) | 10.4±0.6[*] | 27.3±0.3[*] |
| Yang006, *ortho*-Coumaric acid (OCA) | 19.9±0.4[*] | 31.7±0.7[*] |
| Yang004, *para*-Coumaric acid (PCA) | 58.4±7.3[*] | 86.4±13.4[*] |
| Yang033, Salicylic acid (SA) | 12.3±0.5[*] | 29.5±1.7[*] |
| | | |
| HIM | 45.1±5.9 | 118.5±6.4 |
| Yang100, Ethyl *trans*-2-(4-methoxyphenyl)-1-cyclopropanecarboxylate | 43.9±0.7 | 113.0±3.1 |
| Yang101, Methyl *para*-coumate | 28.7±4.7 | 99.8±9.8 |
| Yang102, *trans*-4-Hydroxycinnamide | 34.8±4.2 | 105.7±5.4 |
| Yang103, *trans*-4-Hydroxycinnamohydroxamic acid | 20.8±2.2[*] | 85.0±3.7 |
| Yang104, *para*-Coumaryl alcohol | 49.1±2.6 | 120.1±7.3 |
| Yang105, *trans*-2-(4-Methoxyphenyl)-1-cyclopropanecarboxylic acid | 26.8±1.2 | 86.1±1.2 |
| Yang106, Ethyl *trans*-2-(4-hydroxyphenyl)-1-cyclopropanecarboxylate | 40.4±4.4 | 110.0±8.5 |
| Yang107, *trans*-2-(4-Hydroxyphenyl)-1-cyclopropanecarboxylic acid | 25.4±4.1[*] | 93.7±4.7 |
| Yang108, *trans*-4-Phenylcinnamic acid | 25.2±3.3[*] | 85.6±5.0[*] |
| Yang109, *trans*-4-Chlorocinnamide | 27.8±2.3[*] | 98.3±5.3 |
| Yang114, Diethyl *trans*-2-(4-hydroxyphenyl)-vinylphosphonate | 49.8±3.3 | 121.4±3.0 |
| Yang115, *trans*-2-(4-Hydroxyphenyl)-vinylphosphonic acid | 55.0±3.6 | 123.8±6.9 |
| Yang116, N-(para-Coumaryl)phthalimide | 55.0±3.5 | 128.5±4.8 |
| Yang117, *para*-Coumarylamine | 36.1±2.4[*] | 87.2±0.9[*] |
| Yang118, N-(4-Methoxycinnamyl)phthalimide | 56.7±7.7 | 128.0±8.9 |
| Yang119, *trans*-4-Methoxycinnamylamine | 44.0±3.4 | 86.7±2.3 |
| Yang123, *trans*-2-(4-Hydroxyphenyl)ethenylsulfonic acid tetra(*n*-butyl)ammonium salt | 55.1±1.8 | 124.0±1.7 |
| Yang124, *trans*-4-Hydroxymethylcinnamic acid | 23.8±1.0[*] | 80.9±2.3[*] |
| Yang126, *trans*-4-Methoxycinnamyl alcohol | 36.6±4.5 | 106.3±8.1 |
| Yang127, *trans*-3-Indoleacrylohydroxamic acid | 2.2±0.0[*] | 44.9±6.2[*] |
| Yang128, *trans*-4-Bromocinnamohydroxamic acid | 2.1±0.0[*] | 2.1±0.1[*] |
| | | |
| HIM | 76.2±11.6 | 103.7±11.3 |
| Yang005, *meta*-Coumaric acid (MCA) | 55.4±2.2[*] | 104.0±5.5 |
| Yang008, Hydrocinnamic acid | 47.2±1.8[*] | 105.4±3.2 |
| Yang009, Phenoxyacetic acid | 29.3±0.3[*] | 51.0±6.0[*] |
| Yang010, *trans*-2-Phenylcyclopropane-1-carboxylic acid | 77.7±5.2 | 146.9±8.1 |
| Yang013, *trans*-3-(3-Pyridyl)acrylic acid | 23.7±2.6[*] | 43.0±3.9[*] |
| 035, 3-(2-naphthyl) acrylic acid | 58.7±2.7 | 95.1±5.6 |
| Yang012, *trans*-3-Indoleacrylic acid | 56.7±1.1 | 128.9±1.7 |
| Yang011, *trans*-3-(2-Thienyl)acrylic acid | 31.8±1.9[*] | 76.4±4.6[*] |
| Yang015, *trans*-2-Methoxycinnamic acid | 102.3±1.9[*] | 129.2±6.4[*] |
| Yang018, *trans*-2-Methylcinnamic acid | 81.0±2.1[*] | 118.6±3.2[*] |
| Yang024, *trans*-2-Carboxycinnamic acid | 72.0±5.1 | 94.4±5.4 |
| Yang021, *trans*-2-Chlorocinnamic acid | 115.1±6.7[*] | 156.1±9.5[*] |

FIG. 31 continued

| | | |
|---|---|---|
| Yang030, Methyl *trans*-cinnamate | 79.8±3.3 | 114.7±7.1 |
| Yang032, Cinnamyl alcohol | 92.3±10.8 | 123.1±12.2 |
| Yang014, *trans*-3-(4-Imidazolyl)acrylic acid | 98.1±1.9 | 109.7±1.2 |
| Yang031, *trans*-Cinnamamide | 84.9±3.4 | 105.0±2.7 |
| Yang002, 2,4-Dihydroxycinnamic acid | 84.5±5.0 | 97.4±4.4 |
| Yang007, 3-(4-Hydroxyphenyl)propionic acid | 94.2±2.7 | 148.1±2.5 |
| Yang023, *trans*-4-Chlorocinnamic acid | 68.8±2.2 | 84.2±2.9 |
| Yang017, *trans*-4-Methoxycinnamic acid | 53.2±4.1* | 59.6±4.3* |
| Yang020, *trans*-4-Methylcinnamic acid | 84.5±4.6 | 89.4±4.9 |
| Yang027, *trans*-4-Aminocinnamic acid | 22.0±0.7* | 42.9±1.2* |
| Yang025, *trans*-4-Carboxycinnamic acid | 108.7±10.1 | 116.6±9.0 |
| HIM | 46.7±7.5 | 102.5±10.2 |
| Yang026, *trans*-4-Mercaptocinnamic acid | 37.0±1.0 | 96.8±1.0 |
| Yang003, 3,4-Dihydroxycinnamic acid | 49.0±0.9 | 116.0±2.1 |
| Yang029, *trans*-4-Formylcinnamic acid | 11.9±1.1* | 53.7±6.0* |
| Yang028, *trans*-4-Nitrocinnamic acid | 5.3±0.8* | 36.3±4.0* |
| Yang022, *trans*-3-Chlorocinnamic acid | 23.0±1.9* | 54.5±1.9* |
| Yang016, *trans*-3-Methoxycinnamic acid | 35.6±1.0* | 78.1±1.4* |
| Yang019, *trans*-3-Methylcinnamic acid | 32.2±1.0* | 76.4±2.0* |
| Yang110, *trans*-4-Fluorocinnamic acid | 29.0±0.8* | 76.8±1.4* |
| Yang111, *trans*-4-Bromocinnamic acid | 21.1±2.7* | 53.3±7.1* |
| Yang112, *trans*-4-Dimethylaminocinnamic acid | 33.8±6.6* | 77.8±6.6* |
| Yang113, *trans*-4-Trifluoromethylcinnamic acid | 17.7±1.3* | 45.9±1.4* |
| Yang120, Ethyl *trans*-2-(4-methoxyphenyl)-ethenylsulfonate | 41.1±1.6 | 89.5±2.4 |
| Yang121, *trans*-2-(4-Methoxyphenyl)ethenylsulfonic acid tetra(*n*-butyl) ammonium salt | 41.7±5.2 | 97.6±8.6 |
| Yang122, Ethyl *trans*-2-(4-hydroxyphenyl)-ethenylsulfonate | 38.8±4.4 | 88.3±5.1 |
| Yang125, *trans*-4-Methoxycinnamohydroxamic acid | 17.7±2.4* | 61.1±4.1* |
| Yang129, *trans*-2-Hydroxycinnamohydroxamic acid | 2.2±0.0* | 9.4±1.3* |
| Yang130, *trans*-3-Hydroxycinnamohydroxamic acid | 10.3±1.2* | 69.0±6.2* |
| Yang131, *trans*-3,4-Dihydroxycinnamohydroxamic acid | 34.5±2.9* | 72.3±6.3* |
| Yang132, *trans*-Cinnamohydroxamic acid | 3.1±0.2* | 7.5±0.9* |
| Yang133, *trans*-3-(4-Hydroxyphenyl)acrylohydrazide | 24.6±3.2* | 54.8±5.1* |
| HIM | 24.3±1.8 | 28.0±5.3 |
| Yang134, Benzhydroxamic acid | 19.4±0.9 | 25.3±1.6 |
| Yang135, Salicylhydroxamic acid | 4.2±0.2* | 8.1±0.5* |
| Yang136, Phenylpropiolic acid | 15.9±0.7 | 26.8±1.3 |
| Yang137, N-Methyl-4-hydroxycinnamamide | 27.5±1.2 | 34.2±2.7 |
| Yang138, N-(2-Hydroxyethyl)-4-hydroxycinnamamide | 27.9±0.2 | 34.2±1.0 |
| Yang139, 3-Phenylpropionohydroxamic acid | 17.4±1.9 | 29.3±2.5 |
| Yang140, *trans*-4-Phenylcinnamohydroxamic acid | 13.1±2.3* | 14.3±1.7* |
| Yang141, *trans*-4-Fluorocinnamohydroxamic acid | 3.0±0.0* | 4.3±0.1* |
| Yang142, *trans*-4-Methylcinnamohydroxamic acid | 10.1±0.8* | 11.4±0.3* |
| Yang143, 2-Phenoxyacetohydroxamic acid | 14.6±1.4 | 23.8±1.3 |
| HIM | 52.7±4.6 | 64.2±5.7 |
| Yang144, 4-Hydroxybenzoic acid | 48.3±0.1 | 63.1±3.3 |
| Yang145, 3-Hydroxybenzoic acid | 43.2±5.3 | 54.7±3.1 |
| Yang146, *trans*-4-Formylcinnamohydroxamic acid | 41.7±3.0 | 64.5±3.1 |
| Yang147, *trans*-4-Hydroxymethylcinnamohydroxamic acid | 55.9±3.8 | 76.5±4.0 |

FIG. 31 continued

| | | |
|---|---|---|
| Yang148, *trans*-4-Chlorocinnamohydroxamic acid | 3.9±2.7* | 3.1±0.2* |
| Yang149, *trans*-3-Chlorocinnamohydroxamic acid | 4.0±0.2* | 6.4±1.1* |
| Yang150, *trans*-2-Chlorocinnamohydroxamic acid | 9.4±0.4* | 11.9±0.5* |
| Yang151, *trans*-3-Bromocinnamohydroxamic acid | 3.7±0.4* | 5.4±0.5* |
| Yang152, *trans*-2-Bromocinnamohydroxamic acid | 8.9±0.4* | 11.4±0.9* |
| Yang153, *trans*-3-Fluorocinnamohydroxamic acid | 4.1±0.2* | 5.4±0.3* |
| Yang154, *trans*-2-Fluorocinnamohydroxamic acid | 6.2±0.7* | 7.2±1.1* |
| | | |
| HIM | 78.1±17.5 | 84.3±8.7 |
| Yang155, *trans*-4-Nitrocinnamohydroxamic acid | 34.3±3.7* | 41.5±6.2* |
| Yang156, *trans*-3-Nitrocinnamohydroxamic acid | 49.7±5.5* | 59.9±7.3* |
| Yang157, *trans*-2-Nitrocinnamohydroxamic acid | 33.9±2.6* | 47.9±1.6* |
| Yang158, *trans*-3-Methoxycinnamohydroxamic acid | 48.9±4.8* | 57.8±7.7* |
| Yang159, *trans*-2-Methoxycinnamohydroxamic acid | 69.1±20.0 | 87.7±20.8 |
| Yang160, *trans*-2-Methylcinnamohydroxamic acid | 60.1±4.0* | 80.2±13.0 |
| Yang161, *trans*-3-(2-Thienyl)acrylhydroxamic acid | 38.3±1.2* | 53.4±1.4* |
| Yang162, *trans*-2-Phenylcyclopropane-1-carbohydroxamic acid | 59.0±6.9* | 89.9±5.6 |
| Yang163, *trans*-3-(2-Furyl)acrylhydroxamic acid | 30.3±8.0* | 36.7±9.8* |
| Yang164, *trans*-4-(Benzylcarbonyl)cinnamic acid | 45.2±0.5* | 47.0±1.1* |
| Yang165, *trans*-2-[(4'-Benzylcarbonyl]phenylcyclopropane-1-carboxylic acid | 61.8±1.3 | 69.3±1.0 |
| Yang166, *trans*-4-(Carbo-phenylamide)cinnamic acid | 68.0±2.7 | 72.1±4.4 |
| Yang167, *trans*-4-(Carbo-N-methyl-phenylamide)cinnamic acid | 73.4±4.5 | 76.6±2.9 |

[a] HIM was supplemented with 100 µM of the indicated compound. The chemicals were assayed on two or three separate occasions with HIM only (no supplementation) as the control treatment for each set of experiments. The compound numbers listed correspond to those used in Fig. 1.

[b] The promoter activities of DC3000 carrying the GFP reporter plasmid phrpA were determined at 6 h and 9 h of bacterial growth. GFP mean fluorescence intensity (MFI) was determined for gated populations of bacterial cells by flow cytometry. Values are representative of two or three experiments, and three replicates were used in each experiment. Asterisks indicate statistically significant differences in GFP MFI between DC3000 grown in HIM or in HIM supplemented with the indicated compounds. ($P < 0.01$, Student's $t$ test).

FIG. 32

METHODS OF REDUCING VIRULENCE IN BACTERIA

CROSS-REFERENCE TO RELATED APPLICATIONS

This patent application is a national stage filing under 35 U.S.C. §371 of International Application No. PCT/US2010/025082, filed Feb. 16, 2011, which claims the benefit of priority to U.S. Provisional Application No. 61/305,027, filed on Feb. 16, 2010, and U.S. Provisional Application No. 61/332,385, filed on May 7, 2010, each of which is incorporated herein by reference in its entirety. Priority to each application is hereby claimed.

STATEMENT REGARDING FEDERALLY SPONSORED RESEARCH

This invention was made with government support under EF-0332163 awarded by the National Science Foundation. The United States government has certain rights in the invention.

FIELD OF THE INVENTION

The present invention relates to methods and compounds for controlling virulence in bacteria, methods of identifying further compounds for controlling virulence in bacteria, and methods, compounds, and compositions for treating subjects with bacterial infections to reduce virulence of bacteria in said subjects.

BACKGROUND

GacS/GacA is a two component signal transduction system ("TCSTS") that is widely distributed in many bacteria to respond to environmental stimuli and adapt to different environmental conditions. GacS is a putative histidine kinase sensor and GacA is the response regulator. The homologs of the TCSTS of GacS/GacA have been reported in a variety of Gram-negative bacteria, including *E. coli* (BarA/UvrY), *Pectobacterium* spp., *S. typhimurium* (BarA/SirA), *Pseudomonas* spp. (GacS/GacA), *Legionella pneumophila* (LetS/LetA) and *Vibrio* species.

GacS/GacA and homologous systems regulate many virulence factors including, but not limited to, regulatory RNA, quorum sensing ("QS") signals, type III secretion system ("T3SS") genes, pectate lyases, proteases, biofilm formation, and toxins. For example, in *D. dadantii*, the GacS/GacA system is located at the top of a regulatory cascade and functions as a central regulator by controlling an assortment of transcriptional and posttranscriptional factors. Mainly, the influence of the GacS/GacA system on pectinase production and T3SS gene expression is channeled through a regulatory RNA system, the Rsm system, by activating rsmB which binds to and inhibits the T3SS mRNA decay effect of RsmA.

In addition to the GacS/GacA-RsmA-rsmB-hrpL regulatory pathway, the T3SS of *Dickeya dadantii*, which belongs to Group I T3SS of phytobacteria, is regulated by a HrpX/Y-HrpS-HrpL pathway. The two-component system HrpX/HrpY activates the gene encoding HrpS, which is required for expression of hrpL. HrpL, an alternative sigma factor, further activates expression of genes encoding the T3SS apparatus and its secreted products. Thus, the GacS/GacA and HrpX/HrpY TCSTS systems both exert a regulatory effect in *D. dadantii*, in particular through the T3SS system.

SUMMARY OF THE INVENTION

In one embodiment, the invention may provide a method of reducing virulence in a bacterium comprising at least one of a GacS/GacA-type system, a HrpX/HrpY-type system, a T3SS-type system, and a Rsm-type system, the method comprising contacting the bacterium with an effective amount of a compound described herein, such as compounds of Formula (I), Formula (II), Formula (III), Formula (IV), Formula (V), Formula (VI) and Formula (VII) described herein.

In another embodiment, the invention may provide a compound selected from the following:

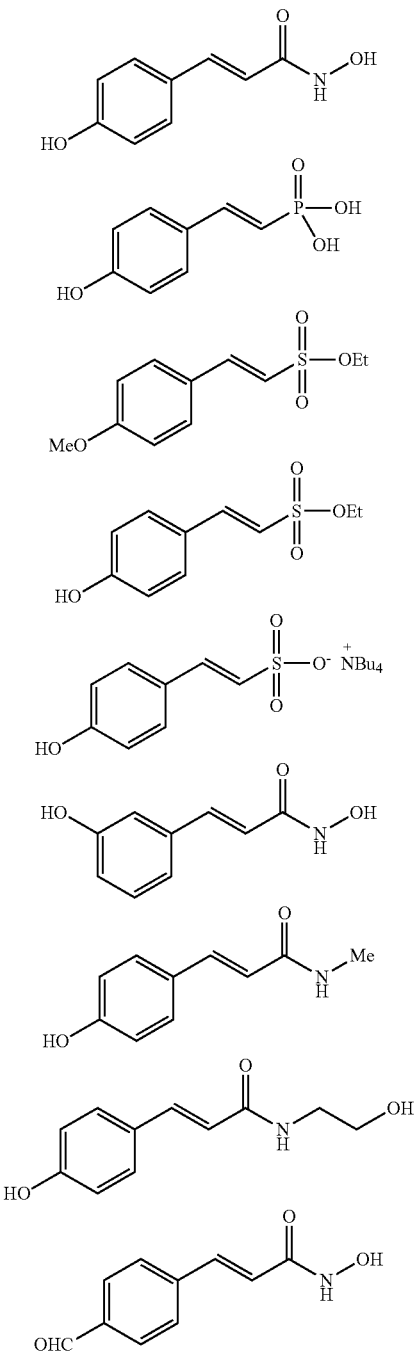

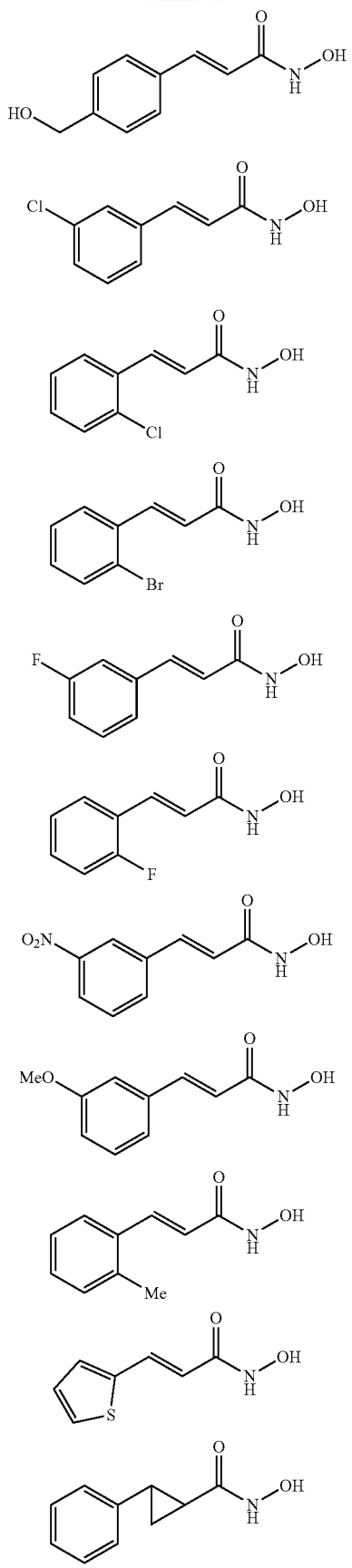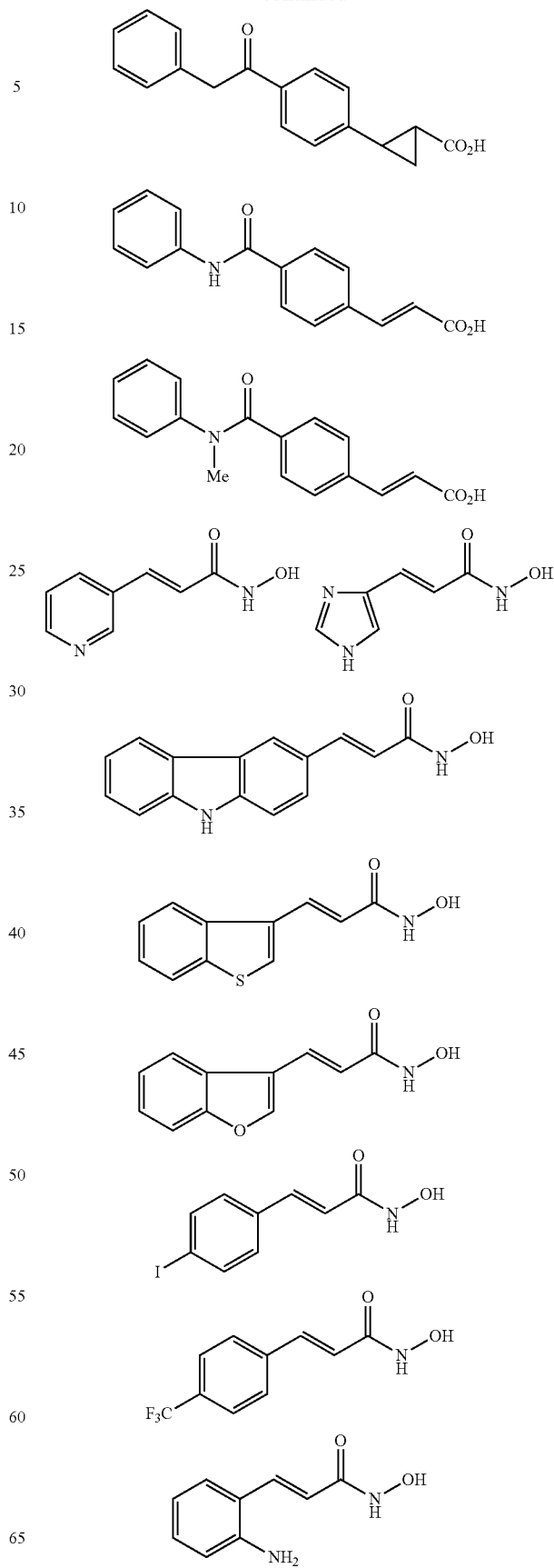

-continued

-continued

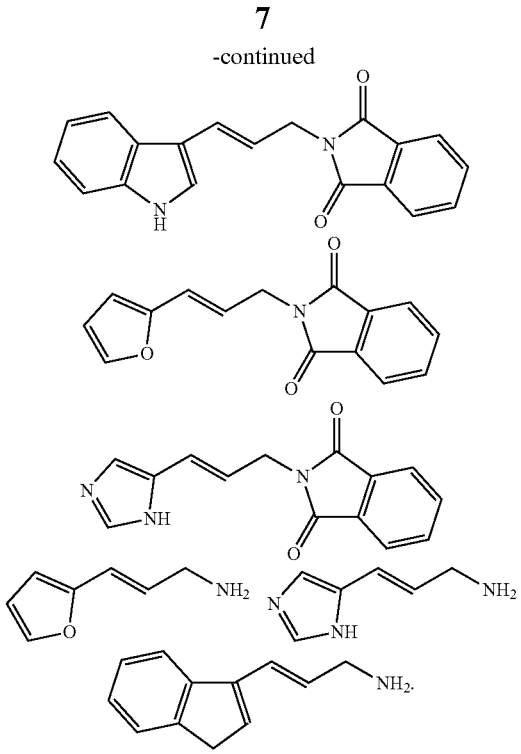

BRIEF DESCRIPTION OF THE DRAWINGS

FIG. 31 shows a Table of Bacterial strains, plasmids, and primers used in this study.

FIG. 32 shows the compounds screened for *Pseudomonas syringae* pv. tomato DC3000 (DC3000) hrpA inducers and inhibitors. Expression of DC3000 hrpA in HIM or HIM supplemented with different compounds.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited.

DETAILED DESCRIPTION OF THE INVENTION

A regulatory role for the two-component system GacS/GacA on the type III secretion system ("T3SS") of *Dickeya dadantii* 3937 (Ech3937) has been demonstrated to channel through a regulator of secondary metabolism (Rsm) system. Rsm is a novel type of post-transcriptional regulatory system that plays a critical role in gene expression. RsmA is a small RNA-binding protein that acts by lowering the half-life of the target mRNA. rsmB is an untranslated regulatory RNA that binds RsmA and inhibits its activity by forming an inactive ribonucleoprotein complex. In Ech3937, GacS/GacA upregulates hrpL mRNA through a post-transcriptional regulation by enhancing the rsmB RNA level, which binds to RsmA and inhibits the hrpL mRNA decay effect of RsmA (FIG. 1).

Figure 1:
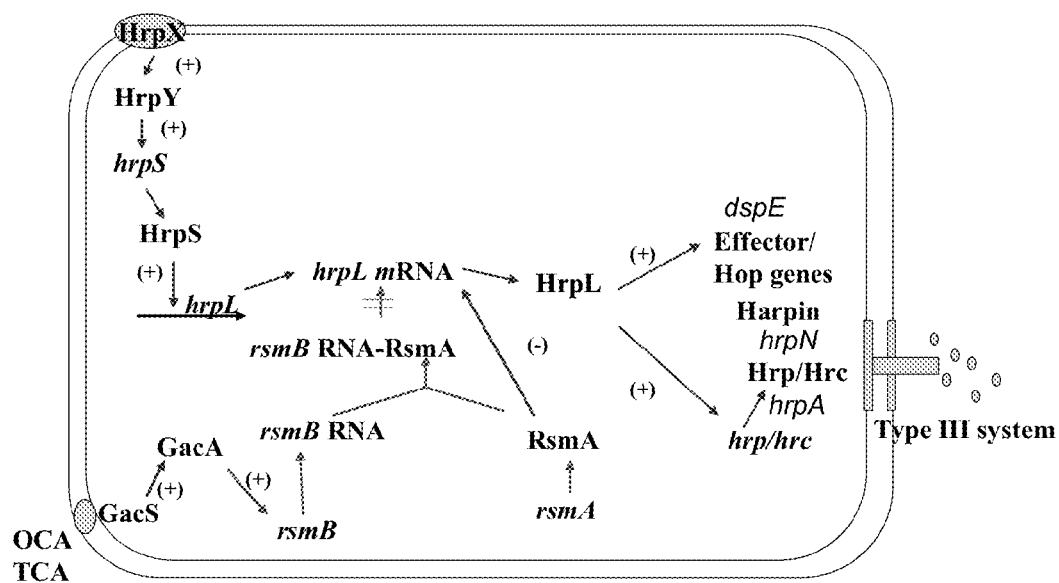
FIG. 1 shows a regulatory network of type III secretion system (T3SS) regulatory pathways of *Dickeya dadantii* 3937 (Ech3937).

FIG. 1 shows a regulatory network of type III secretion system (T3SS) of *Dickeya dadantii* 3937 (Ech3937). Lines with a (+) symbol designate positive regulation, and the line with a (−) symbol indicates negative regulation. The T3SS of Ech3937 is regulated by the HrpX/HrpY-HrpS-HrpL and GacS/GacA-rsmB-HrpL regulatory pathways. The two-component system HrpX/HrpY activates the gene encoding a σ54-enhancer HrpS, which is required for expression of an alternative sigma factor, hrpL. HrpL further activates expression of genes encoding the T3SS apparatus and its secreted products.

The T3SS contributes to bacterial virulence within a host. A gacA deletion mutant of *Dickeya dadantii* (*Erwinia chrysanthemi* 3937) was found to exhibit diminished production of pectate lyase, protease, and cellulose, enzymes that normally lead to loss of structural integrity of plant cell walls. Diminished production of enzymes that attack the plant cell walls leads to diminished bacterial virulence.

Several compounds, including o-coumaric acid ("OCA") and t-cinnamic acid ("TCA"), have been identified as inducers of the GacS/GacA regulatory system. Induction of the GacS/GacA system in turn affects the Rsm system, which further affects the expression of T3SS genes, including pectinase genes.

In further studies the inventors have screened compounds, including t-cinnamic acid, o-coumaric acid, m-coumaric acid, p-coumaric acid, hydrocinnamic acid, phenoxyacetic acid, trans-2-phenylcyclopropane-1-carboxylic acid, trans-3-(3-pyridyl)acrylic acid, trans-3-indoleacrylic acid, 2-methylcinnamic acid, 2-chlorocinnamic acid, methyl trans-cinnamate, and cinnamyl alcohol. Two compounds, p-coumaric acid (PCA) and cinnamyl alcohol, were found to reduce induction of virulence in *Dickeya dadantii*. Without being limited as to theory, PCA appears to reduce virulence through the HrpX/HrpY system (see FIG. 1, Example 10).

Based on the discovery that OCA, TCA, PCA, and cinnamyl alcohol can regulate (i.e. promote or reduce) bacterial virulence, further screening was conducted in order to identify compounds that reduce bacterial virulence. Various compounds were synthesized and screened for their ability to reduce bacterial virulence. The synthesized compounds were tested for an ability to reduce virulence of bacteria having a two-component signal transduction system such as. a GacS/GacA system (or a homolog of the GacS/GacA system), a HrpX/HrpY system (or a homolog of the HrpX/HrpY system), an Rsm system (or homolog), and/or a T3SS system (or homolog).

The compounds produced for testing include compounds referred to herein as "phenylpropanoid derivatives." A description of phenylpropanoid derivatives generally is found in U.S. patent application Ser. No. 12/595,148, filed Oct. 8, 2009, and incorporated herein by reference in its entirety.

Definitions

Each of the groups defined below may be substituted with one or more of the moieties defined herein.

Alkyl: The term "alkyl" as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated (e.g., partially unsaturated, fully unsaturated). Thus, the term "alkyl" includes the sub-classes alkenyl, alkynyl, cycloalkyl, cycloalkyenyl, cylcoalkynyl, etc., discussed below.

In the context of alkyl groups, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$ alkyl" as used herein, pertains to an alkyl group having from 1 to 4 carbon atoms. Examples of groups of alkyl groups include $C_{1-4}$ alkyl ("lower alkyl"), $C_{1-7}$ alkyl, $C_{1-20}$ alkyl and $C_{1-30}$ alkyl. Note that the first prefix may vary according to other limitations; for example, for unsaturated alkyl groups, the first prefix must be at least 2; for cyclic and branched alkyl groups, the first prefix must be at least 3; etc.

Examples of saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl" as used herein, pertains to an alkyl group having one or more carbon-carbon double bonds. Examples of groups of alkenyl groups include $C_{2-4}$ alkenyl, $C_{2-7}$ alkenyl, $C_{2-20}$ alkenyl.

Examples of unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (1-methylvinyl, —C(CH$_3$)=CH$_2$), butenyl ($C_4$), pentenyl ($C_5$), and hexenyl ($C_6$).

Alkynyl: The term "alkynyl" as used herein, pertains to an alkyl group having one or more carbon-carbon triple bonds. Examples of groups of alkynyl groups include $C_{2-4}$ alkynyl, $C_{2-7}$ alkynyl, $C_{2-20}$ alkynyl.

Examples of unsaturated alkynyl groups include, but are not limited to, ethynyl (ethinyl, —C≡CH) and 2-propynyl (propargyl, —CH$_2$—C≡CH).

Cycloalkyl: The term "cycloalkyl" as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g., partially unsaturated, fully unsaturated), which moiety has from 3 to 20 carbon atoms (unless otherwise specified), including from 3 to 20 ring atoms. Thus, the term "cycloalkyl" includes the sub-classes cycloalkyenyl and cycloalkynyl. Preferably, each ring has from 3 to 7 ring atoms. Examples of groups of cycloalkyl groups include $C_{3-30}$ cycloalkyl, $C_{3-20}$ cycloalkyl, $C_{3-10}$ cycloalkyl, $C_{3-7}$ cycloalkyl.

Examples of cycloalkyl groups include, but are not limited to, those derived from: saturated monocyclic hydrocarbon compounds (cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$)); unsaturated monocyclic hydrocarbon compounds (cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$)); saturated polycyclic hydrocarbon compounds (thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$)); unsaturated polycyclic hydrocarbon compounds (camphene ($C_{10}$), limonene ($C_{10}$), pinene ($C_{10}$)); and polycyclic hydrocarbon compounds having an aromatic ring (indene ($C_9$), indane (e.g., 2,3-dihydro-1H-indene) ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$)).

Hydroxyalkyl: The term "hydroxyalkyl" as used herein pertains to an alkyl group in which a hydrogen atom has been replaced with a hydroxyl group.

Heterocyclyl: The term "heterocyclyl" as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms. For example, the term "$C_{5-6}$ heterocyclyl" as used herein, pertains to a heterocyclyl group having 5 or 6 ring atoms. Examples of groups of heterocyclyl groups include $C_{3-30}$ heterocyclyl, $C_{3-20}$ heterocyclyl, $C_{5-20}$ heterocyclyl, $C_{3-15}$ heterocyclyl, $C_{5-15}$ heterocyclyl, $C_{3-12}$ heterocyclyl, $C_{5-12}$ heterocyclyl, $C_{3-10}$ heterocyclyl, $C_{5-10}$ heterocyclyl, $C_{3-7}$ heterocyclyl, $C_{5-7}$ heterocyclyl, and $C_{5-6}$ heterocyclyl.

Examples of monocyclic heterocyclyl groups include, but are not limited to, those derived from: $N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$); $O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$); $S_1$: thiirane ($C_3$), thietane ($C_4$), thiolane (tetrahydrothiophene) ($C_5$), thiane (tetrahydrothiopyran) ($C_6$), thiepane ($C_7$); $O_2$: dioxolane ($C_5$), dioxane ($C_6$), and dioxepane ($C_7$); $O_3$: trioxane ($C_6$); $N_2$: imidazolidine ($C_5$), pyrazolidine (diazolidine) ($C_5$), imidazoline ($C_5$), pyrazoline (dihydropyrazole) ($C_5$), piperazine ($C_6$); $N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$); $N_1S_1$: thiazoline ($C_5$), thiazolidine ($C_5$), thiomorpholine ($C_6$); $N_2O_1$: oxadiazine ($C_6$); $O_1S_1$: oxathiole ($C_5$) and oxathiane (thioxane) ($C_6$); and $N_2O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Aryl: The term "aryl" as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms. Examples of groups of aryl groups include $C_{3-30}$ aryl, $C_{3-20}$ aryl, $C_{5-20}$ aryl, $C_{5-15}$ aryl, $C_{5-12}$ aryl, $C_{5-10}$ aryl, $C_{5-7}$ aryl, $C_{5-6}$ aryl, $C_5$ aryl, and $C_6$ aryl.

The ring atoms may be all carbon atoms, as in "carboaryl groups". Examples of carboaryl groups include $C_{3-20}$ carboaryl, $C_{5-20}$ carboaryl, $C_{5-15}$ carboaryl, $C_{5-12}$ carboaryl, $C_{5-10}$ carboaryl, $C_{5-7}$ carboaryl, $C_{5-6}$ carboaryl and $C_6$ carboaryl.

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g., 2,3-dihydro-1H-indene) ($C_9$), indene ($C_9$), isoindene ($C_{10}$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of heteroaryl groups include $C_{3-20}$ heteroaryl, $C_{5-20}$ heteroaryl, $C_{5-15}$ heteroaryl, $C_{5-12}$ heteroaryl, $C_{5-10}$ heteroaryl, $C_{5-7}$ heteroaryl, $C_{5-6}$ heteroaryl, $C_5$ heteroaryl, and $C_6$ heteroaryl.

Examples of monocyclic heteroaryl groups include, but are not limited to, those derived from: $N_1$: pyrrole (azole) ($C_5$), pyridine (azine) ($C_5$); $O_1$: furan (oxole) ($C_5$); $S_1$: thiophene (thiole) ($C_5$); $N_1O_1$: oxazole ($C_5$), isoxazole ($C_5$), isoxazine ($C_6$); $N_2O_1$: oxadiazole (furazan) ($C_5$); $N_3O_1$: oxatriazole ($C_5$); $N_1S_1$: thiazole ($C_5$), isothiazole ($C_5$); $N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$); $N_3$: triazole ($C_5$), triazine ($C_6$); and $N_4$: tetrazole ($C_5$).

Examples of heteroaryl groups which comprise fused rings, include; but are not limited to: $C_9$ heteroaryl groups (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$); $C_{10}$ heteroaryl groups (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$); $C_{11}$ heteroaryl groups (with 2 fused rings) derived from benzodiazepine ($N_2$); $C_{1-3}$ heteroaryl groups (with 3 fused rings) derived from carbazole (NO, dibenzofuran (OA dibenzothiophene ($S_1$), carboline ($N_2$), perimidine ($N_2$), pyridoindole ($N_2$); and $C_{1-4}$ heteroaryl groups (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heteroaryl groups which have a nitrogen ring atom in the form of an —NH— group may be N-substituted, that is, as —NR—. For example, pyrrole may be N-methyl substituted, to give N-methylpyrrole. Examples of N-substituents include, but are not limited to $C_{1-7}$ alkyl, $C_{3-20}$ heterocyclyl, $C_{5-20}$ aryl, and acyl groups.

Heterocyclic groups (including heteroaryl groups) which have a nitrogen ring atom in the form of an —N=group may be substituted in the form of an N-oxide, that is, as —N(→O)= (also denoted —N$^+$(→O$^-$)=). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (=O) groups on ring carbon atoms.

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR)$_2$, wherein each R is independently an acetal substituents, for example, a $C_{1-7}$ alkyl group, a $C_{3-20}$ heterocyclyl group, or a $C_{3-20}$ aryl group, preferably a $C_{1-7}$ alkyl group, or, in the case of a "cyclic" acetal group, $R^1$ and $R^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR), wherein R is a hemiacetal substituent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH)(OMe) and —CH(OH)(OEt).

Ketal: —CR(OR)$_2$, where each R is defined as for acetals, and each R is independently a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR), where R is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), a $C_{5-20}$ aryl group (also referred to as $C_{5-20}$ arylacyl), preferably a $C_{1-7}$ alkyl group or a halo. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), —C(=O)Ph (benzoyl, phenone), —C(=O)Cl.

Carboxy (carboxylic acid): —C(=O)OH.
Thiocarboxy (thiocarboxylic acid): —C(=S)SH.
Thiolocarboxy (thiolocarboxylic acid): —C(=O)SH.
Thionocarboxy (thionocarboxylic acid): —C(=S)OH.
Imidic acid: —C(=NH)OH.
Hydroxamic acid: —C(=NOH)OH.
Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$_2$, wherein each R is independently an amino substituent, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, both R's, taken together with the nitrogen atom to which they are attached, form a heterocyclic ring having from 4 to 8 ring atoms. Amino groups may be primary (—NH$_2$), secondary (—NHR), or tertiary (—NHR$_2$), and in cationic form, may be quaternary (—$^+$NR$_3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$_2$, wherein each R is independently an amino substituent, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which both R's, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$_2$, wherein each R is independently an amino substituent, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^{10}$C(=O)R$^{11}$, wherein R$^{10}$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and R$^{11}$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. R$^{10}$ and R$^{11}$ may together form a cyclic structure, as in, for example, succinimidyl, maleimidyl, and phthalimidyl:

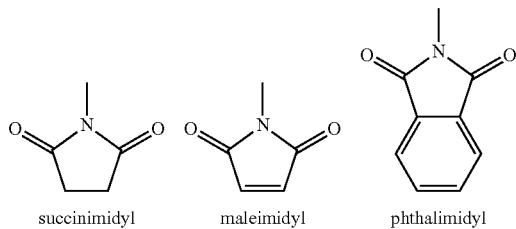

succinimidyl    maleimidyl    phthalimidyl

Aminocarbonyloxy: —OC(=O)NR$_2$, wherein each R is independently an amino substituent, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^{12}$)CONR$_2$ wherein each R is independently an amino substituent, as defined for amino groups, and R$^{12}$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$alkyl group. Examples of imino groups include, but are not limited to, =NH, =NMe, and =NEt.

Amidine (amidino): —C(=NR)NR$_2$, wherein each R is independently an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.
Nitroso: —NO.
Azido: —N$_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.
Thioether (sulfide): —SR, wherein R is a thioether substituent, for example, a $C_{1-7}$ alkyl group (also referred to as a $C_{1-7}$alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$ C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a $C_{1-7}$ alkyl group, a $C_{3-20}$ heterocyclyl group, or a $C_{5-20}$ aryl group, preferably a $C_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a $C_{1-7}$ alkyl group, a $C_{3-20}$ heterocyclyl group, or a $C_{5-20}$ aryl group, preferably a $C_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$_2$, wherein each R is independently an amino substituent, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$_2$, wherein each R is independently an amino substituent, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NRS(=O)$_2$OH, wherein R is an amino substituent, as defined for amino groups. Examples of sulfamino groups include, but are not limited to, —NHS(=O)$_2$OH and —N(CH$_3$)S(=O)$_2$OH.

Sulfonamino: —NR$^{13}$S(=O)$_2$R, wherein R$^{13}$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^{13}$S(=O)R, wherein R$^{13}$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)CH$_3$ and —N(CH$_3$)S(=O)C$_6$H$_5$.

Silyl: —SiR$_3$, wherein each R is independently a silyl substituent, for example, H, a $C_{1-7}$ alkyl group, a $C_{3-20}$ heterocyclyl group, or a $C_{5-20}$ aryl group, preferably a $C_{1-7}$ alkyl group.

Phosphino (phosphine): —PR$_2$, wherein each R is independently a phosphino substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein each R is independently a phosphinyl substituent, for example, a $C_{1-7}$ alkyl group, a $C_{3-20}$ heterocyclyl group, or a $C_{5-20}$ aryl group, preferably a $C_{1-7}$ alkyl group or a $C_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, wherein each R is independently a phosphonate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, wherein each R is independently a phosphate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, wherein each R is independently a phosphite substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR)—NR$_2$, wherein each R is independently a phosphoramidite substituent, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR)—NR$_2$, wherein each R is independently a phosphoramidate substituent, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

The term "alkylene", as used herein, pertains to a bidentate moiety obtained by removing two hydrogen atoms, either both from the same carbon atom, or one from each of two different carbon atoms, of a hydrocarbon compound having from 1 to 12 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkylene, etc., discussed below.

Examples of linear saturated alkylene groups include, but are not limited to, —(CH$_2$)$_n$— where n is an integer from 3 to 12, for example, —CH$_2$CH$_2$CH$_2$— (propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH—$_2$CH$_2$CH$_2$CH$_2$— (heptylene).

Examples of branched saturated alkylene groups include, but are not limited to, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated alkylene groups (alkenylene, and alkynylene groups) include, but are not limited to, —CH═CH—CH$_2$—, —CH$_2$—CH═CH$_2$—, —CH═CH—CH$_2$—CH$_2$—, —CH═CH—CH$_2$—CH$_2$—, —CH═CH—CH═CH—, —CH═CH—CH═CH—CH$_2$—, —CH═CH—CH$_2$—CH═CH—, —CH═CH—CH$_2$—CH$_2$—CH═CH—, and —CH$_2$—C≡C—CH$_2$—.

Examples of branched partially unsaturated alkylene groups (alkenylene and alkynylene groups) include, but are not limited to, —C(CH$_3$)═CH—, —C(CH$_3$)═CH—CH$_2$—, —CH═CH—CH(CH$_3$)— and —C≡C—CH(CH$_3$)—.

Examples of alicyclic saturated alkylene groups (cycloalkylenes) include, but are not limited to, cyclopropylene (e.g. cycloprop-1,2-ylene), cyclobutylene (e.g. cyclobut-1,2-ylene), cyclopentylene (e.g. cyclopent-1,3-ylene), and cyclohexylene (e.g. cyclohex-1,4-ylene).

Examples of alicyclic partially unsaturated alkylene groups (cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

The term "C$_{1-3}$ alkylene" as used herein, is an alkylene as defined above group and having from 1 to 3 carbon atoms. Alkylene includes cyclopropylene groups.

The term "heteroalkylene", as used herein, pertains to an alkylene group in which at least one carbon atom has been replaced with a heteroatom such as O, S or NR, wherein R is hydrogen, a C$_{1-7}$ alkyl group, a C$_{3-20}$ heterocyclyl group, or a C$_{5-20}$ aryl group, preferably H or a C$_{1-7}$ alkyl group. Examples of heteroalkylene groups include, but are not limited to, —O—CH$_2$—, —NH—CH$_2$—, —S—CH$_2$—, —O—CH$_2$—CH$_2$—, —S—CH$_2$—CH$_2$—, —NH—CH$_2$—CH$_2$—, —CH$_2$—O—CH$_2$—, —CH$_2$—S—CH$_2$— and —CH$_2$—NH—CH$_2$—. Heteroalkylene groups also include cyclic heteroalkylene (heterocycloalkylene) groups, examples of which include, but are not limited to, oxirane, oxetane, aziridine and azetidine rings from which two hydrogen atoms are removed.

The term "GacS/GacA-type system" refers to the signal transduction system in *D. dadantii* as well as homologous systems in other bacteria (e.g. *E. coli* (BarA/UvrY), *Pectobacterium* spp., *S. typhimurium* (BarA/SirA), *Pseudomonas* spp. (GacS/GacA), and *Legionella pneumophila* (LetS/LetA), *Vibrio* species) that have a similar structure and function to the GacS/GacA system of *D. dadantii*, even though the homologous regulatory system may be known by a different name in other bacteria. Similarly, "GacA-type polypeptide" and "GacS-type polypeptide" refer to the respective polypeptides in *D. dadantii* as well as homologous polypeptides having similar structure and function in other bacteria.

The term "HrpX/HrpY-type system" refers to the signal transduction system in *D. dadantii* as well as homologous systems in other bacteria that have a similar structure and function to the HrpX/HrpY system of *D. dadantii*, even though the homologous regulatory system may be known by a different name in other bacteria. Similarly, "HrpY-type polypeptide" and "HrpX-type polypeptide" refer to the respective polypeptides in *D. dadantii* as well as homologous polypeptides having similar structure and function in other bacteria.

The term "Rsm-type system" refers to the regulator of secondary metabolism (Rsm) system of *D. dadantii* as well as homologous systems in other bacteria that have a similar structure and function to the Rsm system of *D. dadantii*, even though the homologous regulatory system may be known by a different name in other bacteria.

The term "T3SS-type system" refers to the type III secretion system (T3SS) of *D. dadantii* as well as homologous systems in other bacteria that have a similar structure and function to the T3SS of *D. dadantii*, even though the homologous regulatory system may be known by a different name in other bacteria.

As used herein, the terms "reducing" or "reduced" are used relative to an untreated sample or other suitable control. For example, "reducing expression" of a polynucleotide in a bacterium in response to contacting the bacterium with a test compound means lowering the amount of expression of the polynucleotide (e.g. lowering the amount of polynucleotide-encoded mRNA or protein formed) relative to the level of expression of the polynucleotide in the same bacterium under control conditions. The control conditions may include exposing the bacterium to the same conditions without contacting the bacterium with the test compound.

"Reducing virulence" in a bacterium refers to altering expression of genes associated with virulence, including regulators of virulence. Reducing virulence also refers to physical and biochemical manifestations of virulence including those manifestations associated with any step of the bacterial life cycle when it is associated with a host, including without limitation the adherence, invasion, replication, evasion of host defenses, and transmittal to a new host. Reduced bacterial virulence may be manifested in the form of reduced symptoms in a host, and thus may be detected by monitoring the host for a reduced reaction to the bacteria associated therewith. Reduced virulence may arise as a result of either inhibition or stimulation of a two-component regulatory system such as a GacS/GacA-type system or a HrpX/HrpY-type system, which could lead to increases or decreases of polynucleotide and polypeptide production. For example, reduced virulence may be associated with increase production of a repressor, reduced production of a transcription factor, or increased production of enzymes or toxins. Regulation of bacterial virulence may lead to alterations in the production of pectinase, exoprotease, syringomycin, syringolin, alginate, tolaasin, siderophores, pyocyanin, cyanide, lipase, type III secretion system (T3SS) genes, cholera toxin, polyhydroxybutyrate, or a polynucleotide controlled by a GacS/GacA-type system or a HrpX/HrpY-type system in a Gram negative bacterium. A reduction in virulence may be at least about a 1% reduction, at least about a 10% reduction, at least about a 20% reduction, at least about a 30% reduction, at least about a 40% reduction, at least about a 50% reduction, at least about a 60% reduction, at least about a 70% reduction, at least about a 80% reduction, at least about a 90% reduction, or at least about a 100% reduction of virulence, as measured by any assay described herein or known to those of skill in the art, when measured against a suitable control.

"Components" of a GacS/GacA-type system, a HrpX/HrpY-type system, a T3SS-type system, and a Rsm-type system include without limitation polynucleotides and polypeptides that are part of the respective systems (including genes and gene products of the named operons) as well as polynucleotides, polypeptides, and other molecules that regulate the systems including genes and gene products that are upstream or downstream of the system. "Components" also includes molecules that are products of the genes or gene products of the systems as well as genes or gene products that generate posttranslational modifications of polynucleotides or polypeptides of the systems. A "regulator" is a component that changes (increases or decreases) an expression or activity level of a component. A "repressor" is a component that decreases an expression or activity level of a component, arising from either an increase or a decrease in the amount or activity level of the repressor. An "effector" is a component that puts into effect the activity of the system, e.g. exoenzymes of the T3SS-type system are nonlimiting examples of effectors. A component is "associated with virulence" if a change in an amount or activity of the component leads, directly or indirectly, to an increase or reduction in some aspect of bacterial virulence.

A "phenylpropanoid-type inhibitory compound" as used herein includes phenylpropanoid compounds, such as p-coumaric acid or cinnamyl alcohol, that reduce bacterial virulence. In addition, "phenylpropanoid-type inhibitory compound" also includes phenylpropanoid derivative that have been found to be "active compounds," i.e. compounds that have shown through screening to have bacterial virulence-reducing activity.

A bacterium is "associated with" (or "associated therewith") a host or subject such as a plant or animal (including a human) when the bacterium is in or on the host or subject. For a plant host or subject, an associated bacterium can be on a plant part such as a root, stem, leaf, flower, or fruit of the plant, or in the soil adjacent to the roots or base of the stem. For an animal host or subject, an associated bacterium can be on the outer surface of the animal or on an inner surface such as an intestinal surface, or the associated bacterium can be within the animal, e.g. in a tissue or fluid of the animal or any other internal portion of the animal.

"Treating" or "treatment," as used herein in the context of treating a condition, pertains generally to treatment and therapy, whether of a human, an animal (e.g. in veterinary applications), or plants, in which some desired therapeutic effect is achieved, for example, the reduction of the progress of the condition, and includes a reduction in the rate of progress, a halt in the rate of progress, amelioration of the condition, and cure of the condition. Treatment as a prophylactic measure (i.e. prophylaxis) is also included. "Treating" and "treatment" also refer to reducing the symptoms associated with the condition that is being treated.

"Effective amount," when used herein in the context of contacting a bacterium associated with a plant with a compound described herein, refers to an amount of a compound that can be therapeutically effective to inhibit, prevent or treat the symptoms of particular disease, disorder, or side effect, particularly those associated with bacterial virulence. An effective amount of the active compound may be used alone or as part of a composition as described herein. In various embodiments, an effective amount of active compound in the composition may be from about 0.1 µg/g to about 0.9 g/g, about 1 µg/g to about 100 mg/g, about 10 µg/g to about 10 mg/g, and about 100 µg/g to about 1 mg/g. The amount of active compound applied to a surface (e.g. soil, stem, or a leaf) may be about 0.1 µg/sq.ft., about 1 µg/sq.ft., about 10 µg/sq.ft., about 100 µg/sq.ft., about 1 mg/sq.ft., about 10 mg/sq.ft., about 100 mg/sq.ft., about 1 g/sq.ft., about 10 g/sq.ft., or about 100 g/sq.ft.

"Effective amount," when used herein in the context of contacting a bacterium associated with an animal (e.g., a human) with a compound described herein, refers to an amount of a compound that can be therapeutically effective to inhibit, prevent or treat the symptoms of particular disease, disorder, or side effect, particularly those associated with bacterial virulence. Thus, an effective amount of the active compound may be used alone or as part of a composition as described herein to treat an animal subject having a bacterium associated therewith in order to reduce the virulence of the bacterium. The composition may be prepared as appropriate for oral, topical, pulmonary, parenteral, or other route of administration. The concentration of active compound in the composition may be from about 0.1 µg/g to about 0.9 g/g, about 1 µg/g to about 100 mg/g, about 10 µg/g to about 10 mg/g, and about 100 µg/g to about 1 mg/g. When administered internally (e.g. parenterally or orally), the dose to the subject may be about 0.1 µg/kg body weight to about 1.0 g/kg body weight, about 1 µg/kg body weight to about 100 mg/kg body weight, about 10 µg/kg body weight to about 10 mg/kg body weight, and about 100 µg/kg body weight to about 1 mg/kg body weight.

"Effective amount," when used herein in the context of contacting a bacterium associated with a surface with a compound described herein, refers to an amount of the active compound that can be effective to reduce virulence of a bacterium associated with a surface when the compound, or a composition comprising the compound, is administered to a surface that includes the bacterium. An effective amount of the active compound may be used alone or as part of a composition as described herein. In various embodiments, an effective amount of the active compound in the composition may be from about 0.1 µg/g to about 0.9 g/g, about 1 µg/g to about 100 mg/g, about 10 µg/g to about 10 mg/g, and about 100 µg/g to about 1 mg/g. The amount of active compound applied to a surface may be about 0.1 µg/sq.ft., about 1 µg/sq.ft., about 10 µg/sq.ft., about 100 µg/sq.ft., about 1 mg/sq.ft., about 10 mg/sq.ft., about 100 mg/sq.ft., about 1 g/sq.ft., about 10 g/sq.ft., or about 100 g/sq.ft.

The term "pharmaceutically acceptable" as used herein pertains to compounds, materials, compositions, and/or dosage forms which are, within the scope of sound medical judgment, suitable for use in contact with the tissues of a subject (e.g., human or other animal) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Where substituent groups are specified by their conventional chemical formulae, written from left to right, they optionally encompass substituents resulting from writing the structure from right to left, e.g., —$CH_2O$— optionally also recites —$OCH_2$—.

Compounds

Compounds that may be used in the methods described herein include compounds of formula (I):

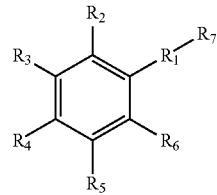

(I)

wherein $R_1$ is selected from alkylene, heteroalkylene, oxygen, sulfur and a bond;
$R_2$, $R_3$, $R_4$, $R_5$, and $R_6$ are each independently selected from hydrogen, alkyl, alkenyl, alkynyl, hydroxy, hydroxyalkyl, alkoxy, sulfhydryl, thioether, sulfo, silyl, phosphono, halo, carboxy, nitro, amino, alkylamino, formyl and heterocyclyl groups; and
$R_7$ is selected from hydroxy, hydroxyalkyl, alkoxy, carboxy, hydroxamic acid, hydrazide, hydrazinocarbonyl, aryl, ester, amino, amido, thioamido, sulfonyl, sulfinic acid, sulfonic acid, sulfinate, sulfonate, phosphonate, substituted or unsubstituted bicyclic heteroaromatic, and carboxamide groups.
or a salt thereof.

In some embodiments, in the compound of formula (I):
$R_1$ is selected from alkylene, heteroalkylene, oxygen, sulfur and a bond;
$R_2$, $R_5$, and $R_6$ are each independently selected from hydrogen, hydroxy, hydroxyalkyl, alkoxy, alkyl, alkenyl, alkynyl, halo, carboxy, and amino groups;
$R_3$ is selected from hydrogen, hydroxy, hydroxyalkyl and alkoxy groups;
$R_4$ is selected from hydrogen, alkyl, alkenyl, alkynyl, halo, hydroxy, hydroxyalkyl and alkoxy groups; and
$R_7$ is selected from hydroxy, hydroxyalkyl, alkoxy, carboxy, hydroxamic acid, hydrazide, hydrazinocarbonyl, aryl, ester, amino, amido, thioamido, sulfonyl, sulfinic acid, sulfonic acid, sulfinate, sulfonate, phosphonate, substituted or unsubstituted bicyclic heteroaromatic, and carboxamide groups.

In some embodiments, $R_1$ is $C_2$-$C_3$ alkylene (e.g., $C_2$-$C_3$ alkenylene or $C_2$-$C_3$ alkynylene. In some embodiments, $R_1$ is heteroalkylene, such as —O—CH$_2$— or —S—CH$_2$—. In some embodiments, $R_1$ is cycloalkenylene, such as cyclopropylene. In some embodiments, $R_1$ is heterocycloalkylene, such as oxetane or aziridine. In some embodiments, $R_1$ is a bond. In some embodiments, $R_4$ is alkoxy (e.g., methoxy) or hydroxy. In some embodiments, $R_7$ is hydroxamic acid, allylic alcohol, hydroxy, carboxy, alkoxy (e.g., methoxy), or ester (e.g., CO$_2$Et). In some embodiments, $R_7$ is hydroxamic acid.

In some embodiments, the compound is compound 103:

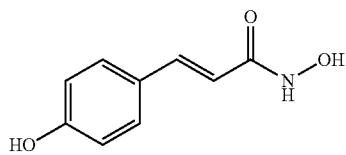

103

Compounds that may be used in the methods described herein include compounds of formula (II):

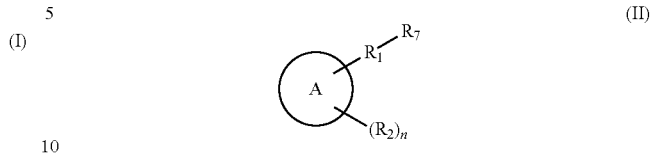

(II)

wherein A is aryl or heteroaryl;
$R_1$ is selected from alkylene, heteroalkylene, oxygen, sulfur and a bond;
n is 0, 1, 2, 3, 4 or 5;
each $R_2$ is independently selected from alkyl, alkenyl, alkynyl, hydroxy, hydroxyalkyl, alkoxy, sulfhydryl, thioether, sulfo, silyl, phosphono, halo, carboxy, nitro, amino, alkylamino, formyl and heterocyclyl groups; and
$R_7$ is selected from hydroxy, hydroxyalkyl, alkoxy, carboxy, hydroxamic acid, hydrazide, hydrazinocarbonyl, aryl, ester, amino, amido, thioamido, sulfonyl, sulfinic acid, sulfonic acid, sulfinate, sulfonate, phosphonate, substituted or unsubstituted bicyclic heteroaromatic, and carboxamide groups.

In some embodiments, A is aryl (e.g., phenyl or naphthyl). In some embodiments, A is heteroaryl (e.g., thiophene, furan, indole, pyridyl, imidazole, benzofuran, benzothiofuran, quinoline or carbazole.) In some embodiments $R_1$ is $C_2$-$C_3$ alkylene (e.g., $C_2$-$C_3$ alkenylene or $C_2$-$C_3$ alkynylene). In some embodiments, $R_1$ is heteroalkylene, such as —O—CH$_2$— or —S—CH$_2$—. In some embodiments, $R_1$ is cycloalkenylene, such as cyclopropylene. In some embodiments, $R_1$ is heterocycloalkylene, such as oxetane or aziridine. In some embodiments, $R_1$ is a bond. In some embodiments, n is at least 1. In some embodiments, at least one $R_2$ is alkoxy (e.g., methoxy) or hydroxy. In some embodiments, $R_7$ is hydroxamic acid, allylic alcohol, hydroxy, carboxy, alkoxy (e.g., methoxy), or ester (e.g., CO$_2$Et).

In some embodiments, the compound is compound 127:

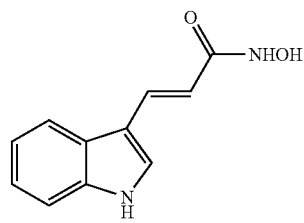

127

Compounds that may be used in the methods described herein include compounds of formula (III):

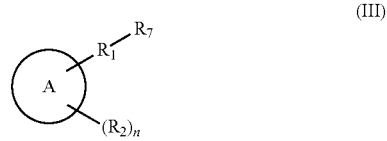

(III)

wherein:
A is aryl or heteroaryl;
$R_1$ is selected from oxygen, sulfur and a bond;
n is 0, 1, 2, 3, 4 or 5;

each $R_2$ is independently selected from alkyl, alkenyl, alkynyl, hydroxy, hydroxyalkyl, alkoxy, sulfhydryl, thioether, sulfo, silyl, phosphono, halo, carboxy, nitro, amino, formyl, aryl, haloalkyl, ester, amido and heterocyclyl groups; and $R_7$ is selected from hydroxy, hydroxyalkyl, alkoxy, carboxy, hydroxamic acid, hydrazide, hydrazinocarbonyl, aryl, ester, amino, amido, thioamido, sulfonyl, sulfinic acid, sulfonic acid, sulfinate, sulfonate, phosphonic acid, phosphonate, and substituted or unsubstituted bicyclic heteroaromatic groups;

or a salt thereof.

In some embodiments, A is aryl (e.g., phenyl). In some embodiments, A is heteroaryl (e.g., indole, pyridyl, imidazole, thiophene, furan, oxazole, thiazole, quinoline, benzofuran, benzothiofuran or carbazole). In some embodiments, $R_1$ is a bond. In some embodiments, n is 0. In some embodiments, n is 1 or 2. In some embodiments, each $R_2$ is independently selected from alkyl (e.g., methyl), hydroxy, hydroxyalkyl (e.g., —CH$_2$OH), alkoxy (e.g., methoxy), sulfhydryl, halo (e.g., fluoro, chloro or bromo), carboxy, nitro, amino (e.g., —NH$_2$ or —NMe$_2$), formyl, aryl (e.g., phenyl), haloalkyl (e.g., trifluoromethyl), ester and amido groups. In some embodiments, $R_7$ is selected from hydroxy, carboxy, hydroxamic acid, hydrazinocarbonyl, ester (e.g., —C(O)OMe or —C(O)OEt), amino (e.g., —NH$_2$), amido (e.g., —C(O)NH$_2$ or —C(O)NHMe), sulfonic acid, sulfonate (e.g., —S(O)$_2$OEt), phosphonic acid, phosphonate (e.g., —P(O)(OEt)$_2$), and substituted or unsubstituted bicyclic heteroaromatic groups (e.g., phthalimido). In some embodiments, $R_7$ is carboxy. In some embodiments, $R_7$ is hydroxamic acid.

Compounds that may be used in the methods described herein include compounds of formula (IV):

$$\text{(IV)} \quad A{\displaystyle \mathop{}_{(R_2)_n}^{R_1-R_7}}$$

wherein:

A is aryl or heteroaryl;

$R_1$ is selected from alkylene, heteroalkylene, oxygen, sulfur and a bond;

n is 0, 1, 2, 3, 4 or 5;

each $R_2$ is independently selected from alkyl, alkenyl, alkynyl, hydroxy, hydroxyalkyl, alkoxy, sulfhydryl, thioether, sulfo, silyl, phosphono, halo, carboxy, nitro, amino, formyl, aryl, haloalkyl, ester, amido and heterocyclyl groups; and $R_7$ is selected from hydroxamic acid, hydrazide, hydrazinocarbonyl, aryl, amino, amido, thioamido, sulfonyl, sulfinic acid, sulfonic acid, sulfinate, sulfonate, phosphonic acid, phosphonate, and substituted or unsubstituted bicyclic heteroaromatic groups;

or a salt thereof.

In some embodiments, A is aryl (e.g., phenyl). In some embodiments, A is heteroaryl (e.g., indole, pyridyl, imidazole, thiophene, furan, oxazole, thiazole, quinoline, benzofuran, benzothiofuran or carbazole). In some embodiments, $R_1$ is alkylene such as a $C_2$-$C_3$ alkylene (e.g., —CH=CH—, —CH$_2$—CH$_2$—, —CH=CH—CH$_2$— or —C≡C—). In some embodiments, $R_1$ is heteroalkylene, such as —O—CH$_2$— or —S—CH$_2$—. In some embodiments, $R_1$ is cycloalkylene, such as cyclopropylene. In some embodiments, $R_1$ is heterocycloalkylene, such as oxetane or aziridine. In some embodiments, $R_1$ is a bond. In some embodiments, n is 0. In some embodiments, n is 1 or 2. In some embodiments, each $R_2$ is independently selected from alkyl (e.g., methyl), hydroxy, hydroxyalkyl (e.g., —CH$_2$OH), alkoxy (e.g., methoxy), sulfhydryl, halo (e.g., fluoro, chloro or bromo), carboxy, nitro, amino (e.g., —NH$_2$ or —NMe$_2$), formyl, aryl (e.g., phenyl), haloalkyl (e.g., trifluoromethyl), ester and amido groups. In some embodiments, $R_7$ is selected from hydroxamic acid, hydrazinocarbonyl, amino (e.g., —NH$_2$), amido (e.g., —C(O)NH$_2$ or —C(O)NHMe), sulfonic acid, sulfonate (e.g., —S(O)$_2$OEt), phosphonic acid, phosphonate (e.g., —P(O)(OEt)$_2$), and substituted or unsubstituted bicyclic heteroaromatic groups (e.g., phthalimido). In some embodiments, $R_7$ is hydroxamic acid.

Compounds that may be used in the methods described herein include compounds of formula (V):

$$\text{(V)} \quad A{\displaystyle \mathop{}_{(R_2)_n}^{R_1-R_7}}$$

wherein:

A is aryl or heteroaryl;

$R_1$ is selected from alkylene, heteroalkylene, oxygen, sulfur and a bond;

n is 1, 2, 3, 4 or 5;

each $R_2$ is independently selected from alkyl, alkenyl, alkynyl, hydroxyalkyl, alkoxy, sulfhydryl, thioether, sulfo, silyl, phosphono, fluoro, bromo, iodo, carboxy, nitro, amino, formyl, aryl, haloalkyl, ester, amido and heterocyclyl groups; and $R_7$ is selected from hydroxy, hydroxyalkyl, alkoxy, carboxy, hydroxamic acid, hydrazide, hydrazinocarbonyl, aryl, ester, amino, amido, thioamido, sulfonyl, sulfinic acid, sulfonic acid, sulfinate, sulfonate, phosphonic acid, phosphonate, and substituted or unsubstituted bicyclic heteroaromatic groups;

or a salt thereof.

In some embodiments, A is aryl (e.g., phenyl). In some embodiments, A is heteroaryl (e.g., indole, pyridyl, imidazole, thiophene, furan, oxazole, thiazole, quinoline, benzofuran, benzothiofuran or carbazole). In some embodiments, $R_1$ is alkylene such as a $C_2$-$C_3$ alkylene (e.g., —CH=CH—, —CH$_2$—CH$_2$—, —CH=CH—CH$_2$— or —C≡C—). In some embodiments, $R_1$ is heteroalkylene, such as —O—CH$_2$— or —S—CH$_2$—. In some embodiments, $R_1$ is cycloalkylene, such as cyclopropylene. In some embodiments, $R_1$ is heterocycloalkylene, such as oxetane or aziridine. In some embodiments, $R_1$ is a bond. In some embodiments, n is 0. In some embodiments, n is 1 or 2. In some embodiments, each $R_2$ is independently selected from alkyl (e.g., methyl), hydroxyalkyl (e.g., —CH$_2$OH), alkoxy (e.g., methoxy), sulfhydryl, fluoro, bromo, carboxy, nitro, amino (e.g., —NH$_2$ or —NMe$_2$), formyl, aryl (e.g., phenyl), haloalkyl (e.g., trifluoromethyl), ester and amido groups. In some embodiments, $R_7$ is selected from hydroxy, carboxy, hydroxamic acid, hydrazinocarbonyl, ester (e.g., —C(O)OMe or —C(O)OEt), amino (e.g., —NH$_2$), amido (e.g., —C(O)NH$_2$ or —C(O)NHMe), sulfonic acid, sulfonate (e.g., —S(O)$_2$OEt), phosphonic acid, phosphonate (e.g., —P(O)(OEt)$_2$), and substituted or unsubstituted bicyclic heteroaromatic groups (e.g., phthalimido). In some embodiments, $R_7$ is carboxy. In some embodiments, $R_7$ is hydroxamic acid.

Compounds that may be used in the methods described herein include compounds of formula (VI):

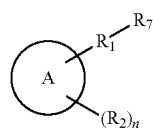

(VI)

wherein:

A is selected from imidazole, thiophene, furan, oxazole, thiazole, quinoline, benzofuran, benzothiofuran and carbazole;

$R_1$ is selected from alkylene, heteroalkylene, oxygen, sulfur and a bond;

n is 0, 1, 2, 3, 4 or 5;

each $R_2$ is independently selected from alkyl, alkenyl, alkynyl, hydroxy, hydroxyalkyl, alkoxy, sulfhydryl, thioether, sulfo, silyl, phosphono, halo, carboxy, nitro, amino, formyl, aryl, haloalkyl, ester, amido and heterocyclyl groups; and $R_7$ is selected from hydroxy, hydroxyalkyl, alkoxy, carboxy, hydroxamic acid, hydrazide, hydrazinocarbonyl, aryl, ester, amino, amido, thioamido, sulfonyl, sulfinic acid, sulfonic acid, sulfinate, sulfonate, phosphonic acid, phosphonate, and substituted or unsubstituted bicyclic heteroaromatic groups;

or a salt thereof.

In some embodiments, A is imidazole, thiophene or furan. In some embodiments, $R_1$ is alkylene such as a $C_2$-$C_3$ alkylene (e.g., —CH=CH—, —CH$_2$—CH$_2$—, —CH=CH—CH$_2$— or —C≡C—). In some embodiments, $R_1$ is heteroalkylene, such as —O—CH$_2$— or —S—CH$_2$—. In some embodiments, $R_1$ is cycloalkylene, such as cyclopropylene. In some embodiments, $R_1$ is heterocycloalkylene, such as oxetane or aziridine. In some embodiments, $R_1$ is a bond. In some embodiments, n is 0. In some embodiments, n is 1 or 2. In some embodiments, each $R_2$ is independently selected from alkyl (e.g., methyl), hydroxy, hydroxyalkyl (e.g., —CH$_2$OH), alkoxy (e.g., methoxy), sulfhydryl, halo (e.g., fluoro, chloro or bromo), carboxy, nitro, amino (e.g., —NH$_2$ or —NMe$_2$), formyl, aryl (e.g., phenyl), haloalkyl (e.g., trifluoromethyl), ester and amido groups. In some embodiments, $R_7$ is selected from hydroxy, carboxy, hydroxamic acid, hydrazinocarbonyl, ester (e.g., —C(O)OMe or —C(O)OEt), amino (e.g., —NH$_2$), amido (e.g., —C(O)NH$_2$ or —C(O)NHMe), sulfonic acid, sulfonate (e.g., —S(O)$_2$OEt), phosphonic acid, phosphonate (e.g., —P(O)(OEt)$_2$), and substituted or unsubstituted bicyclic heteroaromatic groups (e.g., phthalimido). In some embodiments, $R_7$ is carboxy. In some embodiments, $R_7$ is hydroxamic acid.

Compounds that may be used in the methods described herein include compounds of formula (VII):

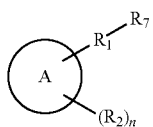

(VII)

wherein:

A is aryl or heteroaryl;

$R_1$ is selected from alkylene, heteroalkylene, oxygen, sulfur and a bond;

n is 2, 3, 4 or 5;

each $R_2$ is independently selected from alkyl, alkenyl, alkynyl, hydroxy, hydroxyalkyl, alkoxy, sulfhydryl, thioether, sulfo, silyl, phosphono, halo, carboxy, nitro, amino, formyl, aryl, haloalkyl, ester, amido and heterocyclyl groups; and $R_7$ is selected from hydroxy, hydroxyalkyl, alkoxy, carboxy, hydroxamic acid, hydrazide, hydrazinocarbonyl, aryl, ester, amino, amido, thioamido, sulfonyl, sulfinic acid, sulfonic acid, sulfinate, sulfonate, phosphonic acid, phosphonate, and substituted or unsubstituted bicyclic heteroaromatic groups;

or a salt thereof.

In some embodiments, A is aryl (e.g., phenyl). In some embodiments, A is heteroaryl (e.g., indole, pyridyl, imidazole, thiophene, furan, oxazole, thiazole, quinoline, benzofuran, benzothiofuran or carbazole). In some embodiments, $R_1$ is $C_2$-$C_3$ alkylene (e.g., $C_2$-$C_3$ alkenylene or $C_2$-$C_3$ alkynylene. In some embodiments, $R_1$ is heteroalkylene, such as —O—CH$_2$— or —S—CH$_2$—. In some embodiments, $R_1$ is cycloalkylene, such as cyclopropylene. In some embodiments, $R_1$ is heterocycloalkylene, such as oxetane or aziridine. In some embodiments, $R_1$ is a bond. In some embodiments, n is 2. In some embodiments, each $R_2$ is independently selected from alkyl (e.g., methyl), hydroxy, hydroxyalkyl (e.g., —CH$_2$OH), alkoxy (e.g., methoxy), sulfhydryl, halo (e.g., fluoro, chloro or bromo), carboxy, nitro, amino (e.g., —NH$_2$ or —NMe$_2$), formyl, aryl (e.g., phenyl), haloalkyl (e.g., trifluoromethyl), ester and amido groups. In some embodiments, $R_7$ is selected from hydroxy, carboxy, hydroxamic acid, hydrazinocarbonyl, ester (e.g., —C(O)OMe or —C(O)OEt), amino (e.g., —NH$_2$), amido (e.g., —C(O)NH$_2$ or —C(O)NHMe), sulfonic acid, sulfonate (e.g., —S(O)$_2$OEt), phosphonic acid, phosphonate (e.g., —P(O)(OEt)$_2$), and substituted or unsubstituted bicyclic heteroaromatic groups (e.g., phthalimido). In some embodiments, $R_7$ is carboxy. In some embodiments, $R_7$ is hydroxamic acid.

Compounds that may be used in the methods described herein also include the following:

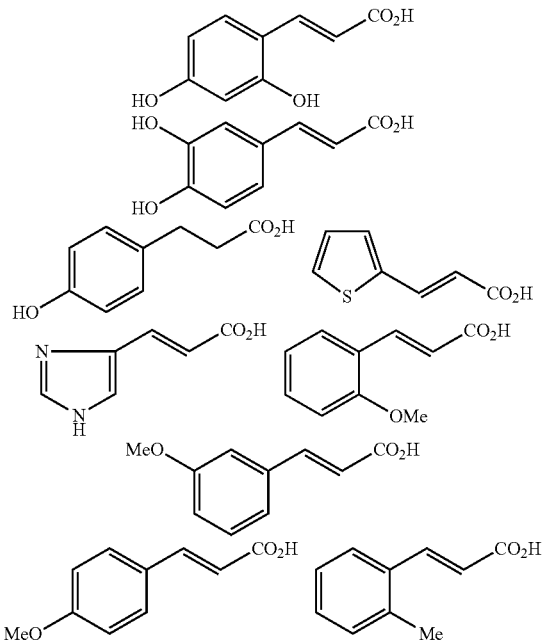

-continued
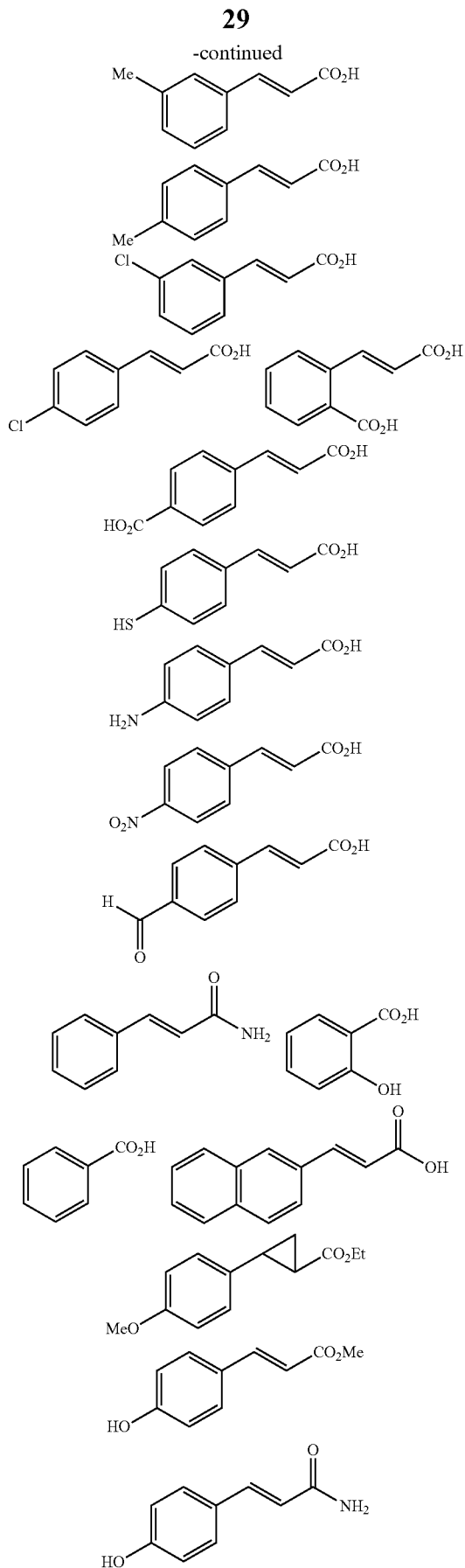
-continued
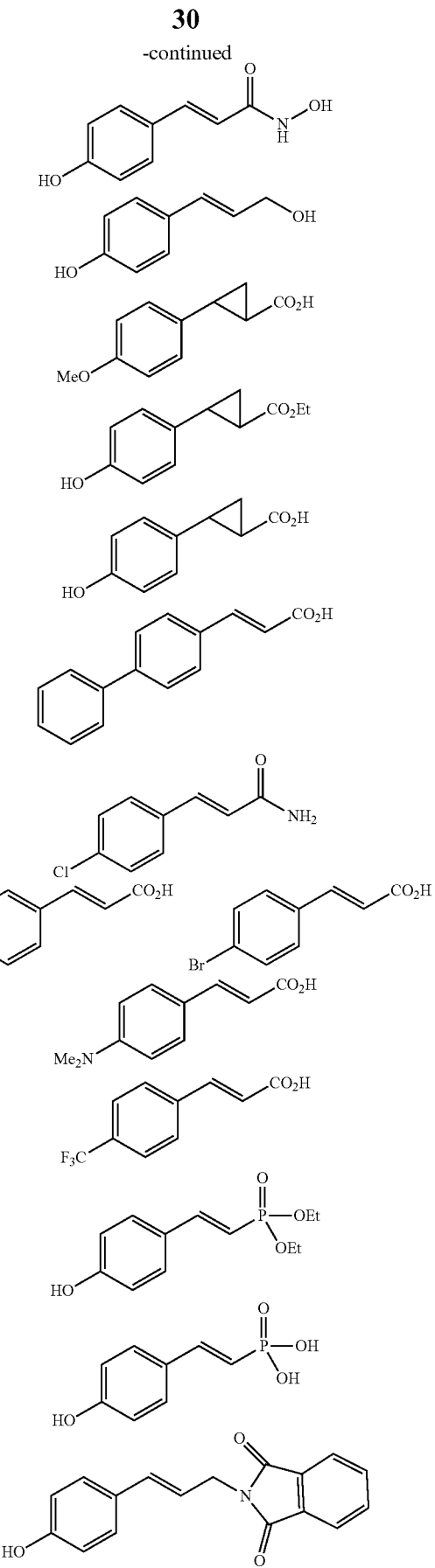

31
-continued
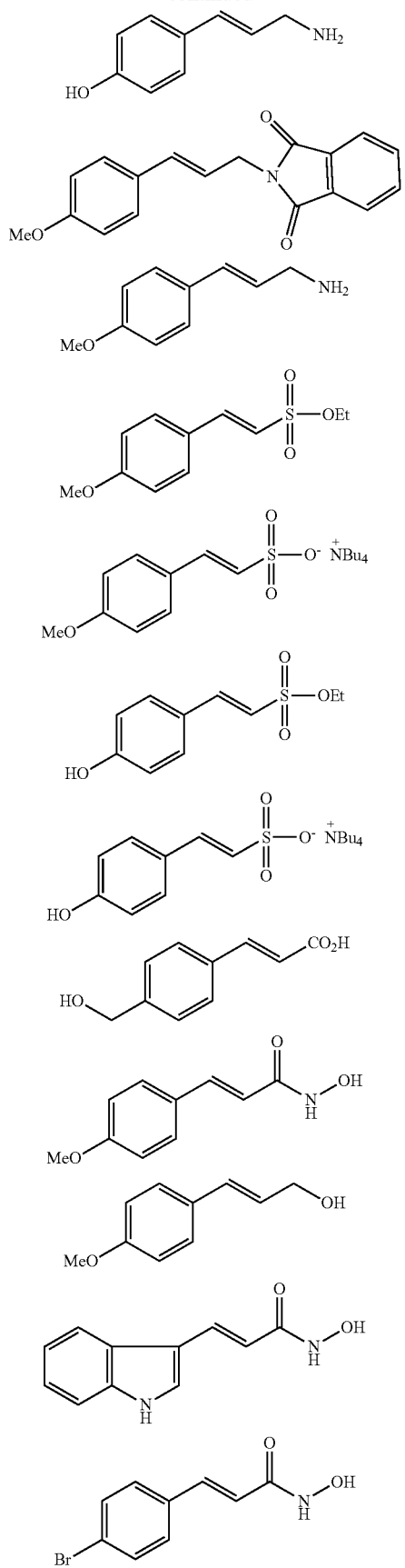
32
-continued
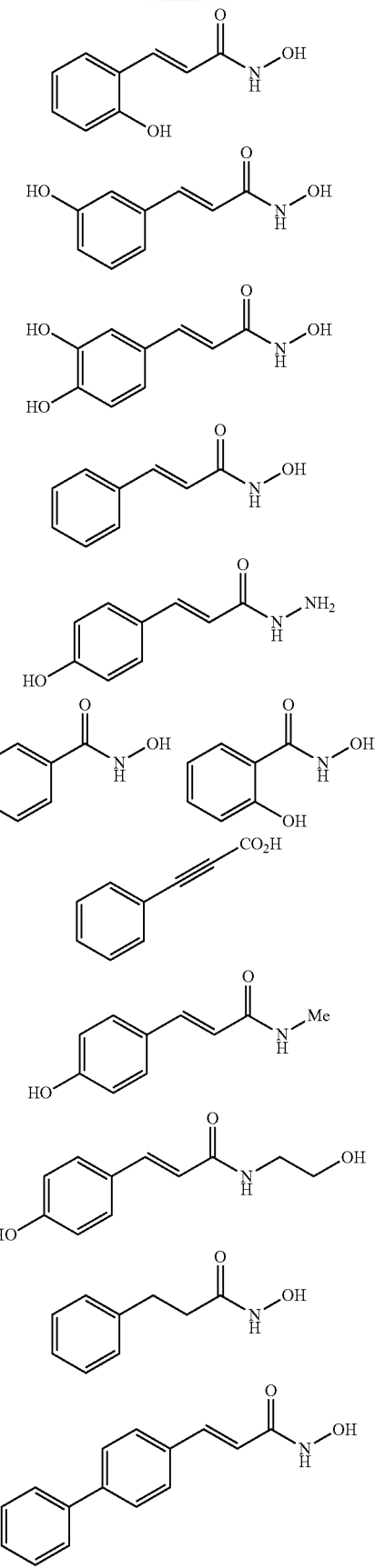

33
-continued
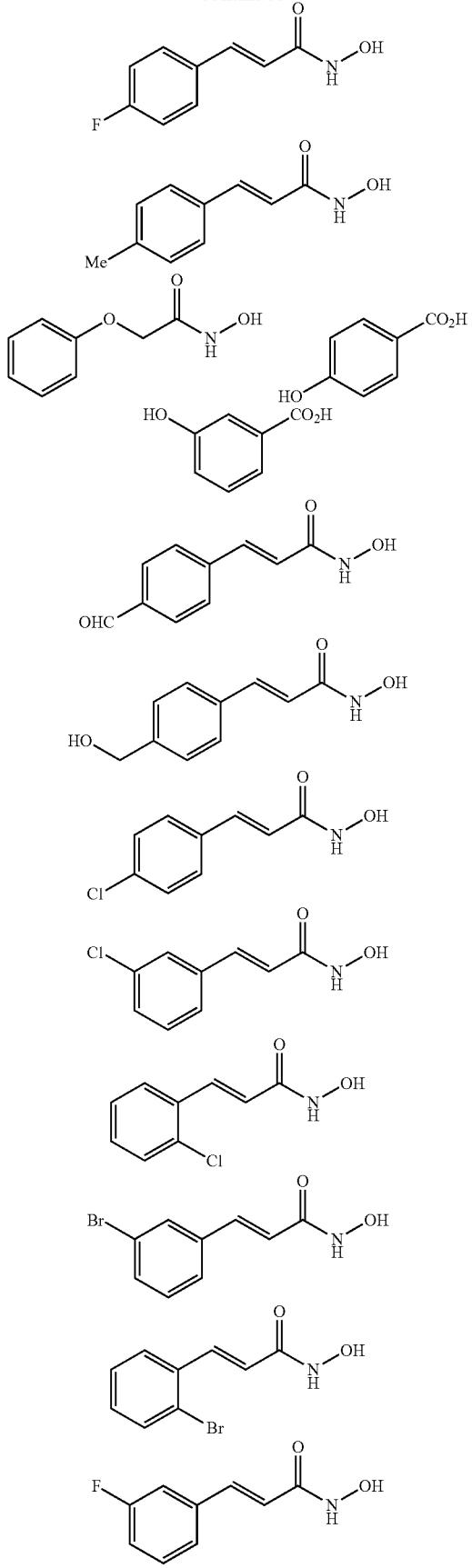
34
-continued
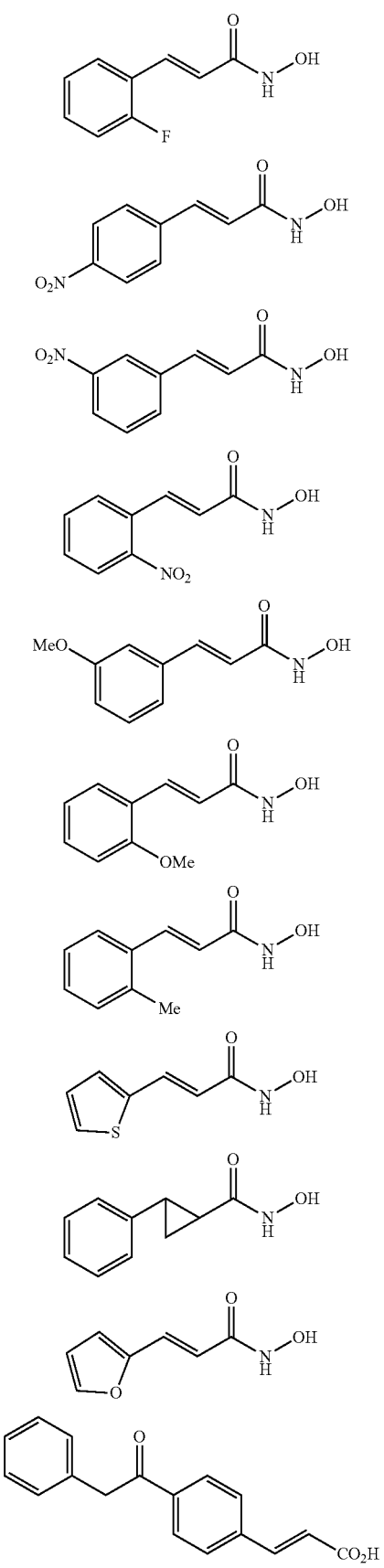

-continued

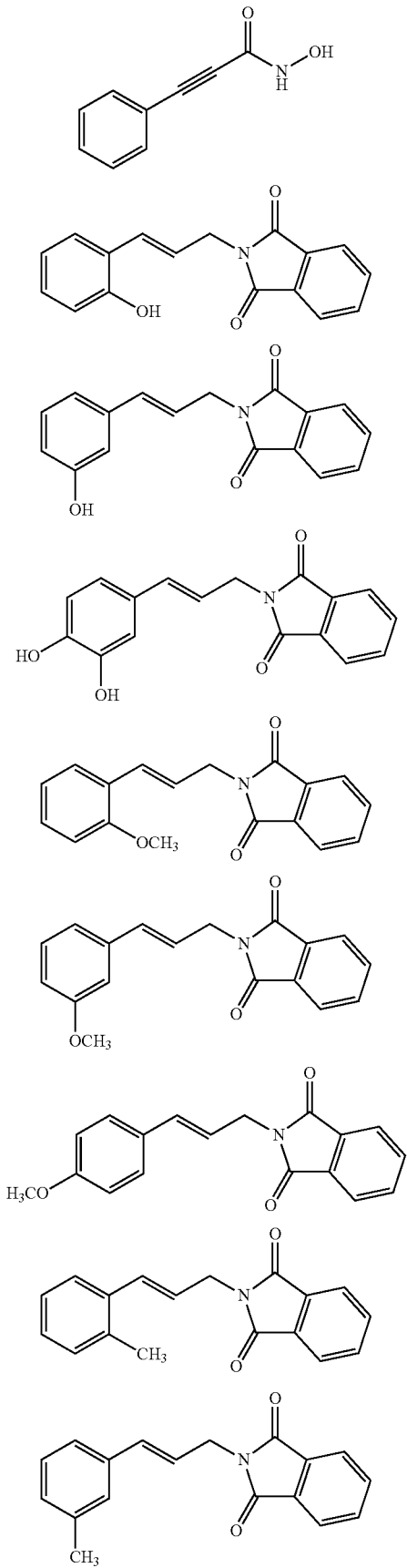
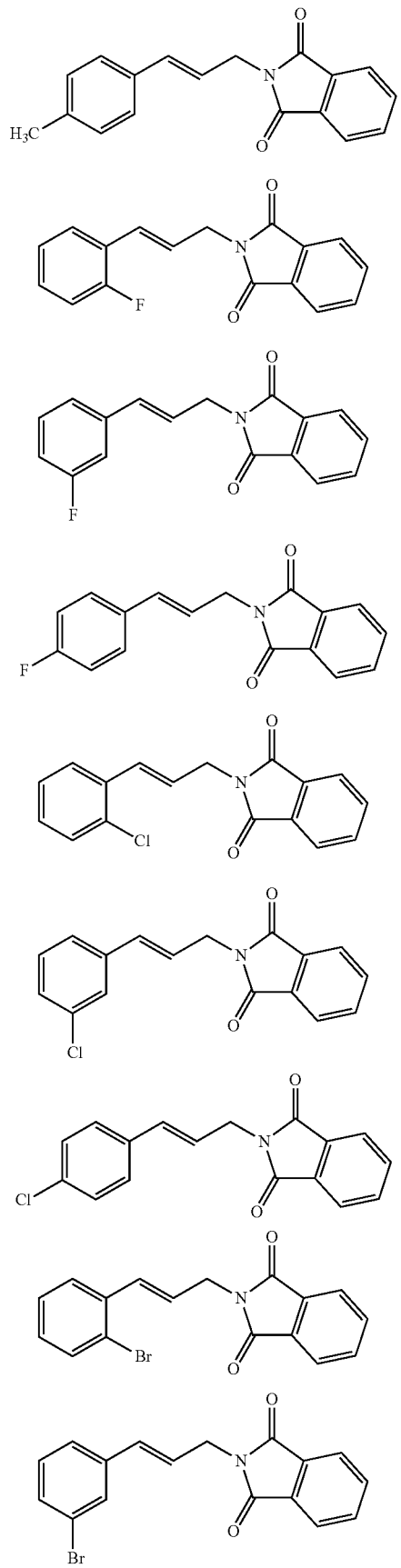

39
-continued
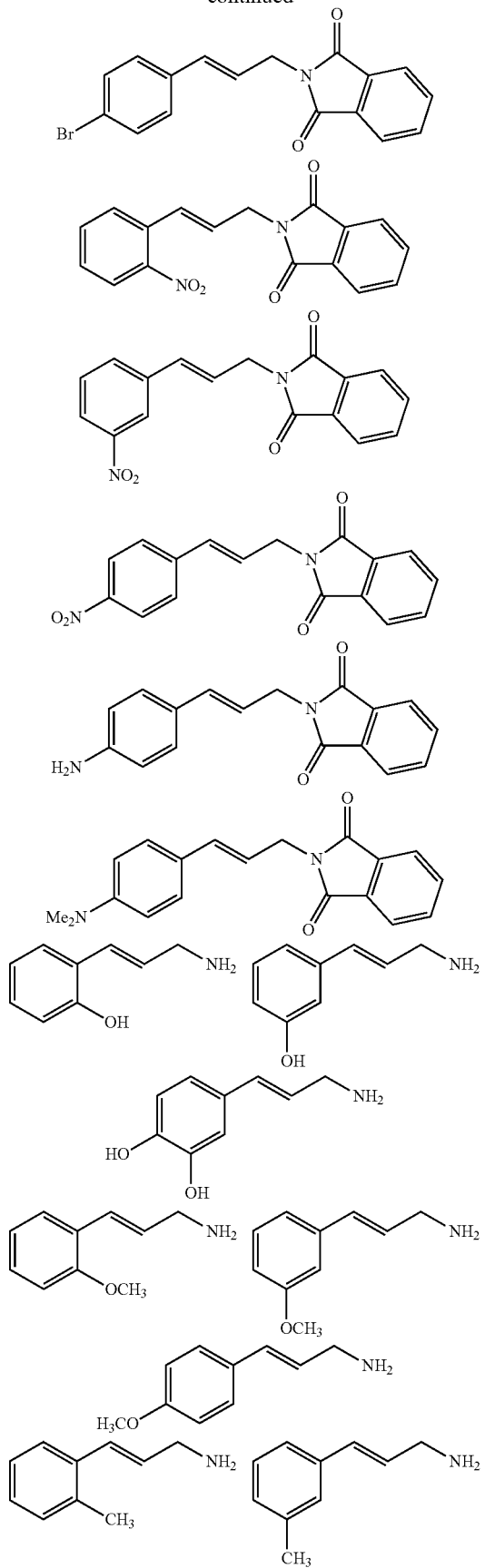
40
-continued
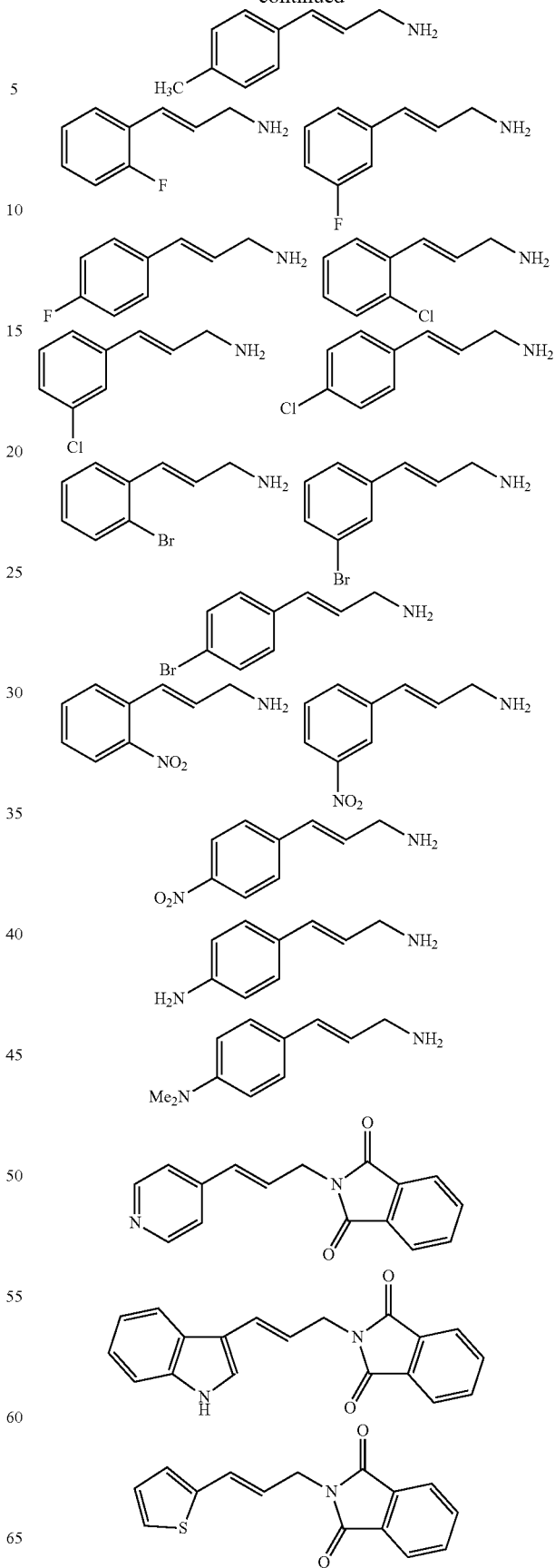

-continued

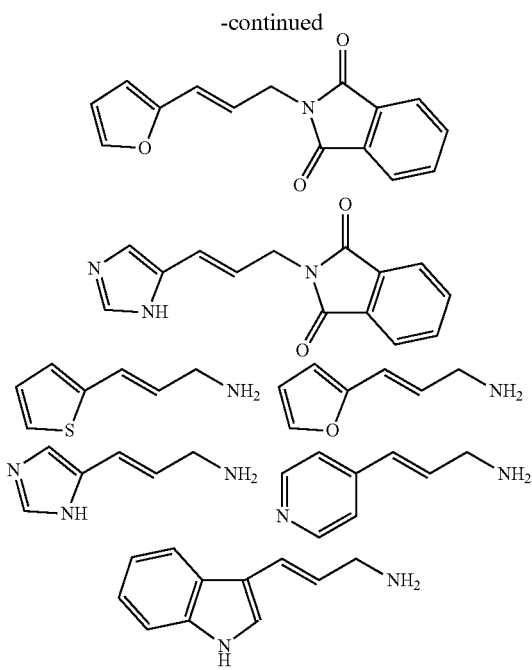

or salts thereof.

Combinations of the substituent groups described above for Formula (I), (II), (III), (IV), (V), (VI) and (VII) are also contemplated as part of this disclosure.

The compounds described herein include compounds that differ only in the presence of one or more isotopically enriched atoms. For example, compounds may have the present structures except for the replacement of hydrogen by deuterium or tritium, or the replacement of a carbon by a $^{13}$C- or $^{14}$C-enriched carbon.

A compound described herein can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al, J. Pharma. Science 1977, 66: 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention may also provide compounds that are in a prodrug form. Prodrugs of the compounds described herein are those compounds that readily undergo chemical changes under physiological conditions to provide the compounds described herein. For instance, prodrugs for carboxylic acid compounds of the invention include a variety of esters. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Synthesis of Compounds

Compounds that may be used in the methods described herein may be synthesized using a variety of methods. Compounds that may be used in the methods described herein include phenylpropanoids, which are plant-derived organic compounds synthesized from phenylalanine. Phenylpropanoid derivatives can be made by adding or removing substituents using methods known to those of skill in the art. As shown in the Examples, phenylpropanoid derivatives such as those disclosed herein can be synthesized de novo or by modifying naturally-occurring compounds.

Figure 18:
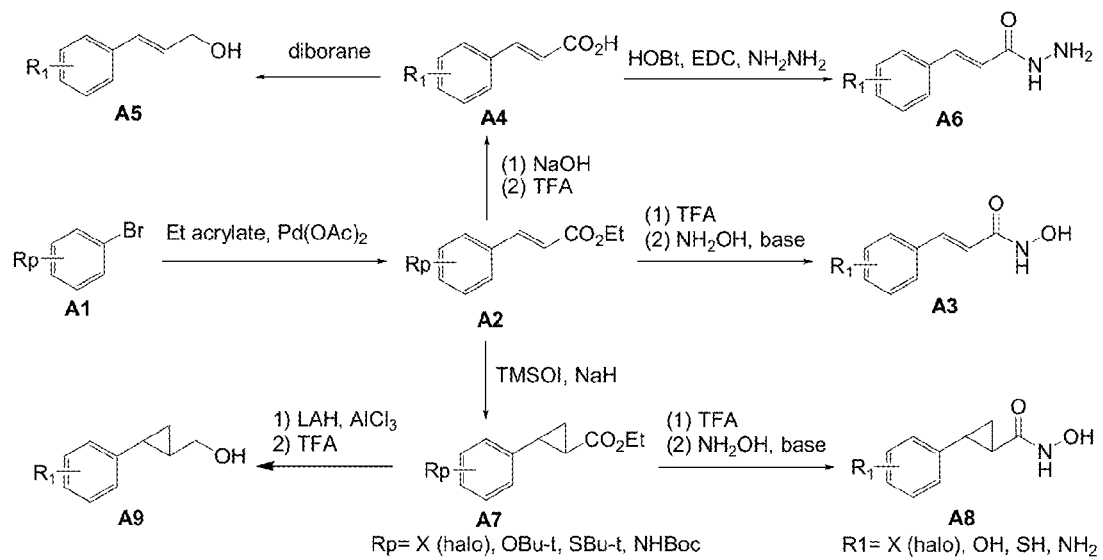
FIG. 18 shows a scheme for synthesis of various compounds.

The synthetic routes for the compounds are described in the schemes presented in FIGS. 18-22 and 24-30. In FIG. 18, aryl bromides A1 are reacted with ethyl acrylate to give ethyl trans-cinnamates A2 under the Heck reaction conditions (Patel, B. A., et al. *J. Org. Chem.* 1977, 42: 3903-3907). After removing the protecting group by trifluoroacetic acid (TFA), the ester was displaced by hydroxylamine to result in hydroxamates A3 with hydroxy, hydroxythio, amino and other groups in phenyl group, respectively. Basic hydrolysis of esters A2 followed by TFA deprotection affords cinnamic acid derivatives A4. The carboxyl group in A4 can be reduced by diborane, resulting in cinnamyl alcohols A5. By following the reported procedure (Zhang, X., et al. *J. Org. Chem.* 2002, 67: 9471-9474), hydrazides A6 can be obtained from acids A4 by treating with HOBt and hydrazine. Under the Corey-Chaykovsky cyclopropanation reaction conditions (TMSOI, NaH, DMSO) (Corey, E. J., Chaykovsky, M. *J. Am. Chem. Soc.* 1965, 87: 1353-1364), ethyl cinnamates A2 are transformed to cyclopropanyl esters A7. The latter can be further converted to cyclopropanyl hydroxamatates A8 by TFA deprotection and reacting with hydroxylamine, or to the corresponding alcohols A9 by LAH reduction and TFA de-protection. The analogs with other heterocycles, such as indolyl, thionaphthyl, naphthyl, and other groups can be synthesized in the similar ways.

Figure 19:
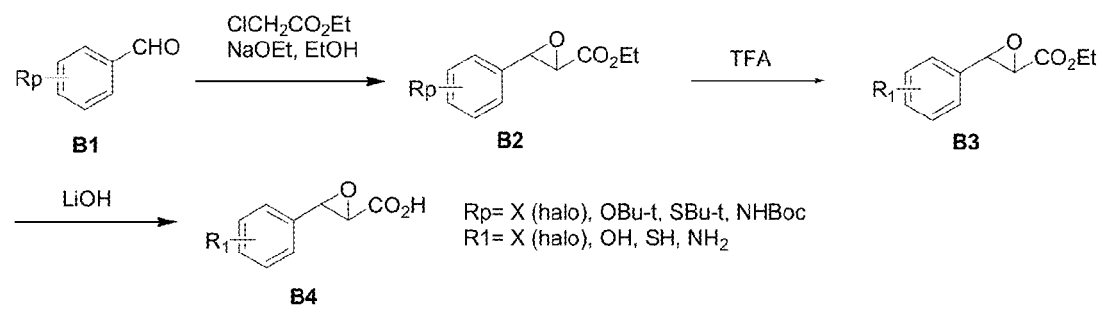
FIG. 19 shows a scheme for synthesis of various compounds.

As shown in FIG. 19, benzaldehydes B1 react with ethyl chloroacetate to afford ethyl oxiranecarboxylates B2 in the presence of sodium ethoxide (Li, S. W., et al. *Bioorg. Chem.* 1998, 26: 45-50). Conversion of B2 to 3-aryl oxiranecarboxylic acids B4 will be accomplished by deprotection with TFA followed by basic hydrolysis (FIG. 19).

Figure 20:
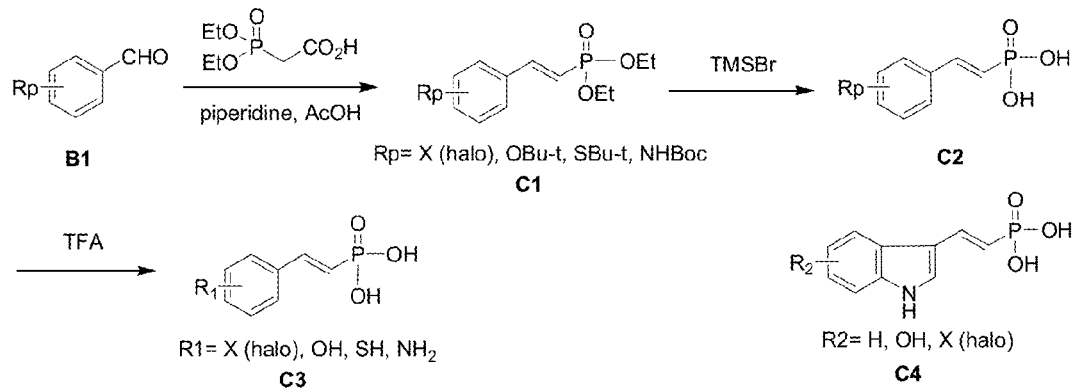
FIG. 20 shows a scheme for synthesis of various compounds.

As shown in FIG. 20, Knoevenagel reaction of benzaldehydes B1 with diethylphosphonoacetic acid leads to the formation of diethyl trans-2-arylvinylphosphonates C1 (Krawczyk, H., Albrecht, L. *Synthesis* 2005, 17: 2887-2896). Upon treatment with trimethylsilyl bromide (TMSBr) and TFA, the phosphonates C1 can be converted to trans-2-arylvinylphosphoric acids C3 (FIG. 20). In the similar way, trans-2-(indol-3-yl)vinylphosphoric acids C4 can be obtained from the corresponding indol-3-aldehydes.

Figure 21:
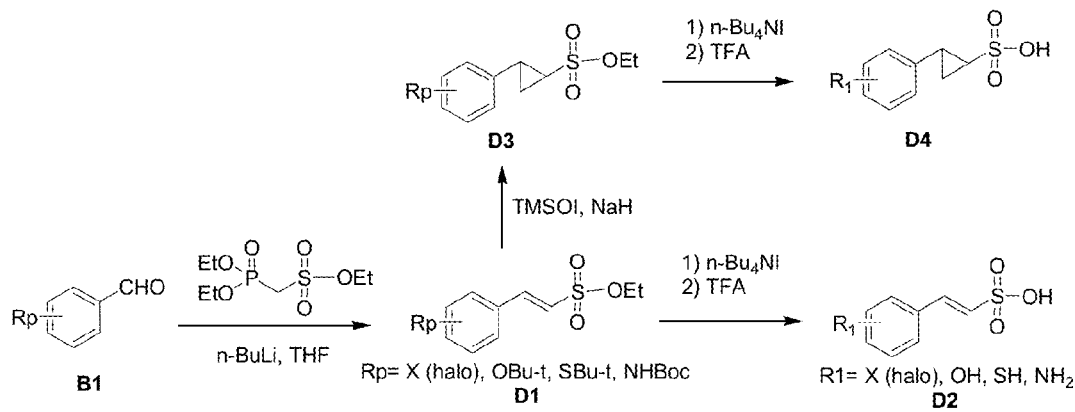
FIG. 21 shows a scheme for synthesis of various compounds.
Figure 22:
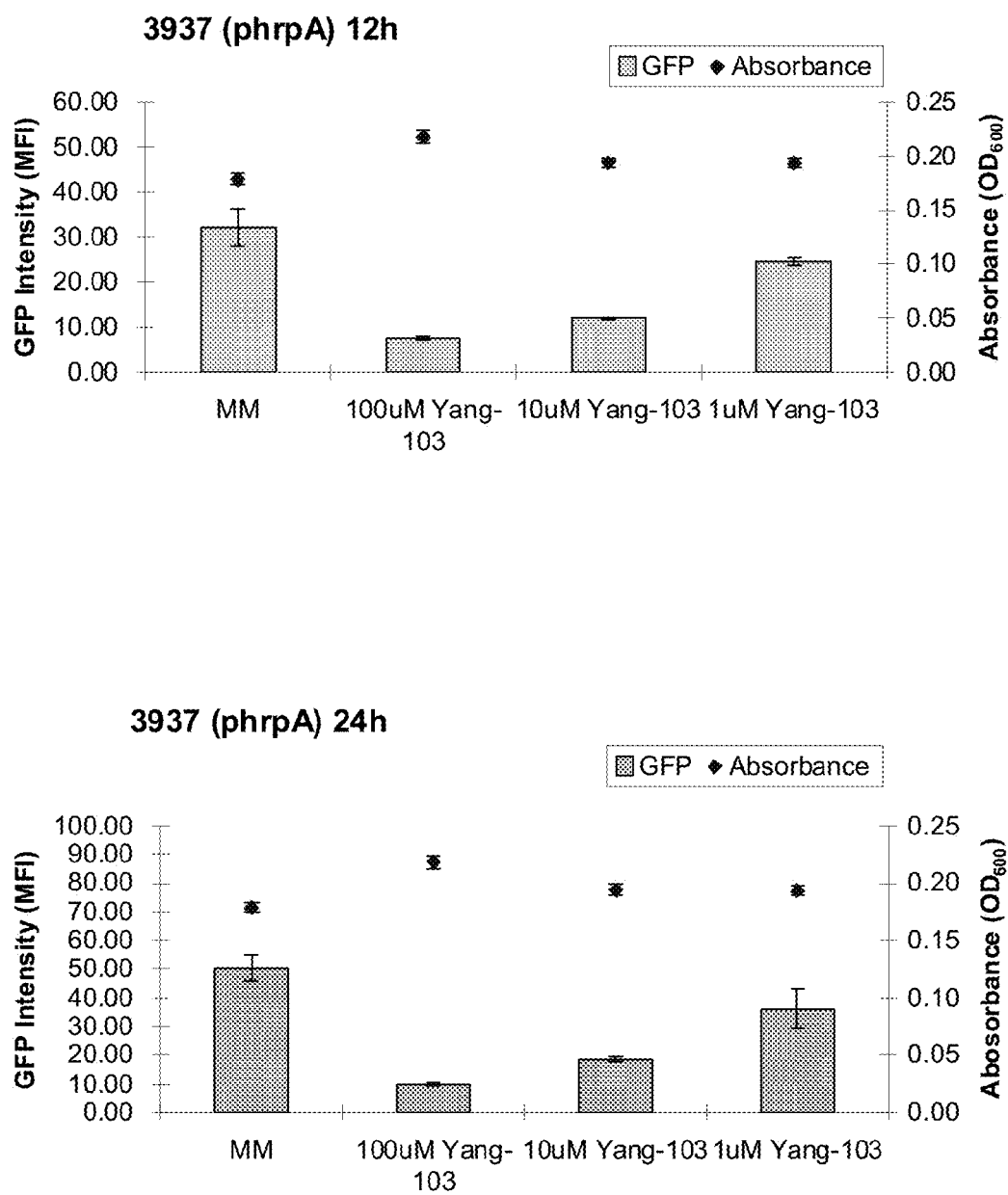
FIG. 22 are graphs of the effect of different concentrations of compound 103 on hrpA expression.

As shown in FIG. 21, In the presence of n-butyllithium, benzaldehydes B1 are reacted with ethyl diethylphosphoryl-methanesulfonate to generate ethyl trans-2-arylethenylsulfonates D1 (Niimi, T., et al. *J. Med. Chem.* 2001, 44: 4737-4740) (FIG. 21). The ethyl sulfonates D1 can be cleaved with tetra-n-butylammonium iodide (n-Bu$_4$NI), and further deprotection with TFA affords the trans-2-arylethenylsulfonic acids D2. Corey-Chaykovsky cyclopropanation reaction of D1 produces cyclopropanyl sulfonates D3, and the corresponding sulfonic acids D4 will be obtained from D3 after treating with n-Bu$_4$NI and TFA.

Figure 24:
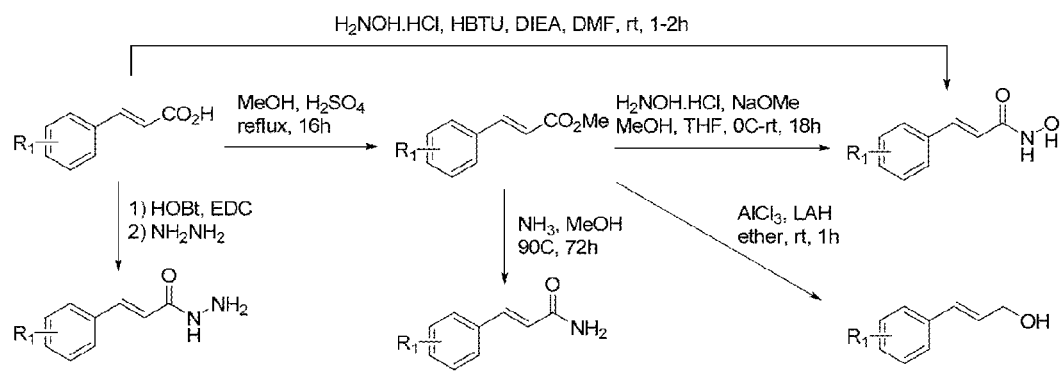
FIG. 24 shows a scheme for synthesis of various compounds.

In FIG. 24, cinnamic acids are converted into the corresponding methyl esters. The latter can be further transformed into hydroxamic acids by treating with hydroxylamine under basic condition. When the substituent in the phenyl group is halo, methyl, methoxy, or other groups which will not form amide/ester, the hydroxamic acids can be obtained directly from the corresponding carboxylic acids. By refluxing with ammonia in methanol, the corresponding amides can be obtained from the methyl esters. The esters can readily reduced by LiAlH$_4$/AlCl$_3$ system, resulting in cinnamyl alcohols. By employing the reported procedure (Zhang et al. 2002), hydrazides can be obtained from cinnamic acids by treating with HOBt and EDC followed by hydrazine.

Figure 25:
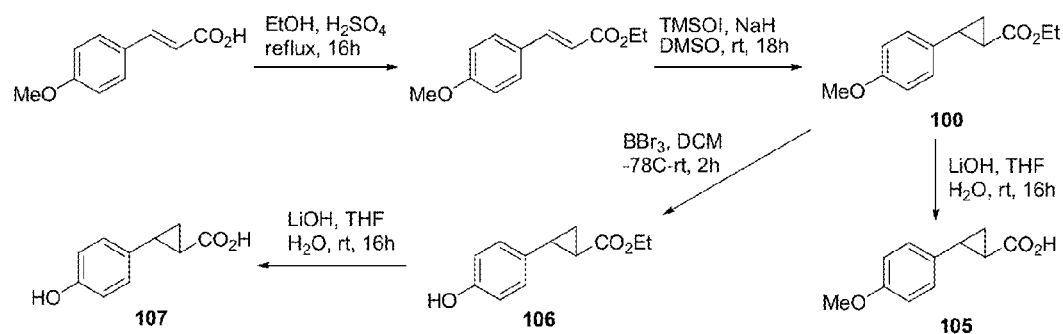
FIG. 25 shows a scheme for synthesis of various compounds.

Under the Corey-Chaykovsky cyclopropanation reaction conditions (Corey and Chaykovsky, 1965), ethyl 4-methoxycinnamate was transformed into cyclopropanyl ester (100). Upon hydrolysis, acid 105 was obtained. Demethylation of 100 with borane tribromide gave 106. The latter was further hydrolyzed with lithium hydroxide to afford the corresponding carboxylic acid 107 (FIG. 25).

Figure 26:
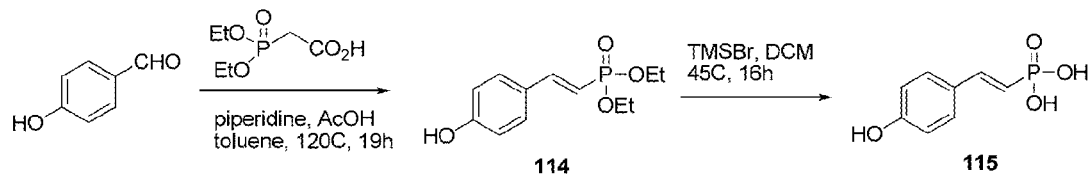
FIG. 26 shows a scheme for synthesis of various compounds.

Knoevenagel reaction (Krawczyk and Albrecht 2005) of 4-hydroxybenzaldehydes with diethylphosphonoacetic acid leads to the formation of diethyl trans-2-arylvinylphosphonates 114. Upon treatment with trimethylsilyl bromide (TMSBr), the phosphonate was converted into vinylphosphoric acid 115 (FIG. 26). In the similar way, other trans-2-arylvinylphosphoric acids can be obtained from the corresponding arylaldehydes.

Figure 27:
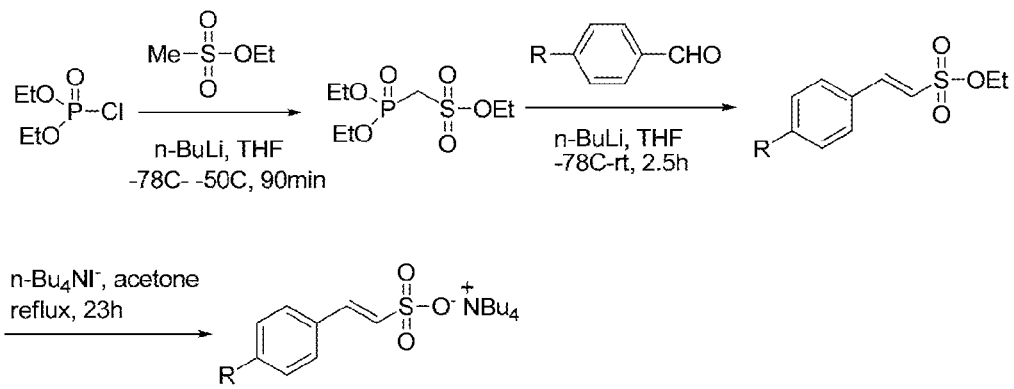
FIG. 27 shows a scheme for synthesis of various compounds.

In the presence of n-butyllithium, benzaldehyde can reacted with ethyl diethylphosphoryl-methanesulfonate to generate ethyl trans-2-arylethenylsulfonates (Niimi et al. 2001) (FIG. 27). The resulting ethyl sulfonates can be cleaved with tetra-n-butylammonium iodide (n-Bu$_4$NI), affording the trans-2-arylethenylsulfonic acids.

Figure 28:
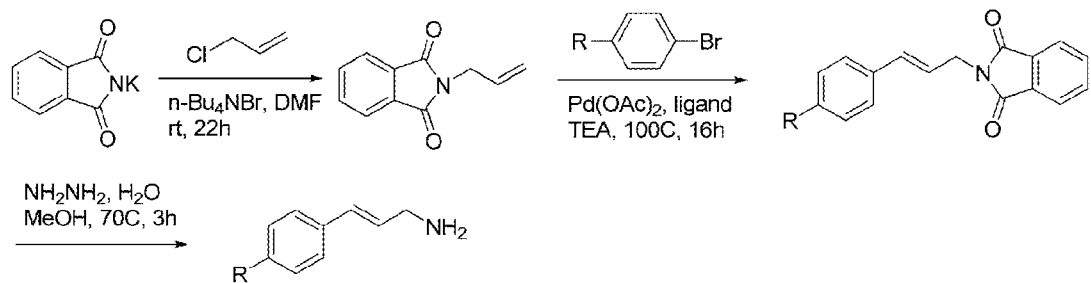
FIG. 28 shows a scheme for synthesis of various compounds.
Figure 29:
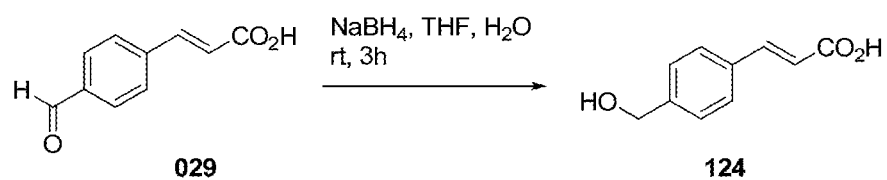
FIG. 29 shows a scheme for synthesis of various compounds.
Figure 30:
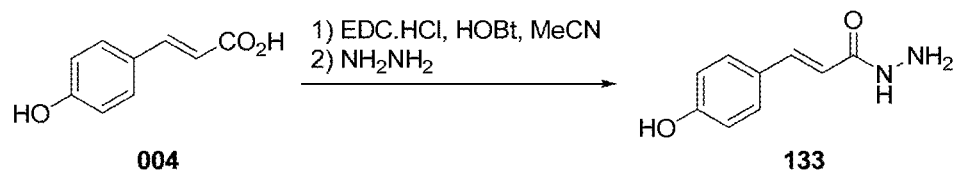
FIG. 30 shows a scheme for synthesis of various compounds.

Phthalimide potassium salt can be alkylated with allyl chloride in DMF to produce N-allylphthalimide. Under the Heck reaction conditions (Patel et al. 1977), N-allylphthalimide reacted with aryl bromide to give N-cinnamyl phthalimide. Upon treatment with hydrazine, cinnamyl amine was obtained from N-cinnamyl phthalimide (FIG. 28).

As can be appreciated by the skilled artisan, alternative methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Activity of Compounds

Activity assays may be carried out on intact bacteria or on isolated bacterial components. For example, receptor portions of the GacS/GacA-type system or HrpX/HrpY-type system may be reconstituted in vitro, e.g. in membrane microsomes, or as isolated, soluble protein components. In one embodiment, the assay includes measurement of binding affinity of a test compound to the GacS-type or HrpX-type polypeptide.

The assays may also be conducted on genetically-engineered bacteria in which the GacS/GacA-type system or HrpX/HrpY-type system is coupled to a reporter. Thus, a test compound can be screened by contacting the compound with an appropriately engineered bacterium so that the binding and/or activation of the GacS/GacA pathway by the compound will be directly reported without the need to assay a downstream target or effector such as a component of the Rsm pathway or T3SS system. The reporter in the genetically-engineered bacterium could be linked to any number of known fluorescent or colorimetric assays, e.g. green fluorescent protein (GFP), to make possible rapid screening of large numbers of compounds.

Various assays may be used to test the efficacy of the compounds, such as any of the assays described herein, including without limitation promoter-probe bioreporter assays, cell sorting (FACS), pectinase activity assays, qRT-PCR analysis, analysis of the phosphorylation of GacA or HrpY, leaf maceraction assays, growth kinetics assays, plate assays, analysis of pellicle formation, analysis of exoenzyme production, and spectrophotometric quantification assays. Assays may be performed using *Dickeya dadantii* or any other suitable bacterial species or strain having a GacS/GacA-type system, a HrpX/HrpY-type system, an Rsm-type system, and/or a T3SS-type system. Leaf maceration assays may be carried out using leaves from any of a variety of plants, including African violet, Chinese cabbage, or witloof chicory leaves.

In addition to the methods described herein, additional methods known to those skilled in the art may be employed as needed in screening and assaying the synthesized compounds. For example, to detect and measure amounts of polypeptides, methods such as SDS-PAGE gel electrophoresis, Western blotting, and enzyme-linked immunoassays (ELISA) may be used, among other techniques. To detect and measure polynucleotides, polymerase-chain reaction (PCR) as well as electrophoretic mobility-based methods such as Southern and Northern blotting may be used, among other techniques.

The bacterium can be any one of a number of virulent bacterial species or strains, including those bacterial species or strains having at least one of a GacS/GacA-type system, a HrpX/HrpY-type system, a Rsm-type system, and/or a T3SS-type system. The suitable bacterial species or strains include without limitation *Pseudomonas* spp., *Erwinia*-related strains, *Azotobacter vinelandii*, *Vibrio cholarae*, *Salmonella enterica*, and *Escherichia coli* strains. The bacterium may be a *Pseudomonas* spp. including *P. aureofaciens*, *P. chlororaphis*, *P. fluorescens*, *P. marginalis*, *Pseudomonas syringae*, *P. tolaasii*, *P. viridiflava*, and *P. aeruginosa*. The bacterium may be an *Erwinia*-related strain including *Dickeya dadantii*, *Erwinia carotovora* (also known as *Pectobacterium carotovorum*), *Erwinia atroseptica* (also known as *Pectobacterium atrosepticum*), and *Erwinia amylovora*. *Dickeya dadantii* is a member of the Enterobacteriaceae family, which includes the plant pathogens *Pectobacterium carotovorum* and *Erwinia amylovora* as well as animal and human pathogens such as *E. coli*, *Salmonella* spp., and *Yersinia* spp (such as *Yersinia pseudotuberculosi*, *Yersinia enterocolitica* and *Yersinia pestis*). Bacteria may further include *Acidovorax* spp. (such as *Acidovorax avenae*), *Aeromonas* spp. (such as *Aeromonas hydrophila*, *Aeromonas veronii* and *Aeromonas salmonicida*), *Bordetella* spp. (such as *Bordetella pertussis*), *Bradyrhizobium* spp. (such as *Bradyrhizobium japonicum* and *Bradyrhizobium liaoningense*), *Burkholderia* spp. (such as *Burkholderia pseudomallei*), *Candidatus* spp., *Cellvibrio* spp., *Chlamydia* spp. (such as *Chlamydia trachomatis* and *Chlamydia pneumoniae*), *Chlamydophilia* spp. (such as *Chlamydophilia psittaci* and *Chlamydophilia pneumoniae*), *Chromobacterium* spp. (such as *Chromobacterium violaceum*), *Citrobacter* spp. (such as *Citrobacter rodentium*), *Cupriavidus* spp., *Desulfovibrio* spp., *Dickeya* spp., *Edwardsiella* spp. (such as *Edwardsiella tarda* and *Edwardsiella ictalun*), *Erwinia* spp. (such as *Erwinia chrysanthemi*), *Escherichia* spp., *Hahella* spp. (such as *Hahella chejuensis*), *Hamiltonella* spp. (such as *Hamiltonella defensa*), *Lawsonia* spp. (such as *Lawsonia intracellularis*), *Mesorhizobium* spp. (such as *Mesorhizobium loti*), *Pantoea* spp. (such as *Pantoea agglomerans*), *Pectobacterium* spp. (such as *Pectobacterium wasabiae*), *Photobacterium* spp., *Photorhabdus* spp. (such as *Photorhabdus asymbiotic*, *Photorhabdus temperata* and *Photorhabdus luminescens*), *Proteus* spp. (such as *Proteus mirabilis*), *Providencia* spp., *Pseudomonas* spp. (such as *Pseudomonas aeruginosa*, *Pseudomonas syringae* pv. *glycinea*, *Pseudomonas syringae* pv. tomato, and *Pseudomonas syringae* pv. *syringae*), *Ralstonia* spp. (such as *Ralstonia solanacearum*), *Rhizobium* spp., (such as *Rhizobium* sp. Strain NGR234), *Salmonella* spp. (such as *Salmonella typhimurium* and *Salmonella enterica*), *Shewanella* spp., *Shigella* spp. (such as *Shigella flexnen*), *Sinorhizobium* spp. (such as *Sinorhizobium fredii*), *Sodalis* spp., *Vibrio* spp. (such as *Vibrio cholerae* and *Vibrio parahaemolyticus*), and *Xanthomonas* spp. (such as *Xanthomonas campestris*, *Xanthomonas axonopodis*, *Xanthomonas otyzae*, *Xanthomonas fuscans* subsp. *Fuscan*, *Xanthomonas campestris* pv. *campestris*, *Xanthomonas campestris* pv. *citri*, *anthomonas campestris* pv. *oryzae*, and *Xanthomonas campestris* pv. *vesicatoria*).

The results of the assays may be evaluated in accordance with the methods described herein and according to the knowledge of one skilled in the art to determine whether the compound that is tested reduces bacterial virulence. Those compounds that demonstrate activity in reducing bacterial virulence in the assays may then be used as antimicrobial compounds, for example as described herein.

Accordingly, the invention may provide a method of screening a compound for an ability to reduce virulence of a bacterium comprising at least one of a GacS/GacA-type system, a HrpX/HrpY-type system, a T3SS-type system, and a Rsm-type system. The method comprises contacting the bacterium with a compound described herein and detecting at least one of: (i) a change in a component of at least one of the GacS/GacA-type system, the HrpX/HrpY-type system, the T3SS-type system, and the Rsm-type system of the bacterium, and (ii) a change in host pathology.

Methods of Use

After the compounds have been screened for their efficacy in reducing induction of virulence, those analogs that show effective reduction (also called "active compounds") may be tested for use in reducing virulence in bacteria that are associated with a subject such as a plant or an animal, including a human. The bacteria may be on the surface of the subject or within the subject or otherwise associated with the subject. Active compounds may be used in a method to treat a subject having a bacterial infection comprising administering to the subject an effective amount of a composition comprising the compound (see Examples). Active compounds may also be applied to a surface to reduce virulence of bacteria associated with the surface.

Accordingly, in one embodiment, the invention may provide a method of treating a subject having a bacterium associated therewith, the bacterium comprising at least one of a GacS/GacA-type system, a HrpX/HrpY-type system, a T3SS-type system, and a Rsm-type system. The method comprises administering to the subject a composition comprising an effective amount of a compound described herein.

In another embodiment, the invention may provide a method of reducing virulence of a bacterium on a surface comprising a bacterium having at least one of a GacS/GacA-type system, a HrpX/HrpY-type system, a T3SS-type system, and a Rsm-type system. The method comprises contacting the surface with a composition comprising an effective amount of a compound described herein.

In another embodiment, the invention may provide a pharmaceutical composition comprising an effective amount of a compound described herein, and a pharmaceutically-acceptable carrier or diluent.

Use on Plants

The active compounds, compositions containing the active compounds, and methods of using the same, may be used with any plant including those having an appropriate TCSTS-containing bacterium associated therewith, including a bacterium having a GacS/GacA-type system or a HrpX/HrpY-type system. These plants may include cultivated, domesticated, or wild plants, including annual crops and longer-term crops such as trees. Agriculturally relevant annual crops include, without limitation, corn, soy, wheat, barley, oats, rice, sorghum, rye, alfalfa, tobacco, and sunflower. The compounds, compositions, and methods may be used either on terrestrial plants or on aquatic plants, including freshwater and marine-dwelling plants.

For application on plants, the compounds may be formulated in compositions such as a liquid suitable for application by spraying or other mode of application; dust; granules; oil; or solid (e.g. as a spike). The composition may be produced in a concentrated form, including a concentrated liquid, powder, solid, or other form, which may be reconstituted prior to use.

The following are suitable as possible formulations: wettable powders (WP), water-soluble powders (SP), emulsifiable concentrates (EC), aqueous solutions or concentrates, emulsions (EW), sprayable solutions, capsule suspensions (CS), dispersions on an oil or water base, suspoemulsions, suspension concentrates (SC), dusting powders (DP), solutions which can be mixed with oils (OL), seed-dressing agents, granules (GR) in the form of microgranules, spray granules, coated granules and adsorption granules, granules for broadcasting and soil application, water-soluble granules (SG), water-dispersible granules (WG), ULV formulations, microcapsules and waxes.

These individual types of formulations are known in principle and are described, for example, in: Winnacker-Kuchler, "Chemische Technologie [Chemical Technology]", Volume 7, C. Hauser Verlag Munich, 4th Ed. 1986; van Valkenburg, "Pesticides Formulations", Marcel Dekker N.Y., 2nd Ed.

1972-73; K. Martens, "Spray Drying Handbook", 3rd Ed. 1979, G. Goodwin Ltd. London.

The formulation auxiliaries required, such as inert materials, surfactants, solvents and other additives are likewise known and are described, for example, in: Watkins, "Handbook of Insecticide Dust Diluents and Carriers", 2nd Ed., Darland Books, Caldwell N.J.; H. V. Olphen, "Introduction to Clay Colloid Chemistry"; 2nd Ed., J. Wiley & Sons, N.Y., Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflachenaktive Athylenoxidaddukte [Surface-active Ethylene Oxide Adducts]", Wiss. Verlagsgesell., Stuttgart 1976; and Winnacker-Kuchler, "Chemische Technologie [Chemical Technology]", Volume 7, C. Hauser Verlag Munich, 4th Ed. 1986.

Combinations with other active substances such as herbicides, fungicides or insecticides, as well as fertilizers and/or growth regulators, may also be prepared on the basis of these formulations, for example in the form of a ready-mix or as a tank mix.

The active compound combinations according to the invention can either be a mixed formulation of the two components which are then diluted with water and applied in a customary manner, or they can be prepared as so-called tank mixes by joint dilution, with water, of the separately formulated components.

Wettable powders are preparations which are uniformly dispersible in water and which, besides the active compound, also contain wetting agents, for example polyoxethylated alkylphenols, polyoxethylated fatty alcohols or fatty amines, alkane- or alkylbenzenesulfonates, and dispersing agents, for example sodium ligninsulfonate, sodium 2,2'-dinaphthylmethane-6,6'-disulfonate, sodium dibutylnaphthalenesulfonate, or alternatively sodium oleylmethyltaurinate, in addition to a diluent or inert substance.

Emulsifiable concentrates may be prepared by dissolving the active compound in an organic solvent, for example butanol, cyclohexanone, dimethylformamide, xylene and also higher-boiling aromatic compounds or hydrocarbons, with the addition of one or more emulsifiers. Examples of emulsifiers which may be used are: calcium salts of an alkylarylsulfonic acid, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting agents may be obtained by grinding the active compound with finely divided solid substances, for example talc or natural clays, such as kaolin, bentonite, pyrophillite or diatomaceous earth.

Granules may be produced either by spraying the active substance onto adsorptive, granulated inert material or by applying active substance concentrates onto the surface of carriers, such as sand, kaolinites or of granulated inert material, by means of binders, for example polyvinyl alcohol, sodium polyacrylate or, alternatively, mineral oils. Suitable active substances may also be granulated in the manner which is conventional for the production of fertilizer granules, if desired in a mixture with fertilizers.

In one embodiment, the concentration of active compound in wettable powders may be, for example, about 10 to about 95% by weight, the remainder to 100% by weight is composed of conventional formulation components. In the case of emulsifiable concentrates, the concentration of active compound may be about 1 to about 85% by weight, preferably about 5 to about 80% by weight. Formulations in the form of dusts usually contain about 1 to about 25% by weight, mostly about 5 to about 20% by weight of active compound, sprayable solutions about 0.2 to about 25% by weight, preferably about 2 to about 20% by weight, of active compound. In the case of granules, such as water-dispersible granules, the active compound content depends partly on whether the active compound is liquid or solid and on which granulation auxiliaries and fillers are used. The content in water-dispersible granules is generally between about 10 and about 90% by weight.

In addition, the active compound formulations mentioned contain, if appropriate, the adhesives, wetting agents, dispersing agents, emulsifiers, penetrants, solvents, fillers or carriers which are conventional in each case.

For use, the formulations, present in commercially-available form, may be diluted, if appropriate, in a customary manner, for example using water in the case of wettable powders, emulsifiable concentrates, dispersions and water-dispersible granules. Preparations in the form of dusts, granules for soil application and/or broadcasting, and also sprayable solutions are usually not further diluted with other inert substances before use.

The application rate required for the compositions varies with the external conditions, such as, inter alia, temperature, humidity, and the nature of the compound and composition used.

Further information regarding formulation and application of compositions for agricultural use are disclosed in U.S. Pat. No. 5,447,903, incorporated herein by reference.

The compositions may be applied to different parts of the plant, including leaves, stems, roots, buds fruits, frill, stump, bark, and roots, as well as to soil in the vicinity of a plant (e.g., the rhizosphere). Methods of application may include spraying, irrigating, dusting, and spreading or broadcasting of granules, powders, or other solid or liquid forms.

The composition may be applied to leaf surfaces, stems of plants including agricultural crops, and irrigated into soil to protect root systems from human and other pathogens (including, for example, E. coli O157:H7 on lettuce, spinach) which may be present as contaminants from exposure to animal waste.

The composition may be applied to the surfaces of stored crops (including without limitation onions, potatoes, grains, squash, melons) to reduce post-harvest infection and contamination by plant, animal, and human pathogens.

The composition may be applied to leaf surfaces, stems, fruits, and other portions of plants intended for consumption by animals including humans, either for fresh consumption or consumption following cooking or other preparation. The composition may be applied at various stages including while the plant is still in the ground; post-harvest; and prior to, during, or after shipping. Application of the composition may reduce post-harvest infection and contamination by plant, animal, and human pathogens.

The composition may be applied once or in repeated applications. Applications may be repeated any number of times daily, weekly, monthly, or annually. Applications may be repeated about 1 to about 100 times per day, week, month, or year, as needed.

Applying a composition comprising an active compound may reduce virulence of bacteria associated with the plant.

Use in Animals Including Humans

The active compound or a pharmaceutical composition comprising the active compound may be administered to an animal subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. Additional modes of administration may include adding the active compound and/or a composition comprising the active compound to a food or beverage, including a water supply for an animal, to supply the active compound as part of the animal's diet.

The subject may include, without limitation, a eukaryote, an animal, a vertebrate animal, a bird, a reptile, an insect, a mammal, a rodent (e.g., a guinea pig, a hamster, a rat, a mouse), canine (e.g., a dog), feline (e.g., a cat), equine (e.g., a horse), ovine (e.g., a sheep), bovine (e.g., a cow), a primate such as a monkey (e.g. marmoset, baboon) or an ape (e.g. gorilla, chimpanzee, orangutan, gibbon), or a human.

While it is possible for the active compound to be administered alone, in some embodiments the active compound may be presented as a pharmaceutical composition (e.g., formulation) comprising at least one active compound, as defined above, together with one or more pharmaceutically-acceptable carriers, adjuvants, excipients, diluents, fillers, buffers, stabilizers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

Suitable carriers, excipients, etc. can be found in standard pharmaceutical texts, for example Remington's Pharmaceutical Sciences, 18th edition, Mack Publishing Company, Easton, Pa., 1990.

The formulations may conveniently be presented in unit dosage form and may be prepared by any method well known in the art of pharmacy. Such methods include the step of bringing into association the active compound with the carrier which constitutes one or more accessory ingredients. In general, the formulations may be prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g., transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents. In addition, a formulation may be added to a conventional bandage, e.g. to a gauze portion that contacts the wound, as an antimicrobial agent.

Formulations suitable for topical administration in the mouth include lozenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active compound.

Formulations suitable for administration by inhalation include those presented as an aerosol spray from a pressurized pack, with the use of a suitable propellant, such as dichlorodifluoromethane, trichlorofluoromethane, dichoro-tetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Suitable emulgents and emulsion stabilizers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilizers, bacteriostats in addition to the active compound, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 1 µg/ml, although other concentrations are possible and are encompassed within the invention. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

Further information regarding formulation of and treatment with pharmaceutical compositions are disclosed in U.S. Pat. No. 7,196,085, incorporated herein by reference.

The composition may be administered once, on a continuous basis (e.g. by an intravenous drip), or on a periodic/intermittent basis, including about once per hour, about once per two hours, about once per four hours, about once per eight hours, about once per twelve hours, about once per day, about once per two days, about once per three days, about twice per week, about once per week, and about once per month. The composition may be administered until a desired reduction of symptoms is achieved, which may be taken as an indication that bacterial virulence has been reduced.

Treatment of an animal subject with an active compound, or a composition comprising an active compound, may reduce virulence of bacteria associated with the animal subject.

Use on Surfaces

In one embodiment, the active compounds may be applied to surfaces to reduce the virulence of bacteria on the surfaces. The active compounds may be formulated in compositions suitable for application to surfaces, including as a gel, powder, liquid, concentrate, spray, or other suitable compositions known to those skilled in the art.

The composition may be applied to surfaces in residential, commercial, medical, industrial, agricultural, and other settings, to reduce virulence of bacteria associated with the surfaces. The composition may be applied to surfaces including without limitation those in bathrooms; kitchens and other food storing or preparation areas; medical facilities including operating rooms and hospital rooms; laundry facilities including laundered articles; restaurant facilities including kitchens and food storage areas; refrigerators and freezers; dishwashing facilities; factories; slaughterhouses; and grocery stores. The active compounds may be incorporated into or applied on packaging, e.g. for medical items or food products, to reduce virulence of bacteria associated therewith.

In one embodiment, the active compound and/or a composition comprising the active compound may be used to reduce or inhibit biofilm formation in medical, industrial, and other equipment, where a biofilm is defined as an aggregation of microorganisms on a solid substrate. The active compound may be applied to external and internal surfaces of the equipment, including pipes and tubing, to reduce or inhibit bacterial virulence and biofilm formation.

The composition may be sprayed, dusted, spread, rubbed, painted, mopped, soaked, or otherwise applied on surfaces. The composition may be applied once or may be repeated on a periodic basis. Periodic application may be about 1 to about 100 times per day, week, month, or year, as needed.

Applying a composition to a surface comprising an active compound may reduce virulence of bacteria on or associated with the surface.

The following non-limiting Examples are intended to be purely illustrative, and show specific experiments that were carried out in accordance with embodiments of the invention.

EXAMPLES

The following methods apply to Examples 1-3:
Bacterial Strains, Plasmids, Media and Chemicals The bacterial strains and plasmids used in this study are listed in Table 1. *E. coli* was grown in LB broth at 37° C. and *D. dadantii* was grown in minimal hrp-inducing medium (MM) at 28° C. Antibiotics (μg/ml) used were: ampicillin, 100; chloramphenicol, 50; kanamycin, 50; spectinomycin, 50. Primers used for Polymerase Chain Reaction (PCR) in this report are also listed in Table 1. Chinese cabbage purchased in a grocery store and African violet, without visible symptom from pathogen infection were used in this study.

TABLE 1

Strains, plasmids, and DNA primers used in this study.

| Strains, plasmids and primers | Characters or sequences (5' to 3')[a] | Reference or source |
|---|---|---|
| Strains | | |
| *E. coli* | | |
| E. coli DH5α | F⁻ φ80IacZΔ.15ΔlacZYA-argF)U169 deoR recA1 endA1 hsdR17 phoA supE44 thi-1 gyrA96 relA1 λ⁻ | Invitrogen, CA |
| E. coli TOP10 | F⁻ mcrA Δmrr-hsdRMS-mcrBC)φ80lacZΔM15 ΔlacX74 deoR recA1 araD139 Δ(ara-leu)7679 galU galK rpsL endA1 nupG | Invitrogen, CA |
| *D. dadantii* | | |
| Ech3937 | wild type, Saintpaulia (African violet) isolate | Hugouvieux-Cotte-Pattat, N. |
| Ech-Rif | Ech3937 rifampicin resistant random mutant | |
| Ech131 | ΔhrpL: : kan; Km$^R$ | Yang et al., 2008 |
| Ech137 | ΔgacA: : kan; Km$^R$ | Yang et al., 2004 |
| Ech138 | ΔiaaM: : kan; Km$^R$ | Yang et al., 2008 |
| WPP96 | ΔhrpL$_{(Δ1-185\ aa)}$: :, aadA. Sp$^R$/Sm$^R$ | Yang et al., 2007 |
| WPP90 | hrpS: : cat; Cm$^R$ | Yap et al., 2005 |
| WPP67 | hrpX: : aadA; Sp$^R$/Sm$^R$ | Yap et al., 2005 |
| WPP92 | hrpY: : kan; Km$^R$ | Yap et al., 2005 |
| Ech3937 (pAT) | Ech3937 containing pPROBE-AT | Yap et al., 2005 |
| Ech3937 (pdspE) | Ech3937 containing pdspE; Ap$^R$ | Peng et al., 2006 |
| Ech131 (pdspE) | ΔhrpL: : kan containing pdspE; Ap$^R$ Km$^R$ | Yang et al., 2004 |
| Ech3937 (phrpA) | Ech3937 containing phrpA; Ap$^R$ | Peng et al., 2006 |
| WPP96 (phrpA) | WPP96 containing phrpA; Ap$^R$ Sp$^R$ | This work |
| Ech3937 (phrpN) | Ech3937 containing phrpN; Ap$^R$ | This work |
| WPP96 (phrpN) | WPP96 containing phrpN; Ap$^R$ Sp$^R$ | Yang et al., 2007 |
| Ech3937 (phrpL) | Ech3937 containing phrpL; Ap$^R$ | Yang et al., 2007 |
| WPP96 (phrpL) | WPP96 containing phrpL; Ap$^R$ Sp$^R$ | Yang et al., 2007 |
| Ech3937 (phrpS) | Ech3937 containing phrpS; Ap$^R$ | Yang et al., 2007 |
| WPP96 (phrpS) | WPP96 containing phrpS; Ap$^R$ Sp$^R$ | This work |
| Ech3937 (pmrp) | Ech3937 containing pmrp; Ap$^R$ | This work |
| Rch3937 (pmrp) | Ech-Rif containing phrpA; Ap$^R$ | Peng et al., 2006 |
| Ech-Rif (phrpA) | Ech137 containing phrpA; Ap$^R$ Km$^R$ | Yang et al., 2008 |
| Ech137 (phrpA) | Ech3937 containing phrpN; Ap$^R$ | Yang et al., 2008 |
| Ech3937 (phrpN) | Ech138 containing phrpN; Ap$^R$ Km$^R$ | Yang et al., 2007 |
| Ech138 (phrpN) | WPP90 containing phrpN; Ap$^R$ Sp$^R$ | Yang et al., 2007 |
| WPP90 (phrpN) | WPP67 containing phrpN; Ap$^R$ Sp$^R$ | This work |
| WPP67 (phrpN) | WPP92 containing phrpN; Ap$^R$ Sp$^R$ | This work |
| WPP92 (phrpN) | | This work |
| Plasmids | | |
| pPROBE-AT | Promoter-probe vector, Ap$^R$ | Miller et al., 1997, 2000 |
| pCR2.1-TOPO | PCR cloning vector, AP$^R$ Km$^R$ | Invitrogen, CA |
| pdspE | pProbe-AT derivative with PCR fragment containing dspE promoter region, AP$^R$ | Yang et al., 2004 |
| phrpA | pProbe-AT derivative with PCR fragment containing 412-by hrpA promoter region, AP$^R$ | This work |

TABLE 1-continued

Strains, plasmids, and DNA primers used in this study.

| Strains, plasmids and primers | Characters or sequences (5' to 3')[a] | Reference or source |
|---|---|---|
| phrpN | pProbe-AT derivative with PCR fragment containing hrpN promoter region, Ap[R] | Yang et al., 2007 |
| phrpL | pProbe-AT derivative with PCR fragment containing hrpL promoter region, Ap[R] | Yang et al., 2007 |
| phrpS | pProbe-AT derivative with PCR fragment containing 709-by hrpS promoter region, AP[R] | This work |
| Primers | | |
| phrpA_F | GTGCCGATAGCCAGTGAT (SEQ ID NO: 1) | This work |
| phrpA_R | TGCTGCTGCGTTAGAAAG (SEQ ID NO: 2) | This work |
| phrpS_F | CAGATTGTATTTGCGGATTG (SEQ ID NO: 3) | This work |
| phrpS_R | CGGATTCATTGCTATTCCTTAT (SEQ ID NO: 4) | This work |
| rplU_RTF | GCGGCAAAATCAAGGCTGAAGTCG (SEQ ID NO: 5) | Yang et al., 2007 |
| rplU_RTR | CGGTGGCCAGCCTGCTTACGGTAG (SEQ ID NO: 6) | Yang et al., 2007 |
| hrpY_RTF | CGGCGACGGCGTAATGAA (SEQ ID NO: 7) | This work |
| hrpY_RTR | TTTCGGCGATGGCATTGACC (SEQ ID NO: 8) | This work |
| hrpS_RTF | TGGAAGGCGAAACCGGCACC (SEQ ID NO: 9) | This work |
| hrpS_RTR | GCACGGCGGCGCAGTTCAC (SEQ ID NO: 10) | This work |
| hrpL_RTF | GATGATGCTGCTGGATGCCGATGT (SEQ ID NO: 11) | Yang et al., 2007 |
| hrpL_RTR | TGCATCAACAGCCTGGCGGAGATA (SEQ ID NO: 12) | Yang et al., 2007 |
| hrpA_RTF | CAGCAATGGCAGGCATGCAG (SEQ ID NO: 13) | Yang et al., 2007 |
| hrpA_RTR | CTGGCCGTCGGTGATTGAGC (SEQ ID NO: 14) | Yang et al., 2007 |
| dspE_RTF | GATGGCGGAGCTGAAATCGTTC (SEQ ID NO: 15) | Yang et al., 2007 |
| dspE_RTR | CCTTGCCGGACCGCTTATCATT (SEQ ID NO: 16) | Yang et al., 2007 |
| rsmB_RTF | AGAGGGATCGCCAGCAAGGATTGT (SEQ ID NO: 17) | This work |
| rsmB_RTR | CGTTTGCAGCAGTCCCGCTACC (SEQ ID NO: 18) | This work |

[a]Ap[R], ampicillin resistance; Cm[R], chloramphenicol resistance; Km[R], kanamycin resistance; Sp[R], spectinomycin resistance.
Hugouvieux-Cotte-Pattat, N., Condemine, G., Nasser, W., and Reverchon, S. (1996) Regulation of pectinolysis in *Erwinia chrysanthemi*. Annu Rev Microbiol 50: 213-257.
Miller, W.G., Leveau, J.H.J., and Lindow, S.E. (2000) Improved gfp and inaZ broad-host-range promoter-probe vectors. Mol Plant-Microbe Interact 13: 1243-1250.
Miller, W.G., and Lindow, S.E. (1997) An improved GFP cloning cassette designed for prokaryotic transcriptional fusions. Gene 191: 149-153.
Peng, Q., Yang, S., Charkowski, A. O., Yap, M. N., Steeber, D. A., Keen, N. T., and Yang, C. H. (2006) Population behavior analysis of dspE and pelD regulation in *Erwinia chrysanthemi* 3937. Mol Plant-Microbe Interact 19: 451-457.
Yang, S., Q. Peng, Q. Zhang, X. Yi, C. J. Choi, R. M. Reedy, A. O. Charkowski, and C.-H. Yang. 2008. Dynamic regulation of GacA in type III secretion system, pectinase gene expression, pellicle formation, and pathogenicity of *Dickeya dadantii*. Mol. Plant-Microbe Interact. 21: 133-142.
Yang, S., Zhang, Q., Guo, J., Charkowski, A. O., Glick, B. R., Ibekwe, A. M. et al. (2007) Global effect of Indole-3-acetic acid (IAA) biosynthesis on multiple virulence factors of *Erwinia chrysanthemi* 3937. Appl Environ Microbiol 73: 1079-1088.
Yang, S., Perna, N. T., Cooksey, D. A., Okinaka, Y., Lindow, S. E., Ibekwe, A. M. et al. (2004) Genome-wide identification of plant-upregulated genes of *Erwinia chrysanthemi* 3937 using a GFP-based IVET leaf array. Mol Plant-Microbe Interact 17: 999-1008.
Yap, M. N., Yang, C. H., Barak, J. D., Jahn, C. E., and Charkowski, A. O. (2005) The *Erwinia chrysanthemi* type III secretion system is required for multicellular behavior. J Bacteriol 187: 639-648.

FACS Analysis

FACS analysis of promoter activity of dspE, hrpA, hrpL, hrpN, and hrpS was carried out as described (Peng et al., 2006). Briefly, the wild-type Ech3937 and the mutant strains carrying the promoter reporter plasmid were grown on LB broth at 28° C. overnight and transferred to appropriate media. For FACS analysis, samples were collected by centrifugation, washed with 1× phosphate buffer saline (PBS) at 13,000 rpm for 1 min, and re-suspended in 1×PBS to ca $10^6$ CFU/ml prior to being run in a FACS Calibur flow cytometer (BD Biosciences, CA). Three replicates were performed for each treatment.

qRT-PCR Analysis

Bacterial strains were grown in MM. Total RNA from the bacterial cells was isolated by using the TRI reagent method (Sigma, Mo.) and treated with Turbo DNA-free DNase kits (Ambion, Tex.) as described (Peng et al., 2006). An iScript cDNA Synthesis Kit (Bio-Rad, CA) was used to synthesize cDNA from 0.5 μg of treated total RNA. The Real Master Mix (Eppendorf, Westbury, N.Y.) was used for qRT-PCR reaction to quantify the cDNA level of target genes in different samples. The rplU was used as the endogenous control for data analysis. qRT-PCR data were analyzed using Relative Expression Software Tool as described (Pfaffl, M. W., Horgan, G. W., and Dempfle, L. (2002) Relative expression software tool (REST) for group-wise comparison and statistical analysis of relative expression results in real-time PCR. *Nucleic Acids Res* 30:e36.).

Example 1

T3SS Gene Expression Induced by Plant Phenolic Compounds

Screening of plant up-regulated genes in Ech3937 has demonstrated that dspE and hrpA were expressed in planta. In this study, the expression of dspE of Ech3937 was further compared in bacterial cells grown in a nutrient rich LB medium, a nutrient-limited medium (MM), and the MM supplemented with Chinese cabbage juice (10% V/V). For this purpose, a GFP reporter plasmid pdspE (pProbe-AT derivative with PCR fragment containing dspE promoter region) was used and cells cultured under different conditions were compared by flow cytometry. A higher total GFP intensity was observed in Ech3937 (pdspE) (Ech3937 cells carrying plasmid pdspE) grown in MM compared with the bacterial cells grown in LB (Table 2). The expression of dspE was further induced in MM supplemented with Chinese cabbage juice in comparison with the bacterial cells grown in MM alone. In addition, low promoter activities of dspE were observed in hrpL mutant Ech131 carrying pdspE grown in MM and MM supplemented with Chinese cabbage (Table 2), suggesting that HrpL is essential for the expression of dspE under inducing conditions.

TABLE 2

The expression of dspE of *Dickeya dadantii* 3937 (Ech3937) and the hrpL mutant Ech131 grown in LB, MM, and MM with Chinese cabbage juice (10% V/V) (MMJ).

| Gene Promoter[a] | LB | MM | MMJ |
|---|---|---|---|
| Ech3937 (pdspE)[b] | 3.2 ± 0.2 | 45 ± 1 | 161 ± 4 |
| Ech131 (pdspE) | 2.1 ± 0.2 | 2.1 ± 0.7 | 1.3 ± 0 |
| Ech3937 (pProbe-AT) | 1.9 ± 0.2 | 1.4 ± 0 | 1.2 ± 0 |

[a]The dspE promoter activities in the wild-type Ech3937 and hrpL mutant Ech131 were compared after 12 h of culture in LB, MM, and MM supplemented with plant juice. GFP intensity was determined on gated populations of bacterial cells by flow cytometry. The fluorescence intensities were an average GFP fluorescence intensity of total bacterial cells.
[b]Values (Mean Fluorescence Intensity) are representative of two experiments. Three replicates were used in this experiment. The values are the average with the standard deviation.

Figure 2A:
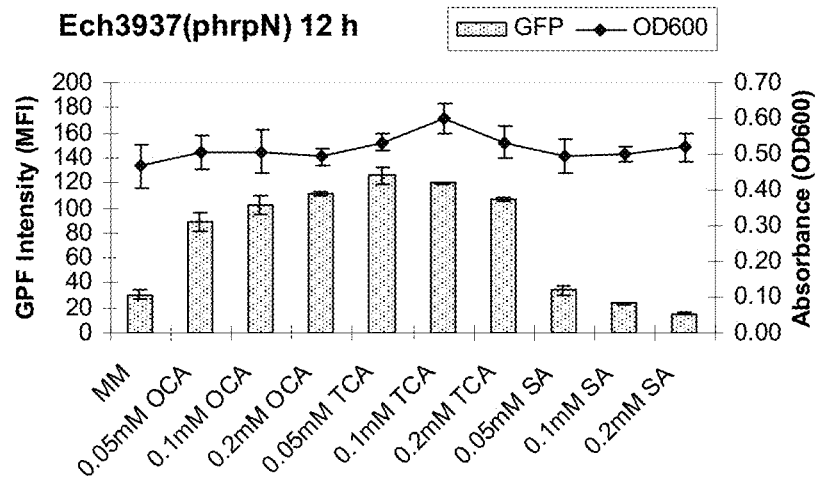
FIGS. 2A and 2B show the promoter activities of hrpN in *Dickeya dadantii* 3937 (Ech3937) using FACS analysis at 12 h (FIG. 2A) and 24 h (FIG. 2B).
Figure 2B:
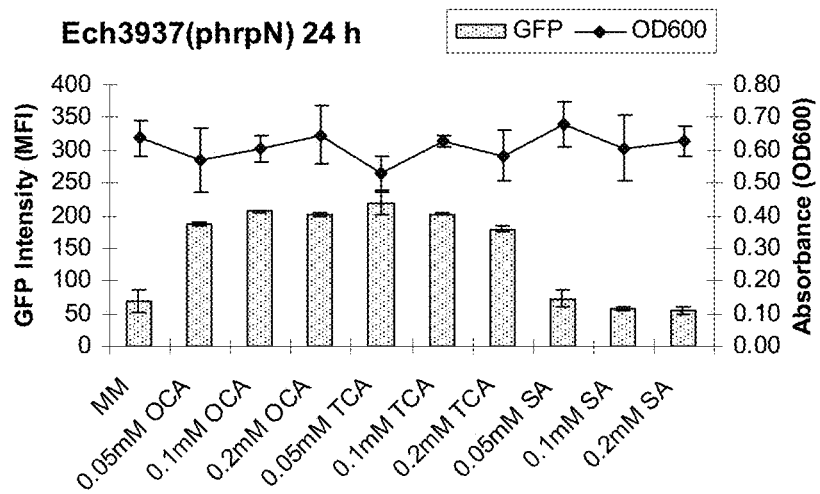

Plant juice induced the expression of T3SS genes of Ech3937, suggesting the existence of compounds in plant tissues that activate the T3SS regulon. Phenolic compounds constitute an important class of organic substances produced by plants. The phenolic compound SA is a signaling molecule that plays a role in host defenses. OCA and TCA are the biosynthetic precursors of SA and are also reported to induce the expression of defense-related genes in plants. OCA, TCA, and SA were examined to elucidate their effects on the expression of T3SS genes. The expression of the T3SS gene hrpN was examined in MM and MM supplemented with OCA, TCA, and SA, at concentrations of 0.05, 0.1, and 0.2 mM, respectively. FIGS. 2A and 2B show the promoter activities of hrpN in *Dickeya dadantii* 3937 (Ech3937) grown in MM and MM supplemented with 0.05, 0.1, and 0.2 mM OCA, TCA, and SA at 12 h (FIG. 2A) and 24 h (FIG. 2B) post-inoculation. GFP intensity was determined on gated populations of bacterial cells by flow cytometry and analyzed with the Cell Quest software (BD Biosciences, San Jose, Calif.). The growth of Ech3937 in MM supplemented with different concentrations of OCA, TCA and SA was recorded. Compared with MM alone, the average GFP fluorescence intensity of bacterial cells of Ech3937 (phrpN) was increased approximately 4-fold when 0.05 mM of OCA and TCA were added to the medium (FIGS. 2A, 2B). The addition of SA did not result in increased GFP fluorescence intensity of Ech3937 (FIGS. 2A, 2B). No reduction of bacterial growth was observed when OCA, TCA, and SA were added into the MM (FIGS. 2A, 2B).

The concentration of the phenolic compound t-cinnamic acid (TCA) in healthy potato leaves is approximately 0.5 µM and levels in the leaves can rise to approximately 10 uM after exposure to a cell-free culture filtrate (CF) of E. c. carotovora. To investigate whether the level of the phenolic compounds in plants is able to induce the expression of T3SS gene, the expression of hrpN was examined using concentrations of TCA comparable to levels found in plants. Ech3937 (phrpN) was grown in MM supplemented with 0.2, 0.5, 5, and 10 µM of TCA, respectively. Compared with Ech3937 (phrpN) in MM alone, a 1.5- to 1.8-fold increase of GFP intensity was observed in the bacterial cells grown in MM supplemented with 0.2 and 0.5 µM TCA (Table 3). Compared with Ech3937 (phrpN) in MM, a 3- to 3.5-fold higher GFP intensity was observed in the bacterial cells grown in MM supplemented with 5 and 10 µM of TCA (Table 2).

TABLE 3

The expression of hrpN of *Dickeya dadantii* 3937 (Ech3937) in MM and MM supplemented with different amount of TCA and SA respectively.

| | GFP Intensity of Ech3937 (phrpN)[b] | |
|---|---|---|
| | 12 h | 24 h |
| MM[a] | 41.6 ± 3.6 | 91.3 ± 11 |
| TCA[a] | | |
| 0.2 µM | 65.1 ± 6.8 | 163 ± 25 |
| 0.5 µM | 73.4 ± 4.2 | 158 ± 20 |
| 5 µM | 134 ± 5.6 | 266 ± 14 |
| 10 µM | 147 ± 18 | 284 ± 12 |
| SA[a] | | |
| 0.2 µM | 53.7 ± 4.0 | 105 ± 28 |
| 0.5 µM | 49.5 ± 5.9 | 99.5 ± 18 |
| 5 µM | 49.9 ± 2.9 | 97.7 ± 9.0 |
| 10 µM | 52.0 ± 2.3 | 104 ± 3.1 |

[a]Minimal medium (MM) alone and MM supplemented with different concentrations of t-cinnamic acid (TCA) or salicylic acid (SA).
[b]The promoter activities of hrpN were measured at 12 and 24 h of growing in the media. GFP intensity was determined on gated populations of bacterial cells by flow cytometry. The fluorescence intensities were an average GFP fluorescence intensity of total bacterial cells. Three replicates were used in this experiment. The value (Mean Fluorescence Intensity) is present as the average of three replicates with standard deviation.

Figure 3:
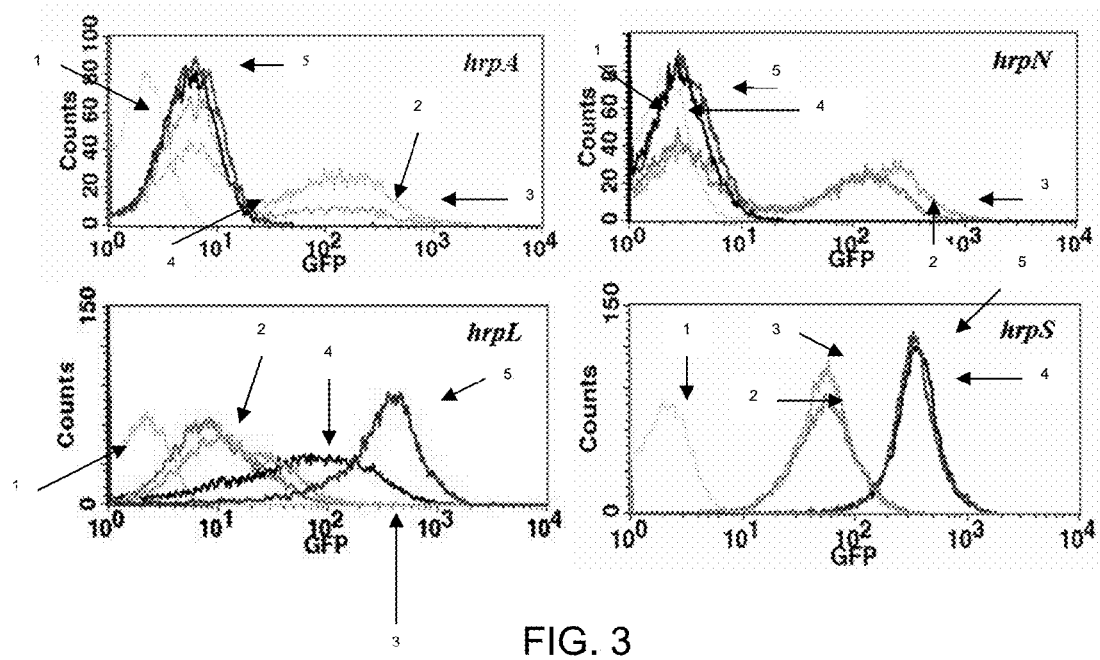
FIG. 3 shows the promoter activities of hrpA, hrpN, hrpL, and hrpS in *Dickeya dadantii* 3937 (Ech3937) and hrpL mutant WPP96 using FACS analysis.

Since OCA and TCA induced the expression of hrpN, the effect of these two phenolic compounds on the expression of hrpA, hrpL, and hrpS was investigated further. FIG. 3 shows the promoter activities of hrpA, hrpN, hrpL, and hrpS in *Dickeya dadantii* 3937 (Ech3937) and hrpL mutant WPP96 grown in MM and MM supplemented with 0.1 mM OCA 12 h post-grown. GFP intensity was determined on gated populations of bacterial cells by flow cytometry and analyzed with the Cell Quest software (BD Biosciences, San Jose, Calif.). The lines labeled "1" stand for the GFP expression control base level of the Ech3937 containing pPROBE-AT vector; lines labeled "2" stand for the promoter activity of hrpS, hrpL, hrpA and hrpN in Ech3937 in MM; lines labeled "3" stand for the promoter activity of Ech3937 in MM supplemented with 0.1 mM OCA; lines labeled "4" stand for the promoter activity of hrpL mutant WPP96 in MM; lines labeled "5" stand for the promoter activity of hrpL mutant WPP96 in MM supplemented with 0.1 mM OCA. Values are representative of at least two experiments. Three biological replicates were used in this experiment, which had similar results, and one replicate was used for the overlay as displayed. Compared with MM alone, the average GFP fluorescence intensity of bacterial cells of Ech3937 (phrpA) was doubled when 0.1 mM of OCA and TCA were added to the medium (Table 4; FIG. 3). Compared with MM alone, a slightly higher promoter activity of hrpL was observed in Ech3937 (hrpL) grown in MM supplemented with OCA and TCA, respectively. Compared with MM alone, a slightly lower GFP intensity of Ech3937 (phrpS) was observed when the bacterial cells were grown in MM supplemented with OCA and TCA (Table 4; FIG. 3). The mrp, whose protein product has an ATPase conserved domain (2e-06), was used as a reference gene in this study. A slightly higher mrp expression was observed in Ech3937 (pmrp) when the bacterial cells were grown in MM and MM supplemented with 0.1 mM OCA and TCA, respectively (Table 4).

TABLE 4

The expression of hrpA, hrpN, hrpL, hrpS, and mrp of *Dickeya dadantii* 3937 (Ech3937) and hrpL mutant WPP96 in MM, MM supplemented with 0.1 mM OCA (MMOCA), and MM supplemented with 0.1 mM TCA (MMTCA).

| Gene Promoter[a] | MM | MMOCA | MMTCA |
|---|---|---|---|
| Ech3937 (phrpA)[b] | 41 ± 3 | 82 ± 1 | 78 ± 0 |
| WPP96 (phrpA) | 6.0 ± 0 | 6.5 ± 0.2 | 6.2 ± 0.6 |
| Ech3937 (phrpN) | 43 ± 4 | 94 ± 3 | 103 ± 1 |
| WPP96 (phrpN) | 3.1 ± 0.1 | 3.3 ± 0.1 | 3.3 ± 0 |
| Ech3937 (phrpL) | 14 ± 1 | 19 ± 0 | 19 ± 1 |
| WPP96 (phrpL) | 103 ± 2 | 313 ± 29 | 331 ± 27 |
| Ech3937 (phrpS) | 63 ± 2 | 56 ± 1 | 54 ± 2 |
| WPP96 (phrpS) | 320 ± 60 | 350 ± 17 | 360 ± 16 |

TABLE 4-continued

The expression of hrpA, hrpN, hrpL, hrpS, and mrp of *Dickeya dadantii* 3937 (Ech3937) and hrpL mutant WPP96 in MM, MM supplemented with 0.1 mM OCA (MMOCA), and MM supplemented with 0.1 mM TCA (MMTCA).

| Gene Promoter[a] | MM | MMOCA | MMTCA |
|---|---|---|---|
| Ech3937 (pmrp) | 93.5 ± 1.4 | 97.7 ± 1.6 | 105 ± 0.3 |
| Ech3937 (pPROBE-AT) | 1.9 ± 0 | 2.0 ± 0 | 1.9 ± 0 |

[a]The promoter activities were compared at 12 h of growing in the media. GFP intensity was determined on gated populations of bacterial cells by flow cytometry. The fluorescence intensities were an average GFP fluorescence intensity of total bacterial cells.
[b]Values (Mean Fluorescence Intensity) are representative of three experiments. Three replicates were used in this experiment. The value is present as the average of three replicates with standard deviation.

Figure 4:
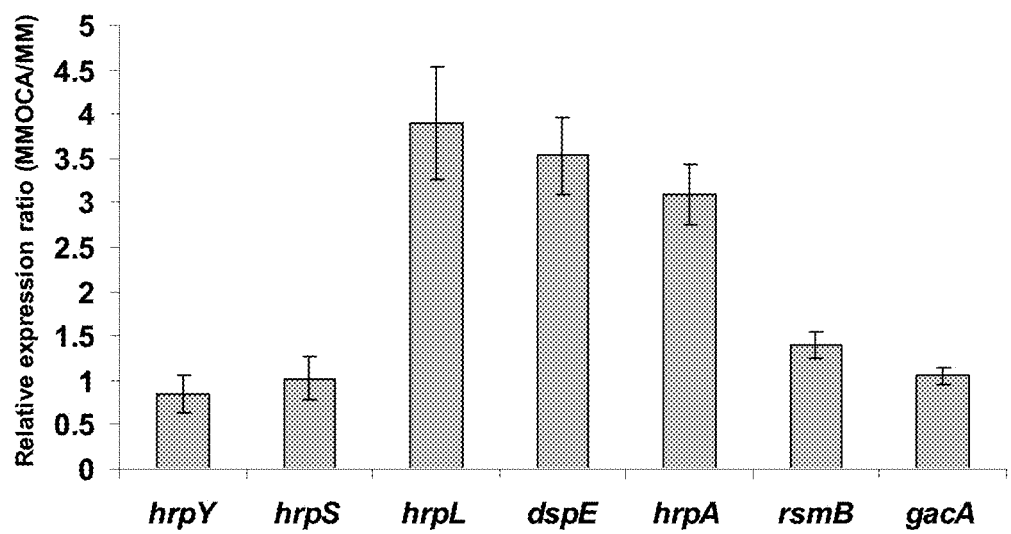
FIG. 4 shows the relative mRNA level of hrpY, hrpS, hrpL, dspE, hrpA, rsmB, and gacA of *Dickeya dadantii* 3937 (Ech3937) using quantitative RT-PCR (qRT-PCR).

To confirm FACS results showing T3SS induction by plant phenolics, the relative mRNA level of hrpY, hrpS, hrpL, dspE, and hrpA of Ech3937 grown in MM and MM supplemented with OCA was examined by qRT-PCR. Compared with MM alone, a significantly higher amount of dspE and hrpA mRNA was observed in Ech3937 supplemented with OCA (FIG. 4). Although only a slight increase of hrpL promoter activity was observed in Ech3937 (phrpL) grown in MM supplemented with OCA (Table 4), Ech3937 cultures with the supplementation of 0.1 mM OCA produced about 3-fold more hrpL mRNAs than those grown in MM alone at 12 h of growth (P<0.01) (FIG. 4). Three replicates were used in this experiment. The p-value was calculated using Relative Expression Software Tool as described by Pfaffl et al. (2002). No significant difference was found between Ech3937 cells grown in MM and MM supplemented with OCA for gene hrpY, hrpS, and gacA with the p>0.5, but gene expression of hrpL, dspE, hrpA, and rsmB are significantly different between MM and MM supplemented with 0.1 mM OCA with p<0.003 (FIG. 4).

Example 2

Regulators Responsible for the OCA and TCA Induction

The expression of T3SS genes dspE, hrpA, and hrpN was reduced in an iaaM mutant Ech138; iaaM encodes an enzyme in the pathway for indole-3-acetic acid (IAA) biosynthesis. To investigate whether IAA biosynthesis is involved in the OCA induction of T3SS, the expression of hrpN in the wild-type Ech3937 and Ech138 was compared with the addition of OCA. As expected, the expression of hrpN was reduced in an iaaM mutant background. However, a similar induction ratio of hrpN by OCA was observed in wild-type Ech3937 and Ech138 at each time point of bacterial growth (Table 5). These results suggest that OCA does not activate T3SS expression through IAA biosynthesis.

TABLE 5

The expression of hrpN of *Dickeya dadantii* 3937 (Ech3937) and iaaM mutant Ech138 in MM and MM supplemented with 0.1 mM OCA (MMOCA), and the expression of hrpA of Ech-Rif and gacA mutant Ech137 in MM, MM supplemented with 0.1 mM OCA (MMOCA).

| | 6 h | | 12 h | | 24 h | |
|---|---|---|---|---|---|---|
| Gene Promoter[a] | MM | MMOCA | MM | MMOCA | MM | MMOCA |
| Ech3937 (phrpN)[b] | 19 ± 2 | 31 ± 3 | 30 ± 3 | 91 ± 8 | 33 ± 2 | 78 ± 8 |
| Ech138 (phrpN) | 5.6 ± 0.7 | 9.1 ± 1.6 | 11 ± 1 | 33 ± 5 | 17 ± 1 | 39 ± 5 |
| Ech-Rif (phrpA) | 13 ± 0 | 18 ± 0 | 22 ± 0 | 51 ± 2 | 16 ± 1 | 49 ± 1 |
| Ech137 (phrpA) | 4.7 ± 0 | 4.9 ± 0.1 | 5.5 ± 0 | 5.9 ± 0.1 | 7.6 ± 0 | 8.3 ± 0 |
| Ech3937 (pPROBE-AT) | 1.9 ± 0 | 2.0 ± 0 | 1.9 ± 0 | 2.0 ± 0 | 1.8 ± 0 | 1.9 ± 0 |

[a]The promoter activities were compared at 6, 12, and 24 h of bacterial growth. GFP intensity was determined on gated populations of bacterial cells by flow cytometry. The fluorescence intensities were an average GFP fluorescence intensity of total bacterial cells.
[b]Values (Mean Fluorescence Intensity) are a representative of two experiments. Three replicates were used in this experiment. The value is present as the average of three replicates with standard deviation (SD).

Ech3937 gacA plays a role in regulating the expression of T3SS genes by a post-transcriptional regulation of hrpL through the Gac-Rsm regulatory pathway (Yang, S., Q. Peng, Q. Zhang, X. Yi, C. J. Choi, R. M. Reedy, A. O. Charkowski, and C.-H. Yang. 2008. Dynamic regulation of GacA in type III secretion system, pectinase gene expression, pellicle formation, and pathogenicity of *Dickeya dadantii*. *Mol. Plant-Microbe Interact*. 21:133-142.). To investigate whether OCA affects T3SS gene expression through the Gac-Rsm regulatory pathway, the expression of hrpA was compared in wild-type Ech-Rif (phrpA) and gacA mutant Ech137 (phrpA) grown in MM and MM supplemented with OCA, respectively. Compared with Ech-Rif (phrpA) grown in MM alone, a higher GFP intensity was observed in bacterial cells grown in MM supplemented with OCA. However, similar GFP intensity was observed in Ech137 (phrpA) cells grown in MM and MM supplemented with OCA, suggesting that OCA may induce the T3SS gene expression through Gac-Rsm pathway (Table 5). To further confirm that the influence of OCA on T3SS is through the Gac-Rsm system, the expression of gacA and rsmB was examined by qRT-PCR. The results showed that, compared with Ech3937 in MM alone (normalized to 1), a significantly higher rsmB mRNA (relative expression ratio 1.4, P=0.003) was observed in the bacterium grown in MM supplemented with OCA (FIG. 4). The effect of TCA on the mRNA level of rsmB of Ech3937 was also examined. Compared with Ech3937 grown in MM alone (normalized to 1), a significantly higher amount of rsmB mRNA was observed in Ech3937 grown in TCA (1.58, P=0.05). However, no significant difference in the level of gacA mRNA was observed in Ech3937 grown in MM and MM supplemented with OCA (FIG. 4).

Figure 5:
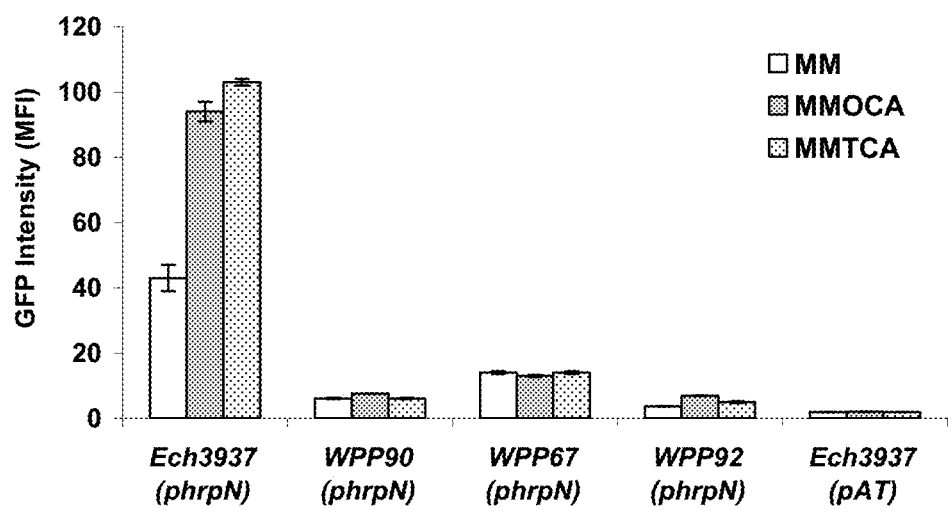
FIG. 5 shows the promoter activity of hrpN of *Dickeya dadantii* 3937 (Ech3937), hrpS mutant WPP90, hrpX mutant WPP67, hrpY mutant WPP92, and Ech3937 (pAT) using FACS analysis.

HrpL appears to be involved in the induction of T3SS gene expression by the phenolic acids OCA and TCA, as the addition of OCA or TCA did not induce the T3SS gene expression (hrpA and hrpN) in the hrpL mutant background (Table 4). Given that T3SS genes are regulated through HrpX/Y-HrpS-HrpL, experiments were performed to investigate whether OCA and TCA were able to induce the expression of T3SS genes in the absence of hrpX, hrpY, and hrpS, respectively. The GFP intensity of the wild-type Ech3937 and hrpX, hrpY, and hrpS mutants carrying phrpN grown in MM and MM supplemented with OCA and TCA, respectively, was measured (FIG. 5). FIG. 5 shows levels of expression of hrpN of Dickeya dadantii 3937 (Ech3937), hrpS mutant WPP90, hrpX mutant WPP67, hrpY mutant WPP92 in MM, MM supplemented with 0.1 mM OCA (MMOCA), and MM supplemented with 0.1 mM TCA (MMTCA). Ech3937 (pAT) is the wild-type containing the pPROBE-AT vector. The promoter activities were compared at 12 h of growth in the media. GFP intensity was determined on gated populations of bacterial cells by flow cytometry. The fluorescence intensities were an average GFP fluorescence intensity of total bacterial cells. Values (Mean Fluorescence Intensity; MFI) are a representative of three experiments. Three replicates were used in this experiment. The value is present as the average of three replicates with standard deviation (SD). The results showed that OCA and TCA induced the expression of hrpN in Ech3937, but not in hrpX, hrpY, and hrpS mutants (FIG. 5).

Example 3

Auto-Regulation of T3SS Regulon

Compared with Ech3937, a higher GFP intensity was observed in the hrpL mutant WPP96 cells carrying phrpS and phrpL, suggesting that HrpL negatively regulated the expression of hrpL and its upstream hrpS (Table 4; FIG. 3). To further confirm the results of GFP-based FACS assays which showed auto-regulation of HrpL, the relative mRNA level of hrpS in Ech3937 and hrpL mutant Ech131 grown in MM was examined by qRT-PCR. Compared with Ech3937, a 4-fold higher level of hrpS mRNA was observed in Ech131 at 6 h of growth in MM (relative expression ratio 5.1, P=0.002). These results suggest that feedback inhibition of HrpL on hrpL itself and hrpS takes place in the bacterium. Similar GFP intensity was observed in Ech3937 and the hrpS mutant carrying phrpS, phrpX and phrpY, respectively, suggesting that HrpS did not regulate the expression of hrpS, hrpX and hrpY. Finally, similar GFP intensity was observed in Ech3937 and the hrpY mutant carrying phrpX and phrpY, respectively, suggesting that HrpY was unable to regulate the expression of hrpX and hrpY.

Examples 4-9

The following methods apply to Examples 4-9:
Bacterial Strains, Plasmids, and Media
The bacterial strains and plasmids used in this group of Examiners are listed in Table 6. Wild-type Ech-Rif, and its mutant strains were stored at −80° C. in 15% glycerol and grown in Luria-Bertani (LB) medium (Sambrook, J., and Russell, D. W. 2001. Molecular Cloning: A Laboratory Manual, 3rd ed. Cold Spring Harbor Laboratory, Cold Spring Harbor, N.Y., U.S.A.) and MM medium (Yang et al. 2007). Antibiotics were added to the media at the following concentrations: kanamycin, 50 µg/ml; rifampicin, 100 µg/ml; ampicillin, 100 µg/ml; and spectinomycin, 50 µg/ml. The gacA deletion mutant was constructed by a crossover PCR mutagenesis approach as described (Yang, C. H., Gavilanes-Ruiz, M., Okinaka, Y., Vedel, R., Berthuy, I., Boccara, M., Chen, J. W., Perna, N. T., and Keen, N. T. 2002. hrp genes of Erwinia chrysanthemi 3937 are important virulence factors. Mol. Plant-Microbe Interact. 15:472-480); the primers used were gacA A, 5' GCA CCC GAT TGC CTG TAC TTA 3' (SEQ ID NO:19); gacA_B, 5' GCA CCA GTT CAT GGT CAT CAA C 3' (SEQ ID NO:20); gacA_C, 5' CGG AGA CAT TGA TTA GTA GTG A 3' (SEQ ID NO:21); and gacA_D, ATT GGG MA CGG GCC GM GT (SEQ ID NO:22).
GFP Reporter Plasmid Construction
The GFP promoter region of dspE and pelD cloned into the reporter plasmid pPROBE-AT (Leveau, J. H., and Lindow, S. E. 2001. Predictive and interpretive simulation of green fluorescent protein expression in reporter bacteria. J. Bacteriol. 183:6752-6762) was constructed previously (Peng et al. 2006). The DNA fragments of promoter regions of hrpA, hrpN, hrpL, and pelL were PCR amplified from Ech3937 chromosomal DNA and ligated into the pCR2.1-TOPO TA cloning vector system (Invitrogen, Carlsbad, Calif., U.S.A.). The primer pair used for pelL promoter in this study is PpelL_F, 5'ATG CGG TAA TGC GGG GAT 3' (SEQ ID NO:23) and PpelL_R, 5'GGC CAG AAC TGA TGT ACT GT 3' (SEQ ID NO:24), which produces a 609-bp pelL promoter region sequence of Ech-Rif. The inserted DNA was further subcloned into the XbaI/SacI sites of the promoter-probe vector pPROBE-AT (Table 6). A plasmid pCLgacA containing a full-length gacA in plasmid pCL1920 also was constructed using the primer set gacAco_F, 5'GCC AAT GTT TCG GGT GTA G3' (SEQ ID NO:25) and gacAco_R, 5'CAT CGA TCT GCC GGA TAC TTT3' (SEQ ID NO:26).

The GFP reporter in combination with the FACS-based approach has been used to evaluate gene activity in several bacteria at the single-cell level. Because the gfp gene in the pPROBE-AT contains its own ribosome binding site, the stability of gfp mRNA should not be interfered with by RsmA when a promoter-containing DNA region of Ech3937 is cloned into the reporter vector.
FACS Investigation of Promoter Activity
The bacterial cells of Ech-Rif and Ech137 carrying GFP reporter plasmid constructs were washed three times with 1× phosphate-buffered saline (PBS) buffer (8.0 g of NaCl, 0.2 g of KCl, 1.44 g of $Na_2HPO_4$, and 0.24 g of $KH_2PO_4$ per liter, pH 7.2 to 7.4) and diluted to approximately 106 CFU/ml before analysis. Bacterial cells were identified based on forward and side light scatter properties and electronically gated for analysis. The promoter activity was determined by FACS (Becton Dickinson, San Jose, Calif., U.S.A.) and the flow cytometry results were analyzed using Cell Quest software (BD Biosciences, San Jose, Calif., U.S.A.).
Real-Time PCR Analysis
Wild-type Ech-Rif and the gacA mutant Ech137 were grown in MM with glucose as carbon source (Yang et al. 2007). Total RNA from the bacteria was isolated by using TRI reagent method (Sigma-Aldrich, St. Louis, Mo.) and treated with Turbo DNA-free DNase kits (Ambion, Austin, Tex., U.S.A.). An iScript cDNA Synthesis Kit (Bio-Rad, Hercules, Calif., U.S.A.) was used to synthesize cDNA from 0.5 µg of treated total RNA. The Real Master Mix (Eppendorf, Westbury, N.Y., U.S.A.) was used for real-time PCR reaction to quantify the cDNA level of hrpL, rsmA, rsmB, rsmC, and rplU in different samples. The rplU was used as the endogenous control for data analysis. The primer pairs used in this study were RplUsF, 5' GCG GCA AAA TCA AGG CTG AAG TCG 3' (SEQ ID NO:27) and RplUsR, 5' CGG TGG CCA GCC TGC TTA CGG TAG 3' (SEQ ID NO:28) for rplU; HrpLsF, 5' GAT GAT GCT GCT GGA TGC CGA TGT 3'

(SEQ ID NO:29) and HrpLsR, 5' TGC ATC AAC AGC CTG GCG GAG ATA 3' (SEQ ID NO:30) for hrpL; rsmAf, 5' TTT TGA CTC GTC GAG TTG GCG AAA 3' (SEQ ID NO:31) and rsmAr, 5' GCG CGT TAA CAC CGA TAC GAA CCT 3' (SEQ ID NO:32) for rsmA; rsmBf, 5' AGA GGG ATC GCC AGC AAG GAT TGT 3' (SEQ ID NO:33) and rsmBr, 5' CGT TTG CAG CAG TCC CGC TAC C 3' (SEQ ID NO:34) for rsmB; and rsmCf, 5' ACG AAG TGC TCC CGG TTA ATG TCC 3' (SEQ ID NO:35) and rsmCr, 5' ACG AGA GCG TAC TGA GCG GCT TTT 3' (SEQ ID NO:36) for rsmC. Reactions were run and data were collected by the Opticon 2 system (Bio-Rad). Real-time PCR data were analyzed using Relative Expression Software Tool as described (Pfaffl et al., 2002).

Pellicle Formation and Exoenzyme Production

For pellicle formation assay, bacterial strains were grown in SOBG broth at 28° C. as described (Yap et al. 2005). Due to the slow formation of pellicle in Ech137, 10-day-old pellicles from Ech-Rif and Ech137 were used for SEM observation. The samples of pellicle were fixed in 2% glutaraldehyde in PBS buffer (pH 7.0) for 2 h and post-fixed in 1% osmium tetroxide in the same buffer for 1 h. After dehydration in the graded series of ethanol, specimens were infiltrated with polyethylene glycol (PEG). Cross sections of the pellicles were cut using an ultramicrotome. Then, PEG was extracted from the blocks by soaking in several changes of warm ethanol. After critical-point drying, the specimen was mounted on a stub coated with Duco cement, sputter coated with gold, and examined with a Hitachi S-570 Scanning Electron Microscope.

Plate assays for activity of Pel, Cel, and Prt and the spectrophotomeric assay of Pel activity for Ech-Rif, Ech137, and the complemented strain Ech137 (pCLgacA) were carried out as described (Matsumoto, H., Muroi, H., Umehara, M., Yoshitake, Y., and Tsuyumu, S. 2003. Peh production, flagellum synthesis, and virulence reduced in *Erwinia carotovora* subsp. *carotovora* by mutation in a homologue of cytR. *Mol. Plant-Microbe Interact.* 16:389-397). Three biological replicates were performed for each treatment.

Virulence Assay, Growth Kinetics, and in Planta Pel Production

The local leaf maceration assay was carried out as described (Yang et al. 2004; Yang, C. H., Gavilanes-Ruiz, M., Okinaka, Y., Vedel, R., Berthuy, I., Boccara, M., Chen, J. W., Perna, N. T., and Keen, N. T. 2002. hrp genes of *Erwinia chrysanthemi* 3937 are important virulence factors. *Mol. Plant-Microbe Interact.* 15:472-480). Briefly, wild-type bacterial cells and gacA mutant Ech137 cells were syringe-infiltrated in the middle of each symmetric side of the same leaf with approximately 50 μl of a bacterial suspension at 106 CFU/ml. Phosphate buffer (50 mM, pH 7.4) was used to suspend the bacterial cells. Three replicate plants with a total of at least 12 leaves were inoculated. In the systemic invasion assay, the pathogenicity of the bacterium was evaluated as described (Franza, T., Sauvage, C., and Expert, D. 1999. Iron regulation and pathogenicity in *Erwinia chrysanthemi* 3937: Role of the fur repressor protein. *Mol. Plant-Microbe Interact.* 12:119-128), with minor modification. A volume of a 50 μl of the bacterial suspension with an optical density at 600 nm of 0.01 was inoculated into the front edge of the African violet leaf. For each bacterial strain, 12 plants were inoculated. Inoculated plants were kept in growth chambers at 28° C., 95% relative humidity, and a photoperiod of 16 h. Development of symptoms induced by bacterial strains in African violet plants was considered as systemic when at least one leaf and its petiole were macerated. Progression of the symptoms was scored daily for 12 days.

Growth kinetics in planta was carried out in African violet cv. Gauguin as described (Yang et al. 2002). Briefly, leaves were syringe infiltrated with approximately 50 μl of bacterial suspension at $10^6$ CFU/ml with a 1-ml syringe. Leaf discs (4 mm in diameter) around the maceration area were harvested at different intervals following infiltration and ground in 50 mM phosphate buffer (pH 7.4). The bacterial concentration, (CFU/cm2) was determined by plating serial dilutions of leaf extracts on LB agar plates. A spectrophotomeric assay was used to monitor the Pel production of Ech-Rif and Ech137 during the in planta growth. A 10-μi supernatant of the plant juice from African violet leaves inoculated with the bacteria was added into 990 μl of Pel reaction buffer and the Pel production was quantified using the spectrophotomeric assay (Matsumoto et al. 2003). Pel production was the ratio of the optical density at 230 nm unit to the log unit of the bacterial concentration (U/log [$CFU/cm^2$]). Three replicate plants with a total of six leaves per plant were used in each sampling time for the in planta Pel production and bacterial growth kinetics assays.

Example 4

GacA Affects Biofilm-Pellicle Formation

Figure 6A:
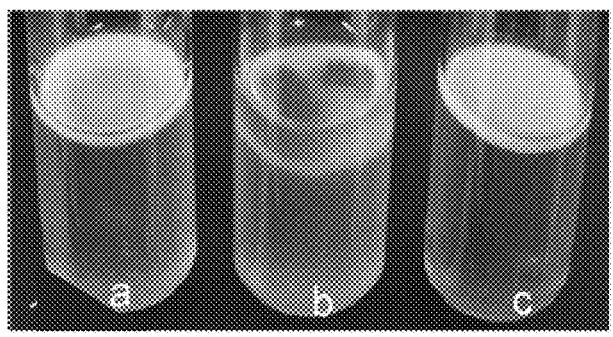
FIG. 6A shows biofilm and pellicle formation in SOBG broth.
Figure 6B:
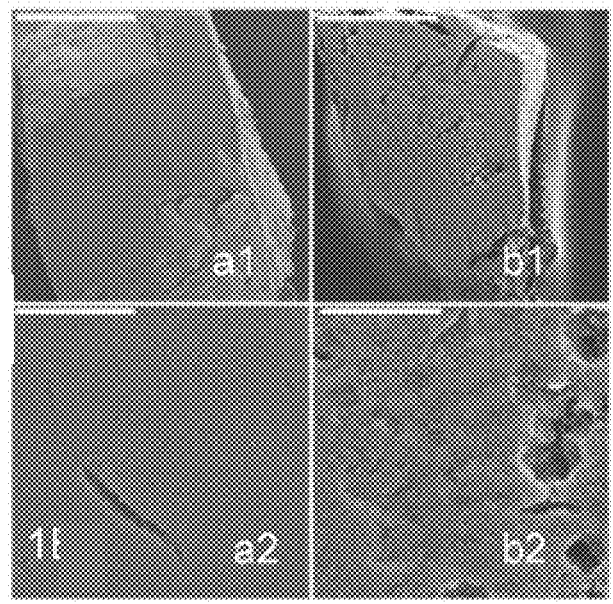
FIG. 6B shows cross sections of the pellicle observed with scanning electron microscopy at different magnifications.

Ech3937 is capable of forming a biofilm and pellicle in SOBG broth. A spontaneous rifampicin-resistant derivative of Ech3937, Ech-Rif, was used as a wild-type in this study (Table 6). A gacA deletion mutant Ech137 of Ech-Rif was constructed and confirmed by DNA sequencing analysis. The gacA gene of Ech137 was deleted with only 20 by of the gacA open reading frame remaining. No significant difference in growth between Ech-Rif and the gacA mutant Ech137 was observed in M9 minimal medium (MM). Ech-Rif formed biofilm-pellicle in SOBG broth grown for 2 days at 28° C. However, no visible biofilm-pellicle was observed in Ech137 until grown for 3 days in SOBG broth. This delayed biofilm-pellicle formation phenotype of the mutant could be restored nearly to the wild-type level when Ech137 was complemented with a low-copy-number plasmid pCLgacA (FIG. 6A). The pellicles of Ech-Rif and Ech137 were sectioned using an ultramicrotome and the interior textures of the pellicles of the bacteria were compared using a scanning electron microscope. A more compact texture in 10-day-old pellicles was observed in Ech-Rif in comparison with Ech137 (FIG. 6B). Pellicles of both Ech-Rif and Ech137 treated with cellulose disintegrated, suggesting that the major component, cellulose, was not altered in Ech137.

FIG. 6A shows biofilm and pellicle formation in SOBG broth (Yap et al. 2005). FIG. 6A(a) shows biofilm and pellicle formed in wild-type Ech-Rif in SOBG cultures grown for 3 days at 28° C. FIG. 6A(b) shows delayed biofilm and pellicle formation in Ech137, the gacA mutant in SOBG cultures grown for 3 days at 28° C. FIG. 6A(c) shows the gacA gene expressed on plasmid pCLgacA restored biofilm and pellicle formation to the gacA mutant Ech137 in SOBG cultures grown for 3 days at 28° C. FIG. 6B shows cross sections of the pellicle observed with scanning electron microscopy at different magnifications. FIG. 6B(a1) shows Ech-Rif; FIG. 6B(b1) shows Ech137; FIG. 6B(a2) shows Ech-Rif; and FIG. 6B(b2) shows Ech137. The size bars in the micrographs in FIG. 6B(a1) and FIG. 6B(b1) are 1 mm, while in FIG. 6B(a2) and FIG. 6B(b2) the size bars are 100 μm.

TABLE 6

Bacterial Strains and Plasmids.

| Strains, plasmids | Characteristics[a] | Reference or source |
|---|---|---|
| Strains | | |
| *Escherichia coli* S17-1 λ-pir | λ-pir Lysogen of S17-1 | V. de Lorenzo, Madrid |
| Ech3937 | Wild-type strain isolated from *Saintpaulia ionantha* | D. Expert, Paris |
| Ech-Rif | Ech3937 rifampicin resistant random mutant | This work |
| Ech137 | ΔgacA::Kan, Km$^R$, Ech-Rif derivative | This work |
| Ech-Rif (pDspE) | Ech3937-Rif containing plasmid pDspE | This work |
| Ech137(pDspE) | Ech137 containing plasmid pDspE | This work |
| Ech-Rif (pHrpA) | Ech3937-Rif containing plasmid pHrpA | This work |
| Ech137(pHrpA) | Ech137 containing plasmid pHrpA | This work |
| Ech-Rif (pHrpN) | Ech3937-Rif containing plasmid pHrpN | This work |
| Ech137(pHrpN) | Ech137 containing plasmid pHrpN | This work |
| Ech-Rif (pHrpL) | Ech3937-Rif containing plasmid pHrpL | This work |
| Ech137(pHrpL) | Ech137 containing plasmid pHrpL | This work |
| Ech-Rif (pPelD) | Ech3937-Rif containing plasmid pPelD | This work |
| Ech137(pPelD) | Ech137 containing plasmid pPelD | This work |
| Ech-Rif (pPelL) | Ech3937-Rif containing plasmid pPelL | This work |
| Ech137(pPelL) | Ech137 containing plasmid pPelL | This work |
| Ech137 (pCLgacA) | Ech137 containing pCLgacA | This work |
| Plasmids | | |
| pWM91 | Sucrose-based counter-selectable plasmid, Ap$^R$ | Metcalf et al. 1995 |
| pCR2.1-TOPO | PCR cloning vector, Ap$^R$, Km$^R$ | Invitrogen. Carlsbad, CA. U.S.A. |
| pPROBE-AT | GFP promoter-probe vector, Ap$^R$ | Miller et al. 2000 |
| pCL1920 | Low copy number plasmid | Lerner and Inouye 1990 |
| pDspE | pProbe-AT derivative with PCR fragment containing dspE promoter region, Ap$^R$ | Yang et al. 2004 |
| pHrpA | pProbe-AT derivative with PCR fragment containing 412-bp hrpA promoter region, Ap$^R$ | Unpublished data |
| pHrpN | pProbe-AT derivative with PCR fragment containing 396-bp hrpN promoter region, Ap$^R$ | Unpublished data |
| pHrpL | pProbe-AT derivative with PCR fragment containing hrpL promoter region, Ap$^R$ | Unpublished data |
| pPelD | pProbe-AT derivative with PCR fragment containing pelD promoter region, Ap$^R$ | Peng et al. 2006 |
| pPelL | pProbe-AT derivative with PCR fragment containing 609-bp pelL promoter region, Ap$^R$ | This work |
| pCLgacA | pCL1920 with a 1.548-bp PCR product containing full length of gacA, Sp$^R$ | This work |

[a]Ap$^R$, Km$^R$, Rif$^R$, and Sp$^R$, ampicillin, kanamycin, rifampicin, and spectinomycin resistance, respectively;
PCR, polymerase chain reaction; and
GFP, green fluorescent protein.
Metcalf, W. W., Jiang, W., Daniels, L. L., Kim, S. K., Haldimann, A., and Wanner, B. L. 1996. Conditionally replicative and conjugative plasmids carrying lacZ alpha for cloning, mutagenesis, and allele replacement in bacteria. *Plasmid* 35: 1-13.
Lerner C. G., and Inouye M. 1990. Low copy number plasmids for regulated low-level expression of cloned genes in *Escherichia coli* with blue/white insert screening capability. *Nucleic Acids* Res. 18: 4631.

Example 5

GacA Regulates Exoenzyme Production

Figure 7:
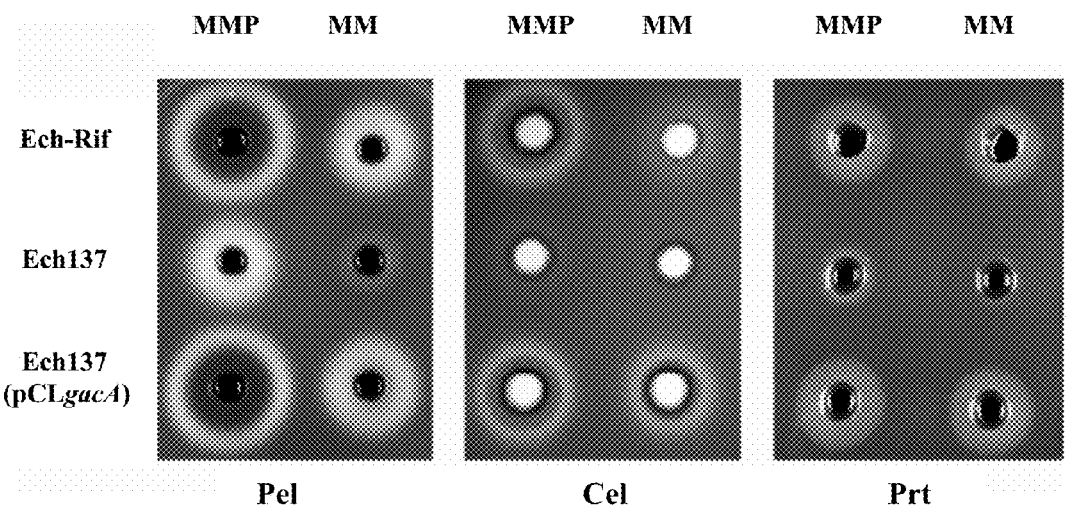
FIG. 7 shows pectate lyase (Pel), protease (Prt), and cellulase (Cel) production of wild-type Ech-Rif, gacA mutant Ech137, and gacA mutant complemented strain Ech137 (pCLgacA) examined by plate assays.

Production of exoenzymes, including pectate lyase (Pel), protease (Prt), and cellulase (Cel) in wild-type Ech-Rif, gacA mutant Ech137, and gacA mutant complemented strain Ech137 (pCLgacA) grown in minimal medium (MM) and MM supplemented with 1% polygalacturonate (MMP) at 36 h, was examined with semi-quantitative plate assays. Values are a representative of two experiments. Three replicates were used in this experiment. Compared with Ech-Rif, reduced Pel, Cel, and Prt production was observed in Ech137 grown in MM and MM supplemented with 1% polygalacturonate (PGA) (MMP) at 36 h (FIG. 7).

Figure 8:
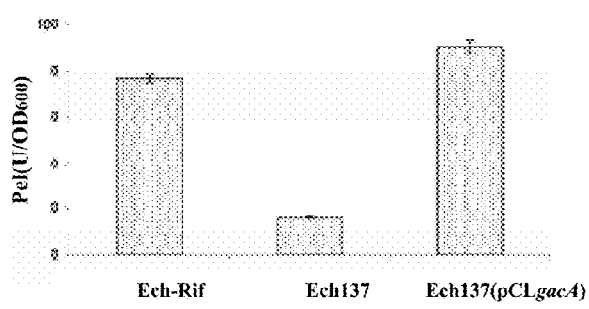
FIG. 8 shows spectrophotometric quantification of pectate lyase (Pel) activity for Ech-Rif, gacA mutant Ech137, and the complementary strain Ech137 (pCLgacA).

A spectrophotomeric assay was used to quantify Pel activity in the bacterial strains. FIG. 8 shows spectrophotometric quantification of pectate lyase (Pel) activity (U/optical density at 600 nm [OD600]) in Ech-Rif, gacA mutant Ech137, and the complementary strain Ech137 (pCLgacA) grown in minimal medium supplemented with 1% polygalacturonate at 36 h. Values are a representative of two experiments. Three replicates were used in this experiment; the value is present as average of three replicates and the standard deviation. Consistent with the results from the plate assay, lower Pel production by Ech137 was observed by the spectrophotomeric assay when the bacterial cells were grown at 36 h (late stationary phase) (FIG. 8). Compared with the Ech-Rif, a lower Pel production of Ech137 also was observed by the spectrophotomeric assay when the bacterial cells were grown at exponential phase (12 h) and beginning of stationary phase (24 h). The Pel, Cel, and Prt production of Ech137 was restored nearly to the wild-type bacterium level by introducing the plasmid pCLgacA containing wild-type gacA gene into the mutant (FIGS. 7 and 8).

Example 6

GacA Regulates the Expression of Pel and T3SS Genes

PelD and PelL of *D. dadantii* encode endo-Pels. PelD has higher activity on nonmethylated pectins and PelL prefers partially methylated pectins. The promoter regions of pelD and pelL, respectively, were cloned into pPROBE-AT to produce pPelD and pPelL (Table 6). The Ech-Rif and Ech137 cells carrying these GFP promoter plasmids were grown in MM-supplemented 1% PGA and the fluorescence intensity of the bacterial cells was measured with an FACS. The fluorescence intensity collected by FACS was analyzed in a four-decade log scale using CellQuest Pro software from Becton Dickinson, and the gene expression profiles were analyzed as i) total, the average GFP fluorescence intensity of total bacterial cells; ii) GFP+ mean, average GFP fluorescence intensity of GFP expressing bacterial cells; and iii) GFP+%, the percentage of GFP-expressing bacterial cells of the total bacterial cells.

Figure 9:
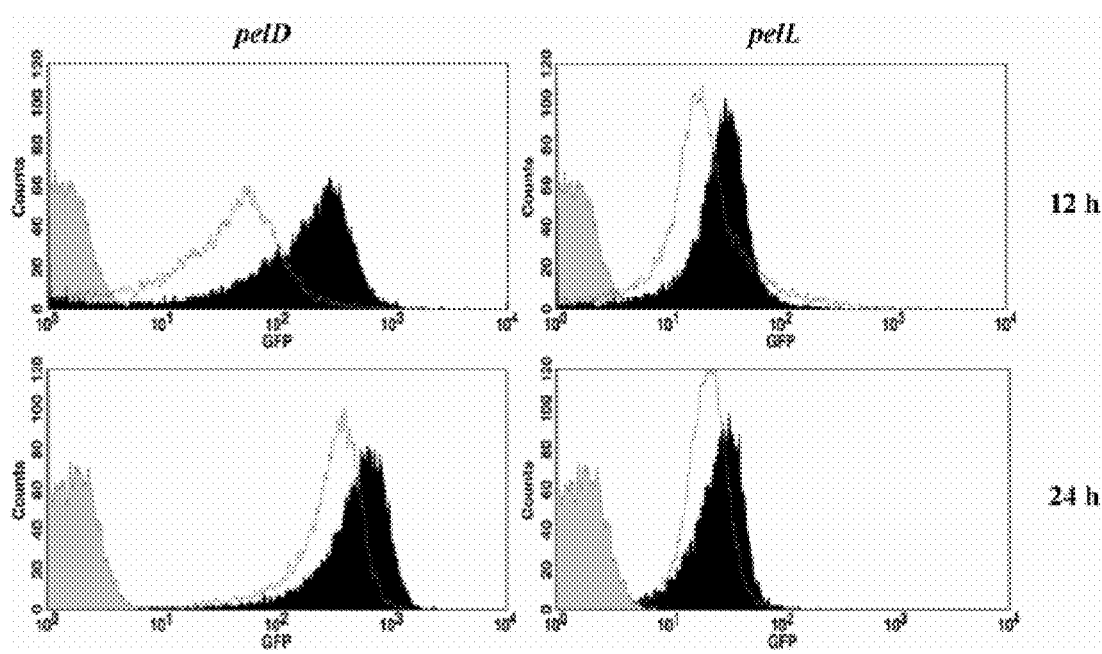
FIG. 9 shows promoter activity of pelD and pelL in Ech-Rif (black line with black filling) and gacA mutant Ech137 (gray line).

To study the influence of GacA on the transcription of pel genes in Ech3937, the promoter activities of pelD and pelL of Ech-Rif and Ech137 were examined. FIG. 9 shows expression of pelD and pelL in Ech-Rif (black line with black filling) and gacA mutant Ech137 (gray line) grown in minimal medium supplemented with 1% polygalacturonate (MMP). The promoter activities were compared after 12 and 24 h of culture in the medium MMP. Green fluorescent protein (GFP) intensity was determined on gated populations of bacterial cells by flow cytometry and analyzed with the Cell Quest software (BD Biosciences, San Jose, Calif., U.S.A.). The gray line with gray filling stands for the GFP expression control base level of the Ech-Rif containing pPROBE-AT vector without insert. Values are a representative of two experiments. Three replicates were used in this experiment and one replicate was used for the overlay as displayed. Compared with Ech-Rif, a considerably lower expression of pelD and pelL was observed in gacA mutant Ech137 at 12 and 24 h of growth in the medium, indicating that GacA upregulated the expression of pelD and pelL (FIG. 9). The pelD expression in wild-type Ech-Rif is more than twofold higher than that of the gacA mutant Ech137 at 12 h postgrown (FIG. 9). The Ech-Rif cells carrying pPelD at 12 and 24 h were expressed at a mean fluorescence intensity (MFI) of 190±17 and 459±73, while the Ech137 cells carrying pPelD at 12 and 24 h were expressed with an MFI of 52±3 and 324±11. Similarly, the pelL promoter activity in the Ech-Rif cells was approximately 50% greater than that in the gacA mutant Ech137 cells. The MFI values of Ech-Rif (pPelL) were 31±0.1 and 28±0 at 12 and 24 h postgrown, respectively (FIG. 9). The MFI values of Ech137 (pPelL) were 19±1 and 22±1 at 12 and 24 h (FIG. 9).

Regulation of the T3SS genes by GacA has been reported in E. carotovora subsp. *carotovora*. To study the influence of GacA on the transcription of T3SS genes in Ech3937, the promoter regions of dspE, hrpA, and hrpN of the bacterium were cloned into the pPROBE-AT to produce plasmids pDspE, pHrpA, and pHrpN (Table 6). The total GFP intensity of Ech-Rif (pDspE) was 15±0.8 at 8 h and 17±1.2 at 12 h grown in hrp-inducing MM (Table 7). A lower total GFP intensity of Ech137 (pDspE) of 3.4±0.01 and 3.4±0.05 was observed at the same period of time. Similarly, compared with Ech-Rif, a lower GFP intensity was observed in the Ech137 cells carrying pHrpA and pHrpN grown in the MM at 8 and 12 h (Table 7). The above data provide evidence that GacA upregulated dspE, hrpA, and hrpN.

TABLE 7

Expression of dspE, hrpA, and hrpN of Ech-Rif and Ech137 grown in minimal medium.

| Gene promoter | Mean fluorescence intensity[a] | |
|---|---|---|
| | 8 h | 12 h |
| Ech-Rif (pDspE) | 15.3 ± 0.8 | 17.0 ± 1.2 |
| Ech137 (pDspE) | 3.4 ± 0.01 | 3.4 ± 0.05 |
| Ech-Rif (pHrpA) | 25.9 ± 1.6 | 39.0 ± 5.0 |
| Ech137 (pHrpA) | 5.4 ± 0.2 | 6.6 ± 0.1 |
| Ech-Rif (pHrpN) | 21.3 ± 1.8 | 38.9 ± 2.4 |
| Ech137 (pHrpN) | 2.6 ± 0.05 | 2.7 ± 0.04 |

[a]Promoter activities were compared after 8 and 12 h of culture in the minimal medium. Values represent total green fluorescent protein intensity and are a representative of two experiments. Three replicates were used in this experiment. The value is present as average of three replicates and the standard deviation.

Example 7

The Gac-Rsm Regulatory Network Controls Pel and T3SS Gene Expression

Figure 10:
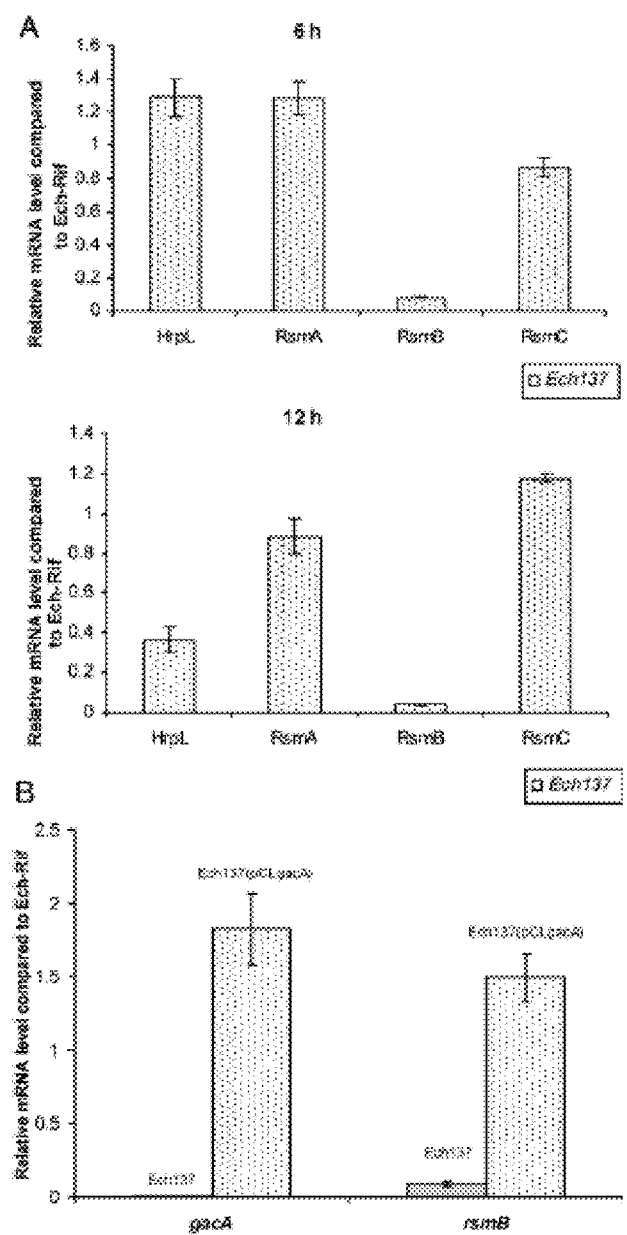
FIG. 10A shows relative levels of rsmA, rsmB, rsmC, and hrpL mRNA in gacA mutant Ech137 compared with wild-type Ech-Rif grown for 6 or 12 h in a minimal medium.
FIG. 10B shows relative levels of gacA and rsmB mRNA in gacA mutant Ech137 and gacA mutant complemented strain Ech137 (pCLgacA) compared with wild-type Ech-Rif grown for 12 h in a minimal medium.

Rsm is a novel type of post-transcriptional regulatory system that plays a critical role in gene expression. To investigate whether the influence of GacA on pectinase gene expression is through the Rsm regulatory pathway, the relative mRNA level of rsmC, rsmB, and rsmA was examined by qRT-PCR. The qRT-PCR data were analyzed using the Relative Expression Software Tool as described by Pfaffl and associates (Pfaffl et al. 2002). FIG. 10A shows relative levels of rsmA, rsmB, rsmC, and hrpL mRNA in gacA mutant Ech137 compared with wild-type Ech-Rif grown for 6 or 12 h in a minimal medium. Three replicates were used in each experiment and the values are presented as the average of the three replicates and the standard deviation. Compared with wild-type, a lower amount of rsmB mRNA was observed in Ech137. Wild-type Ech-Rif produced approximately 10-fold more rsmB mRNA than gacA mutant Ech137 at 6 h and 24-fold more at 12 h, with a P value less than 0.05. No significant differences in amount of rsmC and rsmA mRNA were observed between Ech-Rif and Ech137 (with a P value range from 0.74 to 1) (FIG. 10A).

FIG. 10B shows relative levels of gacA and rsmB mRNA in gacA mutant Ech137 and gacA mutant complemented strain Ech137 (pCLgacA) compared with wild-type Ech-Rif grown for 12 h in a minimal medium. The amount of mRNA was examined by real-time polymerase chain reaction assay and analyzed by Relative Expression Software Tool. The normalized value of mRNA for wild-type was 1.0. Three replicates were used in each experiment and the values are presented as the average of the three replicates and the standard deviation. No detectable mRNA of gacA was observed in Ech137 by qRT-PCR (FIG. 10B). The gacA and rsmB expression of Ech137 was restored by introducing the plasmid pCLgacA into the mutant. The relative mRNA amounts of gacA and rsmB of Ech137 (pCLgacA) are approximately 180 and 150% of the Ech-Rif (FIG. 10B). The higher amounts of gacA and rsmB mRNAs in Ech137 (pCLgacA) compared with Ech-Rif may be due to the copy number effect of the plasmid.

To further investigate whether the influence of GacA on T3SS gene expression is through the GacA-RsmA-rsmB-hrpL regulatory pathway, the amount of hrpL mRNA of the bacteria was examined by qRT-PCR. Compared with Ech-Rif (normalized to 1), a significantly lower hrpL mRNA was observed in gacA mutant Ech137 (0.362±0.065) with a value of 0.001 at 12 h grown in MM (FIG. 10A). A similar amount of hrpL mRNA was observed between Ech-Rif and Ech137 at 6 h (P=1) grown in the medium. Similar promoter activity of hrpL was observed between Ech-Rif and Ech137, suggesting that hrpL was regulated at a post-transcriptional level.

Example 8

GacA Influences the Expression of Pel and T3SS Genes in Planta

To connect the in vitro result with the in vivo condition, the expression of pelL and dspE between Ech-Rif and Ech137 in host plant African violet (*Saintpaulia ionantha*) leaves was examined further. Compared with Ech137, a higher transcription of pelL and dspE in Ech-Rif in *S. ionantha* was observed at 24 h postinoculation, which is approximately threefold more for pelL and fourfold more for dspE (Table 8).

TABLE 8

Expression of pelL and dspE of Ech-Rif and gacA mutant Ech137 in African violet[a].

| Gene promoter | Ech-Rif (pPelL) | Ech137 (pPelL) | Ech-Rif (pDspE) | Ech137 (pDspE) |
|---|---|---|---|---|
| Total | 51.4 ± 20.91 | 11.8 ± 7.4 | 6.0 ± 0.8 | 1.2 ± 0.1 |
| GFP+ mean | 78.2 ± 17.0 | 40.1 ± 0.7 | 54.4 ± 12.2 | 15.8 ± 15.2 |
| GFP+% | 57.1 ± 14.9 | 11.6 ± 11.3 | 8.0 ± 0.5 | 0 ± 0 |

[a]Promoter activities were compared after 24 h of inoculation. Green fluorescent protein (GFP) intensity was determined on gated populations of bacterial cells by flow cytometry. Values are a representative of two experiments. Three replicates were used in this experiment. The value is present as average of three replicates and the standard deviation.

Example 9

The gacA Mutant Reduced Maceration and Systemic Invasion Ability

Figure 11:
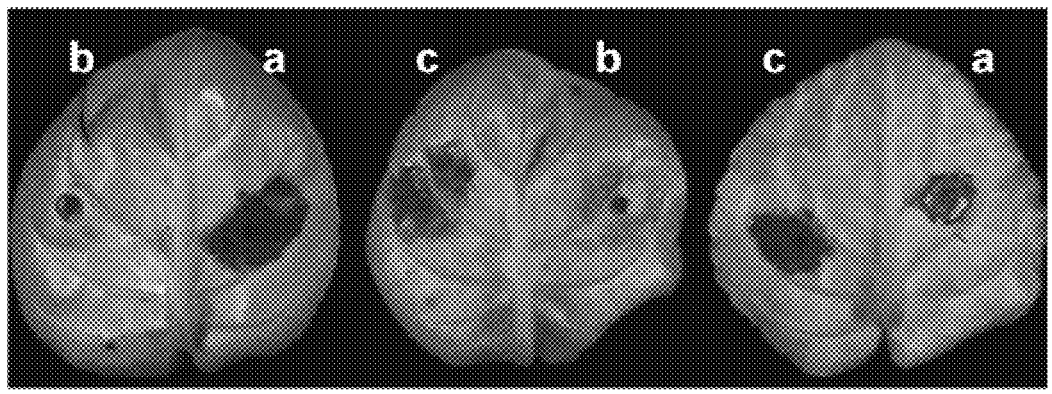
FIG. 11 shows local maceration lesions caused by a, Ech-Rif; b, gacA mutant Ech137; and c, complemented strain Ech137 (pCLgacA).

Because GacA affects multiple phenotypes contributing to pathogenesis, a local maceration assay was carried out with Ech-Rif, Ech137, and the complemented strain Ech137 (pCLgacA) in the African violet cv. Gauguin as previously described (Yang et al. 2002). FIG. 11 shows local maceration lesions caused by a, Ech-Rif; b, gacA mutant Ech137; and c, complemented strain Ech137 (pCLgacA). Bacterial cells were inoculated in the middle of each half side of the same leaf. Phosphate buffer (pH 7.4, 50 mM) was used to suspend the bacterial cells and a volume of a 50 µl of bacterial suspension with a bacterial concentration of 106 CFU/ml was used. The maceration symptom was examined 2 days postinoculation. The experiment has been repeated twice. Compared with Ech-Rif, Ech137 was dramatically reduced in maceration ability in planta 2 days postinoculation (FIG. 11). The maceration ability of Ech137 was restored to near the wild-type Ech-Rif level by pCLgacA (FIG. 11).

Figure 12:
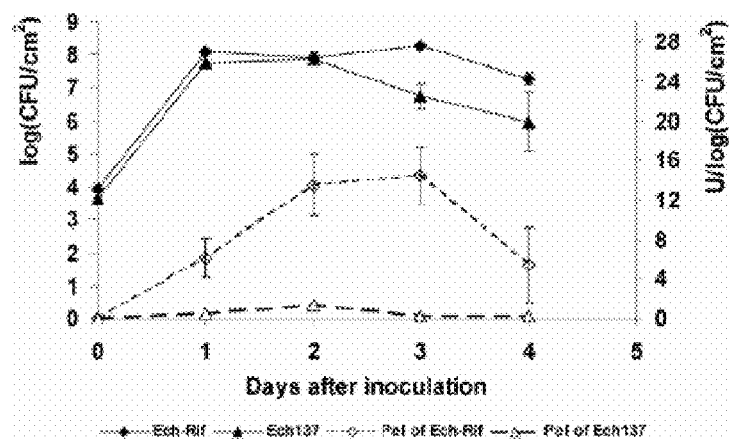
FIG. 12 shows the bacterial population and pectinase activity of Ech-Rif (solid diamonds) and Ech137 (solid triangles) determined by plate assay and spectrophotometric quantification, respectively.

FIG. 12 shows the concentration of Ech-Rif and gacA mutant Ech137 in African violet cv. Gauguin (*Saintpaulia ionantha*). Leaves of African violet were inoculated with a 50-µl bacterial suspension at a concentration of $10^6$ CFU/ml. Six leaves from six replicate plants were used at each sampling time for each bacterial strain, the value is present as average of three replicates and the standard deviation; concentration of Ech-Rif (solid diamonds) and Ech137 (solid triangles). The spectrophotometric quantification was carried out as described to measure the pectinase (Pel) activity in the inoculated leaves from the same sample for population kinetics; Pel production of Ech-Rif (open diamonds) and Ech137 (open triangles). Interestingly, although a lower Pel activity also was observed in plant leaves inoculated with Ech137, in comparison with the leaves inoculated with wild-type Ech-Rif (FIG. 12), there was no difference in bacterial concentration between the wild-type Ech-Rif and Ech137 in African violet leaves at day 2 postinoculation analyzed by a paired sample t test (P=0.23) (FIG. 12). Compared with Ech-Rif, a lower bacterial concentration of Ech137 in plants was observed at day 3 (P=5.9×10$^{-11}$) and day 4 (P=1.7×10$^{-4}$).

Figure 13:
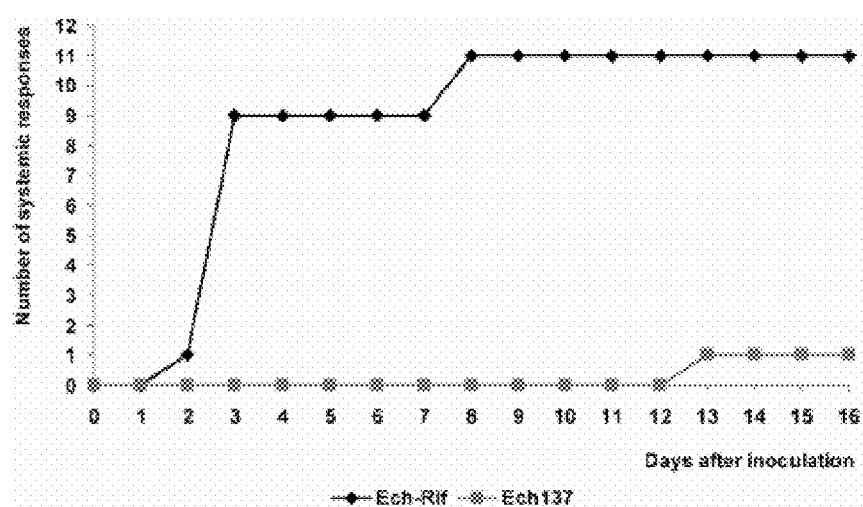
FIG. 13 shows the development of systemic symptoms caused by Ech-Rif and Ech137 strains in African violet cv. Gauguin (*Saintpaulia ionantha*) plants.

A systemic invasion assay (Franza et al. 1999) was further applied to investigate the role of GacA of the bacterium in *S. ionantha*. For each bacterial strain (Ech-Rif and Ech137), 12 plants (one leaf per plant) were inoculated. Response was considered as systemic when at least one leaf and its petiole were macerated. Values are a representative of two experiments. Eight days after inoculation, 11 of the 12 plants inoculated with Ech-Rif developed systemic invasion symptoms (FIG. 13). In contrast, the Ech137 showed a reduced ability to develop a systemic invasion in the plant host; only one plant developed a systemic invasion with the gacA mutant 16 days postinoculation.

Example 10

Identification of T3SS Inhibitors

To identify potential compounds that repress activation of T3SS, analogs and isomers of TCA and intermediates of salicylic acid and phenypropanoid biosynthesis pathways in plants were further screened for their effect on Ech3937 hrpA expression by flow cytometry (Table 9). A green fluorescent protein (GFP) reporter plasmid phrpA (pProbe-AT derivative with PCR fragment containing hrpA promoter region) was constructed, resulting in a transcriptional fusion of hrpA promoter with GFP gene. Bacterial cells containing phrpA plasmid were grown in MM supplemented with 0.1 mM of each compound. GFP intensity, which is a measurement of hrpA promoter activity, was measured by flow cytometry. The TCA analogs p-coumaric acid (PCA) and cinnamyl alcohol were discovered to be inhibitors of the expression of hrpA (Table 9).

TABLE 9

The expression of hrpA of *Dickeya dadantii* 3937 (Ech3937) in MM and MM supplemented with different isomers and analogs of t-cinnamic acid.

| Phenolic compound[a] | 6 h[b] | 12 h | 24 h |
|---|---|---|---|
| MM | 8.3 ± 0.7 | 78.7 ± 6.3 | 92.1 ± 17.1 |
| t-Cinnamic acid | 22.3 ± 2.1 | 133.9 ± 12.9 | 203.7 ± 16.1 |
| o-Coumaric acid | 15.5 ± 1.1 | 115.5 ± 7.9 | 225.8 ± 15.6 |
| m-Coumaric acid | 12.1 ± 0.0 | 133.0 ± 38.2 | 203.3 ± 9.6 |
| p-Coumaric acid | 6.9 ± 0.1 | 10.2 ± 0.4 | 11.4 ± 1.0 |
| Hydrocinnamic acid | 13.7 ± 1.0 | 200.3 ± 35.8 | 213.5 ± 18.9 |
| Phenoxyacetic acid | 18.0 ± 3.1 | 222.7 ± 64.3 | 205.7 ± 11.8 |
| trans-2-Phenylcyclopropane-1-carboxylic acid | 7.2 ± 0.1 | 67.0 ± 18.4 | 84.0 ± 14.3 |
| trans-3-(3-Pyridyl)acrylic acid | 13.1 ± 0.4 | 184.9 ± 35.6 | 204.0 ± 16.8 |
| trans-3-indoleacrylic acid | 7.9 ± 0.2 | 23.9 ± 1.3 | 121.0 ± 6.2 |
| 2-Methylcinnamic acid | 22.8 ± 0.6 | 157.2 ± 11.7 | 342.5 ± 16.6 |
| 2-Chlorocinnamic acid | 25.7 ± 0.2 | 166.2 ± 17.8 | 319.8 ± 48.3 |
| Methyl trans-cinnamate | 9.7 ± 0.1 | 135.8 ± 8.1 | 219.2 ± 14.5 |
| Cinnamyl alcohol | 6.3 ± 0.1 | 27.8 ± 5.0 | 53.8 ± 2.9 |

[a]Minimum medium (MM) and MM supplemented with 0.1 mM of different compounds.
[b]Ech3937 cells carrying GFP reporter phrpA was used in this study. The promoter activities were compared at 6, 12, and 24 h of bacterial growth. GFP intensity was determined on gated populations of bacterial cells by flow cytometry. The fluorescence intensities were an average GFP fluorescence intensity of total bacterial cells. Values (Mean Fluorescence Intensity) of GFP are a representative of three experiments. Three replicates were used in this experiment. The value is present as the average of three replicates with standard deviation (SD).

Figure 16A:
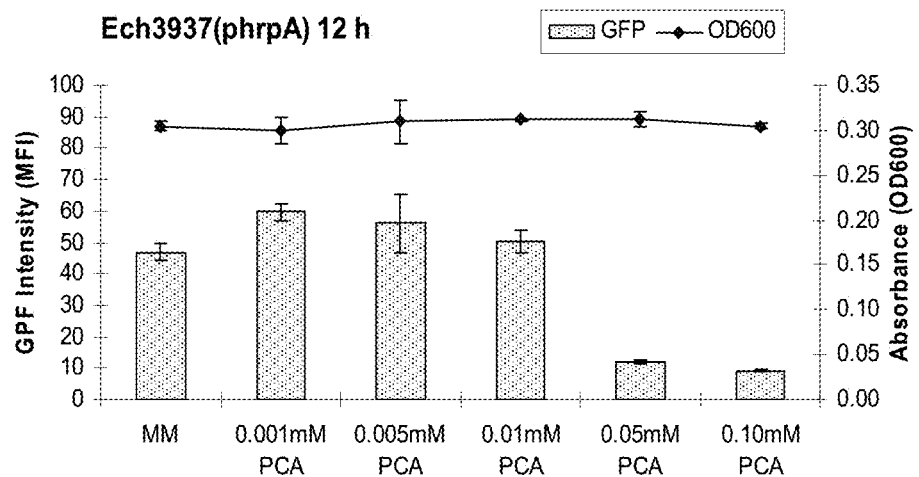
FIGS. 16A and 16B show the promoter activities of hrpA in *Dickeya dadantii* 3937 (Ech3937) grown in minimum medium (MM) and MM supplemented with different amount of p-coumaric acid (PCA) at 12 h (FIG. 16A) and 24 h (FIG. 16B).
Figure 16B:
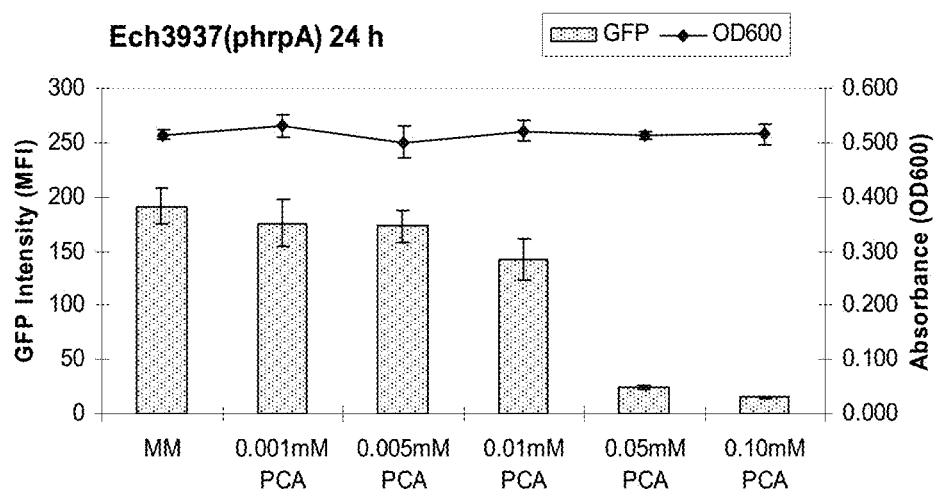

The expression of the T3SS gene hrpA was further examined in MM and MM supplemented with PCA at concentrations of 0.001, 0.005, 0.01, 0.05 and 0.1 mM respectively. FIGS. 16A and 16B show the promoter activities of hrpA in Dickeya dadantii 3937 (Ech3937) grown in minimum medium (MM) and MM supplemented with different amount of p-coumaric acid (PCA) at 12 h (FIG. 16A) and 24 h (FIG. 16B) post-inoculation. GFP intensity was determined on gated populations of bacterial cells by flow cytometry and analyzed with the Cell Quest software (BD Biosciences, San Jose, Calif.). The growth of Ech3937 in MM supplemented with different concentrations of PCA was recorded. Compared with MM alone, the average GFP fluorescence intensity of bacterial cells of Ech3937 (phrpA) was reduced more than 4-fold when 0.05 and 0.1 mM of PCA were added to the medium (FIGS. 16A, 16B). The addition of PCA at concentrations at 0.001, 0.005 and 0.01 did not result in substantial reduction of GFP fluorescence intensity of Ech3937. Inhibition of bacterial growth was not observed when PCA was added into the MM (FIGS. 16A, 16B).

Figure 14:
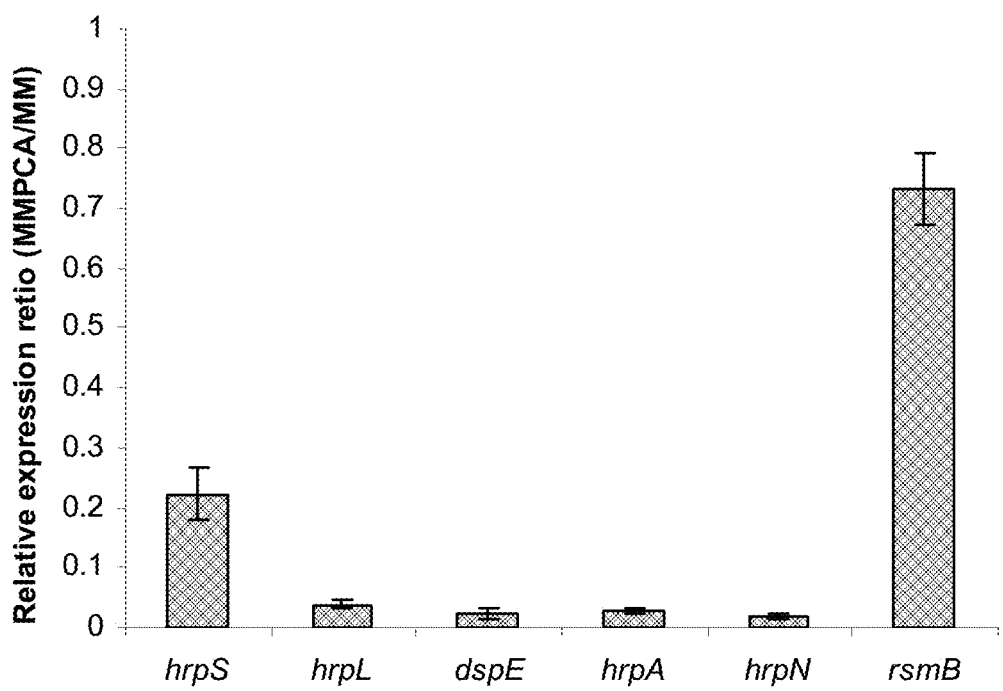
FIG. 14 shows the relative mRNA level of hrpS, hrpL, dspE, hrpA, hrpN, and rsmB of *Dickeya dadantii* 3937 (Ech3937) in minimum medium (MM) supplemented with 0.1 mM p-coumaric acid (PCA) compared to those in MM without PCA.

To confirm the inhibitory effect of PCA on T3SS of Ech3937, the promoter activity of hrpN of Ech3937 was also examined. A reduced expression of hrpN was observed in MM supplemented with 0.1 mM PCA in comparison with the bacterial cells grown in MM alone (Table 10). The mrp, whose protein product has an ATPase conserved domain (2e-06), was used as a reference gene. Similar mrp expression was observed in Ech3937 (pmrp) when the bacterial cells were grown in MM and MM supplemented with 0.1 mM PCA respectively (Table 10). The repression effect of PCA on T3SS gene expression was further demonstrated by a qRT-PCR assay. FIG. 14 shows the relative mRNA level of hrpS, hrpL, dspE, hrpA, hrpN, and rsmB of Dickeya dadantii 3937 (Ech3937) in minimum medium (MM) supplemented with 0.1 mM p-coumaric acid (PCA) compared to those in MM without PCA. The amount of mRNA was determined by qRT-PCR. Three replicates were used in this experiment. The p-value was calculated using Relative Expression Software Tool as described by Pfaffl et al. (2002). Levels of gene expression of hrpS, hrpL, dspE, hrpA, and hrpN are significantly different between MM and MM supplemented with 0.1 mM PCA with p<0.001. Compared with Ech3937 in MM alone (normalized to 1), a significantly lower amount of mRNA of dspE (P=0.001), hrpA (P=0.001), and hrpN (P=0.001) was observed in the bacterium grown in MM supplemented with PCA (FIG. 14).

TABLE 10

The expression of type III secretion genes hrpA and hrpN of Dickeya dadantii 3937 (Ech3937) in minimum medium (MM) and MM supplemented with 0.1 mM PCA (MMPCA).

| Gene | 12 h | | 24 h | |
|---|---|---|---|---|
| Promoter[a] | MM | MMPCA | MM | MMPCA |
| Ech3937 (phrpA) | 64.3 ± 0.9[b] | 10.3 ± 1.3 | 150.8 ± 4.4 | 18.5 ± 3.5 |
| Ech3937 (phrpN) | 39.8 ± 5.8 | 6.8 ± 0.8 | 133.3 ± 3.2 | 11.3 ± 3.4 |
| Ech3937 (phrpS) | 72.7 ± 11.3 | 37.9 ± 1.3 | 95.0 ± 17.7 | 43.6 ± 2.6 |
| Ech3937 (phrpL) | 12.8 ± 0.1 | 7.8 ± 0.1 | 27.2 ± 1.0 | 11.1 ± 3.3 |
| Ech3937 (pmrp) | 113.0 ± 7.7 | 124.1 ± 2.7 | 93.4 ± 2.6 | 98.9 ± 1.0 |
| Ech3937 (pPROBE-AT) | 2.1 ± 0.1 | 2.2 ± 0.2 | 13.4 ± 8.4 | 14.0 ± 10.1 |

[a]The promoter activities were compared at 12 and 24 h of bacterial growth in p-coumaric acid (PCA).
[b]GFP intensity was determined on gated populations of bacterial cells by flow cytometry. The fluorescence intensities were an average GFP fluorescence intensity of total bacterial cells. Values (Mean Fluorescence Intensity) are a representative of two experiments. Three replicates were used in this experiment. The value is present as the average of three replicates with standard deviation (SD).

Figure 17:
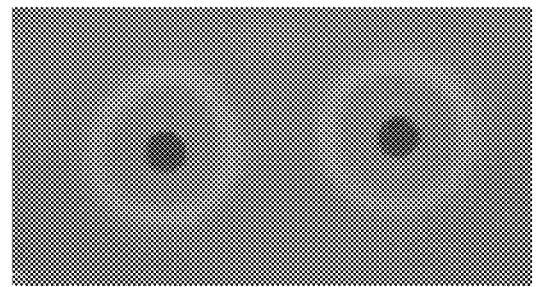
FIG. 17 shows pectate lyase (Pel) production of *Dickeya dadantii* 3937 (Ech3937) grown in minimal medium (MM) and MM supplemented with 0.1 mM of p-coumaric acid (PCA) at 12 h.

GacS/GacA also induced the production of pectate lyase of Ech3937. To investigate whether PCA affects the T3SS gene expression through the Gac-Rsm regulatory pathway, the expression of rsmB was further examined by qRT-PCR. FIG. 17 shows pectate lyase (Pel) production of Dickeya dadantii 3937 (Ech3937) grown in minimal medium (MM) and MM supplemented with 0.1 mM of p-coumaric acid (PCA) at 12 hexamined by plate assays as described (Matsumoto et al. 2003). Values are a representative of two experiments. Three replicates were used in this experiment. No significant difference was observed between Ech3937 grown in MM and MM supplemented with PCA for gene rsmB with the p=0.928 (FIG. 14). This result shows that the repression T3SS expression by PCA is not through the Gac-Rsm pathway. That the Gac-Rsm pathway is not interfered by PCA is further suggested by a pectinase assay. Similar pectate lyase production was observed between Ech3937 grown in MM and MM supplemented with 0.1 mM PCA, demonstrating that GacS/GacA is not influenced by PCA (FIG. 17).

Along with GacS/GacA-RsmA-rsmB-hrpL regulatory pathway, the T3SS of Ech3937, which belongs to Group I T3SS of phytobacteria, is primarily regulated by a HrpX/Y-HrpS-HrpL pathway. The two-component system HrpX/HrpY activates the gene encoding HrpS, which is required for expression of hrpL. HrpL, an alternative sigma factor, further activates expression of genes encoding the T3SS apparatus and its secreted substrates. To investigate whether PCA represses T3SS gene expression through HrpX/Y-HrpS-HrpL pathway, the promoter activity of hrpS and hrpL was further examined. Compared with Ech3937(phrpS) and Ech3937 (phrpL) in MM, a lower GFP intensity was observed in the bacterial cells carrying phrpS and phrpL grown in MM supplemented with 0.1 mM PCA (Table 10). The expression of hrpS and hrpL was also confirmed by qRT-PCR. The result showed that, compared with Ech3937 in MM alone (normalized to 1), a significantly lower amount of mRNA of hrpS (relative expression ratio 0.223, P=0.001) and hrpL (relative expression ratio 0.039, P=0.001) was observed in bacteria grown in MM supplemented with PCA (FIG. 14).

Figure 15:
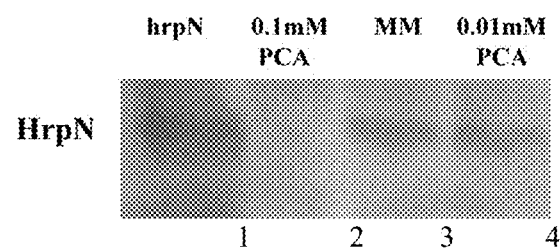
FIG. 15 shows HrpN protein expression of *Dickeya dadantii* 3937 (Ech3937) in minimum medium (MM) and MM supplemented with p-Coumaric acid (PCA).

To further elucidate whether T3SS gene expression is mainly regulated through the HrpX/Y-HrpS-HrpL regulatory pathway, the expression of hrpA and hrpN in wild-type Ech3937 and hrpX (WPP67), hrpY (WPP92), hrpS (WPP90), and hrpL (WPP96) mutants in MM were examined. The result showed that compared with Ech3937 carrying phrpA and phrpN, very low expression of hrpA and hrpN was observed in WPP67, WPP92, WPP90, and WPP96 grown in MM. Similar expression of hrpA and hrpN was observed among WPP67, WPP92, WPP90 and WPP96 carrying phrpA and phrpN grown in MM and MM supplemented with PCA. These results demonstrate that hrpX, hrpY, hrpS and hrpL are crucial for the T3SS gene expression and PCA inhibits expression of T3SS genes through HrpX/Y-HrpS-HrpL regulatory pathway (Table 11). Since PCA represses the expression of several T3SS genes such as hrpN, the effect of PCA on protein production of HrpN was further examined. FIG. 15 shows HrpN protein expression of Dickeya dadantii 3937 (Ech3937) in minimum medium (MM) and MM supplemented with 0.1 mM of p-Coumaric acid (PCA). Lane 1 of FIG. 15 shows a HrpN overexpression strain. Lane 2 shows Ech3937 grown in MM supplemented with 0.1 mM PCA. Lane 3 shows Ech3937 grown in MM. Lane 4 shows Ech3937 grown in MM supplemented with 0.01 mM PCA. Compared with MM alone, a lower amount of HrpN was observed in Ech3937 grown in MM supplemented with 0.1 mM of PCA (FIG. 15).

TABLE 11

The expression of hrpA and hrpN of wild-type Dickeya dadantii 3937 (Ech3937) and hrpX (WPP67), hrpY (WPP92), hrpS (WPP90) and hrpL (WPP96) mutants in minimum medium (MM) and MM supplemented with 0.1 mM PCA (MMPCA).

| Gene | 12 h | | 24 h | |
|---|---|---|---|---|
| Promoter[a] | MM | MMPCA | MM | MMPCA |
| Ech3937 (phrpA) | 53.0 ± 5.8[b] | 9.2 ± 0.4 | 139.3 ± 22.2 | 12.7 ± 0.3 |
| WPP67 (phrpA) | 8.3 ± 0.1 | 7.9 ± 0.2 | 10.3 ± 1.1 | 9.0 ± 1.3 |

TABLE 11-continued

The expression of hrpA and hrpN of wild-type *Dickeya dadantii* 3937 (Ech3937) and hrpX (WPP67), hrpY (WPP92), hrpS (WPP90) and hrpL (WPP96) mutants in minimum medium (MM) and MM supplemented with 0.1 mM PCA (MMPCA).

| Gene Promoter[a] | 12 h MM | 12 h MMPCA | 24 h MM | 24 h MMPCA |
|---|---|---|---|---|
| WPP92 (phrpA) | 9.3 ± 0.2 | 6.9 ± 0.1 | 9.1 ± 0.2 | 9.4 ± 0.7 |
| WPP90 (phrpA) | 7.7 ± 0.4 | 7.9 ± 0.2 | 8.1 ± 0.0 | 9.3 ± 0.2 |
| WPP96 (phrpA) | 7.6 ± 0.3 | 7.3 ± 0.1 | 7.6 ± 0.1 | 9.0 ± 1.6 |
| Ech3937 (phrpN) | 49.0 ± 3.3 | 4.3 ± 0.1 | 112.2 ± 6.7 | 8.8 ± 2.1 |
| WPP67 (phrpN) | 4.4 ± 0.4 | 3.5 ± 0.2 | 9.4 ± 1.4 | 6.3 ± 0.7 |
| WPP92 (phrpN) | 3.8 ± 0.1 | 3.6 ± 0.1 | 5.7 ± 0.4 | 5.5 ± 0.3 |
| WPP90 (phrpN) | 3.6 ± 0.2 | 3.5 ± 0.1 | 5.0 ± 0.3 | 5.1 ± 0.1 |
| WPP96 (phrpN) | 3.0 ± 0.0 | 3.0 ± 0.0 | 3.9 ± 0.1 | 4.3 ± 0.1 |
| Ech3937 (Pprobe-AT) | 2.2 ± 0.1 | 2.3 ± 0.1 | 4.3 ± 0.2 | 4.9 ± 0.1 |

[a]The promoter activities were compared at 12 and 24 h of bacterial growth in p-Coumaric acid (PCA).
[b]GFP intensity was determined on gated populations of bacterial cells by flow cytometry. The fluorescence intensities were an average GFP fluorescence intensity of total bacterial cells. Values (Mean Fluorescence Intensity) are a representative of two experiments. Three replicates were used in this experiment. The value is present as the average of three replicates with standard deviation (SD).

Example 11

Synthesis of Compounds

The compounds in Table 12 were synthesized or purchased commercially.

TABLE 12

| ID | Structure |
|---|---|
| 001 | cinnamic acid (Ph-CH=CH-CO₂H) |
| 002 | 2,4-dihydroxycinnamic acid |
| 003 | 3,4-dihydroxycinnamic acid (caffeic acid) |
| 004 | 4-hydroxycinnamic acid (p-coumaric acid) |
| 005 | 3-hydroxycinnamic acid |
| 006 | 2-hydroxycinnamic acid |
| 007 | 3-(4-hydroxyphenyl)propanoic acid |
| 008 | 3-phenylpropanoic acid |
| 009 | phenoxyacetic acid |
| 010 | 2-phenylcyclopropane-1-carboxylic acid |
| 011 | (E)-3-(thiophen-2-yl)acrylic acid |
| 012 | (E)-3-(1H-indol-3-yl)acrylic acid |
| 013 | (E)-3-(pyridin-3-yl)acrylic acid |
| 014 | (E)-3-(1H-imidazol-4-yl)acrylic acid |
| 015 | 2-methoxycinnamic acid |
| 016 | 3-methoxycinnamic acid |
| 017 | 4-methoxycinnamic acid |
| 018 | 2-methylcinnamic acid |

TABLE 12-continued

| ID | Structure |
|---|---|
| 019 | 3-methylcinnamic acid (Me on meta position, CO₂H) |
| 020 | 4-methylcinnamic acid (Me on para position, CO₂H) |
| 021 | 2-chlorocinnamic acid (Cl on ortho, CO₂H) |
| 022 | 3-chlorocinnamic acid (Cl on meta, CO₂H) |
| 023 | 4-chlorocinnamic acid (Cl on para, CO₂H) |
| 024 | 2-carboxycinnamic acid (CO₂H on ortho, CO₂H) |
| 025 | 4-carboxycinnamic acid (HO₂C on para, CO₂H) |
| 026 | 4-mercaptocinnamic acid (HS on para, CO₂H) |
| 027 | 4-aminocinnamic acid (H₂N on para, CO₂H) |
| 028 | 4-nitrocinnamic acid (O₂N on para, CO₂H) |
| 029 | 4-formylcinnamic acid (OHC on para, CO₂H) |
| 030 | methyl cinnamate (CO₂Me) |
| 031 | cinnamamide (C(O)NH₂) |
| 032 | cinnamyl alcohol (OH) |
| 033 | salicylic acid (CO₂H, OH) |
| 034 | benzoic acid (CO₂H) |
| 035 | 2-naphthylacrylic acid (naphthyl, CO₂H) |
| 100 | ethyl 2-(4-methoxyphenyl)cyclopropanecarboxylate (MeO, CO₂Et) |
| 101 | methyl 4-hydroxycinnamate (HO, CO₂Me) |
| 102 | 4-hydroxycinnamamide (HO, C(O)NH₂) |
| 103 | 4-hydroxycinnamohydroxamic acid (HO, C(O)NHOH) |
| 104 | 4-hydroxycinnamyl alcohol (HO, OH) |
| 105 | 2-(4-methoxyphenyl)cyclopropanecarboxylic acid (MeO, CO₂H) |

TABLE 12-continued

| ID | Structure |
|---|---|
| 106 | 4-HO-C6H4-cyclopropyl-CO2Et |
| 107 | 4-HO-C6H4-cyclopropyl-CO2H |
| 108 | biphenyl-4-CH=CH-CO2H |
| 109 | 4-Cl-C6H4-CH=CH-C(O)NH2 |
| 110 | 4-F-C6H4-CH=CH-CO2H |
| 111 | 4-Br-C6H4-CH=CH-CO2H |
| 112 | 4-Me2N-C6H4-CH=CH-CO2H |
| 113 | 4-F3C-C6H4-CH=CH-CO2H |
| 114 | 4-HO-C6H4-CH=CH-P(O)(OEt)2 |
| 115 | 4-HO-C6H4-CH=CH-P(O)(OH)2 |
| 116 | 4-HO-C6H4-CH=CH-CH2-phthalimide |
| 117 | 4-HO-C6H4-CH=CH-CH2-NH2 |
| 118 | 4-MeO-C6H4-CH=CH-CH2-phthalimide |
| 119 | 4-MeO-C6H4-CH=CH-CH2-NH2 |
| 120 | 4-MeO-C6H4-CH=CH-S(O)2-OEt |
| 121 | 4-MeO-C6H4-CH=CH-S(O)2-O⁻ NBu4⁺ |
| 122 | 4-HO-C6H4-CH=CH-S(O)2-OEt |
| 123 | 4-HO-C6H4-CH=CH-S(O)2-O⁻ NBu4⁺ |
| 124 | 4-(HOCH2)-C6H4-CH=CH-CO2H |
| 125 | 4-MeO-C6H4-CH=CH-C(O)NHOH |
| 126 | 4-MeO-C6H4-CH=CH-CH2-OH |

TABLE 12-continued

| ID | Structure |
|---|---|
| 127 | (E)-3-(1H-indol-3-yl)-N-hydroxyacrylamide |
| 128 | (E)-3-(4-bromophenyl)-N-hydroxyacrylamide |
| 129 | (E)-N-hydroxy-3-(2-hydroxyphenyl)acrylamide |
| 130 | (E)-N-hydroxy-3-(3-hydroxyphenyl)acrylamide |
| 131 | (E)-3-(3,4-dihydroxyphenyl)-N-hydroxyacrylamide |
| 132 | (E)-N-hydroxycinnamamide |
| 133 | (E)-3-(4-hydroxyphenyl)acrylohydrazide |
| 134 | N-hydroxybenzamide |
| 135 | N,2-dihydroxybenzamide |
| 136 | 3-phenylpropiolic acid |
| 137 | (E)-3-(4-hydroxyphenyl)-N-methylacrylamide |
| 138 | (E)-N-(2-hydroxyethyl)-3-(4-hydroxyphenyl)acrylamide |
| 139 | N-hydroxy-3-phenylpropanamide |
| 140 | (E)-3-(biphenyl-4-yl)-N-hydroxyacrylamide |
| 141 | (E)-3-(4-fluorophenyl)-N-hydroxyacrylamide |
| 142 | (E)-N-hydroxy-3-p-tolylacrylamide |
| 143 | N-hydroxy-2-phenoxyacetamide |
| 144 | 4-hydroxybenzoic acid |
| 145 | 3-hydroxybenzoic acid |

TABLE 12-continued
| ID | Structure |
|---|---|
| 146 | 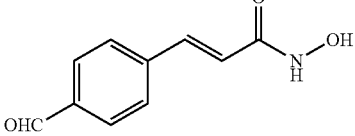 |
| 147 | 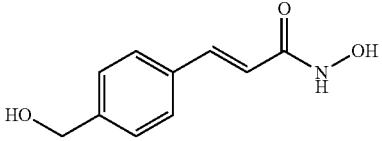 [SMILES: O=C(/C=C/c1ccc(CO)cc1)NO] |
| 148 | 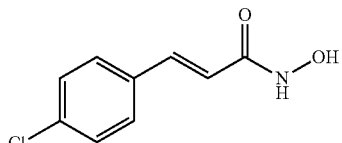 |
| 149 | 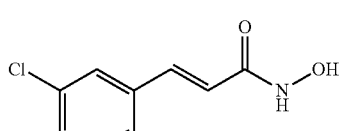 |
| 150 | 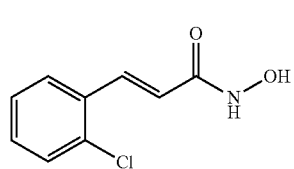 |
| 151 | 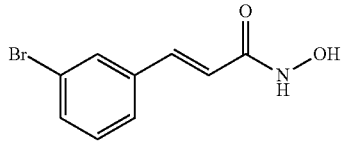 [SMILES: O=C(/C=C/c1cccc(Cl)c1)NO] |
| 152 | 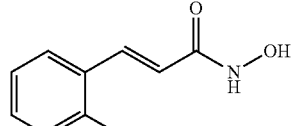 |
| 153 | 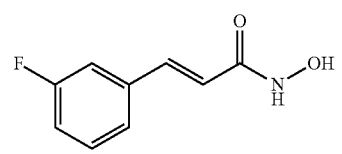 [SMILES: O=C(/C=C/c1cccc(F)c1)NO] |
| 154 | 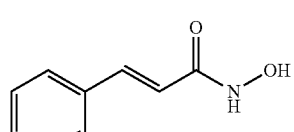 |
| 155 | 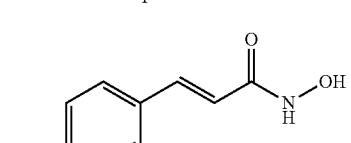 |
| 156 | 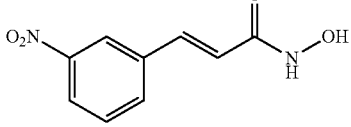 |
| 157 | 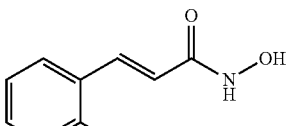 |
| 158 | 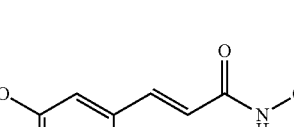 |
| 159 | 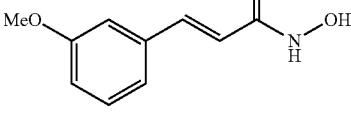 |
| 160 | 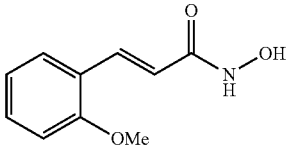 [SMILES: COc1ccccc1/C=C/C(=O)NO] |
| 161 | 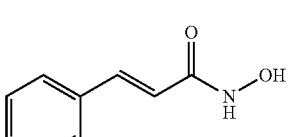 |
| 162 | 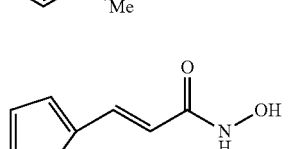 |
| 163 | 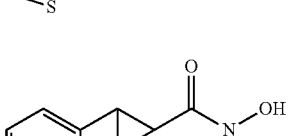 |
| 164 | 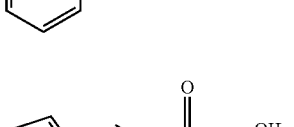 |

TABLE 12-continued

| ID | Structure |
|---|---|
| 165 | (phenylacetyl)phenyl cyclopropane carboxylic acid |
| 166 | N-phenyl 4-(carboxyvinyl)benzamide |
| 167 | N-methyl-N-phenyl 4-(carboxyvinyl)benzamide |

The following compounds will be synthesized or purchased commercially:

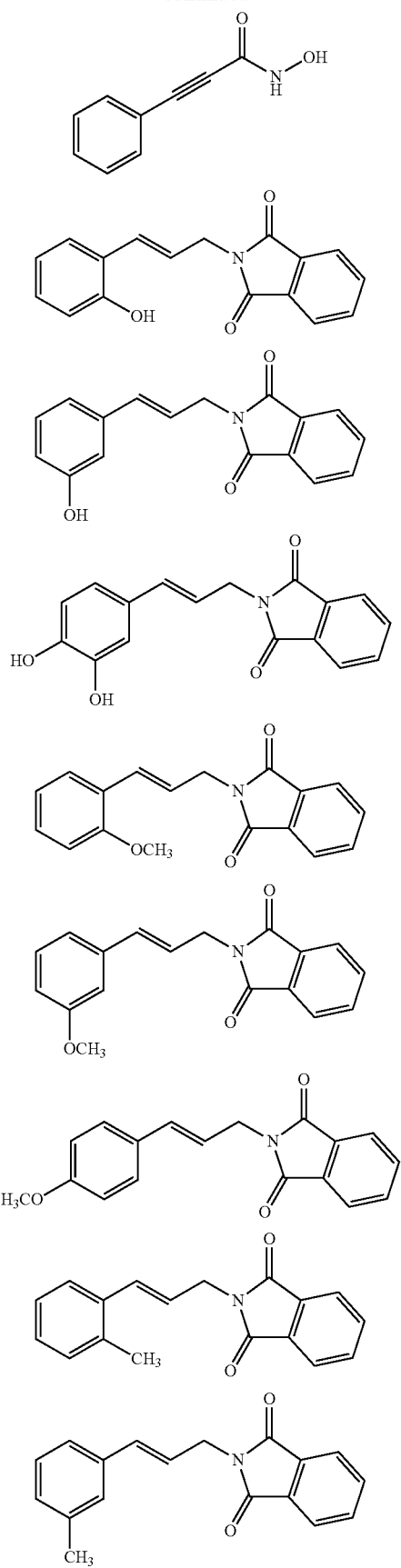
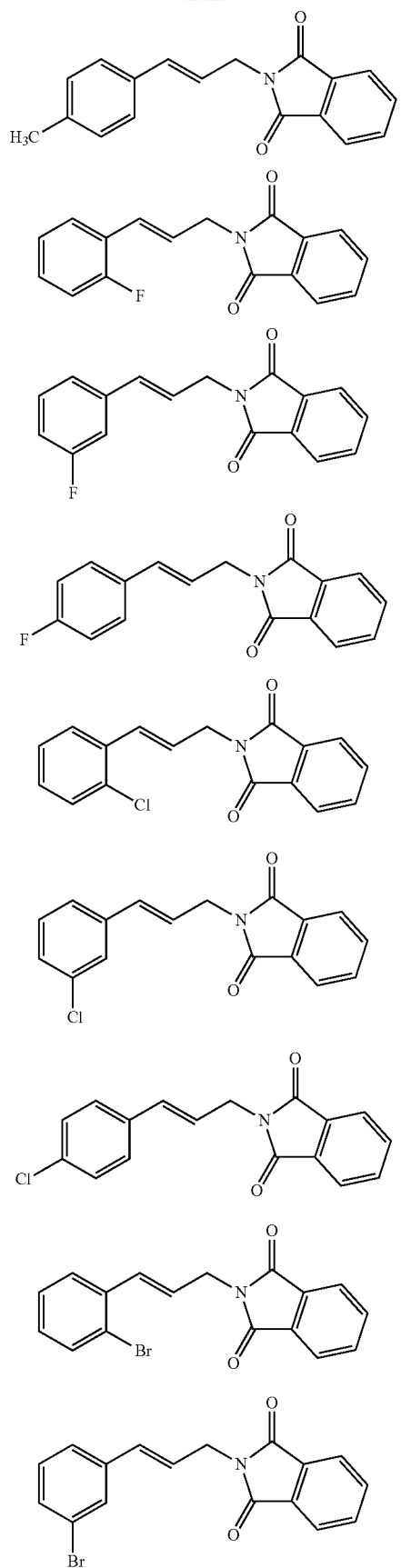

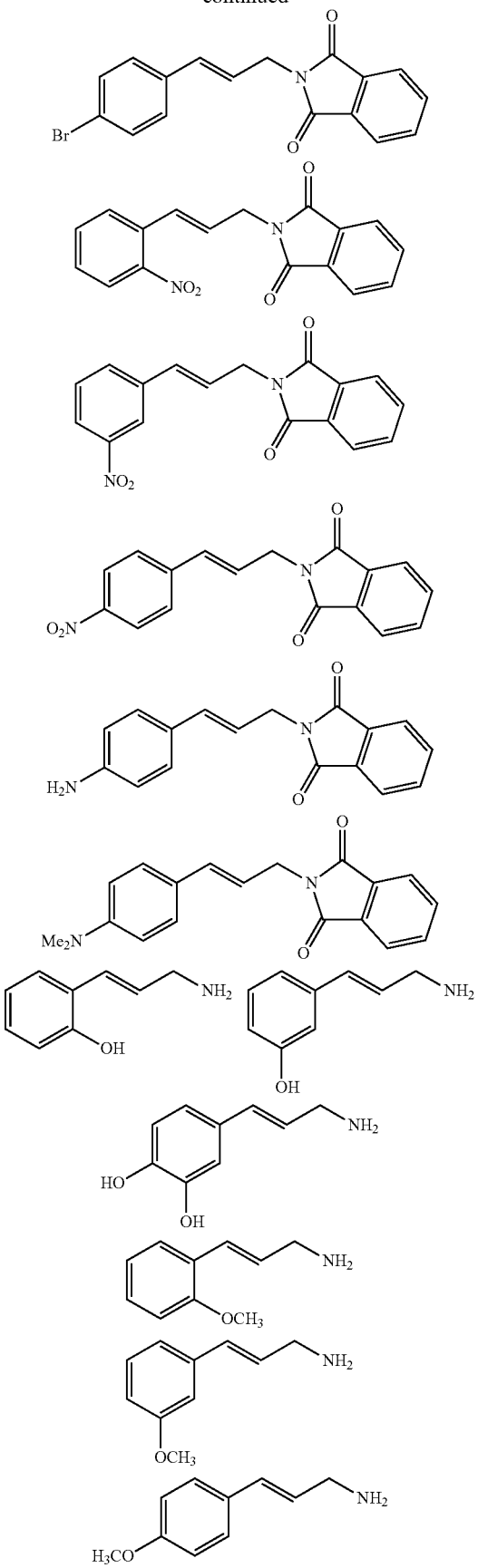
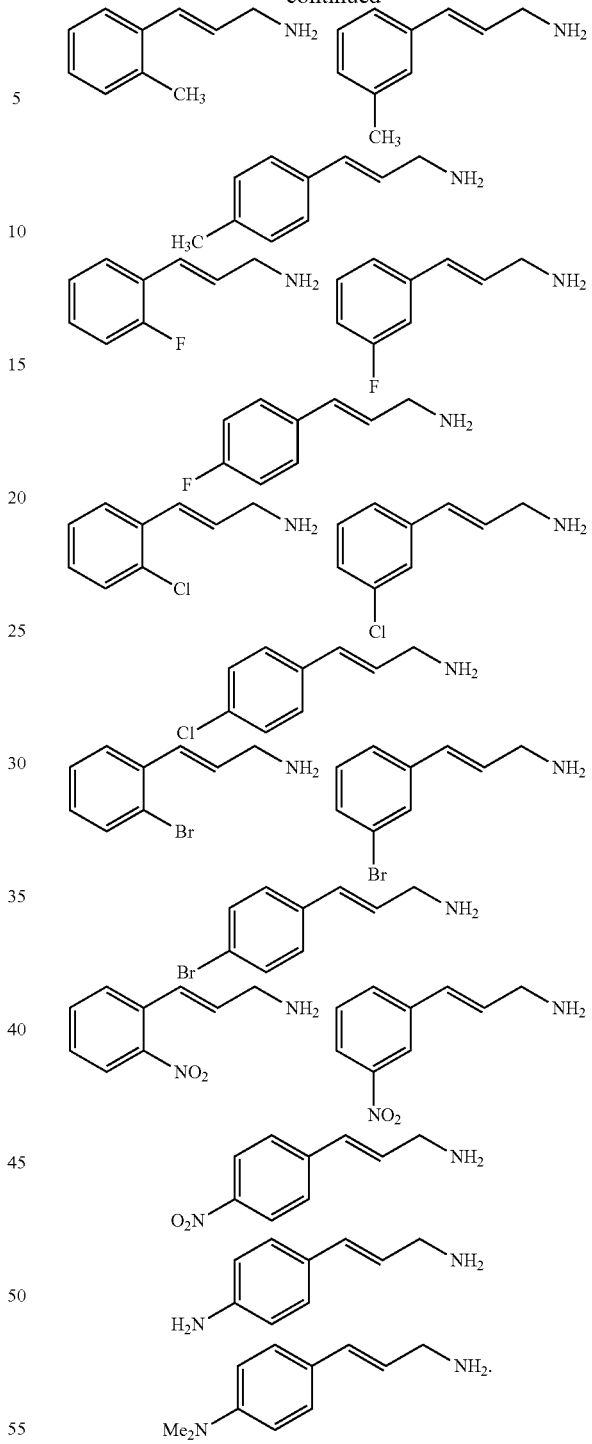

Synthesis of Hydroxamates (103, 125, 127, 128, 129, 130, 131, 132)

Method A: A mixture of cinnamic acid (25 mmol) and concentrated $H_2SO_4$ (0.1 mL) in anhydrous MeOH (25 mL) was refluxed at 80° C. (bath temperature) for 16 h. After the excess MeOH was removed by a rotary evaporator, the residue was treated with $H_2O$ (50 mL), and the resulting mixture was extracted with EtOAc (3×50 mL). The combined extracts were washed with $H_2O$ (50 mL) and brine (50 mL), and dried (anhydrous $Na_2SO_4$). The solvent was evaporated to dryness, and the crude products were purified by flash silica gel chromatography (eluting with 10-60% hexane in EtOAc) to afford methyl cinnamate. To an ice-cold solution of methyl cinnamate described above (8 mmol) dissolved in anhydrous MeOH (10 mL) and THF (10 mL) was added hydroxylamine hydrochloride (1.67 g, 24 mmol, 3 equiv) followed by 25% sodium methoxide in methanol solution (8.4 mL, 36 mmol, 4.5 equiv). The reaction mixture was stirred under argon and at 0° C. for 2 h, then allowed to warm to ambient temperature with the stirring was continued overnight (16 h). The resulting yellow suspension was condensed to dryness with a rotary evaporator, and the residue was treated with 1N HCl aqueous solution (30 mL). The mixture was extracted with EtOAc (3×50 mL), and dried (anhydrous $Na_2SO_4$). Evaporation of the solvent afforded the crude products (480 mg), which was purified by flash silica gel chromatography (eluting with 5-15% MeOH in DCM) to afford the hydroxamate.

Using Method A, Compounds 103, 125, 129, 130, and 131 were synthesized. The carboxyl acid of PCA was converted to hydroxamite to synthesize compound 103 by reacting methyl ester 101 with hydroxylamine under basic conditions. Compound 103 was a light-brown solid, obtained at 25% yield (based on the methyl ester). The hydroxyl group of 103 was replaced by methoxy group, resulting in the hydroxamate 125. Compound 125 was light-brown solid, obtained at 67% yield. Compound 129 was light-brown solid, obtained at 21% yield. Compound 130 was an off-white solid, obtained at 63% yield. Compound 131 was a grey solid, obtained at 25% yield. Identity of compounds was verified by $^1$H NMR (75 MHz, $CD_3OD$).

Method B: To a stirred mixture of cinnamic acid (7 mmol) and diisopropylethylamine (DIEA) (2.45 mL, 17 mmol) in anhydrous DMF (20 mL) was added HBTU (2.92 g, 7.7 mmol) at room temperature, followed by adding a solution of hydroxylamine hydrochloride (0.98 g, 14 mmol) and DBU (2.13 g, 14 mmol) in anhydrous DMF (8 mL), and then the whole reaction mixture was stirred at room temperature for 1 h. After most of the DMF was removed with a rotary evaporator, the residue was dissolved in EtOAc (150 mL), then washed with $H_2O$ (50 mL) and brine (50 mL), and dried (anhydrous $Na_2SO_4$). Evaporation of the solvent afforded the crude products, which was purified by flash silica gel chromatography (eluting with 5-15% MeOH in DCM) to afford the hydroxamate.

Using Method B, compounds 127, 128, and 132 were synthesized. The indole hydroxamate 127 was synthesized by reacting the corresponding methyl esters with hydroxylamine under basic conditions. Compound 127 was a yellow solid, obtained at 35% yield. Compound 128 was a white solid, obtained at 50% yield. Compound 132 was a white solid, obtained at 60% yield. Identity of compounds was verified by $^1$H NMR (400 MHz, $CD_3OD$ for 127; 300 MHz, DMSO-$d_6$ for 128 and 132).

Synthesis of Cinnamyl Alcohols (104, 126)

Compound 101 was reduced with aluminium hydride to generate the $_{AlCl3}$ (1.33 g, 4-hydroxycinnamyl alcohol 104. A cold solution of 10 mmol) in anhydrous diethyl ether (25 mL) was added dropwise to an ice-cold stirred suspension of $LiAlH_4$ (1.33 g, 35 mmol) in anhydrous diethyl ether (25 mL). After completion of the addition, the mixture was allowed to warm to ambient temperature, with stirring for 30 min, resulting in a grey suspension. To this grey suspension was added dropwise a solution of methyl cinnamate (10 mmol) dissolved in anhydrous diethyl ether (25 mL) within 10 min, and the reaction mixture was stirred at room temperature for 1 h. The reaction mixture was cooled with an ice bath, and carefully treated with EtOAc (50 mL) and 1 N HCl solution (100 mL). The resulting mixture was extracted with EtOAc (3×50 mL). The combined extracts were washed with $H_2O$ (50 mL) and brine (50 mL), and dried (anhydrous $Na_2SO_4$). The solvent was evaporated to dryness, and the crude products were purified by flash silica gel chromatography (eluting with 20-50% hexane in EtOAc) to afford the cinnamyl alcohol. Compound 104 was a yellow solid, obtained at: 43% yield. Compound 126 was a white solid, obtained at 79% yield. Identity of compounds was verified by $^1$H NMR (75 MHz, $CD_3OD$ for 104; 400 MHz, $CDCl_3$ for 126).

Synthesis of Preparing Cinnamamide (102)

PCA was converted into its methyl ester 101 by refluxing in methanol in the presence of sulfonic acid. Compound 101 was transformed to amide 102 by reacting with ammonia. A solution of methyl cinnamate (28 mmol) and 7 M ammonia in MeOH (30 mL) was sealed in a 100 mL thick-wall round bottom flashed, and heated at 90° C. with stirring for 72 h, resulting in a brown solution. After the solvent was removed by a rotary evaporator, the crude products were purified by flash silica gel chromatography (eluting with 2-10% MeOH in DCM) to afford cinnamamide. Compound 102 was a yellow solid, obtained at 30% yield. Identity was confirmed by $^1$H NMR (300 MHz, $CD_3OD$).

Synthesis of 2-arylcyclopropane-1-Carboxylic Acids (100, 105, 106, 107)

Compounds 100, 105, 107, and 106 were synthesized under the Corey-Chaykovsky cyclopropanation reaction conditions (TMSOI, NaH, DMSO). A mixture of trans-4-methoxycinnamic acid (18 g, 101 mmol) and concentrated $H_2SO_4$ (0.5 mL) in absolute EtOH (100 mL) was refluxed at 90° C. (bath temperature) for 16 h. After the excess EtOH was removed by a rotary evaporator, the residue was treated with $H_2O$ (100 mL), and the resulting mixture was extracted with ether (3×120 mL). The combined extracts were washed with 1N aq. NaOH (2×50 mL), $H_2O$ (80 mL) and brine (80 mL), and dried (anhydrous $Na_2SO_4$). The solvent was evaporated to dryness to give ethyl trans-4-methoxycinnamate (20 g, 96% yield) as light yellow oil.

To a mixture of trimethylsulfoxonium iodide (TMSOI) (22 g, 100 mmol, 2.6 eq) and 60% NaH (4 g, 100 mmol, 2.6 eq) was added anhydrous DMSO (120 mL) in one portion at room temperature, and the mixture was stirred at room temperature under nitrogen for 1.5 h. A solution of trans-4-methoxycinnamate (7.91 g, 38.4 mmol) in anhydrous DMSO (40 mL) was added dropwise within 10 min to the resulting suspension at room temperature, and the whole mixture was stirred at room temperature for 18 h. The reaction mixture was cooled with an ice bath, and quenched with brine (250 mL). The resulting mixture was extracted with ether (5×100 mL), washed with brine (2×60 mL), and dried. The solvent was evaporated by a rotary evaporator to dryness, and the crude product was purified by flash column chromatography (eluting with 2-10% EtOAc in hexane) to afford 100 (1.6 g, 19% yield) as white solid. Identity was verified by $^1$H NMR (300 MHz, $CDCl_3$).

Lithium hydroxide monohydrate (252 mg, 6 mmol) was added to a solution of 100 (440 mg, 2 mmol) dissolved in THF/$H_2O$ (1:1, 20 mL), and the mixture was stirred at room temperature for 16 h. After most of the THF was removed by a rotary evaporator, the aqueous residue was acidified to pH=1-2 with 1 N HCl (20 mL). The resulting white suspension was extracted with EtOAc (2×50 mL). The combined organic layers were washed with $H_2O$ (30 mL) and brine (40 mL), and dried (anhydrous $Na_2SO_4$). The solvents were evaporated with rotary evaporator to dryness, and the crude product (400 mg) was recrystallized from hexane/EtOAc in a −20° C. freezer to afford 105 (320 mg, 83% yield) as white solid. Identity was confirmed by $^1$H NMR (300 MHz, CD$_3$OD).

A solution of 100 (880 mg, 4 mmol) dissolved in anhydrous DCM (20 mL) was chilled to −78° C. with a dry ice/acetone bath, and 1 M BBr$_3$ DCM (6 mL, 6 mmol) was added dropwise within 6 min. The reaction mixture was stirred at −78° C. for 30° C., at 0° C. for additional 1 h, then allowed to warm to ambient temperature, and with stirring for additional 30 min. The reaction mixture was rechilled to 0° C. with an ice bath, and treated with saturated NaHCO$_3$ (40 mL). The resulting mixture was extracted with DCM (3×50 mL), washed with H$_2$O (40 mL) and brine (40 mL), and dried. The solvent was evaporated by a rotary evaporator to dryness, and the crude product was purified by flash column chromatography (eluting with 10-20% EtOAc in hexane) to afford 106 (480 mg, 58% yield) as white solid.

The double bond of PCA was replaced with a cyclopropanyl group, resulting in the cyclopropanic acid 107. Lithium hydroxide monohydrate (326 mg, 7.8 mmol) was added to a solution of 106 (320 mg, 1.5 mmol) dissolved in THF/H$_2$O (1:1, 16 mL), and the mixture was stirred at room temperature for 20 h. After most of the THF was removed by a rotary evaporator, the aqueous residue was acidified to pH=1-2 with 1 N HCl (20 mL). The resulting white suspension was extracted with EtOAc (2×50 mL). The combined organic layers were washed with brine (40 mL), and dried (anhydrous Na$_2$SO$_4$). The solvents were evaporated with rotary evaporator to dryness, and the crude product (320 mg) was recrystallized from hexane/EtOAc in a −20° C. freezer to afford 107 (150 mg, 56% yield) as white solid. Identity was confirmed by $^1$H NMR (300 MHz, CD$_3$OD).

Synthesis of Vinyl Phosphoric Acid (114, 115)

A mixture of diethylphosphonoacetic acid (1.96 g, 10 mmol), 4-hydroxybenzaldehyde (1.46 g, 12 mmol, 1.2 equiv), piperidine (0.23 g, 2.7 mmol, 0.27 equiv) and AcOH (0.12 g, 2 mmol, 0.2 equiv) in toluene (60 mL) was heated at reflux for 19 h. After the solvent was removed by a rotary evaporator, the residue was taken up in DCM (200 mL), washed with saturated NaHCO$_3$ solution (2×50 mL), H$_2$O (50 mL) and brine (50 mL), and dried. Evaporation of the solvent under reduced pressure afforded the crude product, which was purified by flash silica gel column chromatography (eluting with 2-8% MeOH in DCM) to give pure vinylphosphonate 114 (2 g, 78% yield) as yellow oil.

The carboxyl group of PCA was replaced with phosphoric group, resulting in 2-(4-hydroxyphenyl)vinylphosphoric acid 115. Compound 115 was prepared by Knoevenagel reaction of 4-hydroxybenzaldehyde with diethylphosphonoacetic acid and followed by treating with trimethylsilyl bromide. Bromotrimethylsilane (2 mL) was added to a solution of 114 (760 mg, 3 mmol) in anhydrous DCM (12 mL), and the mixture was refluxed at 45° C. for 16 h, resulting in a brown solution. After the excess bromotrimethylsilane were evaporated to dryness under the reduced pressure, the oily residue was dissolved in DCM (5 mL) and H$_2$O (5 mL), and stirred at room temperature for 2 h. The resulting white suspension was filtered off, and the solid was washed with DCM (2×10 mL), and air-dried. 115 (370 mg, 61% yield) was collected as off-white solid. Identity was confirmed by $^1$H NMR (400 MHz, CD$_3$OD).

Synthesis of Cinnamyl Amines (117, 119)

To a stirred mixture of phthalimide potassium salt (20 g, 108 mmol) and tetrabutylammonium bromide (1.04 g, 3.24 mmol, 0.03 equiv) in anhydrous DMF (75 mL) was added allyl chloride (8.84 mL, 108 mmol) at room temperature, and the mixture was stirred at room temperature for 22 h, resulting in a light-yellow suspension. The reaction was quenched by adding cold H$_2$O (150 mL), and the mixture was stirred for 10 min (an ice bath was applied during this time to aid the precipitation). The resulting white suspension was filtered off, washed with H$_2$O (3×50 mL), and air-dried to give N-allylphthalimide (8.5 g, 42% yield) as white solid.

Aryl bromide (10 mmol), N-allylphthalimide (1.93 g, 10.3 mol, 1.03 equiv) and triethylamine (2.78 mL, 20 mmol, 2 equiv) were placed in a 50 mL three-necked round bottom flask, palladium acetate (23 mg, 0.1 mmol, 0.01 equiv) and tri-O-tolylphosphine (61 mg, 0.2 mmol, 0.02 equiv) were added to the flask under the flash of argon, and the whole mixture was heated at 100° C. (bath temperature) under argon and with stirring for 16 h. After the reaction mixture was cooled to ambient temperature, DCM (50 mL) and H$_2$O (50 mL) were added, and stirred at room temperature for 10 min. The DCM layer was separated, and the aqueous layer was extracted with DCM (2×50 mL). The combined DCM layers were washed with H$_2$O (50 mL) and brine (50 mL), and dried. The solvent was evaporated by a rotary evaporator to dryness, and the crude product was purified by flash column chromatography (eluting with 30-80% EtOAc in hexane) to afford N-cinnamyl phthalimide (116 or 118).

N-cinnamyl phthalimide (3 mmol) was mixed with 65% hydrazine hydrate (6 mmol, 2 equiv) and MeOH (10 mL), and the mixture was heated at 70° C. for 2 h. After the solvent was removed by a rotary evaporator, the solid residue was treated with 1 N NaOH (30 mL), and the resulting mixture was extracted with EtOAc (4×50 mL) and dried. Evaporation of the solvent under reduced pressure afforded the crude product, which was purified by flash silica gel column chromatography (eluting with 5-20% MeOH in DCM) to give cinnamyl amine. Compound 117 (white solid) was obtained at 30% yield, and compound 119 (off-white solid) was obtained at 80% yield. Identity was confirmed by $^1$H NMR (400 MHz, CD$_3$OD).

Synthesis of Ethyl Vinylsulphonates and Tetrabutylammonium Vinylsulphonates (120, 121, 122, 123)

The carboxyl group of PCA was replaced with sulfonic group, resulting in 2-(4-hydroxyphenyl)ethenylsulfonic acid 123. Compound 123 and its derivatives 114, 120, 121, and 122 were synthesized by four-step from the corresponding benzaldehydes. To a stirred solution of ethyl methanesulphonate (4.11 mL, 40 mmol) in dry THF (100 mL) was added dropwise at −78° C. 2.5 M n-BuLi in hexane (17.8 mL, 44.4 mmol) within 10 min. After the mixture was stirred for 15 min, ethyl chlorophosphate (3.2 mL, 22.2 mmol) was added slowly at the same temperature. The solution was stirred at −78° C. for 30 min, then allowed to warm to −45° C. and with stirring for additional 1 h. The reaction was quenched by adding 4.4 M NH$_4$Cl solution (11 mL), and the mixture was warmed to ambient temperature. After the organic solvents were removed by a rotary evaporator, the residue was treated with H$_2$O (50 mL), and extracted with DCM (3×70 mL), washed with brine (40 mL) and dried. Evaporation of the solvent under reduced pressure afforded the crude product, which was purified by flash silica gel column chromatography (eluting with 30-100% EtOAc in hexane) to give ethyl diethylphosphorylmethanesulphonate (4.6 g, 80% yield) as light-yellow oil.

2.5 M n-BuLi hexane solution (3.36 mL, 8.4 mmol) was added dropwise to a stirred solution of ethyl diethylphosphorylmethanesulphonate (2.19 g, 8.4 mmol) in anhydrous THF (20 mL) at −78° C., and stirred at the same temperature for 30 min. A solution of aryl aldehyde (7 mmol) dissolved in anhydrous THF (15 mL) was added dropwise, and the mixture was stirred at −78° C. for 30 min, then allowed to warm to ambient temperature within 30 min, and the stirring was continued at rt for additional 1 h (18 h for 122). After the reaction was quenched by adding AcOH (0.53 mL, 9.2 mmol, 1.1 equiv to n-BuLi), the solvents were removed by a rotary evaporator. The oily residue was treated with $H_2O$ (50 mL), extracted with EtOAc (3×50 mL), washed with $H_2O$ (50 mL) and brine (50 mL), and dried. The crude product was purified by flash silica gel column chromatography (eluting with 10-50% EtOAc in hexane) to give ethyl vinylsulphonates. Compound 120 (light-yellow oil) was obtained at 100% yield and its identity verified by $^1H$ NMR (300 MHz, $CD_3OD$). Compound 122 (white solid) was obtained at 71% yield and its identity verified by $^1H$ NMR (300 MHz, $CD_3OD$).

A mixture of ethyl vinylsulphonates (2 mmol) and tetrabutylammonium bromide (2.2 mmol, 1.2 equiv) in acetone (12 mL) was refluxed for 21 h. After acetone was removed by a rotary evaporator, the residue was dissolved in DCM (100 mL), washed with $H_2O$ (30 mL) and brine (30 mL), and dried. The crude product was purified by flash silica gel column chromatography (eluting with 5-10% MeOH in DCM) to give tetrabutylammonium vinylsulphonates. Compound 121 (white solid) was obtained at 85% yield and its identity verified by $^1H$ NMR (300 MHz, $CD_3OD$). Compound 123 (white solid) was obtained at 40% yield and its identity verified by $^1H$ NMR (300 MHz, $CD_3OD$).

Synthesis of 4-hydroxymethylcinnamic Acid (124)

The hydroxyl group of PCA was replaced by hydroxymethyl group, resulting in compound 4-hydroxymethylcinnamic acid 124. Compound 124 was obtained by reducing 4-formylcinnamic acid with sodium borohydride in aqueous tetrahedron.

A solution of $NaBH_4$ (0.53 g, 14 mmol) in $THF/H_2O$ (4:1) (12 mL) was added dropwise to an ice-cold stirred solution of 4-formylcinnamic acid (2.47 g, 14 mmol) in THF (25 mL), and the mixture was stirred at room temperature for 3 h. The reaction was quenched by adding 4 N HCl (20 mL), and the THF was removed by a rotary evaporator. The solid residue was treated with $H_2O$ (20 mL), and extracted with EtOAc (4×50 mL). The EtOAc extracts were washed with $H_2O$ (50 mL) and brine (50 mL), and dried. The crude product was recrystallized from EtOAc to afford pure 4-hydroxymethylcinnamic acid 124 (1.3 g, 52% yield) as yellow solid, with its identity verified by $^1H$ NMR (300 MHz, $CD_3OD$).

Synthesis of trans-3-(4-hydroxyphenyl)-2-propenohydrazide (133)

To a stirred solution of p-coumaric acid (3.28 g, 20 mmol) in anhydrous acetonitrile (40 mL) was added HOBt (3.24 g, 24 mmol) and EDC.HCl (4.6 g, 24 mmol) at room temperature, and the mixture was stirred at room temperature for 2 h. The resulting yellow suspension was cooled with an ice-bath, and an ice-cold solution of hydrazine (1.25 mL, 40 mmol) and cyclohexene (0.61 mL, 6 mmol) in acetonitrile (30 mL) was added in one portion. The mixture was stirred at 0° C. for 20 min and followed by an additional 1 h at room temperature. The resulting yellow suspension was filtered off, and the solid was washed with MeOH (3×30 mL), $H_2O$ (2×30 mL), saturated $NaHCO_3$ (2×30 mL), $H_2O$ (2×20 mL) and EtOAc (2×20 mL) successively, and finally air-dried, obtaining 133 (1.3 g, 36% yield), with its identity verified by $^1H$ NMR (300 MHz, DMSO-$d_6$).

Commercially Available Compounds

Compound III, with the hydroxyl group of PCA replaced by bromo in the phenyl ring, was commercially available (Sigma-Aldrich, St. Louis, Mo.). Compounds 108, 110, 112 and 113, had the hydroxyl group substituted by phenyl, fluoro, dimethylamino, and trifluoromethyl groups respectively, and were commercially available (Sigma-Aldrich, St. Louis, Mo.; Alfa Aesar, Ward Hill, Mass.). Compound 109 was also commercially available (Alfa Aesar, Ward Hill, MA).

Example 12

Activity of Compounds phrpA Reporter Plasmid

The minimal inhibitory concentration of the compounds on hrpA was measured by supplement compounds at various concentrations, and the reporter plasmid phrpA was used to measure the effects of these compounds on hrpA expression. Compounds 101, 102, 104, 105, 106, 113, 116, 125, 126, and 127 showed inhibitory effect on hrpA expression at a concentration of 100 µM. Compound 103 showed inhibitory effect on hrpA expression at a concentration of 10 µM.

To test for an inhibitory effect on T3SS hrpS expression, the reporter plasmid phrpS was used to measure the effects of these compounds on hrpA expression. Compounds 103, 104, 106, 111, 125, 126, and 127 inhibited hrpS, suggesting that these compounds also inhibit T3SS through HrpX/Y-HrpS-HrpL pathway.

hrpA encodes the T3SS pilus required for protein translocation into plant cells. To test for an inhibitory effect on T3SS hrpA expression, the reporter plasmid phrpA was used to measure the effects of these compounds on hrpA expression. The reporter plasmid phrpA encodes a transcriptional fusion of the hrpA promoter controlling expression of green fluorescent protein (gfp). 50 µL of bacterial suspension of D. dadantii 3937 carrying the hrpA reporter (optical density at 600 nm $OD_{600}$=1.0) was used as the initial inoculum and added to 5 mL of MM or MM supplemented with 100 µM of one of the compounds. The expression level of hrpA of these bacterial cells was measured by measuring GFP intensity of gated populations of the bacterial cells by flow cytometry and analyzed with Cell Quest software (BD Biosciences, San Jose, Calif.). The fluorescence intensities were an average GFP fluorescence intensity of total bacterial cells. Compounds were assayed two different times (12 and 24 h of bacterial growth) with T3SS minimal media (MM) as the control treatment for each set of experiment. Results are shown in Table 13 and Table 14. Values presented in Table 14 are mean fluorescence intensity of GFP, representative of two experiments, presented as the average of three replicates with standard deviation (SD). Briefly, 101, 103, 104, 106, 111, 112, 116, 125, 126, and 127 showed inhibitory effect on the expression of hrpA. Compound 103 was examined further at various concentrations, with results presented in FIG. 22.

Compound 124 did not show any inhibitory activity (data not shown).

Compound 111 exhibited moderate potency (Table 13).

Compounds 108, 110, 112 and 113 were all inactive for inhibition of T3SS gene expression.

Compound 107 demonstrated no inhibitory activity against T3SS gene expression (data not shown). However, its ethyl ester 106 showed strong inhibitory potency (Table 13).

Compounds 115 and 123, as well as their derivatives 114, 120, 121, and 122, did not exhibit any activity against T3SS gene expression (data not shown).

Compound 101 showed weak inhibitory activity comparing to PCA (data not shown). However, 102 did not show any inhibitory activity against T3SS gene expression (data not shown).

No inhibitory effect on hrpA was observed when 10 µM of PCA was added to a T3SS-inducing minimal medium (MM). However, the expression of hrpA was reduced approximately 4-fold when 10 μM of 103 was added to the medium, suggesting that 103 is a more potent inhibitor than PCA. Compared with PCA, a higher potent inhibitory activity was observed with 103 against T3SS gene (data not shown).

Compound 125 still showed potent inhibitory activity against T3SS gene (Table 13).

Compound 127 showed moderate potency.

Compound 104 showed potent inhibitory activity. Similarly, allylic alcohol 126 was also a potent inhibitor of T3SS gene expression.

Allylic amines 117 and 119 did not show any inhibitory activity.

Compound 116 exhibited moderated inhibitory activity.

The results demonstrated the potential of PCA hydroxamates and allylic alcohols as potent inhibitors of T3SS gene expression.

TABLE 13

The eight compounds listed below showed inhibitory effect on T3SS hrpA expression, using the reporter plasmid, phrpA.

| Phenolic compound | Mean Fluorescence Intensity of GFP |
|---|---|
| (Trial 1) | |
| MM[a] | 30.5 ± 0.7 |
| p-coumaric acid | 9.4 ± 0.1 |
| 103 | 9.3 ± 0.3 |
| 104 | 6.0 ± 1.4 |
| 106 | 9.4 ± 0.1 |
| 111 | 16.5 ± 0.8 |
| Phenolic compound | |
| (Trail 2) | |
| MM[a] | 68.3 ± 5.2 |
| p-coumaric acid | 9.3 ± 0.2 |
| 116 | 27.0 ± 2.1 |
| 125 | 25.9 ± 1.0 |
| 126 | 9.5 ± 0.7 |
| 127 | 26.2 ± 2.6 |

[a]T3SS-inducing minimal medium (MM) and MM supplemented with different compounds at 100 μM repectively.

TABLE 14

The hrpA expression of D. dadantii 3937 in MM and MM supplemented with different isomers and analogs of PCA, TCA, and OCA.

| Phenolic compound[a] | 12 h[b] | 24 h |
|---|---|---|
| MM | 35.4 ± 0.8 | 90.6 ± 11.7 |
| 100 | 45.3 ± 3.4* | 119.1 ± 22.1 |
| 101 | 17.5 ± 0.7* | 19.9 ± 0.5* |
| 102 | 21.1 ± 1.2* | 60.8 ± 10.6 |
| 103 | 8.7 ± 0.3* | 11.9 ± 0.8* |
| 104 | 3.0 ± 0.1* | 12.9 ± 1.8* |
| 105 | 22.9 ± 2.6* | 82.4 ± 5.8 |
| 106 | 10.5 ± 0.8* | 49.4 ± 4.1* |
| 107 | 45.9 ± 2.7* | 122.1 ± 17.9 |
| 108 | 31.6 ± 2.5 | 109.0 ± 19.8 |
| 109 | 35.7 ± 6.3 | 81.5 ± 3.8 |
| 110 | 63.4 ± 8.0* | 183.8 ± 19.2* |
| 111 | 23.9 ± 5.2 | 54.7 ± 7.2 |
| 112 | 23.8 ± 4.3 | 60.7 ± 6.4 |
| 113 | 24.4 ± 0.9* | 68.5 ± 5.7 |
| MM-pAT | 2.0 ± 0.0* | 3.4 ± 0.3* |
| MM | 51.4 ± 6.7 | 77.1 ± 9.1 |
| 114 | 55.4 ± 1.0 | 76.5 ± 5.6 |
| 115 | 57.9 ± 1.6 | 79.6 ± 3.3 |
| 116 | 24.3 ± 1.5* | 39.3 ± 3.5* |
| 117 | 49.8 ± 1.6 | 73.1 ± 2.0 |
| 118 | 59.0 ± 0.4 | 83.8 ± 1.7 |
| 119 | 47.8 ± 3.2 | 68.2 ± 10.4 |
| 120 | 49.9 ± 2.6 | 68.6 ± 6.0 |
| 121 | 57.1 ± 10.0 | 72.2 ± 10.6 |
| 122 | 38.6 ± 1.8 | 60.9 ± 0.8 |
| 123 | 52.3 ± 2.0 | 77.7 ± 6.8 |
| 124 | 44.9 ± 3.5 | 78.1 ± 3.4 |
| 125 | 17.4 ± 0.9* | 25.6 ± 2.0* |
| 126 | 7.8 ± 0.2* | 13.4 ± 0.3* |
| 127 | 21.0 ± 3.0* | 35.1 ± 3.0* |

*Means statistically significant different in GFP intensity between bacterial cells grown in MM and MM supplemented with different compounds (P < 0.01, Student's t-test)

Northern Blot Analysis

Figure 23:
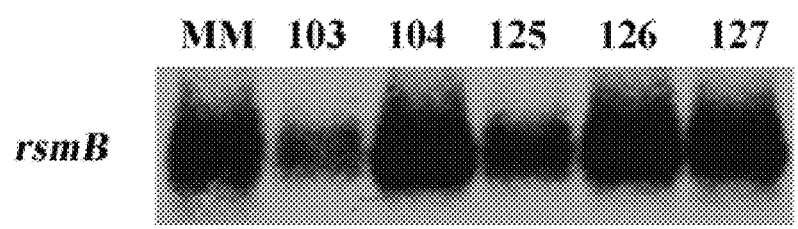
FIG. 23 shows a Northern blot for rsmB RNA of bacterial cells cultured in media supplemented with compound 103.

Northern blot analysis was used to quantify rsmB RNA of D. dadanti 3937. As shown in FIG. 23, T3SS inhibitors 103 and 125 reduced rsmB mRNA and inhibited regulatory RNA rsmB expression in the bacterial cells. These results suggested 103 and 125 inhibited T3SS through HrpX/Y-HrpS-HrpL and GacS/A-rsmB-HrpL pathways as well.

Expression of Other Genes in the Presence of Compound 103

The effect of compound 103 on the expression of other T3SS genes hrpA, hrpN, hrpS and hrpL of Dickeya dadantii 3937, shown in Table 15, was examined. The GFP reporter plasmids phrpA, phrpN, phrpS, and phrpL were used to measure the effects of these compounds on the expression of hrpA, hrpN, hrpS, and hrpL. The promoter activities were compared at 12 and 24 h of bacterial growth in the presence of compound 103. GFP intensity was determined on gated populations of bacterial cells by flow cytometry. Results are shown in Table 16. The fluorescence intensities were an average GFP fluorescence intensity of total bacterial cells. Values presented in Table 16 are mean fluorescence intensity values, representative of two experiments, and presented as the average of three replicates with standard deviation (SD).

TABLE 15

Strains and plasmids used

| Strains, plasmids and primers | Characters[a] | Reference or source |
|---|---|---|
| Strains | | |
| D. dadantii | | |
| 3937 | Wild type, Saintpaulia (African violet) isolate | Hugouvieux-Cotte-Pattat, N. |
| 3937 (pAT) | 3937 containing pPROBE-AT | Peng et al., 2006(14) |
| 3937 (phrpA) | 3937 containing phrpA; Ap[R] | Yang et al., 2008(22) |
| 3937 (phrpN) | 3937 containing phrpN; Ap[R] | Yang et al., 2007(23) |

TABLE 15-continued

Strains and plasmids used

| Strains, plasmids and primers | Characters[a] | Reference or source |
|---|---|---|
| 3937 (phrpL) | 3937 containing phrpL; Ap[R] | Yang et al., 2007(23) |
| 3937 (phrpS) | 3937 containing phrpS; Ap[R] | |
| 3937 (pmrp) | 3937 containing pmrp; Ap[R] | Peng et al., 2006(14) |
| Plasmid | | |
| pPROBE-AT | Promoter-probe vector, Ap[R] | Miller et al., 2000(11) |
| phrpA | pProbe-AT derivative with PCR fragment containing hrpA promoter region, Ap[R] | Yang et al., 2008(22) |
| phrpN | pProbe-AT derivative with PCR fragment containing hrpN promoter region, Ap[R] | Yang et al., 2007(23) |
| phrpL | pProbe-AT derivative with PCR fragment containing hrpL promoter region, Ap[R] | Yang et al., 2007(23) |
| phrpS | pProbe-AT derivative with PCR fragment containing 709-bp hrpS promoter region, Ap[R] | This work |
| pmrp | pProbe-AT derivative with PCR fragment containing mrp promoter region, Ap[R] | Peng et al., 2006(14) |

TABLE 16

The expression of T3SS genes hrpA, hrpN, hrpS and hrpL of *Dickeya dadantii* 3937 in MM and MM supplemented with 100 μM 103 (MM103).

| | 12 h | | 24 h | |
|---|---|---|---|---|
| Gene Promoter[a] | MM | MM103 | MM | MM103 |
| 3937 (phrpA) | 58.7 ± 6.1[b] | 8.9 ± 0.7* | 66.5 ± 5.4 | 8.9 ± 0.2* |
| 3937 (phrpN) | 46.8 ± 2.9 | 5.8 ± 0.7* | 49.9 ± 2.1 | 5.4 ± 0.3* |
| 3937 (phrpS) | 73.2 ± 0.6 | 27.7 ± 1.5* | 90.9 ± 1.2 | 26.4 ± 0.6* |
| 3937 (phrpL) | 20.2 ± 1.8 | 7.6 ± 0.2* | 21.5 ± 0.5 | 7.7 ± 0.2* |
| 3937 (pmrp) | 70.6 ± 0.2 | 81.2 ± 0.7* | 80.9 ± 0.9 | 67.7 ± 2.5* |
| 3937 (pPROBE-AT) | 4.2 ± 0.5 | 3.0 ± 0.6 | 5.7 ± 1.8 | 4.3 ± 0.6 |

*Means statistically significant different in GFP intensity between bacterial cells grown in MM and MM103 (P < 0.01, Student's t-test).

Example 13

Synthesis of Compounds

Compounds were synthesized at Duke University Small Molecule Synthesis Facility (Durham, N.C.). The synthetic routes for the compounds are described below and in FIGS. 24-30.

NMR ($^1$H, $^{13}$C and $^{32}$P) spectra were measured on either a Varian Mercury 300 or Inova 400 spectrometer using TMS as the internal standard. Electrospray ionization mass spectrometry (ESI-MS) was performed on an Agilent 1100 Series LC/MSD Trap Spectrometer with a Daly conversion dynode detector. Ionization was achieved in the positive or negative ion mode by application of +5 or −5 kV at the entrance to the capillary. Thin-layer chromatography (TLC) was performed on precoated silica gel 60 $F_{254}$ plates (Merck, 0.25 mm, purchased from Sigma-Aldrich Company).

All chemical reagents were purchased from commercial sources and used as received. All dry solvents (diethyl ether, DMF, DMSO, DCM, THF, MeOH, EtOH) were of anhydrous quality purchased from Sigma-Aldrich Company. Commercial grade solvents were used for routine purposes without further purification. All moisture-sensitive reactions were carried out using dry solvents and under a slight pressure of ultra-pure quality argon. Glassware was dried in an oven at 140° C. for at least 12 h prior to use, and then assembled quickly while hot, sealed with rubber septa, and allowed to cool under a stream of argon. Reactions were stirred magnetically using Teflon-coated magnetic stirring bars. Commercially available disposable syringes were used for transferring reagents and solvents.

In FIG. 24, cinnamic acids were converted into the corresponding methyl ester. The latter were further transformed into hydroxamic acids by treating with hydroxylamine under basic condition. When the substituent in the phenyl group is halo, methyl, methoxy, or other groups which will not form amide/ester, the hydroxamic acids could be obtained directly from the corresponding carboxylic acids. By refluxing with ammonia in methanol, the corresponding amides were obtained from the methyl esters. The esters were readily reduced by $LiAlH_4/AlCl_3$ system, resulting in cinnamyl alcohols. By employing the reported procedure (Zhang et al. 2002), hydrazides were obtained from cinnamic acids by treating with HOBt and EDC followed by hydrazine.

Under the Corey-Chaykovsky cyclopropanation reaction conditions (Corey and Chaykovsky, 1965), ethyl 4-methoxycinnamate was transformed into cyclopropanyl ester (100). Upon hydrolysis, acid 105 was obtained. Demethylation of 100 with borane tribromide gave 106. The latter was further hydrolyzed with lithium hydroxide to afford the corresponding carboxylic acid 107 (FIG. 25).

Knoevenagel reaction (Krawczyk and Albrecht 2005) of 4-hydroxybenzaldehydes with diethylphosphonoacetic acid lead to the formation of diethyl trans-2-arylvinylphosphonates 114. Upon treatment with trimethylsilyl bromide (TMSBr), the phosphonate was converted into vinylphosphoric acid 115 (FIG. 26). In the similar way, other trans-2-arylvinylphosphoric acids can be obtained from the corresponding arylaldehydes.

In the presence of n-butyllithium, benzaldehyde was reacted with ethyl diethylphosphoryl-methanesulfonate to generate ethyl trans-2-arylethenylsulfonates (Niimi et al. 2001) (FIG. 27). The resulting ethyl sulfonates was cleaved with tetra-n-butylammonium iodide (n-$Bu_4NI$), affording the trans-2-arylethenylsulfonic acids.

Phthalimide potassium salt was alkylated with allyl chloride in DMF to produce N-allylphthalimide. Under the Heck reaction conditions (Patel et al. 1977), N-allylphthalimide reacted with aryl bromide to give N-cinnamyl phthalimide. Upon treatment with hydrazine, cinnamyl amine was obtained from N-cinnamyl phthalimide (FIG. 28).

General Procedure for Preparing Cinnamyl Hydroxamates

Method A: A mixture of cinnamic acid (25 mmol) and concentrated $H_2SO_4$ (0.1 ml) in anhydrous MeOH (25 ml) was refluxed at 80° C. (bath temperature) for 16 h. After the excess MeOH was removed by a rotary evaporator, the residue was treated with $H_2O$ (50 ml), and the resulting mixture was extracted with EtOAc (3×50 ml). The combined extracts were washed with $H_2O$ (50 ml) and brine (50 ml), and dried (anhydrous $Na_2SO_4$). The solvent was evaporated to dryness, and the crude products were purified by flash silica gel chromatography (eluting with 10-60% hexane in EtOAc) to afford methyl cinnamate.

To an ice-cold solution of methyl cinnamate (8 mmol) dissolved in anhydrous MeOH (10 ml) and THF (10 ml) was added hydroxylamine hydrochloride (1.67 g, 24 mmol, 3 equiv) followed by 25% sodium methoxide in methanol solution (8.4 ml, 36 mmol, 4.5 equiv). The reaction mixture was stirred under argon and at 0° C. for 2 h, then allowed to warm to ambient temperature with continuous stirring overnight (16 h). The resulting yellow suspension was condensed to dryness with a rotary evaporator, and the residue was treated with 1N HCl aqueous solution (30 ml). The mixture was extracted with EtOAc (3×50 ml), and dried (anhydrous $Na_2SO_4$). Evaporation of the solvent afforded the crude products (480 mg), which was purified by flash silica gel chromatography (eluting with 5-15% MeOH in DCM) to afford the hydroxamic acid.

103 ($R_1$=4-OH):

25% yield (based on the methyl ester); light-brown solid; $^1$H NMR (300 MHz, $CD_3OD$): δ6.28 (d, J=15.6 Hz, 1H), 6.75 (d, J=8.1 Hz, 2H), 7.38 (d, J=8.1 Hz, 2H), 7.49 (d, J=15.6 Hz, 1H); $^{13}$C NMR (75 MHz, $CD_3OD$): δ113.61, 115.58, 126.46, 129.38, 140.71, 159.40, 166.00; MS (ESI): m/z 178 (M−1).

125 ($R_1$=4-OMe):

67% yield; light-brown solid; $^1$H NMR (300 MHz, $CD_3OD$): δ3.78 (s, 3H), 6.32 (d, J=15.6 Hz, 1H), 6.89 (d, J=8.4 Hz, 2H), 7.46 (d, J=8.4 Hz, 2H), 7.50 (d, J=15.6 Hz, 1H); $^{13}$C NMR (75 MHz, $CD_3OD$): δ54.66, 114.16, 114.53, 127.57, 129.23, 140.32, 161.44, 165.75; MS (ESI): m/z 192 (M−1).

129 ($R_1$=2-OH):

21% yield; light-brown solid; $^1$H NMR (300 MHz, $CD_3OD$): δ6.64 (d, J=15.9 Hz, 1H), 6.77 (d, J=7.5 Hz, 1H), 6.81 (m, 1H), 7.13 (m, 1H), 7.40 (d, J=7.5 Hz, 1H), 7.86 (d, J=15.9 Hz, 1H); $^{13}$C NMR (75 MHz, $CD_3OD$): δ115.85, 116.84, 119.60, 121.86, 128.87, 130.81, 136.88, 156.81, 166.34; MS (ESI): m/z 178 (M−1).

130 ($R_1$=3-OH):

63% yield; off-white solid; $^1$H NMR (300 MHz, $CD_3OD$): δ6.42 (d, J=15.9 Hz, 1H), 6.81 (d, J=8.1 Hz, 1H), 6.96 (brs, 1H), 6.98 (d, J=8.1 Hz, 1H), 7.17 (m, 1H), 7.48 (d, J=15.9 Hz, 1H); $^{13}$C NMR (75 MHz, $CD_3OD$): δ113.95, 116.91, 117.00, 119.23, 129.82, 136.27, 140.80, 157.77, 165.34; MS (ESI): m/z 178 (M−1).

131 ($R_1$=3,4-diOH):

25% yield; grey solid; $^1$H NMR (300 MHz, $CD_3OD$): δ6.22 (d, J=15.6 Hz, 1H), 6.75 (d, J=8.1 Hz, 1H), 6.89 (d, J=8.1 Hz, 1H), 6.99 (brs, 1H), 7.42 (d, J=15.6 Hz, 1H); $^{13}$C NMR (75 MHz, $CD_3OD$): δ113.56, 113.80, 115.28, 120.92, 127.03, 141.06, 145.54, 147.65, 166.00; MS (ESI): m/z 194 (M−1).

132 ($R_1$=H):

71% yield; white solid; $^1$H NMR (300 MHz, DMSO-$d_6$): δ6.47 (d, J=15.6 Hz, 1H), 7.30-7.55 (m, 5H), 7.46 (d, J=15.6 Hz, 1H); $^{13}$C NMR (75 MHz, DMSO-$d_6$): δ119.74, 128.16, 129.60, 130.14, 135.49, 139.10, 163.49; MS (ESI): m/z 162 (M−1).

Method B: To a stirred mixture of cinnamic acid (7 mmol) and diisopropylethylamine (DIEA) (2.45 ml, 17 mmol) in anhydrous DMF (20 ml) was added HBTU (2.92 g, 7.7 mmol) at room temperature, followed by adding a solution of hydroxylamine hydrochloride (0.98 g, 14 mmol) and DBU (2.13 g, 14 mmol) in anhydrous DMF (8 ml), and then the whole reaction mixture was stirred at room temperature for 1 h. After most of the DMF was removed with a rotary evaporator, the residue was dissolved in EtOAc (150 ml), then washed with $H_2O$ (50 ml) and brine (50 ml), and dried (anhydrous $Na_2SO_4$). Evaporation of the solvent afforded the crude products, which was purified by flash silica gel chromatography (eluting with 5-15% MeOH in DCM) to afford the hydroxamic acid.

127 ($R_1$—Ar=3-indole)

35% yield; yellow solid; $^1$H NMR (400 MHz, $CD_3OD$): δ6.46 (d, J=15.6 Hz, 1H), 7.16-7.23 (m, 3H), 7.44 (d, J=7.5 Hz, 1H), 7.59 (s, 1H), 7.82 (d, J=15.6 Hz, 1H), 7.87 (d, J=8 Hz, 1H); MS (ESI): m/z 201 (M−1).

128 ($R_1$=4-Br):

50% yield; white solid; $^1$H NMR (300 MHz, DMSO-$d_6$): δ6.46 (d, J=15.9 Hz, 1H), 7.40 (d, J=15.9 Hz, 2H), 7.48 (d, J=8.4 Hz, 2H), 7.56 (d, J=8.4 Hz, 1H); $^{13}$C NMR (75 MHz, DMSO-$d_6$): δ120.63, 123.28, 130.12, 132.54, 134.77, 137.80, 163.18; MS (ESI): m/z 241 (M−1).

General Procedure for Cinnamyl Alcohols

Cold solution of $AlCl_3$ (1.33 g, 10 mmol) in anhydrous diethyl ether (25 ml) was added dropwise to an ice-cold stirred suspension of $LiAlH_4$ (1.33 g, 35 mmol) in anhydrous diethyl ether (25 ml). After completion of the addition, the mixture was allowed to warm to ambient temperature, with stirring for 30 min, resulting in a grey suspension. To this grey suspension was added dropwise a solution of methyl cinnamate (10 mmol) dissolved in anhydrous diethyl ether (25 ml) within 10 min, and the reaction mixture was stirred at room temperature for 1 h. The reaction mixture was cooled with an ice bath, and carefully treated with EtOAc (50 ml) and 1N HCl solution (100 ml). The resulting mixture was extracted with EtOAc (3×50 ml). The combined extracts were washed with $H_2O$ (50 ml) and brine (50 ml), and dried (anhydrous $Na_2SO_4$). The solvent was evaporated to dryness, and the crude products were purified by flash silica gel chromatography (eluting with 20-50% hexane in EtOAc) to afford the cinnamyl alcohol.

104 ($R_1$=4-OH):

43% yield; yellow solid; $^1$H NMR (300 MHz, $CD_3OD$): δ4.17 (dd, J=6.0, 1.5 Hz, 2H), 6.18 (dt, J=15.6, 6.0 Hz, 1H), 6.48 (d, J=15.6 Hz, 1H), 6.72 (d, J=8.4 Hz, 2H), 7.23 (d, J=8.4 Hz, 2H); $^{13}$C NMR (75 MHz, $CD_3OD$): δ62.80, 115.16, 125.49, 127.53, 128.83, 130.73, 157.06; MS (ESI): m/z 149 (M−1).

126 ($R_1$=4-OMe):

79% yield; white solid; $^1$H NMR (400 MHz, $CDCl_3$): δ1.78 (brs, 1H, OH), 3.79 (s, 3H), 4.27 (d, J=7.8 Hz, 2H), 6.22 (dt, J=16, 6 Hz, 1H), 6.53 (d, J=16 Hz, 1H), 6.84 (d, J=8.4 Hz, 2H), 7.30 (d, J=8.4 Hz, 2H); MS (ESI): m/z 165 (M11).

General Procedure for Preparing Cinnamamide 5:

A solution of methyl cinnamate (28 mmol) and 7M ammonia in MeOH (30 ml) was sealed in a 100 ml thick-wall round bottom flashed, and heated at 90° C. with stirring for 72 h, resulting in a brown solution. After the solvent was removed by a rotary evaporator, the crude products were purified by flash silica gel chromatography (eluting with 2-10% MeOH in DCM) to afford cinnamamide.

102 ($R_1$=4-OH):

30% yield; yellow solid; $^1$H NMR (300 MHz, $CD_3OD$): δ6.43 (d, J=15.6 Hz, 1H), 6.79 (d, J=8.7 Hz, 2H), 7.40 (d, J=8.7 Hz, 2H), 7.45 (d, J=15.6 Hz, 1H); $^{13}$C NMR (75 MHz, CD$_3$OD): δ115.58, 116.64, 126.37, 129.54, 141.80, 159.51, 170.49; MS (ESI): m/z 162 (M−1).

Procedure for Preparing trans-3-(4-hydroxyphenyl)acrylohydrazide 133

To a stirred solution of 4-hydroxycinnamic acid (3.28 g, 20 mmol) in acetonitrile (40 ml) was added HOBt (3.24 g, 24 mmol) and EDC.HCl (4.6 g, 24 mmol). The mixture was stirred at room temperature for 2 h, and the resulting yellow suspension was cooled to 0° C. by an ice bath. A ice-cold solution of hydrazine (1.25 ml, 40 mmol) and cyclohexene (0.61 ml, 6 mmol) in acetonitrile (30 ml) was added into the suspension in one portion, and the mixture was stirred at 0° C. for 20 min, then allowed to warm to ambient temperature, with the stirring continued for additional 1 h. The yellow suspension was filtered off via suction, washed the solid successively with MeOH (3×30 ml), H$_2$O (2×30 ml), saturated NaHCO$_3$ (2×30 ml), H$_2$O (2×20 ml) and EtOAc (2×20 ml), and air-dried to afford 133 (1.3 g, 36% yield) as yellow solid. $^1$H NMR (300 MHz, DMSO-d$_6$): δ4.40 (brs, 3H), 6.32 (d, J=15.9 Hz, 1H), 6.76 (d, J=8.4 Hz, 2H), 7.33 (d, J=16.2 Hz, 1H), 7.36 (d, J=8.1 Hz, 2H), 9.21 (br s, 1H); $^{13}$C NMR (75 MHz, DMSO-d$_6$): δ116.49, 117.21, 126.44, 129.83, 139.08, 159.72, 165.86; MS (ESI): m/z 179 (M+1).

General Procedure for Preparing 2-arylcyclopropane-1-carboxylic Acids

A mixture of trans-4-methoxycinnamic acid (18 g, 101 mmol) and concentrated H$_2$SO$_4$ (0.5 ml) in absolute EtOH (100 ml) was refluxed at 90° C. (bath temperature) for 16 h. After the excess EtOH was removed by a rotary evaporator, the residue was treated with H$_2$O (100 ml), and the resulting mixture was extracted with ether (3×120 ml). The combined extracts were washed with 1N aq. NaOH (2×50 ml), H$_2$O (80 ml) and brine (80 ml), and dried (anhydrous Na$_2$SO$_4$). The solvent was evaporated to dryness to give ethyl trans-4-methoxycinnamate (20 g, 96% yield) as light yellow oil, which was pure enough for the next step.

To a mixture of trimethylsulfoxonium iodide (TMSOI) (22 g, 100 mmol, 2.6 eq) and 60% NaH (4 g, 100 mmol, 2.6 eq) was added anhydrous DMSO (120 ml) in one portion at room temperature, and the mixture was stirred at room temperature under nitrogen for 1.5 h. A solution of trans-4-methoxycinnamate (7.91 g, 38.4 mmol) in anhydrous DMSO (50 ml) was added dropwise within 10 min to the resulting suspension at room temperature, and the entire mixture was stirred at room temperature for 18 h. The reaction mixture was cooled with an ice bath, and quenched with brine (250 ml). The resulting mixture was extracted with ether (5×100 ml), washed with brine (2×60 ml), and dried. The solvent was evaporated by a rotary evaporator to dryness, and the crude product was purified by flash column chromatography (eluting with 2-10% EtOAc in hexane) to afford 100 (1.6 g, 19% yield) as white solid. $^1$H NMR (300 MHz, CDCl$_3$): δ1.25 (m, 1H), 1.27 (t, J=7.2 Hz, 3H), 1.56 (m, 1H), 1.82 (m, 1H), 2.48 (m, 1H), 3.78 (s, 3H), 4.16 (q, J=7.2 Hz, 2H), 6.82 (d, J=8.4 Hz, 2H), 7.03 (d, J=8.7 Hz, 2H); $^{13}$C NMR (75 MHz, CD$_3$OD): δ14.50, 16.95, 24.09, 25.84, 55.53, 60.85, 114.13, 127.58, 132.31, 158.56, 173.77.

Lithium hydroxide monohydrate (252 mg, 6 mmol) was added to a solution of 100 (440 mg, 2 mmol) dissolved in THF/H$_2$O (1:1, 20 ml), and the mixture was stirred at room temperature for 16 h. After most of the THF was removed by a rotary evaporator, the aqueous residue was acidified to pH=1-2 with 1N HCl (20 ml). The resulting white suspension was extracted with EtOAc (2×50 ml). The combined organic layers were washed with H$_2$O (30 ml) and brine (40 ml), and dried (anhydrous Na$_2$SO$_4$). The solvents were evaporated with rotary evaporator to dryness, and the crude product (400 mg) was recrystallized from hexane/EtOAc in a −20° C. freezer to afford 105 (320 mg, 83% yield) as white solid. $^1$H NMR (300 MHz, CD$_3$OD): δ1.28 (m, 1H), 1.47 (m, 1H), 1.73 (m, 1H), 2.40 (m, 1H), 3.74 (s, 3H), 6.81 (d, J=8.7 Hz, 2H), 7.03 (d, J=8.7 Hz, 2H); $^{13}$C NMR (75 MHz, CD$_3$OD): δ15.91, 23.55, 25.51, 54.48, 113.76, 127.11, 132.12, 158.71, 176.07; MS (ESI): m/z 191 (M−1).

A solution of 100 (880 mg, 4 mmol) dissolved in anhydrous DCM (20 ml) was chilled to −78° C. with a dry ice/acetone bath, and B Br$_3$ (1M DCM solution, 6 ml, 6 mmol) was added dropwise within 6 min. The reaction mixture was stirred at −78° C. for 30° C., at 0° C. for additional 1 h, then allowed to warm to ambient temperature, and with stirring for additional 30 min. The reaction mixture was rechilled to 0° C. with an ice bath, and treated with saturated NaHCO$_3$ (40 ml). The resulting mixture was extracted with DCM (3×50 ml), washed with H$_2$O (40 ml) and brine (40 ml), and dried. The solvent was evaporated by a rotary evaporator to dryness, and the crude product was purified by flash column chromatography (eluting with 10-20% EtOAc in hexane) to afford 106 (480 mg, 58% yield) as white solid.

Lithium hydroxide monohydrate (326 mg, 7.8 mmol) was added to a solution of 106 (320 mg, 1.5 mmol) dissolved in THF/H$_2$O (1:1, 16 ml), and the mixture was stirred at room temperature for 20 h. After most of the THF was removed by a rotary evaporator, the aqueous residue was acidified to pH=1-2 with 1N HCl (20 ml). The resulting white suspension was extracted with EtOAc (2×50 ml). The combined organic layers were washed with brine (40 ml), and dried (anhydrous Na$_2$SO$_4$). The solvents were evaporated with rotary evaporator to dryness, and the crude product (320 mg) was recrystallized from hexane/EtOAc in a −20° C. freezer to afford 107 (150 mg, 56% yield) as white solid. $^1$H NMR (300 MHz, CD$_3$OD): δ1.27 (m, 1H), 1.45 (m, 1H), 1.70 (m, 1H), 2.38 (m, 1H), 6.69 (d, J=8.4 Hz, 2H), 6.94 (d, J=8.4 Hz, 2H); $^{13}$C NMR (75 MHz, CD$_3$OD): δ15.82, 23.47, 25.65, 115.09, 127.15, 130.88, 158.00, 176.21; MS (ESI): m/z 177 (M−1).

Procedure for Preparing Vinyl Phosphoric Acid 115

A mixture of diethylphosphonoacetic acid (1.96 g, 10 mmol), 4-hydroxybenzaldehyde (1.46 g, 12 mmol, 1.2 equiv), piperidine (0.23 g, 2.7 mmol, 0.27 equiv) and AcOH (0.12 g, 2 mmol, 0.2 equiv) in toluene (60 ml) was heated at reflux for 19 h. After the solvent was removed by a rotary evaporator, the residue was taken up in DCM (200 ml), washed with saturated NaHCO$_3$ solution (2×50 ml), H$_2$O (50 ml) and brine (50 ml), and dried. Evaporation of the solvent under reduced pressure afforded the crude product, which was purified by flash silica gel column chromatography (eluting with 2-8% MeOH in DCM) to give pure vinylphosphonate 114 (2 g, 78% yield) as yellow oil.

Bromotrimethylsilane (2 ml) was added to a solution of 114 (760 mg, 3 mmol) in anhydrous DCM (12 ml), and the mixture was refluxed at 45° C. for 16 h, resulting in a brown solution. After the excess bromotrimethylsilane were evaporated to dryness under the reduced pressure, the oily residue was dissolved in DCM (5 ml) and H$_2$O (5 ml), and stirred at room temperature for 2 h. The resulting white suspension was filtered off, and the solid was washed with DCM (2×10 ml), and air-dried. 115 (370 mg, 61% yield) was collected as off-white solid. $^1$H NMR (400 MHz, CD$_3$OD): δ6.20 (t, J=17.6 Hz, 1H), 6.77 (d, J=8.4 Hz, 1H), 7.27 (dd, J=22.8, 17.6 Hz, 1H), 7.36 (d, J=8.4 Hz, 2H); $^{13}$C NMR (100 MHz, CD$_3$OD): δ112.7 (d, J=188.9 Hz), 115.26, 126.75 (d, J=22.7 Hz), 128.88, 145.46 (d, J=5.9 Hz), 159.17; $^{32}$P NMR (CD$_3$OD): δ18.07; MS (ESI): m/z 399 (2M−1).

General Procedure for Preparing Ethyl Vinylsulphonates and Tetrabutylammonium Vinylsulphonates To a stirred solution of ethyl methanesulphonate (4.11 ml, 40 mmol) in dry THF (100 ml) was added dropwise at −78° C. 2.5 M n-BuLi in hexane (17.8 ml. 44.4 mmol) within 10 min. After the mixture was stirred for 15 min, ethyl chlorophosphate (3.2 ml, 22.2 mmol) was added slowly at the same temperature. The solution was stirred at −78° C. for 30 min, then allowed to warm to −45° C. and with stirring for additional 1 h. The reaction was quenched by adding 4.4 M $NH_4Cl$ solution (11 ml), and the mixture was warmed to ambient temperature. After the organic solvents were removed by a rotary evaporator, the residue was treated with $H_2O$ (50 ml), and extracted with DCM (3×70 ml), washed with brine (40 ml) and dried. Evaporation of the solvent under reduced pressure afforded the crude product, which was purified by flash silica gel column chromatography (eluting with 30-100% EtOAc in hexane) to give ethyl diethylphosphorylmethanesulphonate (4.6 g, 80% yield) as light-yellow oil.

2.5 M n-BuLi hexane solution (3.36 ml, 8.4 mmol) was added dropwise to a stirred solution of ethyl diethylphosphorylmethanesulphonate (2.19 g, 8.4 mmol) in anhydrous THF (20 ml) at −78° C., and stirred at the same temperature for 30 min. A solution of aryl aldehyde (7 mmol) dissolved in anhydrous THF (15 ml) was added dropwise, and the mixture was stirred at −78° C. for 30 min, then allowed to warm to ambient temperature within 30 min, and the stirring was continued at room temperature for additional 1 h (18 h for 122). After the reaction was quenched by adding AcOH (0.53 ml, 9.2 mmol, 1.1 equiv to n-BuLi), the solvents were removed by a rotary evaporator. The oily residue was treated with $H_2O$ (50 ml), extracted with EtOAc (3×50 ml), washed with $H_2O$ (50 ml) and brine (50 ml), and dried. The crude product was purified by flash silica gel column chromatography (eluting with 10-50% EtOAc in hexane) to give ethyl vinylsulphonates.

120 (R=4-OMe):

100% yield; light-yellow oil; $^1$H NMR (300 MHz, $CD_3OD$): δ1.34 (t, J=7.2 Hz, 3H), 3.82 (s, 3H), 4.17 (q, J=7.2 Hz, 2H), 6.88 (d, J=15.3 Hz, 1H), 6.96 (d, J=8.7 Hz, 2H), 7.52 (d, J=15.3 Hz, 1H), 7.58 (d, J=8.7 Hz, 2H); $^{13}$C NMR (75 MHz, $CD_3OD$): δ14.05, 54.78, 66.79, 114.42, 118.60, 125.02, 130.48, 144.54, 162.63; MS (ESI): m/z 243 (M+1).

122 (R=4-OH):

71% yield; white solid; $^1$H NMR (300 MHz, $CD_3OD$): δ1.33 (t, J=7.2 Hz, 3H), 4.16 (q, J=7.2 Hz, 2H), 6.81 (d, J=8.7 Hz, 2H), 6.82 (d, J=15.6 Hz, 1H), 7.48 (d, J=15.6 Hz, 1H), 7.49 (d, J=8.7 Hz, 2H); MS (ESI): m/z 227 (M−1).

A mixture of ethyl vinylsulphonates (2 mmol) and tetrabutylammonium bromide (2.2 mmol, 1.2 equiv) in acetone (12 ml) was refluxed for 21 h. After acetone was removed by a rotary evaporator, the residue was dissolved in DCM (100 ml), washed with $H_2O$ (30 ml) and brine (30 ml), and dried. The crude product was purified by flash silica gel column chromatography (eluting with 5-10% MeOH in DCM) to give tetrabutylammonium vinylsulphonates.

121 (R=4-OMe):

85% yield; white solid; $^1$H NMR (300 MHz, $CD_3OD$): δ1.01 (t, J=7.2 Hz, 12H), 1.39-1.72 (m, 16H), 3.25 (m, 8H), 3.80 (s, 3H), 6.80 (d, J=15.6 Hz, 1H), 6.92 (d, J=8.7 Hz, 2H), 7.20 (d, J=15.6 Hz, 1H), 7.43 (d, J=8.7 Hz, 2H); MS (ESI): m/z 213 (M−1).

123 (R=4-H):

40% yield; white solid; $^1$H NMR (300 MHz, $CD_3OD$): δ1.00 (t, J=7.2 Hz, 12H), 1.38-1.68 (m, 16H), 3.25 (m, 8H), 6.74 (d, J=15.6 Hz, 1H), 6.77 (d, J=8.7 Hz, 2H), 7.16 (d, J=15.6 Hz, 1H), 7.33 (d, J=8.7 Hz, 2H); MS (ESI): m/z 199 (M−1).

General Procedure for Preparing Cinnamyl Amines

To a stirred mixture of phthalimide potassium salt (20 g, 108 mmol) and tetrabutylammonium bromide (1.04 g, 3.24 mmol, 0.03 equiv) in anhydrous DMF (75 ml) was added allyl chloride (8.84 ml, 108 mmol) at room temperature, and the mixture was stirred at room temperature for 22 h, resulting in a light-yellow suspension. The reaction was quenched by adding cold $H_2O$ (150 ml), and the mixture was stirred for 10 min (an ice bath was applied during this time to aid the precipitation). The resulting white suspension was filtered off, washed with $H_2O$ (3×50 ml), and air-dried to give N-allylphthalimide (8.5 g, 42% yield) as white solid.

Aryl bromide (10 mmol), N-allylphthalimide (1.93 g, 10.3 mol, 1.03 equiv) and triethylamine (2.78 ml, 20 mmol, 2 equiv) were placed in a 50 ml three-necked round bottom flask, palladium acetate (23 mg, 0.1 mmol, 0.01 equiv) and tri-O-tolylphosphine (61 mg, 0.2 mmol, 0.02 equiv) were added to the flask under the flash of argon, and the whole mixture was heated at 100° C. (bath temperature) under argon and with stirring for 16 h. After the reaction mixture was cooled to ambient temperature, DCM (50 ml) and $H_2O$ (50 ml) were added, and stirred at room temperature for 10 min. The DCM layer was separated, and the aqueous layer was extracted with DCM (2×50 ml). The combined DCM layers were washed with $H_2O$ (50 ml) and brine (50 ml), and dried. The solvent was evaporated by a rotary evaporator to dryness, and the crude product was purified by flash column chromatography (eluting with 30-80% EtOAc in hexane) to afford N-cinnamyl phthalimide.

N-cinnamyl phthalimide (3 mmol) was mixed with 65% hydrazine hydrate (6 mmol, 2 equiv) and MeOH (10 ml), and the mixture was heated at 70° C. for 2 h. After the solvent was removed by a rotary evaporator, the solid residue was treated with 1N NaOH (30 ml), and the resulting mixture was extracted with EtOAc (4×50 ml) and dried. Evaporation of the solvent under reduced pressure afforded the crude product, which was purified by flash silica gel column chromatography (eluting with 5-20% MeOH in DCM) to give cinnamyl amine.

117 (R=4-OH):

30% yield; white solid; $^1$H NMR (400 MHz, $CD_3OD$): δ3.34 (d, J=6.0 Hz, 2H), 6.20 (dt, J=15.6, 6.0 Hz, 1H), 6.43 (d, J=15.6 Hz, 1H), 6.69 (d, J=8.8 Hz, 2H), 7.19 (d, J=8.4 Hz, 1H); $^{13}$C NMR (100 MHz, $CD_3OD$): δ43.12, 115.10, 125.43, 127.17, 129.74, 130.45, 157.29;

MS (ESI): m/z 133 (M−$NH_3$).

119 (R=4-OMe):

80% yield; off-white solid; $^1$H NMR (400 MHz, $CD_3OD$): δ3.32 (d, J=6.0 Hz, 2H), 3.74 (s, 3H), 6.15 (dt, J=15.6, 6.0 Hz, 1H), 6.42 (d, J=15.6 Hz, 1H), 6.82 (d, J=8.8 Hz, 2H), 7.28 (d, J=9.2 Hz, 1H); $^{13}$C NMR (100 MHz, $CD_3OD$): δ43.23, 54.25, 113.52, 127.04, 127.28, 129.52, 129.87, 159.18; MS (ESI): m/z 147 (M−$NH_3$).

Procedure for Preparing 4-hydroxymethylcinnamic Acid 124:

A solution of $NaBH_4$ (0.53 g, 14 mmol) in THF/$H_2O$ (4:1) (12 ml) was added dropwise to an ice-cold stirred solution of 4-formylcinnamic acid (2.47 g, 14 mmol) in THF (25 ml), and the mixture was stirred at room temperature for 3 h. The reaction was quenched by adding 4N HCl (20 ml), and the THF was removed by a rotary evaporator. The solid residue was treated with $H_2O$ (20 ml), and extracted with EtOAc (4×50 ml). The EtOAc extracts were washed with $H_2O$ (50 ml) and brine (50 ml), and dried. The crude product was recrystallized from EtOAc to afford pure 4-hydroxymethylcinnamic acid 124 (1.3 g, 52% yield) as yellow solid. $^1$H NMR (300 MHz, $CD_3OD$): δ4.62 (s, 2H), 6.45 (d, J=16.2 Hz, 1H), 7.38 (d, J=8.1 Hz, 2H), 7.56 (d, J=8.1 Hz, 2H), 7.65 (d, J=16.2 Hz, 1H); $^{13}$C NMR (75 MHz, CD$_3$OD): δ63.53, 117.81, 127.17, 128.08, 133.58, 144.25, 144.92, 169.22; MS (ESI): m/z 177 (M−1).

The remaining compounds were synthesized and characterized analogously, or were purchased if commercially available.

Examples 14-17

Studies in *Pseudomonas syringae* pv. tomato DC3000

The following methods apply to Examples 14-17:
Bacterial Strains, Plasmids, and Growth Conditions.

Bacterial strains and plasmids used in this study are listed in the table in FIG. 31. Wild-type *Pseudomonas* strains were routinely grown in King's B (KB) medium at 28° C. (King 1954), and *E. coli* strains were routinely grown in Luria-Bertani (LB) broth at 37° C. For induction of T3SS genes, DC3000 was grown in HIM supplemented with 10 mM fructose as previously described (Huynh et al. 1989). When necessary, antibiotics were added to growth medium at the following concentrations: kanamycin, 50 μg/ml; rifampin, 34 μg/ml (for sterility of the *Pseudomonas* cells lines). Primers used for PCR in this report are listed in the table in FIG. 31. The promoter-probe plasmid was constructed as follows. The hrpA promoter region was amplified by PCR using phrpAF and phrpAR primers incorporating BamHI and EcoRI restriction sites, respectively. A 496-bp DNA fragment encoding the hrpA promoter was digested with BamHI and EcoRI and cloned into pPROBE-NT digested with the same enzymes. This construct was mobilized into DC3000 by conjugation using *E. coli* S17-1λ-pir as the donor strain.
Promoter Activity Assay.

Expression of hrpA was analyzed using a FACS Calibur flow cytometer as previously described (BD Biosciences, CA) (Peng et al. 2006). Wild-type DC3000 carrying the promoter-probe phrpA or pPROBE-NT (vector control) was grown in KB broth overnight and transferred to HIM or HIM supplemented with different compounds as described (Li et al. 2009). The promoter activity of hrpA in DC3000 was monitored by measuring GFP intensity using flow cytometry.
Hypersensitive Response and Virulence Assays Bacterial cells from overnight cultures grown in KB broth were resuspended in sterile dH$_2$O. Cell suspensions were mixed with chemicals and allowed to sit for 30 minutes before plant inoculation. *Nicotiana tabacum* cv. Xanthi plants were used for HR assays. Tobacco leaves were pressure infiltrated by use of a needless syringe (Fu et al. 2006) with 1×10$^8$ cells/ml and 25 μM, 50 μM, 100 μM, 250 μM, or 500 μM TCA. Plants were photographed and assessed for macroscopic tissue collapse indicative of HR 18 h post-inoculation.

Virulence assays were performed in 4-5 week old tomato plants. Bacterial cell suspensions were adjusted to 6×10$^5$ cells/ml in dH$_2$O with 0.02% Silwet L-77 (Lehle Seeds, Round Rock, Tex.). *Lycopersicon esculentum* cv. Moneymaker plants were dip-inoculated into negative control solution (dH$_2$O with 0.02% Silwet L-77 and DMSO), positive control solution (DC3000 in dH$_2$O with 0.02% Silwet L-77 and DMSO), or with a chemical treatment solution (DC3000 in dH$_2$O with 0.02% Silwet L-77 and 250 μM TCA). Leaves were air-dried and plants were covered with a plastic dome and returned to the growth chamber. Plants were scored for disease symptoms using a modified scoring system (Kozik and Nowakowska 2010) five days post-inoculation. Lesions of bacterial speck on tomato were counted and the plants were scored using the following DSI scale: 0=no lesions per plant, 1=1-10 lesions, 2=11-20 lesions, 3=21-40 lesions, 4=>40 lesions.
RNA Extraction and Real-Time PCR Analysis.

DC3000 was cultured in KB medium overnight at 28° C. and subcultured in HIM medium supplemented with DMSO or with 250 μM TCA for 9 h. Total bacterial RNA was isolated using RNeasy Mini Kit (QIAGEN, Valencia, Calif.) and treated with Turbo DNA-free DNase kit (Ambion, Austin, Tex.). cDNA was synthesized using iScript cDNA Synthesis Kit (Bio-Rad, Hercules, Calif.) from 0.8 μg of total RNA. The Real Master Mix SYBR ROX (5 PRIME, Gaithersburg, Md.) was used for real-time PCR reactions to quantify the cDNA level of target genes in different samples. Data were collected by the Opticon 2 system (Bio-Rad) and analyzed using Relative Expression Software Tool as described by Pfaffl and associates (Pfaffl et al. 2002). Two housekeeping genes, gyrA (PSPTO1745) and gap1 (PSPTO1287) were used as endogenous controls for data analysis. The primer pairs used in this study are listed in Table 1. The PCR efficiencies of the primers are: gyrA, 1.93; gap1, 2.08; and hrpW, 1.93.
Immunoblot Analysis The HrpW protein level was determined by immunoblot using anti-HrpW antibody provided by Dr. Alan Collmer (Cornell University, Ithaca, N.Y.). Sample preparation was performed as previously described with modifications (Yuan and He 1996). Wild-type DC3000 was grown overnight in King's B medium at 28° C. The culture was washed with hrp-inducing medium (HIM) and resuspended in 40 ml of the same medium to an optical density (OD) at 600 nm of 0.1. To determine the effect of TCA on the HrpW protein level, TCA dissolved in DMSO was added to the culture at the final concentration of 250 μM and the culture was grown with moderate shaking at 28° C. DMSO was added to a separate culture as a negative control. After 9 h, the cells were collected by centrifugation at 4,000×g for 10 min and resuspended in 1 ml of phosphate buffered saline (PBS; 137 mM NaCl, 2.7 mM KCl, 4.3 mM Na$_2$HPO$_4$, and 1.47 mM KH$_2$PO$_4$ [pH 7.4]). Pelleted cells were resuspended in 1× sample buffer (2% w/v sodium dodecyl sulfate, 2% v/v glycerol, 2 mM (3-mercaptoethanol, 50 mM Tris-HCl [pH6.8], and 0.01% w/v bromophenol blue) and heat-treated at 98° C. for 10 min using Dry Bath Incubator (Fisher Scientific, Pittsburgh, Pa.). The supernatant proteins were concentrated 100-fold with Amicon Ultra-4 Centrifugal Filter Unit (30 kDa cut-off) (Millipore, Billerica, Mass.) and mixed with the same volume of 2× sample buffer and heat-treated. Cell pellets were similarly heat-treated. Sodium dodecyl sulfate-polyacrylamide gel electrophoresis (SDS-PAGE) and immunoblot analysis were performed as previously described (Li et al. 2009). The chemiluminescent detection using BrightStar BioDetect Kit (Ambion, Austin, Tex.) was performed following the manufacturer's instructions.

Example 14

TCA Inhibits Gene Expression of T3SS hrpA but not Bacterial Growth

To determine the maximum concentration of TCA that will inhibit hrpA promoter activity without affecting bacterial growth, DC3000 carrying phrpA was cultured in HIM and HIM supplemented with 25 μM, 50 μM, 100 μM, 250 μM, or 500 μM of TCA. Promoter activity was measured at 6 h and 9 h as mentioned above using flow cytometry. Bacterial growth was determined by withdrawing samples of each culture and spot-plating serial dilutions onto King's B agar (King et al.

Figure 33:
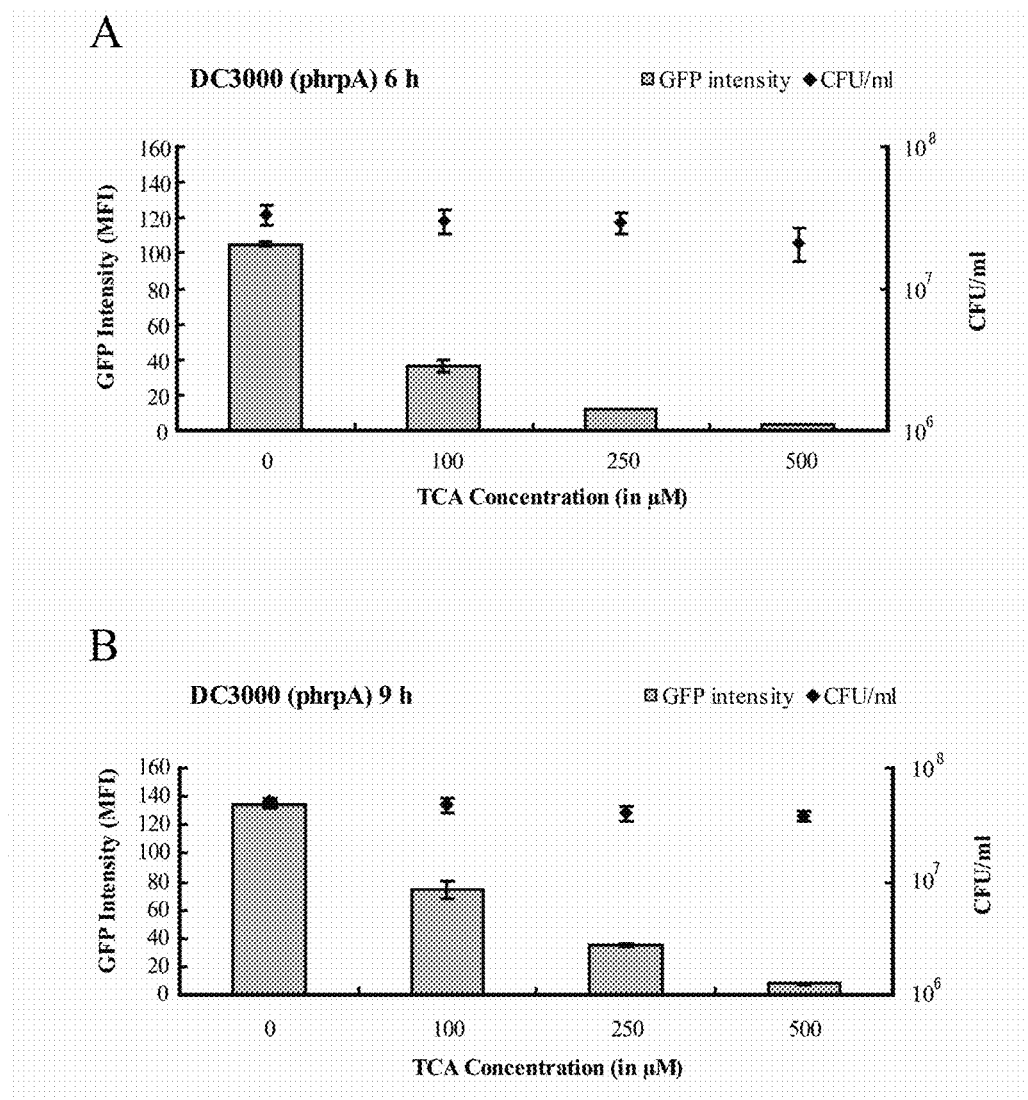
FIG. 33 shows a hrpA promoter activity and growth of *Pseudomonas syringae* pv. tomato DC3000 carrying GFP reporter plasmid phrpA grown in HIM supplemented with different concentrations of TCA at (A) 6 h and (B) 9 h of growth.

1954) in tandem with promoter activity assays. Colonies were counted after 48 h of incubation at 28° C. Addition of 100 µM of TCA to the growth medium (concentration used to screen chemical library) resulted in a 3-fold reduction in hrpA promoter activity, whereas lower concentrations of TCA (25 µM or 50 µM) had a less substantial effect (FIG. 32). HIM supplemented with TCA concentrations of 250 µM and 500 µM caused almost complete repression of hrpA promoter activity which was similar to expression levels measured in the empty vector control (DC3000 containing pPROBE-NT; FIG. 32 and FIG. 33). Colony counts of DC3000 at 6 h and 9 h were similar among the control culture (0 µM TCA) and the cultures to which TCA was added at concentrations of 250 µM or less, whereas colony counts were slightly lower in cultures containing 500 µM TCA (FIG. 33). These results suggest that the degree of inhibition on DC3000 hrpA is proportional to the concentration of TCA added to the growth medium. In addition, TCA does not significantly inhibit nor enhance growth of DC3000 when TCA was added to HIM at or below concentrations of 250 µM.

Example 15

TCA Suppresses Ability of DC3000 to Elicit HR in Tobacco

In DC3000, mutations in genes which encode components of the T3SS result in the inability to elicit HR in non-hosts (Collmer et al. 2000). Since TCA represses expression of hrpA (a major component of the T3SS) in vitro, the ability of TCA to suppress HR in planta was examined. DC3000 ($OD_{600}$=0.1) with 25 µM, 50 µM, 100 µM, 250 µM, or 500 µM of TCA in DMSO was injected into leaves of tobacco (*Nicotiana tabacum* cv. Xanthi). Concentrations of DMSO which correspond to similar amounts of TCA were also injected into the tobacco plants as negative controls. Tobacco leaves were assessed for HR symptoms 18 hours post-infiltration. No visible signs of tissue damage or HR were observed when DMSO or TCA was separately infiltrated into the tobacco leaves (data not shown). When bacterial cells were infiltrated into plants in combination with 250 µM of TCA, elicitation of HR by DC3000 was completely suppressed (FIG. 34A). 100 µM of TCA was unable to completely block HR, but the symptoms were slightly less severe than those seen when either 50 µM or 25 µM was infiltrated with bacterial cells into tobacco leaves. These results revealed that TCA not only inhibits expression of the hrpA gene encoding the major structural component of the T3SS pilus, but also functions in planta to suppress the ability of DC3000 to elicit HR on a non-host. This effect is most likely due to lack of a functional T3SS.

Figure 34:
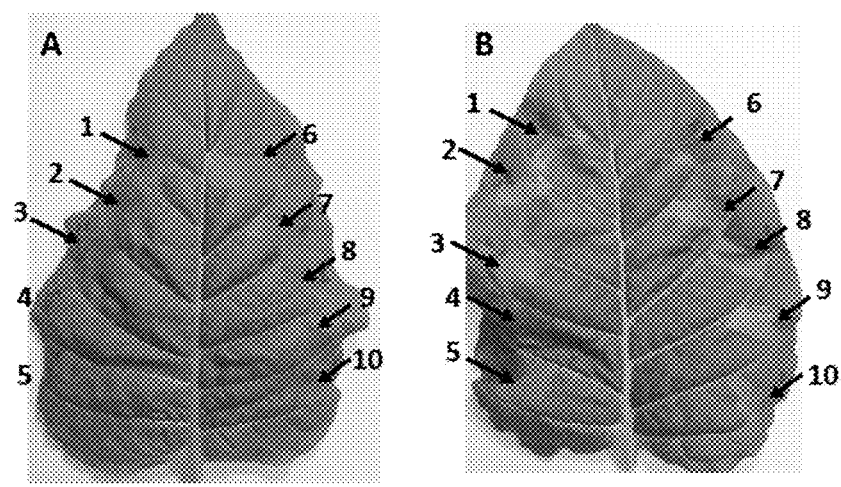
FIG. 34 shows: (A) Tobacco leaves (*N. tabacum* cv. Xanthi) were infiltrated with *Pseudomonas syringae* pv. tomato DC3000 (DC3000) ($OD_{600}$ 0.1) or DC3000 ($OD_{600}$ 0.1) supplemented with different concentrations of the T3SS inhibitor TCA. 1. 25 µM. 2. 50 µM. 3. 100 µM. 4. 250 µM. 5. 500 µM. 6. to 10.: DC3000 alone. (B) Tobacco leaves were infiltrated with DC3000 ($OD_{600}$=0.1) or DC3000 ($OD_{600}$=0.1) supplemented with different concentrations of 104. 1. 25 µM. 2. 50 µM. 3. 100 µM. 4. 250 µM. 5. 500 µM. 6. to 10.: DC3000 alone.

Following the initial screen of the chemical library, several compounds were found to have little or no affect on hrpA promoter activity. One of these TCA analogs (104), was chosen as a negative control to evaluate the specificity of TCA to inhibit T3SS in planta. DC3000 ($OD_{600}$=0.1) with DMSO or with 25 µM, 50 µM, 100 µM, 250 µM, or 500 µM of Y104 (same concentrations as those used to evaluate TCA) was infiltrated into tobacco leaves and scored for HR symptoms after 18 h. 104 was ineffective at suppressing HR at all concentrations tested (FIG. 34B). These results indicate that the inhibitory activity of TCA on the ability of DC3000 to cause HR is specific. In addition, the structure of TCA is important for its repressive effect on HR.

Example 16

Effect of TCA on HrpW of DC3000

Figure 35:
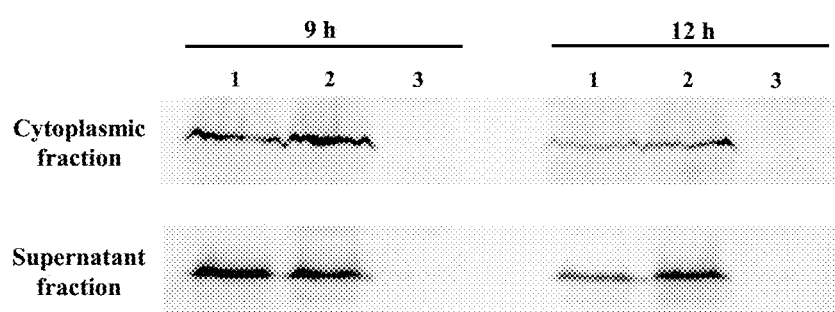
FIG. 35 shows an HrpW immunoblot analysis was performed using anti-HrpW polyclonal antibody. Samples were taken at two different time points; 9 h and 12 h after subculturing cells into HIM medium. Chemiluminescent signals were detected by 6 min and 8 min exposure for cytoplasmic and supernatant fractions, respectively. Lane 1, *Pseudomonas syringae* pv. tomato DC3000 (DC3000) in HIM; lane 2, DC3000 in HIM supplemented with DMSO; lane 3, DC3000 in HIM supplemented with 250 µM TCA.

The T3SS is responsible for the translocation of virulence and accessory proteins which contribute to disease in plants (Lindeberg et al. 2006). HrpW is a T3SS-secreted harpin capable of eliciting HR on tobacco (Charkowski et al. 1998). The amount of hrpW mRNA and HrpW protein levels in the DC3000 cells grown in TCA can serve as an indicator of the HR response in tobacco plants by the bacterium (Wei et al. 2000). Real-time PCR was performed to examine the effect of TCA on hrpW expression. Compared to induction of T3SS in HIM alone, a significantly lower amount of hrpW mRNA (relative expression ratio 0.07, P=0.04) was observed in HIM supplemented with 250 µM TCA. Immunoblot analysis was performed on DC3000 cultured in HIM or in HIM supplemented with 250 µM TCA. When DC3000 cells were grown in HIM supplemented with 250 µM of TCA, HrpW was absent from the culture supernatants and was also undetectable in the whole cell lysates (FIG. 35). These results indicate that TCA inhibited the production and secretion of HrpW protein from the cells. Our results showed that the HrpW protein was detected at similar levels of intensity when DC3000 was grown in HIM or in HIM with DMSO (TCA solvent), which suggests that the concentrations of DMSO used in this study did not cause alteration of HrpW production in the bacterium.

Example 17

TCA Prevents DC3000 from Causing Disease in Tomato

Figure 36:
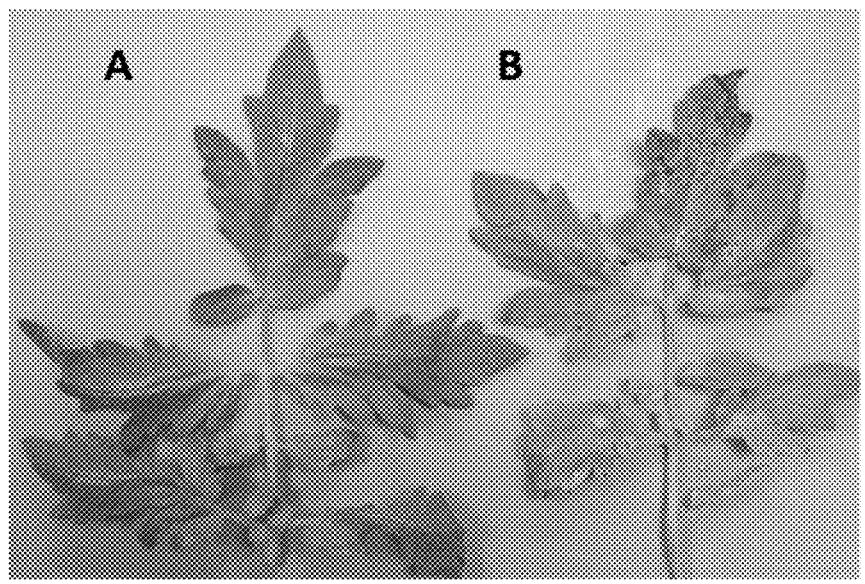
FIG. 36 shows: Bacterial suspension of *Pseudomonas syringae* pv. tomato DC3000 (DC3000) was diluted to $6 \times 10^5$ CFU/ml in $dH_2O$ and 0.02% Silwet L-77 for dip-inoculation. (A) DC3000 supplemented with 250 µM of 001. No lesions of bacterial speck were observed in tomato plants treated with TCA. (B) DC3000 alone.

Taken together, the above results indicate that TCA specifically blocks the action of T3SS by inhibiting its expression. The effects of TCA on virulence in tomato plants were examined. *Lycopersicon esculentum* cv. Moneymaker plants were dip-inoculated with a negative control treatment ($dH_2O$ with 0.02% Silwet L-77 and DMSO), a positive control treatment (DC3000 in $dH_2O$ with 0.02% Silwet L-77 and DMSO), or with a chemical treatment (DC3000 in $dH_2O$ with 0.02% Silwet L-77 and 250 µM TCA) as described in the methods. The lesions of bacterial speck on leaves per plant were counted and plants were classified with a disease severity index (DSI) as described in the methods. At five days post-inoculation, no bacterial speck lesions were observed in tomato plants treated with DC3000 and 250 µM TCA or with the negative control treatment (FIG. 36A), which were all scored with a DSI of zero. Plants treated with DC3000 were all scored with a DSI of four (FIG. 36B).

Example 18

Screening for Inhibitors/Inducers of the T3SS of *P. aeruginosa*

Figure 37:
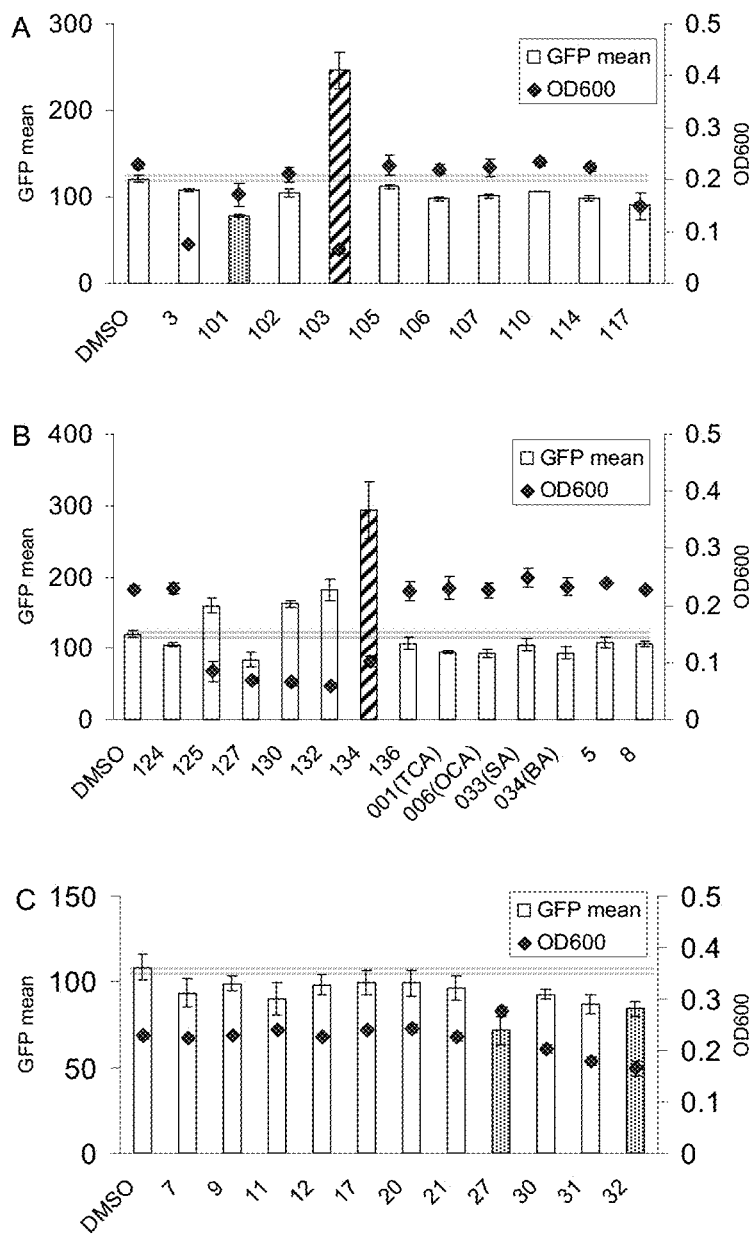
FIG. 37 shows the effects of compounds on exoS expression and bacterial growth. Gray lines represent the exoS expression levels of the cells treated with DMSO.
Figure 37:
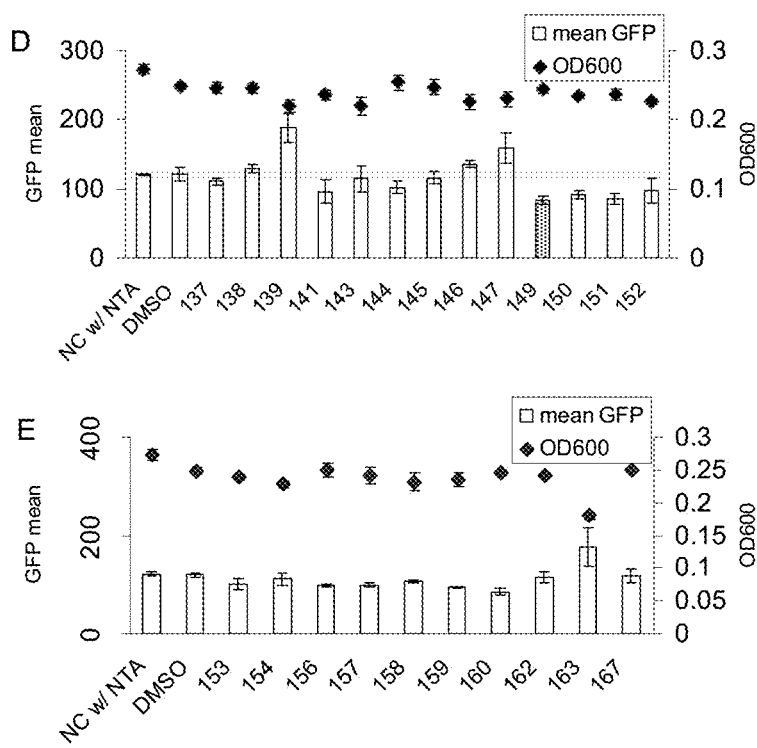

To identify T3SS inhibitors of PA01, a promoter-probe vector pPROBE-AT containing the promoterless green fluorescent protein (gfp) gene was used to construct an exoS promoter-gfp plasmid reporter, pATexoS. PA01 containing pATexoS was cultured in T3SS-inducing medium containing dimethyl sulfoxide (DMSO; solvent of chemical compounds), or supplemented with 250 µM of each compound, and promoter activity was assessed at 6 h by measuring GFP intensity using flow cytometry. 101 compounds (58 synthesized and 43 commercially available) were screened. Compounds 027, 032, 101, and 149 repressed exoS expression at the final concentration of 250 µM by at least one standard deviation below the sample average (Z score≤−1) (FIG. 37 A-E). Z score (or standard score) indicates how many standard deviations an observation or datum is above or below the mean [$z=(x-\mu)/\sigma$, where x is a raw score to be standardized, $\mu$ is the mean of the population, and $\sigma$ is the standard deviation of the population]. 027, 032, 101, and 149 were found to function as T3 inhibitors of *P. aeruginosa* with minor alterations in bacterial growth at 250 µM (FIGS. 37 A, C, and D). Additionally, two compounds 103 and 134 were found to induce exoS expression at the same concentration by at least 4 standard deviations above the sample average (Z score≥4) (FIGS. 37A and B). However, 103 and 134 showed some inhibition on bacterial growth.

Example 19

Figure 38:
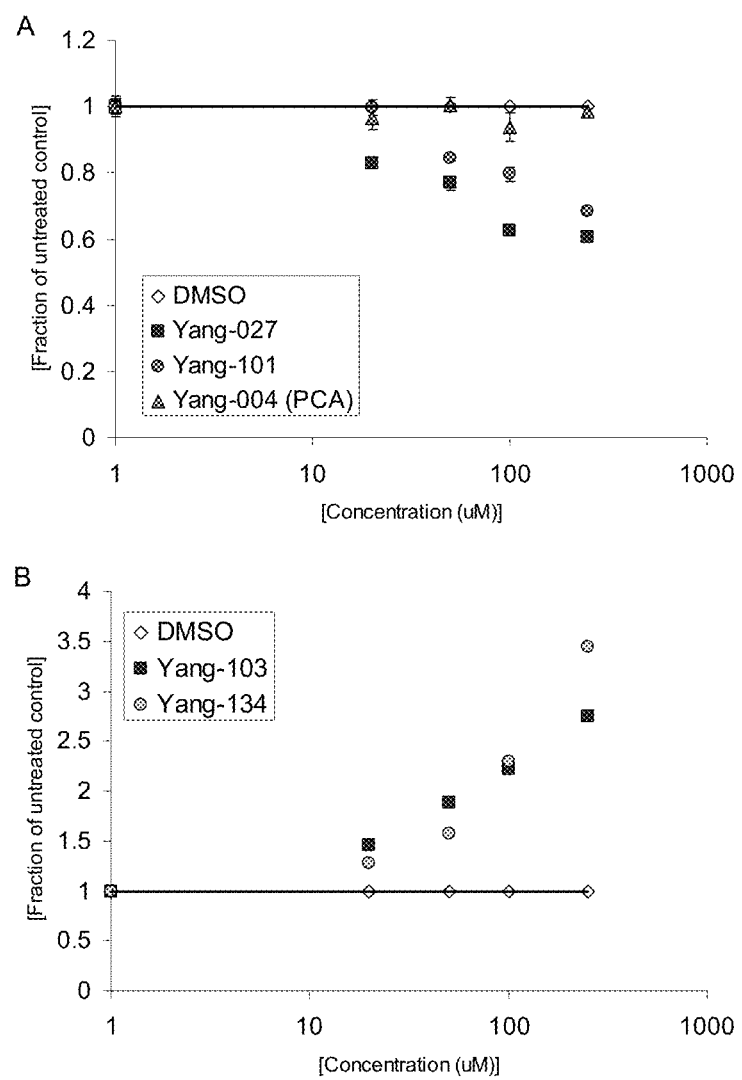
FIG. 38 shows an evaluation of the dose-dependent effect of compounds on exoS expression. Dose-dependent effect of (A) T3 inhibitors or (B) T3 inducers on exoS expression. X-axis represents the relative exoS expression level (compound/DMSO). Black lines represent asymptotic lines for the DMSO-treated samples.
Figure 39:
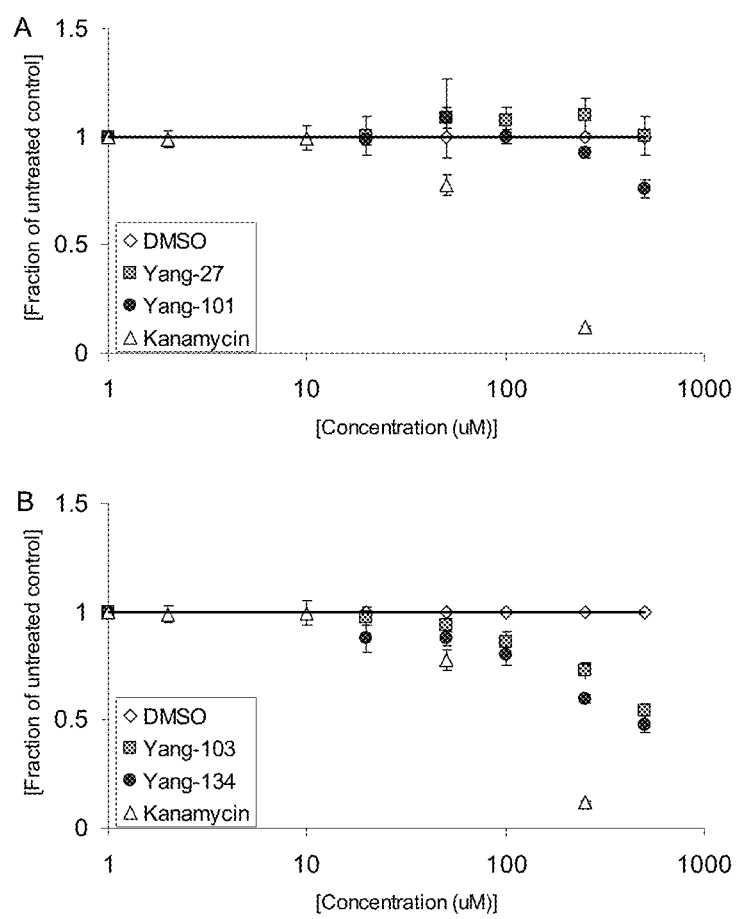
FIG. 39 shows an evaluation of the dose-dependent effect of compounds on *P. aeruginosa* growth. Dose-dependent effect of (A) T3 inhibitors or (B) T3 inducers on *P. aeruginosa* growth. X-axis represents the relative cell density (compound/DMSO). Black-lines represent asymptotic lines for the DMSO-treated samples.
Figure 40:
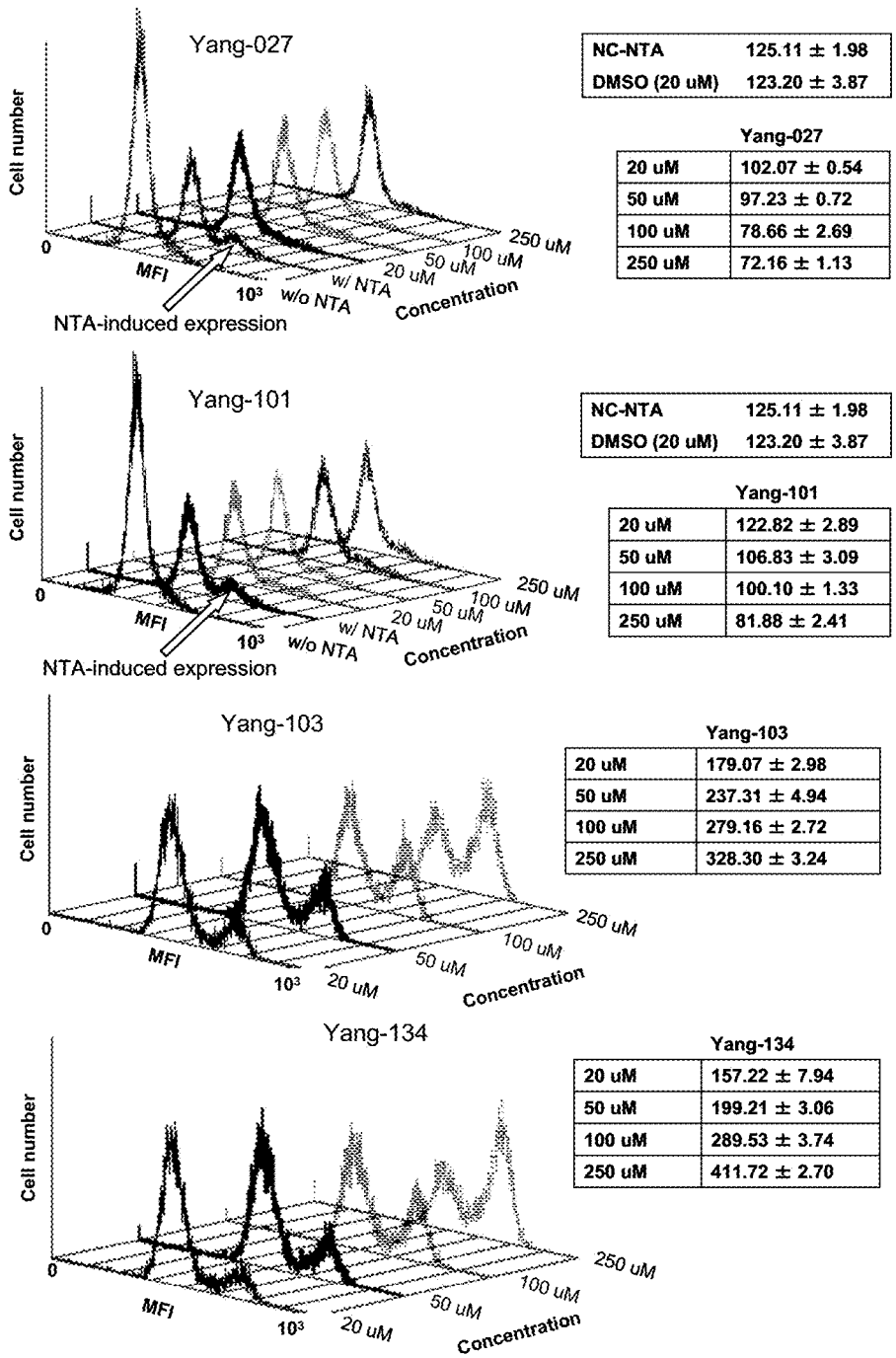
FIG. 40 shows an evaluation of the dose-dependent effect of compounds on exoS expression and cell populations. X-axis, MFI (mean fluorescence intensity); Y-axis, cell number; Z-axis, concentration of the compound.

Evaluation of the Dose-Dependent Effects of Compounds on exoS Expression and Bacterial Growth To determine the effective concentration of compounds, the dose-dependent effect of potential inhibitors on exoS expression and bacterial growth were tested. *P. aeruginosa* cells carrying pATexoS were pre-cultured in LB supplemented with 200 mM NaCl and transferred to fresh LB with 200 mM NaCl, 10 mM NTA, and various concentrations of compounds (20, 50, 100, and 250 µM) or DMSO for 6 h. As shown in FIG. 37A and Table 17, 027 inhibited exoS expression at 20 µM but 101 did not. At 50 µM dosage, both 027 and 101 inhibited exoS expression at similar levels, and this inhibitory effect increased as compound concentration increased (FIG. 38A and Table 17). These two compounds had only minor effects on bacterial growth at different compound concentrations (up to 250 µM for 101 and up to 500 µM for 027) (FIG. 39A). On the other hand, two T3 inducers 103 and 134 showed significant induction of exoS expression at 20 µM (FIG. 38B and Table 17). This induction effect increased as compound concentration increased (FIG. 38B and Table 17), and inverse relationship was observed between the compound concentration and bacterial growth (FIG. 39B). These inhibitions/inductions of exoS expression are caused by the shifting bacterial population between low-state expression cells and high-state expression cells (FIG. 40).

TABLE 17

Actual readings of flow cytometry (exoS expression) at various concentrations of compounds.
NC 50.42 ± 0.51
NC-NTA 125.11 ± 1.98

|  | 20 uM | 50 uM | 100 uM | 250 uM |
|---|---|---|---|---|
| DMSO | 123.20 ± 3.87 | 126.30 ± 0.57 | 125.78 ± 1.27 | 119.34 ± 0.66 |
| Yang-027 | 102.07 ± 0.54 | 97.23 ± 0.72 | 78.66 ± 2.69 | 72.16 ± 1.13 |
| Yang-101 | 122.82 ± 2.89 | 106.83 ± 3.09 | 100.10 ± 1.33 | 81.88 ± 2.41 |
| Yang-004 (PCA) | 119.08 ± 1.82 | 127.05 ± 4.43 | 118.16 ± 2.73 | 117.74 ± 5.09 |
| Yang-103 | 179.07 ± 2.98 | 237.31 ± 4.94 | 279.16 ± 2.72 | 328.30 ± 3.24 |
| Yang-134 | 157.22 ± 7.94 | 199.21 ± 3.06 | 289.53 ± 3.74 | 411.72 ± 2.70 |

Example 20

Structure-Activity Relationships (SARs)

While screening for T3SS inhibitors, several compounds were found to have little or no effect on exoS promoter activity, such as 004, 132, and 137. Comparison of the effective T3SS inhibitors vs. non-effective chemicals reveals that the structure of 027 is identical to that of 004 except the hydroxyl group of the phenol ring has been replaced with an amide group (Table 18). Also, 101 is similar to 004 (carboxyl group was replaced with a carboxymethyl group) (Table 18). Given that 004 has almost no effect on exoS expression (FIG. 38A and Table 17) signifies that these two functional groups may be important for their exoS-inhibitory effect. Meanwhile, the *P. aeruginosa* T3 inducer 103 shares its structure with less-functional 132 (no hydroxyl group on the phenol ring) and nonfunctional 137 (the hydroxyl group on the carbonyl-nitrogen group was replaced with a methyl group), indicating that of these two functional groups, one enhances the effect of the compound and the other is crucial for its induction activity, respectively (Table 18).

TABLE 18

Structure-activity relationships.

| Compound ID | Structure | Fraction of untreated control |
|---|---|---|
| Yang-027 | [4-aminophenyl acrylic acid, $CO_2H$] | 0.66 ± 0.04 |
| Yang-101 | [4-hydroxyphenyl methyl acrylate, $CO_2Me$] | 0.65 ± 0.03 |
| Yang-004 | [4-hydroxyphenyl acrylic acid, $CO_2H$] | 0.94 ± 0.05 |
| Yang-103 | [4-hydroxyphenyl N-hydroxy acrylamide] | 2.04 ± 0.13 |

TABLE 18-continued

Structure-activity relationships.

| Compound ID | Structure | Fraction of untreated control |
|---|---|---|
| Yang-132 | (E)-cinnamohydroxamic acid (PhCH=CH-C(O)-NHOH) | 1.53 ± 0.19 |
| Yang-137 | (E)-N-methyl-4-hydroxycinnamamide (HO-C6H4-CH=CH-C(O)-NHMe) | 0.92 ± 0.05 |

Example 21

Studies in *Erwinia amylovora* 273

Wild-type *Erwinia amylovora* 273 was used in this study. The promoter-probe plasmid phrpA was constructed as follows. The hrpA promoter region of *Erwinia amylovora* 273 was amplified and cloned into pPROBE-NT to produce PhrpA. Plasmid PhrpA was electroporated into *Erwinia amylovora* 273. Expression of hrpA was analyzed using a FACS Calibur flow cytometer (BD Biosciences, CA). Wild-type *Erwinia amylovora* 273 containing phrpA was cultured in a hrp-inducing medium (HIM) containing dimethyl sulfoxide (DMSO; solvent of chemical compounds), or HIM supplemented with 100 μM of each compound, and promoter activity was assessed at 6 h and 9 h by measuring GFP intensity using flow cytometry (Table 19). Treatment:

Ea273 (pPROBE-NT): *Erwinia amylovora* 273 carrying pPROBE-NT (vector control)

Ea273 (phrpA): *Erwinia amylovora* 273 carrying phrpA

HIM: hrp inducing medium

: HIM supplemented with the indicated compound

TABLE 19

Expression of Erwinia amylovora273 hrpA in HIM or HIM supplemented with the indicated compound.

| | Avg MFI ± SD[b] at: | |
|---|---|---|
| Compound No. | 6 h | 9 h |
| Ea273 (pPROBE-NT) | 1.4 ± 0.2 | 1.2 ± 0.1 |
| HIM | 1229.4 ± 39.2 | 1024.3 ± 52.9 |
| 024, trans-2-Carboxycinnamic acid | 361.1 ± 76.1 | 332.2 ± 19.6 |
| 030, Methyl trans-cinnamate | 674.8 ± 252.1 | 668.5 ± 31.2 |
| 032, Cinnamyl alcohol | 681.6 ± 217.9 | 784.0 ± 53.3 |
| 027, trans-4-Aminocinnamic acid | 255.6 ± 7.4 | 132.1 ± 8.5 |
| 026, trans-4-Mercaptocinnamic acid | 159.7 ± 22.0 | 44.7 ± 2.7 |
| 029, trans-4-Formlycinnamic acid | 285.1 ± 40.8 | 218.3 ± 9.9 |
| 028, trans-4-Nitrocinnamic acid | 14.4 ± 16.9 | 4.0 ± 0.3 |
| 101, Methyl para-coumate | 1443.4 ± 49.4 | 1227.8 ± 41.6 |
| 102, trans-4-Hydroxycinnamaide | 1134.0 ± 36.7 | 766.4 ± 94.8 |
| 103, trans-4-Hydroxycinnamohydroxamic acid | 206.9 ± 3.9 | 168.2 ± 24.9 |
| 104, para-Coumaryl alcohol | 814.7 ± 55.2 | 556.9 ± 40.3 |
| 105, trans-2-(4-Methoxyphenyl)-1-cyclopropanecarboxylic acid | 345.3 ± 11.9 | 200.2 ± 11.0 |
| 106, Ethyl trans-2-(4-hydroxyphenyl)-1-cyclopropanecarboxylate | 1289.3 ± 46.5 | 1110.9 ± 67.5 |
| 107, trans-2-(4-Hydroxyphenyl)-1-cyclopropanecarboxylic acid | 1464.3 ± 76.5 | 1348.0 ± 82.6 |
| 108, trans-4-Phenylcinnamic acid | 173.7 ± 7.9 | 79.4 ± 1.8 |
| 109, trans-4-Chlorocinnamide | 172.9 ± 20.5 | 90.6 ± 12.0 |
| 110, trans-4-Fluorocinnamic acid | 279.2 ± 5.3 | 152.4 ± 0.7 |
| 111, trans-4-Bromocinnamic acid | 102.8 ± 23.5 | 61.8 ± 4.2 |
| 112, trans-4-Dimethylaminocinnamic acid | 87.0 ± 4.0 | 37.3 ± 3.7 |
| HIM | 1476.7 ± 63.8 | 1649.1 ± 96.9 |
| 006, Ortho-coumaric acid | 443 ± 16.9 | 437.8 ± 21.1 |
| 001, trans-cinnamic acid | 471.2 ± 12.6 | 432.6 ± 17.8 |
| 004, para-coumaric acid | 920.6 ± 29.1 | 993.8 ± 43.3 |
| 005, meta-coumaric acid | 1212 ± 47.6 | 1439.1 ± 97.9 |
| 033, Salicylic acid | 49.8 ± 13.9 | 34.3 ± 4.2 |
| 034, Benzoic acid | 48.1 ± 5.4 | 32.6 ± 1.9 |
| HIM | 1242.1 ± 27.0 | 1672.5 ± 126.0 |
| 122, Ethyl trans-2-(4-hydroxyphenyl)-ethenylsulfonate | 2042.8 ± 20.7 | 2900.6 ± 120.1 |
| 123, trans-2-(4-Hydroxyphenyl)ethenylsulfonic acid tetra(n-butyl)ammonium salt | 1073.4 ± 107.7 | 1377.3 ± 81.1 |
| 124, trans-4-Hydroxymethylcinnamic acid | 419.8 ± 12.2 | 444.3 ± 11.4 |
| 125, trans-4-Methoxycinnamohydroxamic acid | 215.5 ± 6.5 | 230.0 ± 4.4 |
| 126, trans-4-Methoxycinnamyl alcohol | 386.9 ± 9.4 | 401.4 ± 10.8 |
| 127, trans-3-Indoleacrylohydroxamic acid | 91.4 ± 4.9 | 102.7 ± 0.5 |
| 128, trans-4-Bromocinnamohydroxamic acid | 17.6 ± 2.8 | 5.7 ± 2.2 |
| 129, trans-2-Hydroxycinnamohydroxamic acid | 187.9 ± 1.2 | 181.0 ± 0.7 |
| 130, trans-3-Hydroxycinnamohydroxamic acid | 431.4 ± 4.1 | 491.0 ± 10.2 |
| 131, trans-3,4-Dihydroxycinnamohydroxamic acid | 1057.5 ± 41.2 | 1515.1 ± 39.1 |
| 132, trans-Cinnamohydroxamic acid | 145.7 ± 1.2 | 147.8 ± 4.2 |
| 133, trans-3-(4-Hydroxyphenyl)acrylohydrazid | 1716.5 ± 33.1 | 2780.9 ± 58.5 |
| 136, Phenylpropiolic acid | 261.7 ± 1.0 | 307.0 ± 9.3 |
| 134, Benzhydroxamic acid | 679.0 ± 12.7 | 921.6 ± 10.3 |
| 135, Salicylhydroxamic acid | 124.7 ± 7.7 | 147.8 ± 4.3 |

TABLE 19-continued Expression of Erwinia amylovora273 hrpA in HIM or HIM supplemented with the indicated compound.

| Compound No. | Avg MFI ± SD[b] at: 6 h | 9 h |
|---|---|---|
| HIM | 1068.6 ± 170.9 | 1157.8 ± 58.7 |
| 008, Hydrocinnamic acid | 395.9 ± 16.0 | 342.0 ± 11.7 |
| 009, Phenoxyacetic acid | 342.7 ± 24.8 | 269.9 ± 15.2 |
| 010, trans-2-Phenylcyclopropane-1-carboxylic acid | 336.7 ± 28.1 | 293.0 ± 4.7 |
| 013, trans-3-(3-Pyridyl)acrylic acid | 468.3 ± 7.7 | 245.7 ± 3.1 |
| 035, 3-(2-naphthyl) acrylic acid | 178.9 ± 9.7 | 89.0 ± 6.2 |
| 012, trans-3-Indoleacrylic acid | 33.7 ± 8.9 | 47.9 ± 6.9 |
| 011, trans-3-(2-Thienyl)acrylic acid | 230.1 ± 5.8 | 167.3 ± 8.2 |
| 015, trans-2-Methoxycinnamic acid | 342.6 ± 7.0 | 255.1 ± 1.7 |
| 018, trans-2-Methylcinnamic acid | 303.8 ± 8.7 | 262.5 ± 9.3 |
| 021, trans-2-Chlorocinnamic acid | 225.7 ± 35.8 | 192.7 ± 8.6 |
| 014, trans-3-(4-Imidazolyl)acrylic acid | 874.6 ± 23.1 | 839.2 ± 17.6 |
| 002, 2,4-Dihydroxycinnamic acid | 1365.3 ± 104.9 | 1479.8 ± 72.9 |
| 007, 3-(4-Hydroxyphenyl)propionic acid | 1093.1 ± 62.8 | 1211.0 ± 58.7 |
| 023, trans-4-Chlorocinnamic acid | 171.8 ± 7.7 | 125.8 ± 3.9 |
| 017, trans-4-Methoxycinnamic acid | 132.5 ± 5.5 | 76.4 ± 2.7 |
| 020, trans-4-Methylcinnamic acid | 208.5 ± 2.7 | 145.4 ± 3.7 |
| 003, 3,4-Dihydroxycinnamic acid | 783.4 ± 80.2 | 787.3 ± 25.2 |
| 108, trans-4-Phenylcinnamic acid | 197.7 ± 5.5 | 99.3 ± 3.3 |
| 022, trans-3-Chlorocinnamic acid | 332.9 ± 16.9 | 238.3 ± 8.7 |
| 016, trans-3-Methoxycinnamic acid | 265.3 ± 24.4 | 198.5 ± 20.0 |
| 019, trans-3-Methylcinnamic acid | 311.5 ± 18.6 | 251.6 ± 13.3 |
| HIM | 458.1 ± 10.2 | 587.4 ± 360 |
| 025, trans-4-Carboxycinnamic acid | 421.0 ± 10.6 | 496.7 ± 98.9 |
| 031, trans-Cinnamamide | 98.0 ± 18.4 | 88.1 ± 4.6 |
| 100, Ethyl trans-2-(4-methoxyphenyl)-1-cyclopropanecarboxylate | 447.8 ± 20.2 | 594.6 ± 3.5 |
| 113, trans-4-Trifluoromethylcinnamic acid | 84.2 ± 7.5 | 97.4 ± 23.6 |
| 114, Diethyl trans-2-(4-hydroxyphenyl)-vinylphosphonate | 495.8 ± 14.2 | 661.2 ± 134.3 |
| 115, trans-2-(4-Hydroxyphenyl)-vinylphosphonic acid | 442.4 ± 2.3 | 553.3 ± 32.7 |
| 116, N-(para-Coumaryl)phthalimide | 889.1 ± 61.8 | 1466.4 ± 17.8 |
| 117, para-Coumarylamine | 452.6 ± 9.5 | 547.9 ± 112.4 |
| 118, N-(4-Methoxycinnamyl)phthalimide | 361.3 ± 28.6 | 520.4 ± 16.2 |
| 119, trans-4-Methoxycinnamylamine | 208.6 ± 18.6 | 232.9 ± 44.4 |
| 120, Ethyl trans-2-(4-methoxyphenyl)-ethenylsulfonate | 371.5 ± 29.7 | 492.0 ± 37.6 |
| 121, trans-2-(4-Methoxyphenyl)ethenylsulfonic acid tetra(n-butyl)ammonium salt | 358.3 ± 24.0 | 477.4 ± 40.0 |
| HIM | 1100.1 ± 30.8 | 1351.9 ± 62.4 |
| 153, trans-3-Fluorocinnamohydroxamic acid | 177.1 ± 11.9 | 110.6 ± 3.2 |
| 154, trans-2-Fluorocinnamohydroxamic acid | 111.4 ± 15.1 | 77.8 ± 1.3 |
| 155, trans-4-Nitrocinnamohydroxamic acid | 108.4 ± 8.5 | 132.5 ± 2.6 |
| 156, trans-3-Nitrocinnamohydroxamic acid | 67.8 ± 17.9 | 99.5 ± 4.9 |
| 157, trans-2-Nitrocinnamohydroxamic acid | 104.6 ± 7.3 | 96.2 ± 3.3 |
| 158, trans-3-Methoxycinnamohydroxamic acid | 216.2 ± 12.5 | 250.6 ± 13.9 |
| 159, trans-2-Methoxycinnamohydroxamic acid | 256.3 ± 10.8 | 337.3 ± 15.2 |
| 160, trans-2-Methylcinnamohydroxamic acid | 122.7 ± 1.9 | 95.7 ± 3.7 |
| 161, trans-3-(2-Thienyl)acrylhydroxamic acid | 132.4 ± 13.2 | 145.0 ± 11.7 |
| 162, trans-2-Phenylcyclopropane-1-carbohydroxamic acid | 711.1 ± 2.8 | 701.9 ± 2.8 |
| 163, trans-3-(2-Furyl)acrylhydroxamic acid | 231.5 ± 7.0 | 196.5 ± 14.9 |
| 164, trans-4-(Benzylcarbonyl)cinnamic acid | 155.7 ± 22.2 | 116.4 ± 6.7 |
| 165, trans-2-[(4'-Benzylcarbonyl]phenylcyclopropane-1-carboxylic acid | 292.8 ± 17.1 | 229.4 ± 15.0 |
| 166, trans-4-(Carbo-phenylamide)cinnamic acid | 105.0 ± 53.0 | 221.2 ± 22.2 |
| 167, trans-4-(Carbo-N-methyl-phenylamide)cinnamic acid | 729.7 ± 67.5 | 707.3 ± 55.9 |
| HIM | 1132.3 ± 93.6 | 1295.0 ± 86.5 |
| 137, N-Methyl-4-hydroxycinnamamide | 1064.1 ± 99.3 | 1121.1 ± 52.1 |
| 138, N-(2-Hydroxyethyl)-4-hydroxycinnamamide | 1474.5 ± 30.4 | 1907.0 ± 39.8 |
| 139, 3-Phenylpropionohydroxamic acid | 306.3 ± 11.9 | 286.3 ± 10.0 |
| 140, trans-4-Phenylcinnamohydroxamic acid | 101.7 ± 17.1 | 82.8 ± 4.3 |
| 141, trans-4-Fluorocinnamohydroxamic acid | 167.6 ± 4.7 | 119.0 ± 7.1 |
| 142, trans-4-Methylcinnamohydroxamic acid | 126.2 ± 5.6 | 106.0 ± 13.6 |
| 143, 2-Phenoxyacetohydroxamic acid | 228.7 ± 4.6 | 178.5 ± 27.1 |
| 144, 4-Hydroxybenzoic acid | 434.4 ± 22.1 | 424.7 ± 24.8 |
| 145, 3-Hydroxybenzoic acid | 559.4 ± 23.6 | 529.9 ± 32.0 |
| 146, trans-4-Formylcinnamohydroxamic acid | 414.3 ± 31.6 | 435.2 ± 36.2 |
| 147, trans-4-Hydroxymethylcinnamohydroxamic acid | 688.6 ± 39.2 | 746.8 ± 96.3 |
| 148, trans-4-Chlorocinnamohydroxamic acid | 22.5 ± 3.7 | 21.8 ± 25.2 |
| 149, trans-3-Chlorocinnamohydroxamic acid | 31.2 ± 34.1 | 21.7 ± 28.5 |
| 150, trans-2-Chlorocinnamohydroxamic acid | 25.9 ± 3.2 | 30.5 ± 3.3 |
| 151, trans-3-Bromocinnamohydroxamic acid | 6.3 ± 1.2 | 3.9 ± 1.2 |
| 152, trans-2-Bromocinnamohydroxamic acid | 15.7 ± 2.3 | 11.1 ± 1.2 |

Throughout this disclosure, various aspects of this invention may be presented in a range format. It should be understood that the description in range format is merely for convenience and brevity, and should not be construed as an inflexible limitation on the scope of the invention. Accordingly, as will be understood by one skilled in the art, for any and all purposes, particularly in terms of providing a written description, all ranges disclosed herein also encompass any and all possible subranges and combinations of subranges thereof, as well as integral and fractional numerical values within that range. The above detailed description of the invention is illustrative of certain embodiments of the invention and is not intended to limit the scope of the invention.

All patents, publications and references cited herein are hereby fully incorporated by reference. In case of conflict between the present disclosure and incorporated patents, publications and references, the present disclosure should control.

The invention claimed is:

1. A method of reducing virulence in a bacterium comprising at least one of a GacS/GacA-type system, a HrpX/HrpY-type system, a T3SS-type system, and a Rsm-type system, the method comprising contacting the bacterium with an effective amount of a compound of formula (IV):

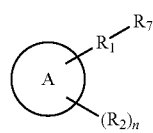

(IV)

wherein:

A is aryl or heteroaryl;

$R_1$ is alkylene;

n is 1;

$R_2$ is selected from halo and nitro; and $R_7$ is hydroxamic acid;

or a salt thereof.

2. A method of reducing virulence in a bacterium comprising at least one of a GacS/GacA-type system, a HrpX/HrpY-type system, a T3SS-type system, and a Rsm-type system, the method comprising contacting the bacterium with an effective amount of a compound of formula (V):

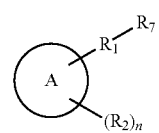

(V)

wherein:

A is aryl or heteroaryl;

$R_1$ is alkylene;

n is 1;

$R_2$ is selected from nitro and aryl; and $R_7$ is carboxy;

or a salt thereof.

3. A method of reducing virulence in a bacterium comprising at least one of a GacS/GacA-type system, a HrpX/HrpY-type system, a T3SS-type system, and a Rsm-type system, the method comprising contacting the bacterium with an effective amount of a compound of formula (VI):

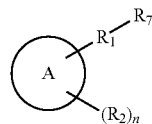

(VI)

wherein:

A is selected from imidazole, thiophene, furan, oxazole, thiazole, quinoline, benzofuran, benzothiofuran and carbazole;

$R_1$ is selected from alkylene, heteroalkylene, oxygen, sulfur and a bond;

n is 0, 1, 2, 3, 4 or 5;

each $R_2$ is independently selected from alkyl, alkenyl, alkynyl, hydroxy, hydroxyalkyl, alkoxy, sulfhydryl, thioether, sulfo, silyl, phosphono, halo, carboxy, nitro, amino, formyl, aryl, haloalkyl, ester, amido and heterocyclyl groups; and $R_7$ is selected from hydroxy, hydroxyalkyl, alkoxy, carboxy, hydroxamic acid, hydrazide, hydrazinocarbonyl, aryl, ester, amino, amido, thioamido, sulfonyl, sulfinic acid, sulfonic acid, sulfinate, sulfonate, phosphonic acid, phosphonate, and substituted or unsubstituted bicyclic heteroaromatic groups;

or a salt thereof.

4. A method of reducing virulence in a bacterium comprising at least one of a GacS/GacA-type system, a HrpX/HrpY-type system, a T3SS-type system, and a Rsm-type system, the method comprising contacting the bacterium with an effective amount of a compound selected from the group consisting of:

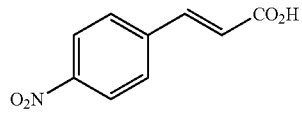

or a salt thereof.

5. The method of claim 1, wherein the bacterium is of a bacterial genus selected from the group consisting of *Pseudomonas, Dickeya, Erwinia, Azotobacter, Vibrio, Yersinia, Pectobacterium, Salmonella, Chlamydia, Xanthomonas, Ralstonia, Shewanella, Shigella* and *Escherichia*.

6. The method of claim 1, wherein the bacterium is a *Pseudomonas* spp. selected from the group consisting of *P. aureofaciens, P. chlororaphis, P. fluorescens, P. marginalis, P. syringae, P. tolaasii, P. viridiflava,* and *P. aeruginosa*.

7. The method of claim 6, wherein the bacterium is *P. aeruginosa*.

8. The method of claim 1, wherein the bacterium is an *Erwinia*-related strain selected from the group consisting of *Dickeya dadantii, Pectobacterium carotovora, Pectobacterium atroseptica,* and *Erwinia amylovora*.

9. The method of claim 1, wherein the bacterium is a *Salmonella* spp. selected from the group consisting of *S. typhimurium* and *S. enterica*.

10. The method of claim 1, wherein the bacterium is *Ralstonia solanacearum*.

11. The method of claim 1, wherein the bacterium is a *Xanthomonas* spp. selected from the group consisting of *X. campestris, X. axonopodis* and *X. oryzae*.

12. The method of claim 1, wherein the bacterium is associated with a subject, and wherein the bacterium is contacted with the compound by administering the compound to the subject.

13. The method of claim 12, wherein the subject is a plant.

14. The method of claim 13, wherein the composition is administered to at least one of leaves, stems, roots, buds, fruits, frill, stump, bark, roots, soil or rhisozphere.

15. The method of claim 13, wherein the composition is sprayed on the plant.

16. The method of claim 12, wherein the subject is an animal.

17. The method of claim 8, wherein the bacterium is on a surface, and wherein the bacterium is contacted with the compound by contacting the surface with the compound.

18. A compound selected from the group consisting of:

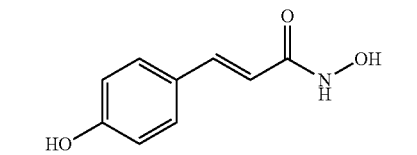 [SMILES: O=C(/C=C/c1ccc(O)cc1)NO]

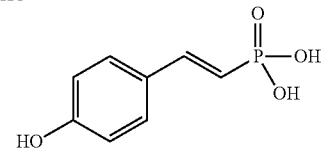

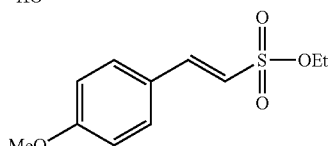

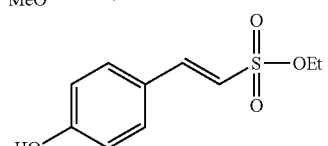

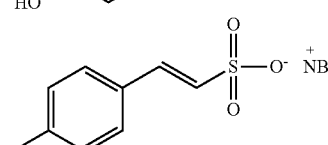

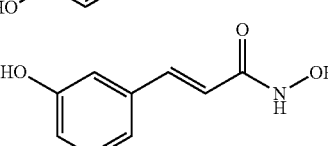

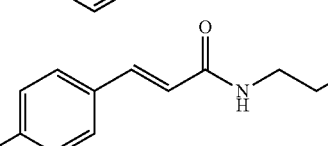

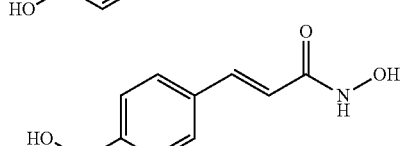

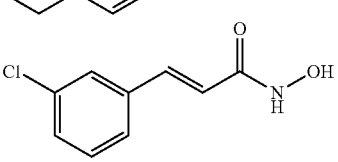

-continued

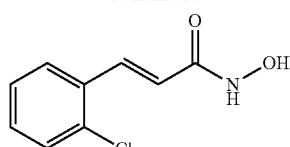

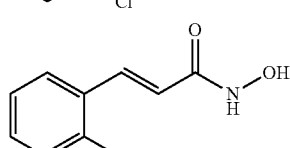

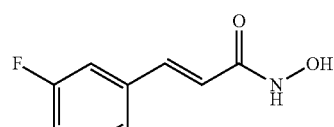

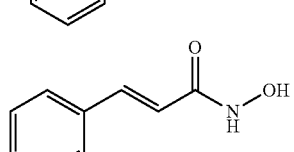

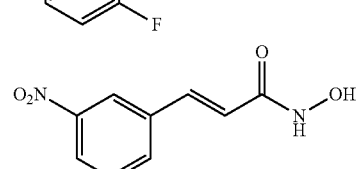

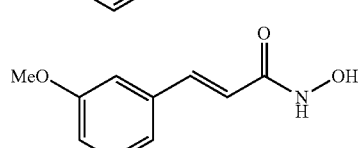

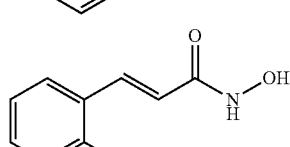

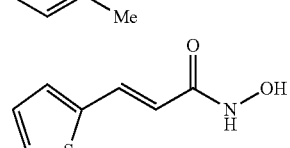

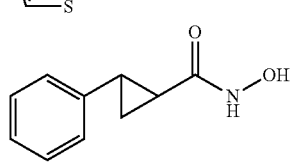

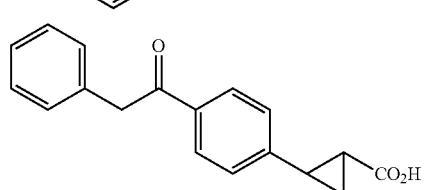

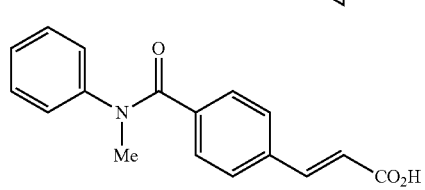

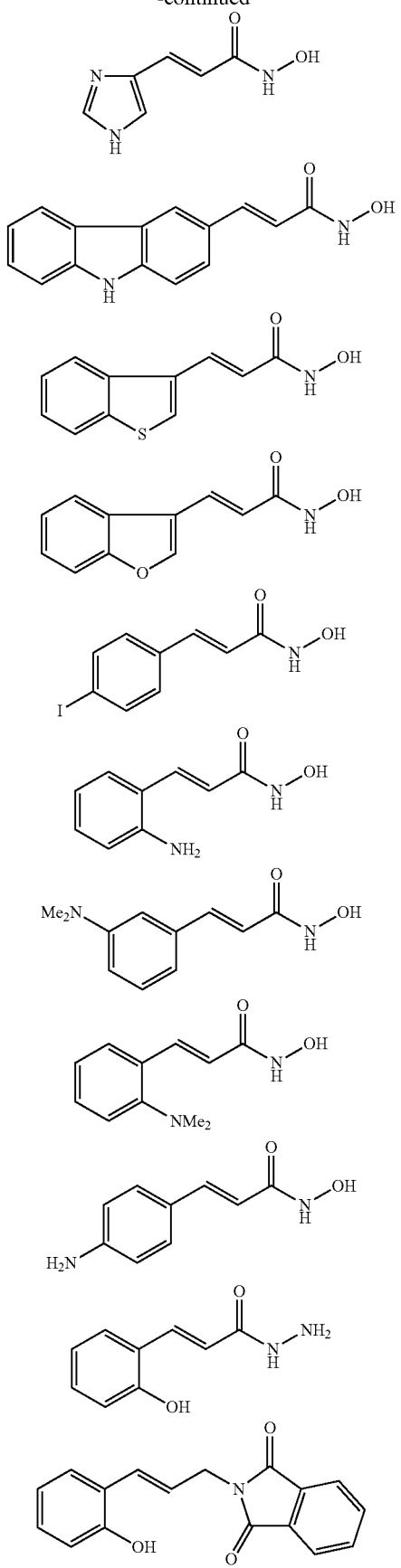
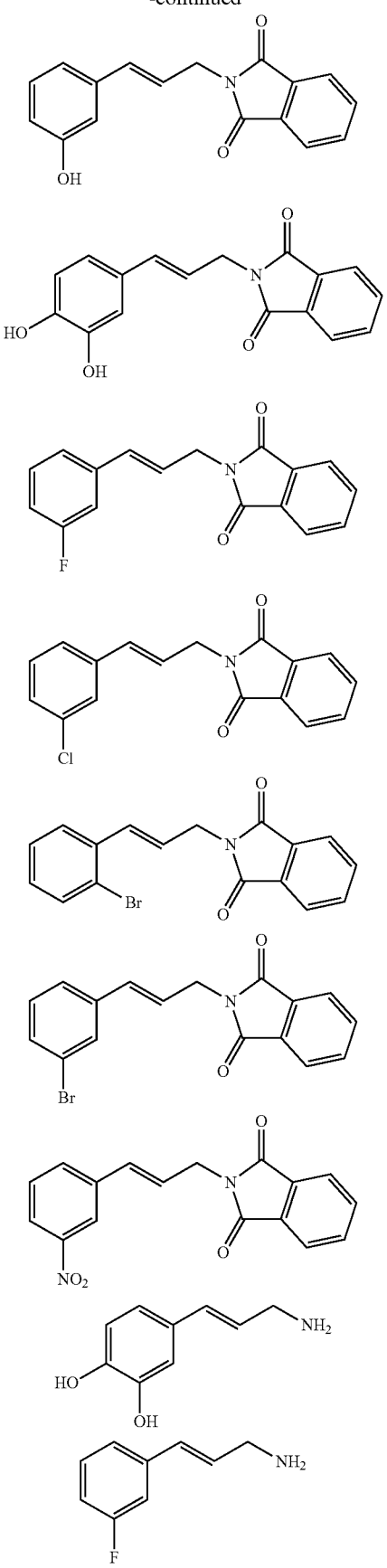

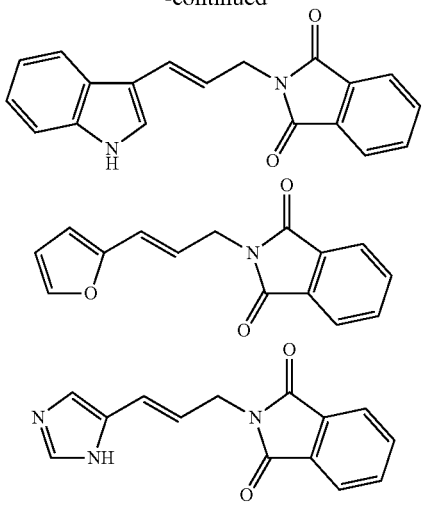

or a salt thereof.

19. A method of reducing virulence in a bacterium comprising at least one of a GacS/GacA-type system, a HrpX/HrpY-type system, a T3SS-type system, and a Rsm-type system, the method comprising contacting the bacterium with an effective amount of a compound selected from the group consisting of:

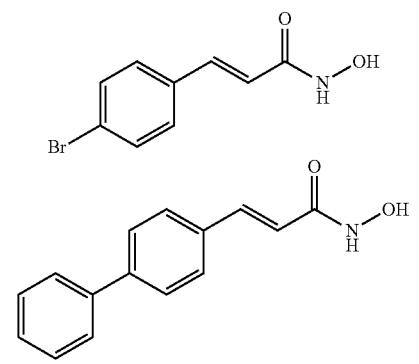

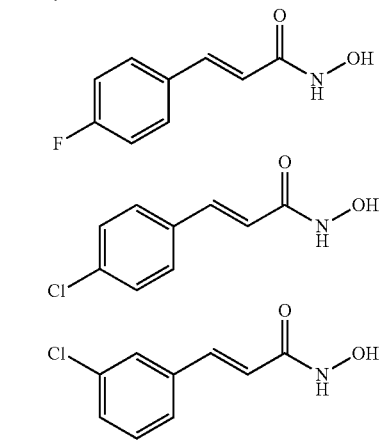

or a salt thereof.

20. A method of reducing virulence in a bacterium comprising at least one of a GacS/GacA-type system, a HrpX/HrpY-type system, a T3SS-type system, and a Rsm-type system, the method comprising contacting the bacterium with an effective amount of a compound:

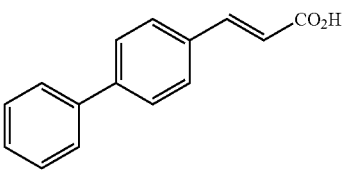 [SMILES: O=C(O)/C=C/c1ccc(-c2ccccc2)cc1]

or a salt thereof.

21. A method of reducing virulence in a bacterium comprising at least one of a GacS/GacA-type system, a HrpX/HrpY-type system, a T3SS-type system, and a Rsm-type system, the method comprising contacting the bacterium with an effective amount of a compound:

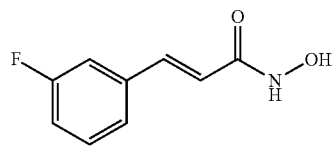 [SMILES: O=C(/C=C/c1cccc(F)c1)NO]
or a salt thereof.
* * * * *